(12) United States Patent
Mutter

(10) Patent No.: US 6,773,883 B2
(45) Date of Patent: Aug. 10, 2004

(54) PROGNOSTIC CLASSIFICATION OF ENDOMETRIAL CANCER

(75) Inventor: George L. Mutter, Chestnut Hill, MA (US)

(73) Assignee: The Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/919,497

(22) Filed: Jul. 31, 2001

(65) Prior Publication Data

US 2002/0106662 A1 Aug. 8, 2002

Related U.S. Application Data

(60) Provisional application No. 60/221,735, filed on Jul. 31, 2000.

(51) Int. Cl.⁷ ................................. C12Q 1/68
(52) U.S. Cl. .............. 435/6; 436/504; 436/64
(58) Field of Search ............... 435/6, 7.1, 7.23; 436/502, 64

(56) References Cited

U.S. PATENT DOCUMENTS 5,468,634 A    11/1995   Liu

OTHER PUBLICATIONS

Marx et al (Sep. 8, 2000, Science vol. 289 pp. 1670–2).*
Tockman et al (Cancer Res., 1992, 52:2711s–2718s).*
Imamura et al., Database GenCore, locus AN D88213, Genomics 40(2): 277–283 (1997).
Zhang et al., Database GenCore, locus AN AF081363 (1998).
O'Bryan et al., Database GenCore, locus AN M76125, *Mol Cell Biol* 11(10): 5016–5031 (1991).
Janssen et al., Database GenCore, locus AN S65125, *Oncogene* 6(11): 2113–2120 (1991).

* cited by examiner

*Primary Examiner*—Larry R. Helms
*Assistant Examiner*—Misook Yu
(74) *Attorney, Agent, or Firm*—Wolf, Greenfield & Sacks, P.C.

(57) ABSTRACT

The invention provided sets of genes that are expressed differentially in normal and malignant endometrium. These sets of genes can be used to discriminate between normal and malignant endometrial tissues. Accordingly, diagnostic assays for classification of tumors, prediction of tumor outcome, selecting and monitoring treatment regimens and monitoring tumor progression/regression also are provided.

1 Claim, No Drawings

PROGNOSTIC CLASSIFICATION OF ENDOMETRIAL CANCER

RELATED APPLICATIONS

This application claims the benefit under 35 U.S.C. §119 (e) of U.S. provisional application 60/221,735, filed Jul. 31, 2000.

FIELD OF THE INVENTION

The invention relates to nucleic acid microarray markers for cancer, particularly for endometrial cancer. The invention also relates to methods for diagnosing cancer as well as optimizing cancer treatment strategies.

BACKGROUND OF THE INVENTION

Endometrioid endometrial adenocarcinomas are the most common gynecologic malignancy, the risk of which is increased by an abnormal endocrine environment or premalignant lesions with loss of tumor suppressor function. The 6000 deaths yearly make uterine cancer the seventh leading cause of death from malignancy in females. It is primarily a disease of postmenopausal women, although 25 percent of cases occur in women below age 50 and 5 percent below age 40 (Harrison's Principles of Internal Medicine 1998).

Although much progress has been made toward understanding the biological basis of cancer and in its diagnosis and treatment, it is still one of the leading causes of death in the United States. Inherent difficulties in the diagnosis and treatment of cancer include among other things, the existence of many different subgroups of cancer and the concomitant variation in appropriate treatment strategies to maximize the likelihood of positive patient outcome.

The prognosis of endometrial cancer depends upon stage, histologic grade, and extent of myometrial invasion. The staging of endometrial cancer requires surgery to establish the extent of disease and the depth of myometrial invasion. Peritoneal fluid should be sampled; the abdomen and pelvis explored; and pelvic and para-aortic lymphadenectomy performed depending upon the histology, grade, and depth of invasion in the uterine specimen on frozen section.

Initial evaluation of patients suspected of endometrial cancer includes a history and physical and pelvic examination followed by an endometrial biopsy or a fractional dilation and curettage. Outpatient procedures such as endometrial biopsy or aspiration curettage can be used but are definitive only when positive. Once a diagnosis is made, the options for treating endometrial cancer are assessed with respect to the needs of the patient. These options traditionally include surgical intervention, radiotherapy, chemotherapy, and adjuvant systemic therapies. Adjuvants may include but are not limited to chemotherapy, radiotherapy, and endocrine therapies with progestational agents such as hydroxyprogesterone, megastrol, and deoxyprogesterone, and the antiestrogen tamoxifen.

It is difficult to predict from standard clinical and pathologic features the clinical course of endometrial cancer. However, it is very important in the treatment of endometrial cancer to select and implement an appropriate combination of therapeutic approaches. The available methods for designing strategies for treating endometrial cancer patients are complex and time consuming. The wide range of cancer subgroups and variations in disease progression limit the predictive ability of the healthcare professional. In addition, continuing development of novel treatment strategies and therapeutics will result in the addition of more variables to the already complex decision-making process involving matching the cancer patient with a treatment regimen that is appropriate and optimized for the cancer stage, extent of myometrial invasion, tumor growth rate, and other factors central to the individual patient's prognosis. Because of the critical importance of selecting appropriate treatment regimens for endometrial cancer patients, the development of guidelines for treatment selection is of key interest to those in the medical community and their patients. Thus, there presently is a need for objective, reproducible, and sensitive methods for predicting endometrial cancer patient outcome and selecting optimal treatment regimens.

SUMMARY OF THE INVENTION

It now has been discovered that particular sets of genes are expressed differentially in normal and malignant endometrium. These sets of genes can be used to discriminate between normal and malignant endometrial tissues. Accordingly, diagnostic assays for classification of tumors, prediction of tumor outcome, selecting and monitoring treatment regimens, and monitoring tumor progression/regression can now be based on the expression of sets of genes.

According to one aspect of the invention, methods for diagnosing endometrial cancer in a subject suspected of having endometrial cancer are provided. The methods include obtaining from the subject an endometrial tissue sample and determining the expression of a set of nucleic acid molecules or expression products thereof in the endometrial tissue sample. The set of nucleic acid molecules includes at least two nucleic acid molecules selected from the group consisting of SEQ ID NOs:1–50. In preferred embodiments, the endometrial tissue sample is suspected of being cancerous.

In some embodiments the set of nucleic acid molecules includes more than 2, and up to all of the nucleic acid molecules set forth as SEQ ID NOs:1–50, and any number of nucleic acid sequences between these two numbers. For example, in certain embodiments the set includes at least 3, 4, 5, 10, 15, 20, 30, 40 or more nucleic acid molecules of the nucleic acid molecules set forth as SEQ ID NOs:1–50.

In other embodiments, the method further includes determining the expression of the set of nucleic acid molecules or expression products thereof in a non-cancerous endometrial tissue sample, and comparing the expression of the set of nucleic acid molecules or expression products thereof in the endometrial tissue sample suspected of being cancerous and the non-cancerous endometrial tissue sample.

The invention in another aspect provides solid-phase nucleic acid molecule arrays. The arrays have a cancer gene marker set that consists essentially of at least two and as many as all of the nucleic acid molecules set forth as SEQ ID NOs:1–50 fixed to a solid substrate. The set of nucleic acid markers can include any number of nucleic acid sequences between these two numbers, selected from SEQ ID NOs:1–50. For example, in certain embodiments the set includes at least 3, 4, 5, 10, 15, 20, 30, 40 or more nucleic acid molecules of the nucleic acid molecules set forth as SEQ ID NOs:1–50. In some embodiments, the solid-phase nucleic acid molecule array also includes at least one control nucleic acid molecule.

In certain embodiments, the solid substrate includes a material selected from the group consisting of glass, silica, aluminosilicates, borosilicates, metal oxides such as alumina and nickel oxide, various clays, nitrocellulose, or nylon. Preferably the substrate is glass.

In other embodiments, the nucleic acid molecules are fixed to the solid substrate by covalent bonding.

According to yet another aspect of the invention, protein microarrays are provided. The protein microarrays include antibodies or antigen-binding fragments thereof, that specifically bind at least two different polypeptides selected from the group consisting of SEQ ID NOs:51–100, fixed to a solid substrate. In some embodiments, the microarray comprises antibodies or antigen-binding fragments thereof, that bind specifically to least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 different polypeptides selected from the group consisting of SEQ ID NOs:51–100. In certain embodiments, the microarray also includes an antibody or antigen-binding fragment thereof, that binds specifically to a cancer-associated polypeptide other than those selected from the group consisting of SEQ ID NOs:51–100, preferably An endometrial cancer associated polypeptide. In some embodiments, the protein microarray also includes at least one control polypeptide molecule. In further embodiments, the antibodies are monoclonal or polyclonal antibodies. In other embodiments, the antibodies are chimeric, human, or humanized antibodies. In some embodiments, the antibodies are single chain antibodies. In still other embodiments, the antigen-binding fragments are F(ab')$_2$, Fab, Fd, or Fv fragments.

According to yet another aspect of the invention, protein microarrays are provided. The protein microarrays include antibodies or antigen-binding fragments thereof, that specifically bind at least two different polypeptides selected from the group consisting of SEQ ID NOs:51–100, fixed to a solid substrate. In some embodiments, the microarray comprises antibodies or antigen-binding fragments thereof, that bind specifically to least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 different polypeptides selected from the group consisting of SEQ ID NOs:51–100. In certain embodiments, the microarray also includes an antibody or antigen-binding fragment thereof, that binds specifically to a cancer-associated polypeptide other than those selected from the group consisting of SEQ ID NOs:51–100, preferably an endometrial cancer associated polypeptide. In some embodiments, the protein microarray also includes at least one control polypeptide molecule. In further embodiments, the antibodies are monoclonal or polyclonal antibodies. In other embodiments, the antibodies are chimeric, human, or humanized antibodies. In some embodiments, the antibodies are single chain antibodies. In still other embodiments, the antigen-binding fragments are F(ab')$_2$, Fab, Fd, or Fv fragments.

In a further aspect of the invention, methods for identifying lead compounds for a pharmacological agent useful in the treatment of endometrial cancer are provided. The methods include contacting an endometrial cancer cell or tissue with a candidate pharmacological agent, and determining the expression of a set of nucleic acid molecules in the endometrial cancer cell or tissue sample under conditions which, in the absence of the candidate pharmacological agent, permit a first amount of expression of the set of nucleic acid molecules. The set of nucleic acid molecules includes at least two and as many as all of the nucleic acid molecules set forth as SEQ ID NOs:1–50. The methods also include detecting a test amount of the expression of the set of nucleic acid molecules, wherein a decrease in the test amount of expression in the presence of the candidate pharmacological agent relative to the first amount of expression indicates that the candidate pharmacological agent is a lead compound for a pharmacological agent that is useful in the treatment of endometrial cancer.

In some embodiments of any of the foregoing methods and products, the differences in the expression of the nucleic acid molecules are determined by nucleic acid hybridization or nucleic acid amplification methods. Preferably the nucleic acid hybridization is performed using a solid-phase nucleic acid molecule array. In other embodiments, the differences in the expression of the nucleic acid molecules are determined by protein expression analysis, preferably SELDI mass spectroscopy.

These and other aspects of the invention will be described in greater detail below.

DETAILED DESCRIPTION OF THE INVENTION

The invention described herein relates to the identification of a set of genes expressed in endometrial cancer tissue that are predictive of the clinical outcome of the cancer. Changes in cell phenotype in cancer are often the result of one or more changes in the genome expression of the cell. Some genes are expressed in tumor cells, and not in normal cells. In addition, different genes are expressed in different subgroups of endometrial cancers, which have different prognoses and require different treatment regimens to optimize patient outcome. The differential expression of endometrial cancer genes can be examined by the assessment of nucleic acid or protein expression in the endometrial cancer tissue.

The genes identified permit, inter alia, rapid screening of cancer samples by nucleic acid microarray hybridization or protein expression technology to determine the expression of the specific genes and thereby to predict the outcome of the cancer. Such screening is beneficial, for example, in selecting the course of treatment to provide to the cancer patient, and to monitor the efficacy of a treatment.

The invention differs from traditional endometrial cancer diagnostic and classification techniques with respect to the speed, simplicity, and reproducibility of the cancer diagnostic assay. The invention also presents targets for drug development because it identifies genes that are differentially expressed in outcome endometrial tumors, which can be utilized in the development of drugs to treat such tumors, e.g., by reducing expression of the genes or reducing activity of proteins encoded by the genes.

The invention simplifies prognosis determination by providing an identified set of genes whose expression in endometrial cancers predicts clinical outcome as defined by tumor metastasis, recurrence, or death. In the invention RNA expression phenotyping was performed using high density microarrays generated from quantitative expression data on over 5000 (estimated 5800) genes, which have been analyzed to identify 50 specific probe sets (genes). The expression gene set has multifold uses including, but not limited to, the following examples. The expression gene set may be used as a prognostic tool for endometrial cancer patients, to make possible more finely tuned diagnosis of endometrial cancer and allow healthcare professionals to tailor treatment to individual patients' needs. The invention can also assess the efficacy of endometrial cancer treatment by determining progression or regression of endometrial cancer in patients before, during, and after endometrial cancer treatment. Another utility of the expression gene set is in the biotechnology and pharmaceutical industries' research on disease pathway discovery for therapeutic targeting. The invention can identify alterations in gene expression in endometrial cancer and can also be used to uncover and test candidate pharmaceutical agents to treat endometrial cancer.

As used herein, a subject is a human, non-human primate, cow, horse, pig, sheep, goat, dog, cat, or rodent. In all embodiments human subjects are preferred. Preferably the subject is a human either suspected of having endometrial cancer, or having been diagnosed with endometrial cancer. In a preferred embodiment of the invention the cancer is endometroid endometrial adenocarcinoma. Methods for identifying subjects suspected of having endometrial cancer may include physical examination, subject's family medical history, subject's medical history, endometrial biopsy, or a number of imaging technologies such as ultrasonography, computed tomography, magnetic resonance imaging, magnetic resonance spectroscopy, or positron emission tomography. Diagnostic methods for endometrial cancer and the clinical delineation of endometrial cancer diagnoses are well known to those of skill in the medical arts.

As used herein, endometrial tissue sample is tissue obtained from an endometrial tissue biopsy using methods well known to those of ordinary skill in the related medical arts. The phrase "suspected of being cancerous" as used herein means an endometrial cancer tissue sample believed by one of ordinary skill in the medical arts to contain cancerous cells. Methods for obtaining the sample from the biopsy include gross apportioning of a mass, microdissection, laser-based microdissection, cytologic sampling of the endometrium using a brush, aspiration curettage, fractional dilation and curettage, or other art-known cell-separation methods.

Because of the variability of the cell types in diseased-tissue biopsy material, and the variability in sensitivity of the diagnostic methods used, the sample size required for analysis may range from 1, 10, 50, 100, 200, 300, 500, 1000, 5000, 10,000, to 50,000 or more cells. The appropriate sample size may be determined based on the cellular composition and condition of the biopsy and the standard preparative steps for this determination and subsequent isolation of the nucleic acid for use in the invention are well known to one of ordinary skill in the art. An example of this, although not intended to be limiting, is that in some instances a sample from the biopsy may be sufficient for assessment of RNA expression without amplification, but in other instances the lack of suitable cells in a small biopsy region may require use of RNA conversion and/or amplification methods or other methods to enhance resolution of the nucleic acid molecules. Such methods, which allow use of limited biopsy materials, are well known to those of ordinary skill in the art and include, but are not limited to: direct RNA amplification, reverse transcription of RNA to cDNA, amplification of cDNA, or the generation of radio-labeled nucleic acids.

As used herein, the phrase "determining the expression of a set of nucleic acid molecules in the endometrial tissue" means identifying RNA transcripts in the tissue sample by analysis of nucleic acid or protein expression in the tissue sample. As used herein, "set" refers to a group of nucleic acid molecules that include 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 different nucleic acid sequences from the group of nucleic acid sequences numbered 1 through 50 in Table 1 (SEQ ID NOs:1–50).

The expression of the set of nucleic acid molecules in the sample from the endometrial cancer patient can be compared to the expression of the set of nucleic acid molecules in a sample of endometrial tissue that is non-cancerous. As used herein, non-cancerous endometrial tissue means tissue determined by one of ordinary skill in the medical art to have no evidence of endometrial cancer based on standard diagnostic methods including, but not limited to, histologic staining and microscopic analysis.

Nucleic acid markers for cancer are nucleic acid molecules that by their presence or absence indicate the presence of absence of endometrial cancer. In tissue, certain nucleic acid molecules are expressed at different levels depending on whether tissue is non-cancerous or cancerous.

Hybridization methods for nucleic acids are well known to those of ordinary skill in the art (see, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York). The nucleic acid molecules from an endometrial cancer tissue sample hybridize under stringent conditions to nucleic acid markers expressed in endometrial cancer. In one embodiment the markers are sets of two or more of the nucleic acid molecules as set forth in SEQ ID NOs:1 through 50.

The endometrial cancer nucleic acid markers disclosed herein are known genes and fragments thereof. It may be desirable to identify variants of those genes, such as allelic variants or single nucleotide polymorphisms (SNPs) in tissues. Accordingly, methods for identifying endometrial cancer nucleic acid markers, including variants of the disclosed full-length cDNAs, genomic DNAs, and SNPs are also included in the invention. The methods include contacting a nucleic acid sample (such as a cDNA library, genomic library, genomic DNA isolate, etc.) with a nucleic acid probe or primer derived from one of SEQ ID NOs:1–50. The nucleic acid sample and the probe or primer hybridize to complementary nucleotide sequences of nucleic acids in the sample, if any are present, allowing detection of nucleic acids related to SEQ ID NOs:1–50. Preferably the probe or primer is detectably labeled. The specific conditions, reagents, and the like can be selected by one of ordinary skill in the art to selectively identify nucleic acids related to sets of two or more of SEQ ID NOs:1 through 50. The isolated nucleic acid molecule can be sequenced according to standard procedures.

In addition to native nucleic acid markers (SEQ ID NOs:1–50), the invention also includes degenerate nucleic acids that include alternative codons to those present in the native materials. For example, serine residues are encoded by the codons TCA, AGT, TCC, TCG, TCT, and AGC. Each of the six codons is equivalent for the purposes of encoding a serine residue. Similarly, nucleotide sequence triplets that encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions, and deletions of one or more nucleotides such as the allelic variants and SNPs described above. In preferred embodiments, these modified nucleic acid molecules and/or the polypeptides they encode retain at least one activity or function of the unmodified nucleic acid molecule and/or the polypeptides, such as hybridization, antibody binding, etc. In certain embodiments, the modified nucleic acid molecules encode modified polypeptides, preferably polypeptides having conservative amino acid substitutions. As used herein, a "conservative amino acid substitution" refers to an amino acid substitution which does not alter the relative charge or size characteristics of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared for use in the methods and products disclosed herein. Each of these nucleic acid molecules can have one, two, or three nucleotide substitutions exclusive of nucleotide changes corresponding to the degeneracy of the genetic code as described herein. Likewise, modified nucleic acid molecules that encode polypeptides having two amino acid changes can be prepared, which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions that code for the amino acid substitutions. Additional nucleic acid molecules that encode polypeptides having additional substitutions (i.e., 3 or more), additions or deletions [e.g., by introduction of a stop codon or a splice site(s)] also can be prepared and are embraced by the invention as readily envisioned by one of ordinary skill in the art. Any of the foregoing nucleic acids can be tested by routine experimentation for retention of structural relation to or activity similar to the nucleic acids disclosed herein.

In the invention, standard hybridization techniques of microarray technology are utilized to assess patterns of nucleic acid expression and identify nucleic acid marker expression. Microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast*, Nature Genetics, Vol.21, January 1999, the entire contents of which is incorporated by reference herein.

According to the present invention, microarray substrates may include but are not limited to glass, silica, aluminosilicates, borosilicates, metal oxides such as alumina and nickel oxide, various clays, nitrocellulose, or nylon. In all embodiments a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of two or more of the nucleic acid molecules set forth as SEQ ID NO:1 through 50 (see also Table 1). Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or olignucleotide to the substrate. These agents or groups may include, but are not limited to: amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photochemical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (Chipping Forecast, 1999) or chromium (Gwynne and Page, 2000). In this embodiment, presynthesized probes are applied to the substrate in a precise, predetermined volume and grid pattern, utilizing a computer-controlled robot to apply probe to the substrate in a contact-printing manner or in a non-contact manner such as ink jet or piezo-electric delivery. Probes may be covalently linked to the substrate with methods that include, but are not limited to, UV-irradiation. In another embodiment probes are linked to the substrate with heat.

Targets are nucleic acids selected from the group, including but not limited to: DNA, genomic DNA, cDNA, RNA, mRNA and may be natural or synthetic. In all embodiments, nucleic acid molecules from human endometrial tissue are preferred. The tissue may be obtained from a subject or may be grown in culture (e.g. from a endometrial cancer cell line).

In embodiments of the invention one or more control nucleic acid molecules are attached to the substrate. Preferably, control nucleic acid molecules allow determination of factors including but not limited to: nucleic acid quality and binding characteristics; reagent quality and effectiveness; hybridization success; and analysis thresholds and success. Control nucleic acids may include but are not limited to expression products of genes such as housekeeping genes or fragments thereof.

To select a set of tumor markers, the expression data generated by, for example, microarray analysis of gene expression, preferably is analyzed to determine which genes in different groups of cancer tissues are significantly differentially expressed. In the methods disclosed herein, the significance of gene expression was determined using Permax computer software, although any standard statistical package that can discriminate significant differences in expression may be used. Permax performs permutation 2-sample t-tests on large arrays of data. For high dimensional vectors of observations, the Permax software computes t-statistics for each attribute, and assesses significance using the permutation distribution of the maximum and minimum overall attributes.

In one embodiment of the invention, expression of nucleic acid markers is used to select clinical treatment paradigms for endometrial cancer. Treatment options, as described herein, may include but are not limited to: radiotherapy, chemotherapy, adjuvant therapy, or any combination of the aforementioned methods. Aspects of treatment that may vary include, but are not limited to: dosages, timing of administration, or duration or therapy; and may or may not be combined with other treatments, which may also vary in dosage, timing, or duration. Another treatment for endometrial cancer is surgery, which can be utilized either alone or in combination with any of the aforementioned treatment methods. One of ordinary skill in the medical arts may determine an appropriate treatment paradigm based on evaluation of differential expression of sets of two or more of the nucleic acid targets ste forth as SEQ ID NOs:1–50. Cancers that express markers that are indicative of a more aggressive cancer or poor prognosis may be treated with more aggressive therapies.

Progression or regression of endometrial cancer is determined by comparison of two or more different endometrial cancer tissue samples taken at two or more different times from a subject. For example, progression or regression may be evaluated by assessments of expression of sets of two or more of the nucleic acid targets, including but not limited to SEQ ID NOs:1–50, in an endometrial cancer tissue sample from a subject before, during, and following treatment for endometrial cancer.

In another embodiment, novel pharmacological agents useful in the treatment of endometrial cancer can be identified by assessing variations in the expression of sets of two or more endometrial cancer nucleic acid markers, from among SEQ ID NOs:1–50, prior to and after contacting endometrial cancer cells or tissues with candidate pharmacological agents for the treatment of endometrial cancer. The cells may be grown in culture (e.g. from an endometrial cancer cell line), or may be obtained from a subject, (e.g. in a clinical trial of candidate pharmaceutical agents to treat endometrial cancer). Alterations in expression of two or more sets of endometrial cancer nucleic acid markers, from among SEQ ID NOs:1–50, in endometrial cancer cells or tissues tested before and after contact with a candidate pharmacological agent to treat endometrial cancer, indicate progression, regression, or stasis of the endometrial cancer thereby indicating efficacy of candidate agents and concomitant identification of lead compounds for therapeutic use in endometrial cancer.

The invention further provides efficient methods of identifying pharmacological agents or lead compounds for agents active at the level of endometrial cancer cellular function. Generally, the screening methods involve assaying for compounds that beneficially alter endometrial cancer nucleic acid molecule expression. Such methods are adaptable to automated, high-throughput screening of compounds.

The assay mixture comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, antimicrobial agents, and the like may also be used.

The mixture of the foregoing assay materials is incubated under conditions whereby, the anti-endometrial cancer candidate agent specifically binds the cellular binding target, a portion thereof or analog thereof. The order of addition of components, incubation temperature, time of incubation, and other paameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the antiendometrial cancer candidate agent and one or more binding targets is detected by any convenient method available to the user. For cell-free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal-to-noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromotograpic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of the anti-cancer agent binding to a target molecule typically encodes a directly or indirectly detectable product, e.g., β-galactosidase activity, luciferase activity, and the like. For cell-free binding assays, one of the components usually comprises, or is coupled to, a detectable label. A wide variety of labels can be used, such as those that provide direct detection (e.g., radioactivity, luminescence, optical, or electron density, etc) or indirect detection (e.g., epitope tag such as the FLAG epitope, enzyme tag such as horseseradish peroxidase, etc.). The label may be bound to an anti-cancer agent binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

The invention provides endometrial cancer gene-specific binding agents, methods of identifying and making such agents, and their use in diagnosis, therapy and pharmaceutical development. For example, endometrial cancer gene-specific pharmacological agents are useful in a variety of diagnostic and therapeutic applications as described herein. In general, the specificity of an endometrial cancer gene binding to a binding agent is shown by binding equilibrium constants. Targets that are capable of selectively binding an endometrial cancer gene preferably have binding equilibrium constants of at least about $10^7 M^{-1}$, more preferably at least about $10^8 M^{-1}$, and most preferably at least about $10^9 M^{-1}$. The wide variety of cell-based and cell-free assays may be used to demonstrate endometrial cancer gene-specific binding. Cell-based assays include one, two and three hybrid screens, assays in which endometrial cancer gene-mediated transcription is inhibited or increased, etc. Cell-free assays include endometrial cancer gene-protein binding assays, immunoassays, etc. Other assays useful for screening agents which bind endometrial cancer polypeptides include fluorescence resonance energy transfer (FRET), and electrophoretic mobility shift analysis (EMSA).

In another aspect of the invention, pre- and post-treatment alterations in expression of two or more sets of endometrial cancer nucleic acid markers including, but not limited to, SEQ ID NOs:1–50 in endometrial cancer cells or tissues may be used to assess treatment parameters including, but not limited to: dosage, method of administration, timing of administration, and combination with other treatments as described herein.

Candidate pharmacological agents may include antisense oligonucleotides that selectively bind to an endometrial cancer nucleic acid marker molecule, as identified herein, to reduce the expression of the marker molecules in endometrial cancer cells and tissues. One of ordinary skill in the art can test of the effects of a reduction of expression of endometrial cancer nucleic acid marker sequences in vivo or in vitro, to determine the efficacy of one or more antisense oligonucleotides.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide, which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions.

Based upon the sequences of endometrial cancer expressed nucleic acids, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases that are complementary to the target, although in certain cases modified oligonucleotides as short as 7 bases in length have been used successfully as antisense oligonucleotides (Wagner et al., 1996). Most preferably, the antisense oligonucleotides comprise a complementary sequence of 20–30 bases. Although oligonucleotides may be chosen that are antisense to any region of the gene or mRNA transcripts, in preferred embodiments the antisense oligonucleotides correspond to N-terminal or 5' upstream sites such as translation initiation, transcription initiation, or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., 1994) and at which proteins are not expected to bind. Finally, although the listed sequences are cDNA sequences, one of ordinary skill in the art may easily derive the genomic DNA corresponding to the cDNA of an endometrial cancer expressed polypeptide. Thus, the present invention also provides for antisense oligonucleotides that are complementary to the genomic DNA corresponding to endometrial cancer expressed nucleic acids. Similarly, the use of antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art-recognized methods, which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways that do not prevent them from hybridizing to their target but which enhance their stability or targeting or which otherwise enhance their therapeutic effectiveness. The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters, and peptides.

The term "modified oligonucleotide" also encompasses oligonucleotides with a covalently modified base and/or sugar. For example, modified oligonucleotides include oligonucleotides having backbone sugars that are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, endometrial cancer expressed nucleic acids, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art.

The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials, which are well known in the art.

Expression of endometrial cancer nucleic acid molecules can also be determined using protein measurement methods to determine expression of SEQ ID NOs:1–50, e.g., by determining the expression of polypeptides encoded by SEQ ID NOs:1–50 (SEQ ID NOs: 51–100). Preferred methods of specifically and quantitatively measuring proteins include, but are not limited to: mass spectroscopy-based methods such as surface enhanced laser desorption ionization (SELDI; e.g., Ciphergen ProteinChip System), non-mass spectroscopy-based methods, and immunohistochemistry-based methods such as 2-dimensional gel electrophoresis.

SELDI methodology may, through procedures known to those of ordinary skill in the art, be used to vaporize microscopic amounts of tumor protein and to create a "fingerprint" of individual proteins, thereby allowing simultaneous measurement of the abundance of many proteins in a single sample. Preferably SELDI-based assays may be utilized to classify endometrial cancer tumors. Such assays preferably include, but are not limited to the following examples. Gene products discovered by RNA microarrays may be selectively measured by specific (antibody mediated) capture to the SELDI protein disc (e.g., selective SELDI). Gene products discovered by protein screening (e.g., with 2-D gels), may be resolved by "total protein SELDI" optimized to visualize those particular markers of interest from among SEQ ID NOs:1–50. Predictive models of tumor classification from SELDI measurement of multiple markers from among SEQ ID NOs:1–50 may be utilized for the SELDI strategies. In an additional embodiment a set of endometrioid endometrial adenocarcinoma tissues may be preferably utilized to determine the risk classification of endometrial cancer based on SELDI results.

The invention also involves agents such as polypeptides that bind to endometrial cancer-associated polypeptides, i.e., SEQ ID NOs:51–100. Such binding agents can be used, for example, in screening assays to detect the presence or absence of endometrial cancer-associated polypeptides and complexes of endometrial cancer-associated polypeptides and their binding partners and in purification protocols to isolate endometrial cancer-associated polypeptides and complexes of endometrial cancer-associated polypeptides and their binding partners. Such agents also may be used to inhibit the native activity of the endometrial cancer-associated polypeptides, for example, by binding to such polypeptides.

The invention, therefore, embraces peptide binding agents which, for example, can be antibodies or fragments of antibodies having the ability to selectively bind to endometrial cancer-associated polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modem Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859, 205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to polypeptides selected from SEQ ID NOs:51–100, and complexes of both endometrial cancer-associated polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the endometrial cancer-associated polypeptide. This process can be repeated through several cycles of reselection of phage that bind to the endometrial cancer-associated polypeptide. Repeated rounds lead to enrichment of phage bearing particular sequences. DNA sequence analysis can be conducted to identify the sequences of the expressed polypeptides. The minimal linear portion of the sequence that binds to the endometrial cancer-associated polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the endometrial cancer-associated polypeptides.

Thus, the endometrial cancer-associated polypeptides of the invention, including fragments thereof, can be used to screen peptide libraries, including phage display libraries, to identify and select peptide binding partners of the endometrial cancer-associated polypeptides of the invention. Such molecules can be used, as described, for screening assays, for purification protocols, for interfering directly with the functioning of endometrial cancer-associated polypeptides and for other purposes that will be apparent to those of ordinary skill in the art. For example, isolated endometrial cancer-associated polypeptides can be attached to a substrate (e.g., chromatographic media, such as polystyrene beads, a filter, or an array substrate), and then a solution suspected of containing the binding partner may be applied to the substrate. If a binding partner that can interact with endometrial cancer-associated polypeptides is present in the solution, then it will bind to the substrate-endometrial cancer-associated polypeptide. The binding partner then may be isolated.

As detailed herein, the foregoing antibodies and other binding molecules may be used for example, to identify tissues expressing protein or to purify protein. Antibodies also may be coupled to specific diagnostic labeling agents for imaging of cells and tissues that express endometrial cancer-associated polypeptides or to therapeutically useful agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium.

The invention further includes protein microarrays for analyzing expression of endometrial cancer-associated peptides selected from SEQ ID NOs:51–100. In this aspect of the invention, standard techniques of microarray technology are utilized to assess expression of the endometrial cancer-associated polypeptides and/or identify biological constituents that bind such polypeptides. The constituents of biological samples include antibodies, lymphocytes (particularly T lymphocytes), and the like. Protein microarray technology, which is also known by other names including: protein chip technology and solid-phase protein array technology, is well known to those,of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," *Science* 289(5485): 1760–1763, 2000.

Preferably antibodies or antigen binding fragments thereof that specifically bind polypeptides selected from the group consisting of SEQ ID NOs:51–100 are attached to the microarray substrate in accordance with standard attachment methods known in the art. These arrays can be used to quantify the expression of the polypeptides identified herein.

In some embodiments of the invention, one or more control peptide or protein molecules are attached to the substrate. Preferably, control peptide or protein molecules allow determination of factors such as peptide or protein quality and binding characteristics, reagent quality and effectiveness, hybridization success, and analysis thresholds and success.

The use of such methods to determine expression of endometrial cancer nucleic acids from among SEQ ID NOs:1–50 and/or proteins from among SEQ ID Nos:51–100 can be done with routine methods known to those of ordinary skill in the art and the expression determined by protein measurement methods may be used as a prognostic method for selecting treatment strategies for endometrial cancer patients.

EXAMPLE

To establish a prognostic tool for designing endometrial cancer treatment regimens, expression patterns in primary endometrialcancer specimens were assessed and correlated with clinical outcome.

Tissue Processing

RNA isolated from normal cycling (proliferative, n=2; secretory, n=2) and neoplastic (endometrioid adenocarcinoma, n=10) human endometrial specimens was reverse transcribed and resultant cDNA used for in vitro transcriptional synthesis of fluorescently labeled nucleic acid probes according to manufacturer's instructions. Each resultant tissue-derived probe was then separately hybridized to an Affymetrix HuFL human expression array and hybridization images analyzed with Affymetrix software to generate a data matrix of named probes by quantitative expression level in each tissue.

Data Normalization

Average differences for each sample were rescaled to sum to 3,000,000 over all genes. Then the average differences with an Affymetrix call of Absent or Marginal were set to 20, and average differences with a call of Present but with less than 20 were also set to 20. This resulted in a dataset truncated on the left tail at a value of 20, in which only genes determined to be "present" by the Affymetrix call were included as positive expression values.

Permax Test

Standard pooled variance t-statistics comparing the 4 normal samples to the 10 tumor samples were computed separately for each gene from their log values. Log values were used because it is natural to think of differences between tissue types as a multiplicative effect or ratio increase/decrease. Only genes with at least 2 values>20 were considered (3665 genes), since the t statistic is undefined for genes with all values=20, and the statistic is either 1.69 or −0.62 with only one value not equal to 20, regardless of the value.

The permutation distribution was used to assess the significance of t-statistics calculated for each gene in the dataset (Permax test). The customized program written in S-plus language to calculate Permax is a data analysis software tool for testing the significance of gene expression. It has been presented by Mutter, et al., 8th International Workshop on Chromosomes in Solid Tumors, Tucson, Ariz., 2000; and is available online from the website of the Dana Farber Cancer Institute, laboratory of Dr George Mutter and from Robert J. Gray, Department of Biostatistical Science, Dana-Farber Cancer Institute, 44 Binney Street Boston, MA 02115. Permax details enclosed therein are incorporated by reference herein. In this approach all 1001 possible ways of dividing the 14 samples into two groups of sizes 4 and 10 were considered. For each of these, the t-statistics were computed for each gene. With unequal group sizes, these distributions are not symmetric, so the significance was assessed separately in each direction. To control the overall error rate, the distributions of the maximum and minimum t-statistics over the genes were used. That is, for each gene, the p-value in the direction with expression higher (lower) in normals is the proportion of permutations with the minimum (maximum) t statistic over all genes less than (greater than) or equal to the observed value for the particular gene. A test declaring as significant any genes with say p<.50 then guarantees that the chance of any false positives being selected is <50%.

The t statistics have a tendency to preferentially select genes with very small variances within a group. Because of this it may be appropriate to also require minimum criteria for differences between the group means. After determining the most significant genes from the t statistics, those genes with absolute differences between means<100, and ratios of means<3 were identified.

Table 1 is a spreadsheet identifying 50 genes which discriminate normal cycling from malignant endometrium.

TABLE 1

| SEQ ID NO | GeneCode | Permax GPT | Fold GPT | Delta GPT | ChrBand | NLX GPT | TX GPT | AffyProbe Set | LocusLink | GenBank | ABREV | Title (from Unigene) |
|---|---|---|---|---|---|---|---|---|---|---|---|---|
| 1 | x6235 | 0.042 | 8.9 | 157.3 | 17q21 | 177 | 20 | D88213_at | 314 | D88213 | AOC2 | amine oxidase, copper containing 2 (retina-specific) |
| 2 | x4535 | 0.2218 | 11.6 | 344.8 | 19q13.1 | 377 | 32 | HG162-HT3165_at | 558 | M76125 | AXL | AXL receptor tyrosine kinase |
| 3 | x2035 | 0.2727 | 45.9 | 898.1 | 11p15.5 | 20 | 918 | M91083_at | 8045 | M91083 | C11ORF13 | chromosome 11 open reading frame 13 |
| 4 | x3265 | 0.468 | 10.1 | 1590.5 | 12p13 | 1766 | 175 | D13639_at | 894 | D13639 | CCND2 | cyclin D2 |
| 5 | x3120 | 0.5 | 8.8 | 446.4 | 16q22.1 | 504 | 57 | D21255_at | 1009 | D21255 | CDH11 | cadherin 11 (OB-cadherin, osteoblast) |
| 6 | x6580 | 0.2587 | 8.9 | 255.1 | 1p21 | 287 | 32 | J04177_at | 1301 | J04177 | COL11A1 | collagen, type XI, alpha 1 |
| 7 | x2140 | 0.1938 | 13.3 | 412.2 | 8q23 | 446 | 33 | Y11710_mal_at | 7373 | Y11710 | COL14A1 | collagen, type XIV, alpha 1; undulin |
| 8 | x1629 | 0.2038 | 8.9 | 158.8 | 2p21 | 179 | 20 | U03688_at | 1545 | U03688 | CYP1B1 | cytochrome P450, subfamily I (dioxin-inducible), polypeptide 1 (glaucoma 3, primary infantile) |
| 9 | x3108 | 0.028 | 13.9 | 258.1 | 17p13.1 | 278 | 20 | U83192_at | 1742 | U83192 | DLG4 | discs, large (Drosophila) homolog 4. |
| 10 | x3342 | 0.426 | 6.5 | 3499.8 | 5q34 | 4140 | 640 | X68277_at | 1843 | X68277 | DUSP1 | dual specificity phosphatase 1 |
| 11 | x4985 | 0.2448 | 4.4 | 113.1 | 8 | 33 | 146 | U15642_s_at | 1875 | U15642 | E2F5 | E2F transcription factor 5, p130-binding |
| 12 | x671 | 0.446 | 11.2 | 597.5 | 4 | 656 | 58 | D11151_at | 1909 | D11151 | EDNRA | endothelin receptor type A |
| 13 | x2341 | 0.2448 | 5.5 | 1078.6 | 8p21.1 | 242 | 1321 | HG4535-HT4940_s_at | 2039 | U28389 | EPB49 | erythrocyte membrane protein band 4.9 (dematin) |
| 14 | x2797 | 0.0959 | 25.4 | 489.0 | 16p13.3-p13.11 | 20 | 509 | L76568_xpt3_f_at | 2072 | L76568 | ERCC4 | excision repair cross-complementing rodent repair deficiency, complementation group 4 |
| 15 | x6244 | 0.3057 | 3.1 | 750.5 | 13q14.1-q14.2 | 1103 | 353 | M13450_at | 2098 | M13450 | ESD | esterase D/formylglutathione hydrolase |
| 16 | x2404 | 0.2128 | 8.7 | 245.1 | Xq22 | 277 | 32 | X97249_at | 2491 | X97249 | FSHPRH1 | FSH primary response (LRPR1, rat) homolog 1 |
| 17 | x4516 | 0.3247 | 39.1 | 761.3 | 3p21.3 | 20 | 781 | U49082_at | 10991 | U49082 | G17 | G17 transporter protein |
| 18 | x4495 | 0.2218 | 55.8 | 3521.2 | 2p12-q11 | 3585 | 64 | M85276_at | 10578 | M85276 | GNLY | granulysin |
| 19 | x1222 | 0.014 | 16.5 | 310.3 | 2q14-q21 | 330 | 20 | M36284_s_at | 2995 | M36284 | GYPC | glycophorin C (Gerbich blood group) |
| 20 | x2590 | 0.1359 | 7.5 | 129.1 | 15q22 | 149 | 20 | U50078_at | 8925 | U50078 | HERC1 | hect (homologous to the E6-AP (UBE3A) carboxyl terminus) domain and RCC1 (CHC1)-like domain (RLD) 1 |
| 21 | x881 | 0.0599 | 10.3 | 185.2 | 2 | 205 | 20 | U44111_at | 3176 | U44111 | HNMT | histamine N-methyltransferase |
| 22 | x5023 | 0.2388 | 11.2 | 395.1 | 2q37.1-q36.3 | 434 | 39 | X77307_at | 3357 | X77307 | HTR2B | 5-hydroxytryptamine (serotonin) receptor 2B |
| 23 | x2719 | 0.2108 | 7.9 | 206.0 | 9p22 | 236 | 30 | J00212_f_at | 3452 | V00540 | IFNA21 | interferon, alpha 21 |
| 24 | x5442 | 0.1618 | 42.3 | 1454.6 | 12q22-q23 | 1490 | 35 | X57025_at | 3479 | X57025 | IGF1 | insulin-like growth factor 1 (somatomedin C) |
| 25 | x5452 | 0.5 | 6.2 | 420.4 | 19p13.1 | 501 | 81 | U61263_at | 10994 | U61263 | ILVBL | ilvB (bacterial acetolactate synthase)-like |
| 26 | x6197 | 0.1808 | 10.4 | 188.0 | 4q34.1-q35.1 | 208 | 20 | X15949_at | 3660 | X15949 | IRF2 | interferon regulatory factor 2 |
| 27 | x3700 | 0.3447 | 7.2 | 124.9 | 3q21-q25 | 145 | 20 | D13626_at | 9934 | D13626 | KIAA0001 | KIAA0001 gene product |
| 28 | x1553 | 0.1728 | 3.7 | 3035.7 | 12q13 | 1115 | 4151 | X12876_s_at | 3875 | X12876 | KRT18 | keratin 18 |
| 29 | x5912 | 0.0669 | 10.2 | 4816.8 | 12q13 | 521 | 5338 | X74929_s_at | 3856 | X74929 | KRT8 | keratin 8 |
| 30 | x197 | 0.035 | 43.7 | 853.4 | 16q22.1 | 873 | 20 | M12625_at | 3931 | M12625 | LCAT | lecithin-cholesterol acyltransferase |
| 31 | x723 | 0.2478 | 5.8 | 7378.3 | 22q13.1 | 8915 | 1537 | J04456_at | 3956 | J04456 | LGALS1 | lectin, galactoside-binding, soluble, 1 (galectin 1) |

TABLE 1-continued

| SEQ ID NO | GeneCode | Permax GPT | Fold GPT | Delta GPT | ChrBand | NLX GPT | TX GPT | AffyProbe Set | LocusLink | GenBank | ABREV | Title (from Unigene) |
|---|---|---|---|---|---|---|---|---|---|---|---|---|
| 32 | x1271 | 0.1299 | 3.8 | 1609.5 | 4q | 583 | 2192 | M93036_at | 4072 | M93036 | M4S1 | membrane component, chromosomal 4, surface marker (35kD glycoprotein) |
| 33 | x6752 | 0.431 | 4.0 | 613.2 | 14 | 818 | 205 | Z24725_at | 10979 | Z24725 | MIG2 | mitogen inducible 2 |
| 34 | x1469 | 0.2038 | 18.2 | 797.4 | 14q11-q12 | 844 | 46 | Z48481_at | 4323 | Z48481 | MMP14 | matrix metalloproteinase 14 (membrane-inserted) |
| 35 | x879 | 0.2458 | 22.3 | 1149.7 | 1q43 | 1204 | 54 | M30269_at HG3510-HT3704_at | 4811 | M30269 | NID | nidogen (enactin) |
| 36 | x1397 | 0.3946 | 11.6 | 724.8 | 5q14 | 793 | 68 | | 7025 | X12795 | NR2F1 | nuclear receptor subfamily 2, group F, member 1 |
| 37 | x2831 | 0.2987 | 6.0 | 204.3 | 10q21.3-q23.1 | 41 | 245 | M24486_s_at | 5033 | M24486 | P4HA1 | procollagen-proline, 2-oxoglutarate 4-dioxygenase (proline 4-hydroxylase), alpha polypeptide 1 |
| 38 | x2670 | 0.2478 | 158.2 | 4966.1 | 9q34 | 4998 | 32 | HG721-HT4827_s_at | 5047 | J04129 | PAEP(alt2) | progestagen-associated endometrial protein (placental protein 14, pregnancy-associated endometrial alpha-2-globulin, alpha uterine protein): Alternate Splice 2 |
| 39 | x5757 | 0.2038 | 12.3 | 3977.7 | 7q22 | 4331 | 353 | L33799_at | 5118 | L33799 | PCOLCE | procollagen C-endopeptidase enhancer |
| 40 | x6701 | 0.3077 | 17.8 | 1101.4 | 4q11-q13 | 1167 | 65 | M21574_at | 5156 | M21574 | PDGFRA | platelet-derived growth factor receptor, alpha polypeptide |
| 41 | x6741 | 0.2068 | 5.1 | 120.6 | Xq21-q27 | 150 | 29 | D00860_at | 5631 | D00860 | PRPS1 | phosphoribosyl pyrophosphate synthetase 1 |
| 42 | x1195 | 0.1099 | 10.2 | 183.7 | Xp22.3-p22.2 | 204 | 20 | Y00971_at | 5634 | Y00971 | PRPS2 | phosphoribosyl pyrophosphate synthetase 2 |
| 43 | x5284 | 0.0789 | 11.6 | 212.7 | 4p15.31 | 233 | 20 | M16447_at | 5860 | M16447 | QDPR | quinoid dihydropteridine reductase |
| 44 | x320 | 0.4076 | 5.6 | 167.7 | 1p31-p22 | 204 | 37 | X98001_at | 5876 | X98001 | RABGGTB | Rab geranylgeranyltransferase, beta subunit |
| 45 | x6986 | 0.3417 | 13.9 | 628.3 | 10q11.1 | 677 | 49 | L36033_at | 6387 | L36033 | SDF1 | stromal cell-derived factor 1 |
| 46 | x1047 | 0.1988 | 3.7 | 297.9 | 5q31 | 408 | 110 | Z11793_at | 6414 | Z11793 | SEPP1 | selenoprotein P, plasma, 1 |
| 47 | x4685 | 0.2218 | 8.3 | 215.8 | Xq28 | 245 | 30 | X92396_at | 6845 | X92396 | SYBL1 | synaptobrevin-like 1 |
| 48 | x5624 | 0.2228 | 3.1 | 666.3 | 15q13 | 988 | 321 | L14837_at | 7082 | L14837 | TJP1 | tight junction protein 1 (zona occludens 1) |
| 49 | x4880 | 0.038 | 13.0 | 239.8 | 11p13 | 260 | 20 | X69950_s_at | 51352 | X69950 | WT1-1 | Wilms tumor associated protein |
| 50 | x860 | 0.1508 | 13.9 | 323.7 | 7q22-q32 | 349 | 25 | X98260_at | 27000 | X98260 | ZRF1 | zuotin related factor 1 |

Key:
SEQ ID NO    Sequence identifier number
GeneCode     Internal lab unique identifier, numbers preceded by an "x"
PermaxGPT    Permax value using GPT datastate
FoldGPT      Ratio of NLXGPT to TXGPT, inverted if needed to yield value >1
DeltaGPT     Arithmetic difference of NLXGPT and TXGPT, absolute value
ChrBand      Karyotypic locus of gene
NLXGPT       Mean expression in GPT units of 4 normal endometria
TXGPT        Mean expression in GPT units of 10 endometrioid endometrial adenocarcinomas
AffyProbeSet Affymetrix probe identifier in HuFL human expression array chip
LocusLink    Locuslink ID number, when available.
GenBank      The GenBank entry for sequence used by Affymetrix to design probes
Abrev        When in full caps, this is the Locuslink recommend nomenclature.
Title        Text description of gene. Usually Locuslink label References 1. Mutter, G. L., Baak, J. P. A., Cai, T., Fitzgerald, J., Gray, R., Gentleman, R., Gullans, S., Ibrahim, J., Neuberg, D., and Wilcox, M. Altered Gene Expression in Endometrioid Endometrial Adenocarcinomas Analyzed by High Density Microarrays. 8th International Workshop on Chromosomes in Solid Tumors (Tucson, Ariz.). 2000. Ref Type: Abstract
2. Gray, R. Permax available online from the Dana Farber Cancer Institute in the laboratory of Dr George Mutter.
3. National Center for Biotechnology Information (USA): Unigene available on line from the National Center for Biotechnology Information.
4. Wheeler D L, Chappey C, Lash A E, Leipe D D, Madden T L, Schuler G D, Tatusova T A, Rapp B A: Database resources of the National Center for Biotechnology Information. Nucleic Acids Res 2000, 28:10–14.
5. National Center for Biotechnology Information (USA): Locuslink [Online]. Available: http://www ncbi nlm nih gov/LocusLink/2000.
6. Pruitt K D, Katz K S, Sicotte H, Maglott D R: Introducing RefSeq and LocusLink: curated human genome resources at the NCBI. Trends Genet 2000, 16:44–47.
7. Harrison's Principles of Internal Medicine, 14/e, (1998) McGraw-Hill Companies, New York.
8. The Chipping Forecast (1999) Nature Genetics, 21(l):1–60.
9. Gwynne, P., and Page, G., (1999) Microarray Analysis: the next revolution in Molecular Biology, Science eMarketplace, Science, August 6. (sciencemag.org/feature/e-market/benchtop/micro.shl)
10. *Molecular Cloning: A Laboratory Manual*, (1989) J. Sambrook, et al., eds., Second Edition, Cold Spring Harbor Laboratory Press, Cold Spring Harbor, N.Y.
11. *Current Protocols in Molecular Biology*, (1999) F. M. Ausubel, et al., eds., John Wiley & Sons, Inc., New York.
12. Wagner et al., Nature Biotechnol. (1996) 14:840–844.
13. Sainio, K., Saarma, M., Nonclercq, D., Paulin, L., and Sariola, H. (1994) Antisense inhibition of low-affinity nerve growth factor receptor in kidney cultures: power and pitfalls. Cell Mol. Neurobiol. 14(5):439–457.

The present invention is not limited in scope by the examples provided, since the examples are intended as illustrations of various aspects of the invention and other functionally equivalent embodiments are within the scope of the invention. Various modifications of the invention in addition to those shown are described herein will become apparent to those skilled in the art for the foregoing description and fall within the scope of the appended claims. The advantages and objects of the invention are not necessarily encompassed by each embodiment of the invention.

All references, patents, and patent publications that are recited in this application are incorporated in their entirety herein by reference.

I claim:

1. A method for diagnosing endometrial cancer in a subject suspected of having endometrial cancer comprising:

obtaining from the subject an endometrial tissue sample suspected of being cancerous, determining expression of a set of nucleic acid molecules or expression products thereof in the endometrial tissue sample, wherein the set of nucleic acid molecules comprises nucleic acid molecules of SEQ ID NOs:14 and 32, and determining the expression of the set of nucleic acid molecules or expression products thereof in a non-cancerous endometrial tissue sample, and comparing the expression of the set of nucleic acid molecules or expression products thereof in the endometrial tissue sample suspected of being cancerous and the non-cancerous endometrial tissue sample wherein increased expression of SEQ ID NO:14 and 32 is diagnostic of endometrial cancer in the subject.

* * * * *

SEQUENCE LISTING

```
<160> NUMBER OF SEQ ID NOS: 100

<210> SEQ ID NO 1
<211> LENGTH: 2572
<212> TYPE: DNA
<213> ORGANISM: Homo sapiens

<400> SEQUENCE: 1
tctgatttca cctctcagca tccaccatgc atctcaagat agtcctggcg ttcctggcac      60
tgtccctcat taccatcttt gccctggcct atgttttgct gaccagccca ggtggttcca     120
gccagcctcc ccactgcccc tctgtatccc atagggccca gccctggcca caccctggcc     180
agagccagct gtttgcagac ctgagccgag aggagttgac agctgtgatg cgcttttctga    240 cccagcggct ggggccaggg ctggtggacg cagcccaggc tcagccctcg gacaactgca     300
tcttctcagt ggagctgcag ctgccccca aggctgcagc cctggcccac ctggacaggg     360 ggagccccc acctgcccgg gaggcactgg ccatcgtcct ctttggtgga caacccaac      420 ccaatgtgag tgagctggtg gtggggccgc tgcctcaccc ctcgtacatg cgggatgtga     480
ctgtggagcg tcacggcggg cccctgccct atcaccgtcg cccggtgctg agagctgagt     540
ttacacagat gtggaggcat ctgaaagatg tggagctacc caaggcaccc atcttcctgt     600
cgtccacctt caactacaat ggctctaccc tggcagctgt gcatgccacc cctcggggct     660
tgcgctcaag ggaacgaact acctggattg gcctctacca taacatctca ggggttggtc     720
ttttccttca ccccgtgggg ctggagctac tactggacca cagggccctg gaccctgccc     780
actggactgt ccagcaggtc ttctaccttg ggcactacta tgcagacttg ggccagttgg     840
aacgggagtt taagtctggc cggttggaag tggttagagt ccctctacct ccaccaaatg     900
gagcttcatc cctgaggtct cggaactctc caggtcctct tccccctctt cagttctcgc     960
```

-continued

```
cccagggttc ccagtacagt gtgcaaggaa acctggtggt atcctccctc tggtcattta    1020
cctttggcca tgggtgttc agcggcctga ggatttttga tgttcggttc cagggtgagc    1080
gaatagccta tgaagtcagt gtccaggagt gtgtatctat ctatggtgcc gattcaccca    1140
agacgatgct gactcgctat ttggatagca gctttggact cggccgtaac agccgaggct    1200
tggtgcgggg agtggactgc ccctatcaag ccacgatggt ggacatccat atattagtgg    1260
gcaaagggc agtccagctg cttccagggg ctgtgtgtgt atttgaggaa gcccagggac    1320
tgccccttcg aaggcaccac aattaccttc aaaatcattt ctatggtggt ttggccagct    1380
cagcccttgt ggtcaggtct gtgtcatctg tgggcaacta tgactacatt tgggactttg    1440
tgttgtaccc aaatggggca cttgaagggc gggtccatgc cacgggttat atcaacacag    1500
ctttcctgaa aggggagag gagggcctcc tctttgggaa ccgtgtgggg aaagagtgc    1560
tgggaacggt gcacacacat gccttccact tcaagctgga cctggatgtg cagggctga    1620
aaaactgggt ggtagctgaa gacgtggtgt ttaaacctgt ggctgccccc tggaacccgg    1680
agcactggct acagcgccca cagctgactc ggcaggtcct gggaaaggag gacctgacag    1740
cttttttcctt gggaagcccc ctaccccgct acctctacct ggctagcaac cagactaatg    1800
cgtggggtca ccagcgcgga taccagcttg tggtgaccca gagaaaggag gaggagtcac    1860
agagcagtag catctatcac cagaatgaca tctggacacc cacagttacc tttgctgact    1920
tcatcaacaa tgaaaccctc ttaggagagg atctggtggc ttgggtcaca gccagcttcc    1980
tgcacattcc ccatgccgag gacatcccaa acacagtgac tctggggaac agagttggct    2040
tcttgctccg accctataac ttctttgatg aggacccctc catcttctcc cctggcagtg    2100
tgtactttga gaagggccag gatgctgggc tctgcagcat caatcctgtg gcctgcctcc    2160
ccgacctggc agcctgtgtc ccggacttac cccctttctc ttaccacggc ttctagtcct    2220
gagggtgtgg cgggcggcgt ggttaggcac atgtactttt ccctgttct actttctatt    2280
ctccgtgttt ttatcacacc tgctccccag attcccaccc cctcaatgtt cctctcacac    2340
gaaaccccca tcagtccctt tggttaattc ttacttcctg ttcatctcta aagtgttaaa    2400
ttataaaaat gatttttaaa tattcaaaga aaaatatcac aaatcctact actcagaaat    2460
aggtggtcac attacatcag acatctcttt atgcatgtgc attcaaaagg aagagtagat    2520
agaattttgt aaaacagatg ttgtatgtaa tttataataa aaagtattaa ag            2572
```

<210> SEQ ID NO 2
<211> LENGTH: 3227
<212> TYPE: DNA
<213> ORGANISM: Homo sapiens

<400> SEQUENCE: 2

```
gctgggcaaa gccggtggca agggcctccc ctgccgctgt gccaggcagg cagtgccaaa      60
tccgggagc ctggagctgg ggggagggcc gggacagcc cggccctgcc ccctccccg        120
ctggagccc agcaacttct gaggaaagtt tggcacccat ggcgtggcgg tgccccagga      180
tgggcagggt cccgctggcc tggtgcttgg cgctgtgcgg ctgggcgtgc atggccccca      240
ggggcacgca ggctgaagaa agtcccttcg tgggcaaccc agggaatatc acaggtgccc      300
gggggactcac gggcacccct cggtgtcagc tccaggttca gggagagccc ccgaggtac     360
attggcttcg ggatggacag atcctggagc tcgcggacag cacccagacc caggtgcccc     420
tgggtgagga tgaacaggat gactggatag tggtcagcca gctcagaatc acctccctgc     480
agctttccga cacgggacag taccagtgtt tggtgttcct gggacatcag accttcgtgt     540
```

```
cccagcctgg ctatgttggg ctggagggct tgccttactt cctggaggag cccgaagaca    600
ggactgtggc cgccaacacc cccttcaacc tgagctgcca agctcaggga cccccagagc    660
ccgtggacct actctggctc caggatgctg tccccctggc cacggctcca ggtcacggcc    720
cccagcgcag cctgcatgtt ccagggctga acaagacatc ctctttctcc tgcgaagccc    780
ataacgccaa gggggtcacc acatcccgca cagccaccat cacagtgctc ccccagcagc    840
cccgtaacct ccacctggtc tcccgccaac ccacggagct ggaggtggct tggactccag    900
gcctgagcgg catctacccc ctgacccact gcacctgca ggctgtgctg tcagacgatg    960
ggatgggcat ccaggcggga gaaccagacc ccccagagga gcccctcacc tcgcaagcat   1020
ccgtgccccc ccatcagctt cggctaggca gcctccatcc tcacacccct tatcacatcc   1080
gcgtggcatg caccagcagc cagggcccct catcctggac ccactggctt cctgtggaga   1140
cgccggaggg agtgccccctg ggccccccta agaacattag tgctacgcgg aatgggagcc   1200
aggccttcgt gcattggcaa gagccccggg cgccctgca gggtaccctg ttagggtacc   1260
ggctggcgta tcaaggccag gacaccccag aggtgctaat ggacataggg ctaaggcaag   1320
aggtgacccct ggagctgcag ggggacgggt ctgtgtccaa tctgacagtg tgtgtggcag   1380
cctacactgc tgctggggat ggaccctgga gcctcccagt accctggag gcctggcgcc   1440
cagtgaagga accttcaact cctgccttct cgtggccctg gtggtatgta ctgctaggag   1500
cagtcgtggc cgctgcctgt gtcctcatct tggctctctt ccttgtccac cggcgaaaga   1560
aggagaccccg ttatggagaa gtgtttgaac caacagtgga aagaggtgaa ctggtagtca   1620
ggtaccgcgt gcgcaagtcc tacagtcgtc ggaccactga agctaccttg aacagcctgg   1680
gcatcagtga agagctgaag gagaagctgc gggatgtgat ggtggaccgg cacaaggtgg   1740
ccctggggaa gactctggga gagggagagt ttggagctgt gatggaaggc cagctcaacc   1800
aggacgactc catcctcaag gtggctgtga agacgatgaa gattgccatc tgcacgaggt   1860
cagagctgga ggatttcctg agtgaagcgg tctgcatgaa ggaatttgac catcccaacg   1920
tcatgaggct catcggtgtc tgtttccagg ttctgaacg agagagcttc cagcacctg   1980
tggtcatctt acctttcatg aaacatggag acctacacag cttcctcctc tattcccggc   2040
tcggggacca gccagtgtac ctgcccactc agatgctagt gaagttcatg gcagacatcg   2100
ccagtggcat ggagtatctg agtaccaaga gattcataca ccgggacctg gcggccagga   2160
actgcatgct gaatgagaac atgtccgtgt gtgtggcgga cttcgggctc tccaagaaga   2220
tctacaatgg ggactactac cgccagggac gtatcgccaa gatgccagtc aagtggatcg   2280
ccattgagag tctagctgac cgtgtctaca ccagcaagag cgatgtgtgg tccttcgggg   2340
tgacaatgtg ggagattgcc acaagaggcc aaacccata tccgggcgtg agaacagcg   2400
agatttatga ctatctgcgc cagggaaatc gcctgaagca gcctgcggac tgtctggatg   2460
gactgtatgc cttgatgtcg cggtgctggg agctaaatcc ccaggaccgg ccaagttta   2520
cagagctgcg ggaagatttg gagaacacac tgaaggcctt gcctcctgcc caggagcctg   2580
acgaaatcct ctatgtcaac atggatgagg gtggaggtta tcctgaaccc cctggagctg   2640
caggaggagc tgacccccca acccagccag accctaagga ttcctgtagc tgcctcactg   2700
cggctgaggt ccatcctgct ggacgctatg tcctctgccc ttccacaacc cctagccccg   2760
ctcagcctgc tgatagggc tccccagcag ccccagggca ggaggatggt gcctgagaca   2820
accctccacc tggtactccc tctcaggatc caagctaagc actgccactg gggaaaactc   2880
cacctttccca cttttccacc ccacgcctta tccccacttg cagccctgtc ttcctaccta   2940
```

-continued

| | |
|---|---|
| tcccacctcc atcccagaca ggtccctccc cttctctgtg cagtagcatc accttgaaag | 3000 |
| cagtagcatc accatctgta aaaggaaggg gttggattgc aatatctgaa gccctcccag | 3060 |
| gtgttaacat tccaagactc tagagtccaa ggtttaaaga gtctagattc aaaggttcta | 3120 |
| ggtttcaaag atgctgtgag tctttggttc taaggacctg aaattccaaa gtctctaatt | 3180 |
| ctattaaagt gctaaggttc taaggcaaaa aaaaaaaaa aaaaaaa | 3227 |

<210> SEQ ID NO 3
<211> LENGTH: 1539
<212> TYPE: DNA
<213> ORGANISM: Homo sapiens

<400> SEQUENCE: 3

| | |
|---|---|
| gaattcgggg ggaggggggca gtgtcctccg agccaggaca gcatgttgt tgggactggc | 60 |
| ggccatggag ctgaaggtgt gggtggatgg catccagcgt gtggtctgtg gggtctcaga | 120 |
| gcagaccacc tgccaggaag tggtcatcgc actagcccaa gcaataggcc agactggccg | 180 |
| ctttgtgctt gtgcagcggc ttcgggagaa ggagcggcag ttgctgccac aagagtgtcc | 240 |
| agtgggcgcc caggccacct gcggacagtt tgccagcgat gtccagtttg tcctgaggcg | 300 |
| cacagggccc agcctagctg ggaggccctc ctcagacagc tgtccacccc cggaacgctg | 360 |
| cctaattcgt gccagcctcc ctgtaaagcc acgggctgcg ctgggctgtg agccccgcaa | 420 |
| aacactgacc cccgagccag ccccagcct ctcacgccct gggcctgcgg ccctgtgac | 480 |
| acccacacca ggctgctgca cagacctgcg gggcctggag ctcagggtgc agaggaatgc | 540 |
| tgaggagctg ggccatgagg ccttctggga gcaagagctg cgccgggagc aggcccggga | 600 |
| gcgagaggga caggcacgcc tgcaggcact aagtgcggcc actgctgagc atgccgcccg | 660 |
| gctgcaggcc ctggacgctc aggcccgtgc cctggaggct gagctgcagc tggcagcgga | 720 |
| ggcccctggg ccccctcac ctatggcatc tgccactgag cgcctgcacc aggacctggc | 780 |
| tgttcaggag cggcagagtg cggaggtgca gggcagcctg gctctggtga gccgggccct | 840 |
| ggaggcagca gagcgagcct tgcaggctca ggctcaggag ctggaggagc tgaaccgaga | 900 |
| gctccgtcag tgcaacctgc agcagttcat ccagcagacc ggggctgcgc tgccaccgcc | 960 |
| cccacggcct gacaggggcc ctcctggcac tcagggccct ctgcctccag ccagagagga | 1020 |
| gtccctcctg ggcgctccct ctgagtccca tgctggtgcc cagcctaggc cccgaggtgg | 1080 |
| cccccatgac gcagaactcc tggaggtagc agcagctcct gccccagagt ggtgtcctct | 1140 |
| ggcagcccag ccccaggctc tgtgacagcc tagtgagggc tgcaagacca tcctgcccgg | 1200 |
| accacagaag gagagttggc ggtcacagag ggctcctctg ccaggcagtg ggaagccctg | 1260 |
| ggtttggcct caggagctgg gggtgcagtg ggggactgcc ctagtccttg ccaggtcgcc | 1320 |
| cagcaccctg gagaagcatg gggcgtagcc agctcggaac ttgccaggcc ccaaaggcca | 1380 |
| cgactgcctg ttggggacag gagatgcatg gacagtgtgc tcaagctgtg ggcatgtgct | 1440 |
| tgcctgcggg agaggtcctt cactgtgtgt acacagcaag agcatgtgtg tgccacttcc | 1500 |
| cctacccccaa cgtgaaaacc tcaataaact gcccgaagc | 1539 |

<210> SEQ ID NO 4
<211> LENGTH: 6478
<212> TYPE: DNA
<213> ORGANISM: Homo sapiens

```
<400> SEQUENCE: 4
agagcgagca ggggagagcg agaccagttt taaggggagg accggtgcga gtaaggcagc      60
cccgaggctc tgctcgccca ccacccaatc ctcgcctccc ttctgctcca ccttctctct     120
ctgccctcac ctctcccccg aaaccccct atttagccaa aggaaggagg tcaggggaac      180
gctctcccct cccccttccaa aaacaaaaa cagaaaaacc cttttccagg ccggggaaag     240
caggagggag aggggccgcc gggctggcca tggagctgct gtgccacgag gtggacccgg     300
tccgcagggc cgtgcgggac cgcaacctgc tccgagacga ccgcgtcctg cagaacctgc     360
tcaccatcga ggagcgctac cttccgcagt gctcctactt caagtgcgtg cagaaggaca     420
tccaacccta catgcgcaga atggtggcca cctggatgct ggaggtctgt gaggaacaga     480
agtgcgaaga agaggtcttc cctctggcca tgaattacct ggaccgtttc ttggctgggg     540
tcccgactcc gaagtcccat ctgcaactcc tgggtgctgt ctgcatgttc ctggcctcca     600
aactcaaaga gaccagcccg ctgaccgcgg agaagctgtg catttacacc gacaactcca     660
tcaagcctca ggagctgctg gagtgggaac tggtggtgct ggggaagttg aagtggaacc     720
tggcagctgt cactcctcat gacttcattg agcacatctt gcgcaagctg ccccagcagc     780
gggagaagct gtctctgatc cgcaagcatg ctcagacctt cattgctctg tgtgccaccg     840
actttaagtt tgccatgtac ccaccgtcga tgatcgcaac tggaagtgtg ggagcagcca     900
tctgtgggct ccagcaggat gaggaagtga gctcgctcac ttgtgatgcc ctgactgagc     960
tgctggctaa gatcaccaac acagacgtgg attgtctcaa agcttgccag gagcagattg    1020
aggcggtgct cctcaatagc ctgcagcagt accgtcagga ccaacgtgac ggatccaagt    1080
cggaggatga actggaccaa gccagcaccc ctacagacgt gcgggatatc gacctgtgag    1140
gatgccagtt gggccgaaag agagacgc gtccataatc tggtctcttc ttctttctgg     1200
ttgtttttgt tctttgtgtt ttagggtgaa acttaaaaaa aaaattctgc ccccacctag    1260
atcatattta aagatctttt agaagtgaga gaaaaggtc ctacgaaaac ggaataataa     1320
aaagcatttg gtgcctattt gaagtacagc ataagggaat cccttgtata tgcgaacagt    1380
tattgtttga ttatgtaaaa gtaatagtaa aatgcttaca ggaaaacctg cagagtagtt    1440
agagaatatg tatgcctgca atatgggaac aaattagagg agactttttt tttcatgtta    1500
tgagctagca catacacccc cttgtagtat aatttcaagg aactgtgtac gccatttatg    1560
gcatgattag attgcaaagc aatgaactca agaaggaatt gaaataagga gggacatgat    1620
ggggaaggag tacaaaacaa tctctcaaca tgattgaacc atttgggatg gagaagcacc    1680
tttgctctca gccacctgtt actaagtcag gagtgtagtt ggatctctac attaatgtcc    1740
tcttgctgtc tacagtagct gctacctaaa aaaagatgtt ttattttgcc agttggacac    1800
aggtgattgg ctcctgggtt tcatgttctg tgacatcctg cttcttcttc caaatgcagt    1860
tcattgcaga caccaccata ttgctatcta atggggaaat gtagctatgg gccataacca    1920
aaactcacat gaaacggagg cagatggaga ccaagggtgg gatccagaat ggagtctttt    1980
ctgttattgt atttaaaagg gtaatgtggc cttggcattt cttcttagaa aaaaactaat    2040
ttttggtgct gattggcatg tctggttcac agtttagcat tgttataaac cattccattc    2100
gaaaagcact ttgaaaaatt gttcccgagc gatagatggg atggtttatg caagtcatgc    2160
tgaatactcc tcccctcttc tcttttgccc cctcccttcc tgcccccagt ctgggttact    2220
cttcgcttct ggtatctggc gttctttggt acacagttct ggtgttccta ccaggactca    2280
agagacaccc cttcctgctg acattcccat cacaacattc ctcagacaag cctgtaaact    2340
```

-continued

```
aaaatctgtt accatctgat ggcacagaag gatcttaatt cccatctcta tacttctcct    2400
ttggacatgg aaagaaaagt tattgctggt gcaaagatag atggctgaac atcagggtgt    2460
ggcatttgt  tcccttttcc gttttttttt ttttattgt  tgttgttaat tttattgcaa    2520
agttgtattc agcgtacttg aattttctt  cctctccact tcttagaggc attcagttag    2580
caaagaggtt ggagcaacaa cttttttttt tttttttgc  acaattgtaa ttgacaggta    2640
atgaagctat ttgttaaaat atttgccttt ttaagtaaaa agaaaaatc  agaacagggc    2700
tatttgaaga attatttat  acacagattc tgccttgttt catagtatga gggttgaaga    2760
cggaaaacaa tctaagggtc tctcatttt  ttaattttgt tttgttcagt ttggtttttt    2820
ttttttttg  cgctgctaag aagctaaagt catccatcct tattcacgtt gacagtacct    2880
agctgtaatg tttcacagag tgtgctgcta ttttataaac atttttataa tatattattt    2940
tactgcttaa attccaagtc ctgaagtaga tggttgagat atgagttctt cgtactggaa    3000
aagcccttcc gtagtttgtt ttcttctggt agcatattca tggttgtttt ttttttttctt   3060
ttttggtttt ttggttttt  ttttttcctc tgatcacatt cttcaaagac ggagtattct    3120
tacctcaggt ttactggaca aaatcaataa ctacaaaagg caatgattca cgcttttgtt    3180
ttcataatac ctcacaaccg tacagtttct gcttgggagc ccattcgcat gaggaataca    3240
gaagcagtgt gagcagggct gactccctct caggtggaag gcaggcggt  ctcactccca    3300
gggaccttt  tggtcatgga ggccatcggg ctcccagtta gaccctggta tcctcatcat    3360
gatgaaaaa  atacattgaa ccaagggatc ctccctcccc ttcaaggcag acgttcagta    3420
caaacatttta tgcggtaggc tcagatgtcg taatttgcac ttaggtacca ggtgtcagga    3480
aacagactaa aaagaattcc accaggctgt ttggagatcc tcatcttgga gcttttcaa     3540
aagcggggct tcatctgcaa agggcccttt catcttgaag ttttttcccct ccgtctttcc   3600
cctcccctgg catggacacc ttgtgtttag gatcatctct gcaggtttcc taggtctgaa    3660
tctgcgagta gatgaacctg cagcaagcag cgtttatggt gcttccttct ccctcctctg    3720
tctcaaactg cgcaggcaag cactatgcaa gcccaggccc tctgctgagc ggtactaaac    3780
ggtcgggttt tcaatcacac tgaattggca ggataagaaa aataggtcag ataagtatgg    3840
gatgatagtt gaagggaggt gaagaggctg cttctctaca gaggtgaaat tccagatgag    3900
tcagtctctt gggaagtgtg tttagaaggg ttcaggactt tgtgagttag catgacccta    3960
aaattctagg ggattctgg  tgggacaatg ggtggtgaat tttgaagttt tggagaggga    4020
agtggagcag ccagcaagta agctagccag agttttctca agagccagct ttgctcagca    4080
cactctcctg ggccccaagg agtcccacgg aatggggaaa gtgggaaccc tggagttctt    4140
gggaatcttg gagcctaaag agaaaccgag gtgcaaattc atttcatggt gactgaccct    4200
tgagcttaaa cagaagcagc aaatgaaaga accggacaaa taaggaaggg cacaagccta    4260
cccgactcta tttacagtct gtaactttcc actcttcctg tagtcccgag gccctgggt     4320
ccttctagct tttctctttc ccatccttgg ggccttgtgt gatgatgggt gtgggctgc     4380
cgatgggaaa gtcgggggtt gttaggcttt tctgcctgct cctgcttaaa cacaagaagg    4440
aatcctggat tttgccctct ccttagctct tagtctcttt ggtaggagtt tgttccaga     4500
ggagctctcc cccttggatt tgaacttgct ctttttgttg ttgttgttct ttctcttctt    4560
tttcttacct cccactaaag gggttccaaa ttatcctggt cttttctac  cttgttgtgt    4620
ttctatctcg tctttacttc catctgtttg tttttttctc catcagtggg ggccgagttg    4680
ttccccccagc ctgccaaatt ttgatccttc ccctcttttg gccaaatcct aggggaaga    4740
```

```
aatcctagta tgccaaaaat atatgctaag cataattaaa ctccatgcgg gtccataaca    4800
gccaagaagc ctgcaggaga aagccaaggg cagttccctc cgcagaacac cccatgcgtg    4860
ctgagaggcg agctccttga agaagggct gttcttccag gaggccttat tttgaactgc     4920
ctcaggaccc cactggagag cacagcatgc cttactactg ggtcatcctt ggtctatgtg    4980
ctctgtactg gaggctctgt tctgcctctt atcagccagg tcaggggcac acatggctta    5040
agtgacaaag ccagaggaga agacaaccct gacagcatca cgctgcatcc cattgctagc    5100
aggattggca actcttcaga cggagctgcg cttccctgca gtctagcacc tctagggcct    5160
ctccagactg tgccctggga gctctgggac tgaaaggtta agaacataag gcaggatcag    5220
atgactctct ccaagagggc aggggaattt tctctccatg gccacaggg  acagggctg     5280 ggagaagaaa tagacttgca ccttatgtca tgtaaataat tgattttcta gttcaagaag    5340
ataatattgg tagtgtggga attggaggta ggaaggggag gaagtctgag taagccagtt    5400
ggcttctaag ccaaaaggat tcctctttgt ttatctctga gacagtccaa ccttgagaat    5460
agctttaaaa gggaaattaa tgctgagatg ataaagtccc cttaagccaa caaaccctct    5520
gtagctatag aatgagtgca ggtttctatt ggtgtggact cagagcaatt tacaagagct    5580
gttcatgcag ccatccattt gtgcaaaata gggtaagaag attcaagagg atatttatta    5640
cttcctcata ccacatggct tttgatgatt ctggattcta aacaacccag aatggtcatt    5700
tcaggcacaa cgatactaca ttcgtgtgtg tctgctttta aacttggctg ggctatcaga    5760
ccctattctc ggctcaggtt ttgagaagcc atcagcaaat gtgtacgtgc atgctgtagc    5820
tgcagcctgc atcccttcgc ctgcagccta ctttgggaa  ataaagtgcc ttactgactg    5880
tagccattac agtatccaat gtcttttgac aggtgcctgt ccttgaaaaa caaagtttct    5940
atttttattt ttaattggtt tagttcttaa ctgctggcca actcttacat ccccagcaaa    6000
tcatcgggcc attggatttt ttccattatg ttcatcaccc ttatatcatg tacctcagat    6060
ctctctctct ctcctctctc tcagttatat agtttcttgt cttggacttt ttttttcttt    6120 tcttttctt tttttttttg ctttaaaaca agtgtgatgc catatcaagt ccatgttatt      6180
ctctcacagt gtactctata agaggtgtgg gtgtctgttt ggtcaggatg ttagaaagtg    6240
ctgataagta gcatgatcag tgtatgcgaa aaggttttta ggaagtatgg caaaaatgtt    6300
gtattggcta tgatggtgac atgatatagt cagctgcctt ttaagaggtc ttatctgttc    6360
agtgttaagt gatttaaaaa aataataacc tgttttctga ctagtttaaa gatggatttg    6420
aaaatggttt tgaatgcaat taggttatgc tatttggaca ataaactcac cttgacct      6478

<210> SEQ ID NO 5
<211> LENGTH: 3867
<212> TYPE: DNA
<213> ORGANISM: Homo sapiens

<400> SEQUENCE: 5
acaggcccgc gacgctcccc tcagctggcg gcggccgcgg agagatgccg cggggggccgc    60 tcgcagccgc cgctgacttg tgaatgggac cgggactggg gccggactg acaccgcagc     120 gcttgccctg cgccagggac tggcggctcg gaggttgcgt ccaccctcaa gggccccaga    180
aatcactgtg ttttcagctc agcggccctg tgacattcct tcgtgttgtc atttgttgag    240
tgaccaatca gatgggtgga gtgtgttaca gaaattggca gcaagtatcc aatgggtgaa    300
gaagaagcta actggggacg tgggcagccc tgacgtgatg agctcaacca gcagagacat    360
tccatcccaa gagaggtctg cgtgacgcgt ccgggaggcc accctcagca agaccaccgt    420
```

-continued

```
acagttggtg gaaggggtga cagctgcatt ctcctgtgcc taccacgtaa ccaaaaatga      480
aggagaacta ctgtttacaa gccgccctgg tgtgcctggg catgctgtgc cacagccatg      540
cctttgcccc agagcggcgg gggcacctgc ggccctcctt ccatgggcac catgagaagg      600
gcaaggaggg gcaggtgcta cagcgctcca agcgtggctg ggtctggaac cagttcttcg      660
tgatagagga gtacaccggg cctgaccccg tgcttgtggg caggcttcat tcagatattg      720
actctggtga tgggaacatt aaatacattc tctcagggga aggagctgga accattttg       780 tgattgatga caaatcaggg aacattcatg ccaccaagac gttggatcga aagagagag       840 cccagtacac gttgatggct caggcggtgg acagggacac caatcggcca ctggagccac      900
cgtcggaatt cattgtcaag gtccaggaca ttaatgacaa ccctccggag ttcctgcacg      960
agacctatca tgccaacgtg cctgagaggt ccaatgtggg aacgtcagta atccaggtga     1020
cagcttcaga tgcagatgac cccacttatg gaaatagcgc caagttagtg tacagtatcc     1080
tcgaaggaca accctatttt tcggtggaag cacagacagg tatcatcaga acagccctac     1140
ccaacatgga cagggaggcc aaggaggagt accacgtggt gatccaggcc aaggacatgg     1200
gtggacatat gggcggactc tcagggacaa ccaaagtgac gatcacactg accgatgtca     1260
atgacaaccc accaaagttt ccgcagagcg tataccagat atctgtgtca gaagcagccg     1320
tccctgggga ggaagtagga agagtgaaag ctaaagatcc agacattgga gaaaatggct     1380
tagtcacata caatattgtt gatggagatg gtatggaatc gtttgaaatc acaacggact     1440
atgaaacaca ggagggggtg ataaagctga aaaagcctgt agattttgaa accaaaagag     1500
cctatagctt gaaggtagag gcagccaacg tgcacatcga cccgaagttt atcagcaatg     1560 gcccctttcaa ggacactgtg accgtcaaga tcgcagtaga agatgctgat gagcccccta     1620
tgttcttggc cccaagttac atcccacgaag tccaagaaaa tgcagctgct ggcaccgtgg     1680
ttgggagagt gcatgccaaa gaccctgatg ctgccaacag cccgataagg tattccatcg     1740
atcgtcacac tgacctcgac agattttca ctattaatcc agaggatggt tttattaaaa      1800
ctacaaaacc tctggataga gaggaaacag cctggctcaa catcactgtc tttgcagcag     1860
aaatccacaa tcggcatcag gaagccaaag tcccagtggc cattagggtc cttgatgtca     1920
acgataatgc tcccaagttt gctgccccctt atgaaggttt catctgtgag agtgatcaga     1980
ccaagccact ttccaaccag ccaattgtta caattagtgc agatgacaag gatgacacgg     2040
ccaatggacc aagatttatc ttcagcctac cccctgaaat cattcacaat ccaaatttca     2100
cagtcagaga caaccgagat aacacagcag gcgtgtacgc ccggcgtgga gggttcagtc     2160
ggcagaagca ggacttgtac cttctgccca tagtgatcag cgatggcggc atcccgccca     2220
tgagtagcac caacacccctc accatcaaag tctgcgggtg cgacgtgaac ggggcactgc     2280
tctcctgcaa cgcagaggcc tacattctga acgccggcct gagcacaggc gccctgatcg     2340
ccatcctcgc ctgcatcgtc attctcctgg gttgcccaag cttaatggaa ccccctctc      2400 ccagggaaga catgagattg ctttatctgg gcttccagct gatgctattt tcctatgtta     2460
aagtaaacag aagattttgt cttctggggg tctttataaa acttcctttc ctctatgtgg     2520
tggctacaga gagtccaacc acacttacgt cattgtagta ttgtttgtga ccctgagaag     2580
gcaaagaaaa gaaccactca ttgtctttga ggaagaagat gtccgtgaga acatcattac     2640
ttatgatgat gaagggggtg gggaagaaga cacagaagcc tttgatattg ccaccctcca     2700
gaatcctgat ggtatcaatg gatttatccc ccgcaaagac atcaaacctg agtatcagta     2760
catgcctaga cctgggctcc ggccagcgcc caacagcgtg gatgtcgatg acttcatcaa     2820
```

| cacgagaata caggaggcag acaatgaccc cacggctcct ccttatgact ccattcaaat | 2880 |
| ctacggttat gaaggcaggg gctcagtggc cgggtccctg agctccctag agtcggccac | 2940 |
| cacagattca gacttggact atgattatct acagaactgg ggacctcgtt ttaagaaact | 3000 |
| agcagatttg tatggttcca agacactttt tgatgacgat tcttaacaat aacgatacaa | 3060 |
| atttggcctt aagaactgtg tctggcgttc tcaagaatct agaagatgtg taaacaggta | 3120 |
| tttttttaaa tcaaggaaag gctcatttaa aacaggcaaa gttttacaga gaggatacat | 3180 |
| ttaataaaac tgcgaggaca tcaaagtggt aaatactgtg aaatacccttt tctcacaaaa | 3240 |
| aggcaaatat tgaagttgtt tatcaacttc gctagaaaaa aaaacacttt ggcatacaaa | 3300 |
| atatttaagt gaaggagaag tctaacgctg aactgacaat gaagggaaat tgtttatgtg | 3360 |
| ttatgaacat ccaagtcttt cttcttttt aagttgtcaa agaagcttcc acaaaattag | 3420 |
| aaaggacaac agttctgagc tgtaatttcg ccttaaactc tggacactct atatgtagtg | 3480 |
| catttttaaa cttgaaatat ataatattca gccagcttaa acccatacaa tgtatgtaca | 3540 |
| atacaatgta caattatgtc tcttgagcat caatcttgtt actgctgatt cttgtaaatc | 3600 |
| tttttgcttc tactttcatc ttaaactaat acgtgccaga tataactgtc ttgtttcagt | 3660 |
| gagagacgcc ctatttctat gtcatttta atgtatctat ttgtacaatt ttaaagttct | 3720 |
| tattttagta tacatataaa tatcagtatt ctgacatgta agaaaatgtt acggcatcac | 3780 |
| acttatattt tatgaacatt gtactgttgc tttaatatga gcttcaatat aagaagcaat | 3840 |
| ctttgaaata aaaaaagatt ttttttt | 3867 |

<210> SEQ ID NO 6
<211> LENGTH: 6158
<212> TYPE: DNA
<213> ORGANISM: Homo sapiens
<220> FEATURE:
<221> NAME/KEY: Unsure
<222> LOCATION: (2434)..(2434)
<223> OTHER INFORMATION: n = a, c, g or t/u

<400> SEQUENCE: 6

| aaccatcaaa tttagaagaa aaagcccttt gactttttcc ccctctccct ccccaatggc | 60 |
| tgtgtagcaa acatccctgg cgataccttg gaaaggacga agttggtctg cagtcgcaat | 120 |
| ttcgtgggtt gagttcacag ttgtgagtgc ggggctcgga gatggagccg tggtcctcta | 180 |
| ggtggaaaac gaaacggtgg ctctgggatt tcaccgtaac aaccctcgca ttgaccttcc | 240 |
| tcttccaagc tagagaggtc agaggagctg ctccagttga tgtactaaaa gcactagatt | 300 |
| ttcacaattc tccagaggga atatcaaaaa caacggggatt ttgcacaaac agaaagaatt | 360 |
| ctaaaggctc agatactgct tacagagttt caaagcaagc acaactcagt gccccaacaa | 420 |
| aacagttatt tccaggtgga actttcccag aagacttttc aatactattt acagtaaaac | 480 |
| caaaaaaagg aattcagtct ttccttttat ctatatataa tgagcatggt attcagcaaa | 540 |
| ttggtgttga ggttgggaga tcacctgttt ttctgtttga agaccacact ggaaaacctg | 600 |
| ccccagaaga ctatcccctc ttcagaactg ttaacatcgc tgacgggaag tggcatcggg | 660 |
| tagcaatcag cgtggagaag aaaactgtga caatgattgt tgattgtaag aagaaaacca | 720 |
| cgaaaccact tgatagaagt gagagagcaa ttgttgatac caatggaatc acggttttttg | 780 |
| gaacaaggat tttggatgaa gaagttttttg agggggacat tcagcagtttt ttgatcacag | 840 |
| gtgatcccaa ggcagcatat gactactgtg agcattatag tccagactgt gactcttcag | 900 |
| cacccaaggc tgctcaagct caggaacctc agatagatga gtatgcacca gaggatataa | 960 |

```
tcgaatatga ctatgagtat ggggaagcag agtataaaga ggctgaaagt gtaacagagg   1020
gacccactgt aactgaggag acaatagcac agacggaggc aaacatcgtt gatgattttc   1080
aagaatacaa ctatggaaca atggaaagtt accagacaga agctcctagg catgtttctg   1140
ggacaaatga gccaaatcca gttgaagaaa tatttactga agaatatcta acgggagagg   1200
attatgattc ccagaggaaa aattctgagg atacactata tgaaaacaaa gaaatagacg   1260
gcagggattc tgatcttctg gtagatggag atttaggcga atatgatttt tatgaatata   1320
aagaatatga agataaacca acaagcccccc ctaatgaaga atttggtcca ggtgtaccag   1380
cagaaactga tattacagaa acaagcataa atggccatgg tgcatatgga gagaaaggac   1440
agaaaggaga accagcagtg gttgagcctg gtatgcttgt cgaaggacca ccaggaccag   1500
caggacctgc aggtattatg ggtcctccag gtctacaagg ccccactgga cccctggtg    1560 accctggcga taggggcccc ccaggacgtc ctggcttacc aggggctgat ggtctacctg   1620
gtcctcctgg tactatgttg atgttaccgt tccgttatgg tggtgatggt tccaaaggac   1680
caaccatctc tgctcaggaa gctcaggctc aagctattct tcagcaggct cggattgctc   1740
tgagaggccc acctggccca atgggtctaa ctggaagacc aggtcctgtg gggggccctg   1800
gttcatctgg ggccaaaggt gagagtggtg atccaggtcc tcagggccct cgaggcgtcc   1860 agggtcccc  tggtccaacg ggaaaaacctg gaaaagggg tcgtccaggt gcagatggag    1920
gaagaggaat gccaggagaa cctggggcaa agggagatcg agggtttgat ggacttccgg   1980
gtctgccagg tgacaaaggt cacagggtg aacgaggtcc tcaaggtcct ccaggtcctc    2040
ctggtgatga tggaatgagg ggagaagatg gagaaattgg accaagaggt cttccaggtg   2100
aagctggccc acgaggtttg ctgggtccaa ggggaactcc aggagctcca gggcagcctg   2160
gtatggcagg tgtagatggc cccccaggac caaaagggaa catgggtccc caaggggagc   2220
ctgggcctcc aggtcaacaa gggaatccag gacctcaggg tcttcctggt ccacaaggtc   2280
caattggtcc tcctggtgaa aaaggaccac aaggaaaacc aggacttgct ggacttcctg   2340
gtgctgatgg gcctcctggt catcctggga agaaggccca gtctggagaa aaggggctc    2400 tgggtcccc  tggtccacaa ggtcctattg gatnnccggg cccccgggga gtaaagggag   2460
cagatggtgt cagaggtctc aagggatcta aaggtgaaaa gggtgaagat ggttttccag   2520
gattcaaagg tgacatgggt ctaaaggtg acagaggaga agttggtcaa attggcccaa   2580
gagggnaaga tggccctgaa ggacccaaag gtcgagcagg cccaactgga gacccaggtc   2640
cttcaggtca gcaggagaa aagggaaaac ttggagttcc aggattacca ggatatccag    2700
gaagacaagg tccaaaggt tccactggat tccctgggt tccaggtgcc aatggagaga    2760
aaggtgcacg gggagtagct ggcaaaccag gccctcgggg tcagcgtggt ccaacgggtc   2820
ctcgaggttc aagaggtgca agaggtccca ctgggaaacc tgggccaaag ggcacttcag   2880
gtggcgatgg ccctcctggc cctccaggtg aaagaggtcc tcaaggacct cagggtccag   2940
ttggattccc tggaccaaaa ggccctcctg gaccaccagg aaggatgggc tgcccaggac   3000
accctgggca acgtggggag actggatttc aaggcaagac cggccctcct gggccagggg   3060
gagtggttgg accacaggga ccaaccggtg agactggtcc aatagggaa cgtgggtatc    3120 ctggtcctcc tggcccctcct ggtgagcaag gtcttcctgg tgctgcagga aaagaaggtc   3180
caaagggtga tccaggtcct caaggtatct cagggaaaga tggaccagca ggattacgtg   3240
gtttcccagg ggaaagaggt cttcctggag ctcagggtgc acctggactg aaaggagggg   3300 aaggtccccca ggggccacca ggtccagttg gctcaccagg agaacgtggg tcagcaggta   3360
```

-continued

```
cagctggccc aattggttta cgagggcgcc cgggacctca gggtcctcct ggtccagctg    3420
gagagaaagg tgctcctgga gaaaaaggtc cccaagggcc tgcagggaga gatggagttc    3480
aaggtcctgt tggtctccca gggccagctg gtcctgccgg ctcccctggg aagacggag     3540 acaagggtga aattggtgag ccgggacaaa aaggcagcaa gggtggcaag ggagaaaatg    3600
gccctcccgg tcccccaggt cttcaaggac cagttggtgc cctggaatt gctggaggtg     3660 atggtgaacc aggtcctaga ggacagcagg ggatgtttgg gcaaaaaggt gatgagggtg    3720
ccagaggctt ccctggacct cctggtccaa taggtcttca gggtctgcca ggcccacctg    3780
gtgaaaaagg tgaaaatggg gatgttggtc catgggggcc acctggtcct ccaggcccaa    3840
gaggccctca aggtcccaat ggagctgatg gaccacaagg accccaggt tctgttggtt     3900 cagttggtgg tgttggagaa aagggtgaac ctggagaagc aggaaaccca gggcctcctg    3960
gggaagcagg tgtaggcggt cccaaaggag aagaggaga gaaggggaa gctggtccac      4020 ctggagctgc tggacctcca ggtgccaagg ggccgccagg tgatgatggc cctaagggta    4080
acccgggtcc tgttggtttt cctggagatc ctggtcctcc tggggaactt ggccctgcag    4140
gtcaagatgg tgttggtggt gacaagggtg aagatgagga tcctggtcaa ccgggtcctc    4200
ctggcccatc tggtgaggct ggcccaccag gtcctcctgg aaaacgaggt cctcctggag    4260
ctgcaggtgc agagggaaga caaggtgaaa aaggtgctaa gggggaagca ggtgcagaag    4320
gtcctcctgg aaaaaccggc ccagtcggtc tcagggacc tgcaggaaag cctggtccag     4380
aaggtcttcg gggcatccct ggtcctgtgg gagaacaagg tctccctgga gctgcaggcc    4440
aagatggacc acctggtcct atgggacctc ctggcttacc tggtctcaaa ggtgaccctg    4500
gctccaaggg tgaaaaggga catcctggtt taattggcct gattggtcct ccaggagaac    4560
aaggggaaaa aggtgaccga gggctccctg gaactcaagg atctccagga gcaaaagggg    4620
atgggggaat tcctggtcct gctggtccct taggtccacc tggtcctcca ggcttaccag    4680
gtcctcaagg cccaaagggt aacaaaggct ctactggacc cgctggccag aaaggtgaca    4740
gtggtcttcc agggcctcct gggcctccag gtccacctgg tgaagtcatt cagccttttac    4800 caatcttgtc ctccaaaaaa acgagaagac atactgaagg catgcaagca gatgcagatg    4860
ataatattct tgattactcg gatggaatgg aagaaatatt tggttccctc aattccctga    4920
aacaagacat cgagcatatg aaatttccaa tgggtactca gaccaatcca gcccgaactt    4980
gtaaagacct gcaactcagc catcctgact tcccagatgg tgaatattgg attgatccta    5040
accaaggttg ctcaggagat tccttcaaag tttactgtaa tttcacatct ggtggtgaga    5100 cttgcatttta tccagacaaa aaatctgagg gagtaagaat ttcatcatgg ccaaaggaga    5160
aaccaggaag ttggttttagt gaatttaaga ggggaaaact gctttcatac ttagatgttg    5220
aaggaaattc catcaatatg gtgcaaatga cattcctgaa acttctgact gcctctgctc    5280
ggcaaaattt cacctaccac tgtcatcagt cagcagcctg gtatgatgtg tcatcaggaa    5340
gttatgacaa agcacttcgc ttcctgggat caaatgatga ggagatgtcc tatgacaata    5400
atccttttat caaaacactg tatgatggtt gtacgtccag aaaaggctat gaaaaaactg    5460
tcattgaaat caatacacca aaaattgatc aagtacctat tgttgatgtc atgatcagtg    5520
actttggtga tcagaatcag aagttcggat ttgaagttgg tcctgttgt tttcttggct    5580 aagattaaga caaagaacat atcaaatcaa cagaaaatgt accttggtgc caccaaccca    5640
ttttgtgcca catgcaagtt ttgaataagg atgtatggaa aacaacgctg catatacagg    5700
taccatttag gaaataccga tgcctttgtg ggggcagaat cacagacaaa agctttgaaa    5760
```

| | |
|---|---|
| atcataaaga tataagttgg tgtggctaag atggaaacag ggctgattct tgattcccaa | 5820 |
| ttctcaactc tccttttcct atttgaattt ctttggtgct gtagaaaaca aaaaaagaaa | 5880 |
| aatatatatt cataaaaaat atggtgctca ttctcatcca tccaggatgt actaaaacag | 5940 |
| tgtgtttaat aaattgtaat tattttgtgt acagttctat actgttatct gtgtccattt | 6000 |
| ccaaaacttg cacgtgtccc tgaattccgc tgactctaat ttatgaggat gccgaactct | 6060 |
| gatggcaata atatatgtat tatgaaaatg aagttatgat ttccgatgac cctaagtccc | 6120 |
| tttctttggt taatgatgaa attcctttgt gtgtgttt | 6158 |

<210> SEQ ID NO 7
<211> LENGTH: 2823
<212> TYPE: DNA
<213> ORGANISM: Homo sapiens

<400> SEQUENCE: 7

| | |
|---|---|
| tatgtaaggc ggccaaggct gacctggtat ttatggtgga tggatcctgg agcattggag | 60 |
| atgaaaattt caataagatc atcagctttc tatacagcac tgttggagcc ctgaacaaga | 120 |
| ttggcacaga tggaacccaa gttgcaatgg ttcagttcac tgatgatccc agaacagaat | 180 |
| ttaaactaaa tgcttacaaa accaaagaga ctcttcttga tgcaattaaa cacatttcat | 240 |
| acaaaggagg aaatacaaaa acaggaaaag caattaagta tgttcgagat accttgttca | 300 |
| ctgcagagtc aggtacaaga aggggcatcc caaaggttat cgtggttata actgatggaa | 360 |
| gatcacaaga tgatgtgaac aaaatctcca gggagatgca attagatggc tatagcattt | 420 |
| ttgcaattgg tgtggccgat gcagattact cggagttggt tagcattggc agtaagccca | 480 |
| gcgcacgcca tgtcttcttt gtggatgact ttgacgcctt taagaaaatc gaagatgagt | 540 |
| taattacttt tgtctgcgaa acagcatcag caacctgtcc agtggtacac aaggatggca | 600 |
| ttgatcttgc aggatttaag atgatggaaa tgtttggttt ggttgaaaaa gattttttcat | 660 |
| cagtggaagg ggtttctatg gagcctggta ccttcaatgt gtttccatgt taccaactcc | 720 |
| ataaagatgc cctggtttcc cagccaacca ggtacttgca cccagaagga ttgccctccg | 780 |
| actacacaat cagttttcta ttccggattc ttcctgacac tccacaggag ccatttgctc | 840 |
| tttgggagat tttaaataaa aattctgacc cattggttgg ggttatttta gacaatggtg | 900 |
| ggaaaactct aacatatttc aactatgacc agagtgggga ttttcaaact gttacttcg | 960 |
| aaggacctga aattaggaaa attttttatg aagctttca caagctacac attgttgtca | 1020 |
| gtgagacttt ggtcaaagtg gttattgact gcaagcaagt gggtgagaag caatgaacg | 1080 |
| catcagctaa tatcacgtca gatggtgtag aagtgctagg gaaatggtt cgatcaagag | 1140 |
| gaccaggtgg aaactctgca ccgttccagt tacagatgtt tgatattgtt tgctccacat | 1200 |
| catgggccaa tacagacaaa tgctgtgaac ttccaggcct gagagatgat gagtcttgcc | 1260 |
| cagaccttcc ccattcctgc tcctgttctg aaaccaatga agtggctctg ggaccagcgg | 1320 |
| gcccaccagg tggtccagga ctccgaggac caaagggcca gcaaggtgaa ccgggtccaa | 1380 |
| agggaccaga tggccctcgg ggtgaaattg gtctgccagg acctcagggt ccacctggac | 1440 |
| ctcaaggacc aagtggtctg tccattcaag gaatgcccgg aatgccagga gaaaaggag | 1500 |
| agaaaggaga tactggcctt ccaggtccac agggtatccc aggaggcgtt ggttcaccag | 1560 |
| gacgtgatgg ctcaccaggc cagaggggcc ttccgggaaa ggatggatcc tcgggacctc | 1620 |
| caggaccacc agggcaata ggcattcctg gcaccctgg agtcccaggg atcacaggaa | 1680 |
| gcatgggacc gcaaggcgcc ctgggaccac ctggtgtccc tggagcaaag ggggaacgag | 1740 |

```
gagagcgggg tgacctgcag tctcaagcca tggtgagatc agtggcgcgt caagtatgcg    1800
aacagctcat ccagagtcac atggccaggt acactgccat cctcaaccag attcccagcc    1860
actcctcatc catccggact gtccaagggc ctcctgggga gcctggggag ccaggctcac    1920
ctggagcccc tggtgaacaa ggaccccag gaacaccagg cttccccgga aatgcaggcg    1980
taccagggac cccaggagaa cgaggtctaa ctggtatcaa aggagaaaaa ggaaatccag    2040
gcgttggaac ccaaggtcca agaggccccc tggaccagc aggaccttca ggggagagtc    2100
ggcctggcag ccctgggccc cctggctctc ctggaccaag aggcccacca ggtcatctgg    2160
gggttcctgg accccaaggt ccttctggcc agcctggata ttgtgacccc tcatcatgtt    2220
ctgcctatgg tgtgagagat ctgatcccct acaatgatta ccagcactga agtggaaatc    2280
ctccactctg gttccattgg ccccagacat ttagctgtgg atacagaact gtcctgtcaa    2340
ccaccaccac caccaagccc ctgcccctaa caatggacac tctgcttccc tgcttcttct    2400
gcatccctgc cttcccactt tcaaacctct gcccactct gctccaaaca tgatggagtg    2460
ataacatcgg aacttaacca atcatatat gtctatttta atagacactg actgctccat    2520
gtcagcctgg atagaggtat atgacgtgtg ccaagaattt atcccagact cccctgtgtg    2580
acagcttcat aataaagtta cttaactgtg cctcttcctc cttcctctcc ccacacagga    2640
tggatgggca tctttctcct tgaccaccct actctccctt cctccctga tcacctcccc    2700 tccctgctct ccctggtga tggacttcta acatgagatt tttttaaaaa atttctattt    2760
cttttataat tttgctgagt tttcagggtt tcttctgtaa ataaaacata atatttaaaa    2820
aaa                                                                  2823

<210> SEQ ID NO 8
<211> LENGTH: 5102
<212> TYPE: DNA
<213> ORGANISM: Homo sapiens

<400> SEQUENCE: 8
gcttctgcga ctccagttgt gagagccgca agggcatggg aattgacgcc actcaccgac      60
ccccagtctc aatctcaacg ctgtgaggaa acctcgactt tgccaggtcc ccaagggcag     120
cggggctcgg cgagcgaggc acccttctcc gtccccatcc caatccaagc gctcctggca     180
ctgacgacgc caagagactc gagtgggagt taaagcttcc agtgagggca gcaggtgtcc     240
aggccgggcc tgcgggttcc tgttgacgtc ttgccctagg caaaggtccc agttccttct     300
cggagccggc tgtcccgcgc cactggaaac cgcacctccc cgcagcatgg gcaccagcct     360
cagcccgaac gacccttggc cgctaaaccc gctgtccatc cagcagacca cgctcctgct     420
actcctgtcg gtgctggcca ctgtgcatgt gggccagcgg ctgctgaggc aacggaggcg     480
gcagctccgg tccgcgcccc cgggccgtt tgcgtggcca ctgatcggaa acgcggcggc     540
ggtgggccag gcggctcacc tctcgttcgc tcgcctggcg cggcgctacg cgacgttttt     600
ccagatccgc ctgggcagct gccccatagt ggtgctgaat ggcgagcgcg ccatccacca     660
ggccctggtg cagcagggct cggccttcgc cgaccggccg gccttcgcct ccttccgtgt     720
ggtgtccggc ggccgcagca tggctttcgg ccactactcg gagcactgga aggtgcagcg     780
gcgcgcagcc cacagcatga tgcgcaactt cttcacgcgc cagccgcgca gccgccaagt     840
cctcgagggc cacgtgctga gcgaggcgcg cgagctggtg gcgctgctgg tgcgcggcag     900
cgcggacggc gccttcctcg acccgaggcc gctgaccgtc gtggccgtgg ccaacgtcat     960
gagtgccgtg tgtttcggct gccgctacag ccacgacgac cccgagttcc gtgagctgct    1020
```

```
cagccacaac gaagagttcg ggcgcacggt gggcgcgggc agcctggtgg acgtgatgcc    1080
ctggctgcag tacttcccca acccggtgcg caccgttttc cgcgaattcg agcagctcaa    1140
ccgcaacttc agcaacttca tcctggacaa gttcttgagg cactgcgaaa gccttcggcc    1200
cggggccgcc ccccgcgaca tgatggacgc ctttatcctc tctgcggaaa agaaggcggc    1260
cggggactcg cacggtggtg gcgcgcggct ggatttggag aacgtaccgg ccactatcac    1320
tgacatcttc ggcgccagcc aggacaccct gtccaccgcg ctgcagtggc tgctcctcct    1380
cttcaccagg tatcctgatg tgcagactcg agtgcaggca gaattggatc aggtcgtggg    1440
gagggaccgt ctgccttgta tgggtgacca gcccaacctg ccctatgtcc tggccttcct    1500
ttatgaagcc atgcgcttct ccagctttgt gcctgtcact attcctcatg ccaccactgc    1560
caacacctct gtcttgggct accacattcc aaggacactg tggtttttg tcaaccagtg     1620 gtctgtgaat catgacccag tgaagtggcc taacccggag aactttgatc agctcgatt     1680 cttggacaag gatggcctca tcaacaagga cctgaccagc agagtgatga ttttttcagt    1740
gggcaaaagg cggtgcattg gcgaagaact ttctaagatg cagcttttc tcttcatctc     1800 catcctggct caccagtgcg atttcagggc caacccaaat gagcctgcga aaatgaattt    1860
cagttatggt ctaaccatta aacccaagtc atttaaagtc aatgtcactc tcagagagtc    1920
catggagctc cttgatagtg ctgtccaaaa tttacaagcc aaggaaactt gccaataaga    1980
agcaagaggc aagctgaaat tttagaaata ttcacatctt cggagatgag gagtaaaatt    2040 cagtttttt ccagttcctc ttttgtgctg cttctcaatt agcgtttaag gtgagcataa     2100
atcaactgtc catcaggtga ggtgtgctcc atacccagcg gttcttcatg agtagtgggc    2160
tatgcaggag cttctgggag attttttga gtcaaagact taagggccc aatgaattat      2220 tatatacata ctgcatcttg gttatttctg aaggtagcat tctttggagt taaaatgcac    2280
atatagacac atacacccaa acacttacac caaactactg aatgaagaag tatttttggta   2340 accaggccat ttttggtggg aatccaagat tggtctccca tatgcagaaa tagacaaaaa    2400
gtatattaaa caaagtttca gagtatattg ttgaagagac agagacaagt aatttcagtg    2460
taaagtgtgt gattgaaggt gataagggaa aagataaaga ccagaaattc ccttttcacc    2520
ttttcaggaa aataacttag actctagtat ttatgggtgg atttatcctt ttgccttctg    2580
gtatacttcc ttactttaa ggataaatca taaagtcagt tgctcaaaaa gaaatcaata     2640
gttgaattag tgagtatagt ggggttccat gagttatcat gaattttaaa gtatgcatta    2700
ttaaattgta aaactccaag gtgatgttgt acctcttttg cttgccaaag tacagaattt    2760
gaattatcag caaagaaaaa aaaaaaagcc agccaagctt taaattatgt gaccataatg    2820
tactgatttc agtaagtctc ataggttaaa aaaaaagtc accaaatagt gtgaaatata     2880
ttacttaact gtccgtaagc agtatattag tattatcttg ttcaggaaaa ggttgaataa    2940
tatatgcctt gtgtaatatt gaaaattgaa agtacaact aacgcaacca agtgtgctaa     3000
aaatgagctt gattaaatca accacctatt tttgacatgg aaatgaagca gggtttcttt    3060
tcttcactca aattttggcg aatctcaaaa ttagatccta agatgtgttc ttattttat     3120 aacatcttta ttgaaattct atttataata cagaatcttg ttttgaaaat aacctaatta    3180
atatattaaa attccaaatt catggcatgc ttaaatttta actaaattt aaagccattc     3240 tgattattga gttccagttg aagttagtgg aaatctgaac attctcctgt ggaaggcaga    3300
gaaatctaag ctgtgtctgc ccaatgaata atggaaaatg ccatgaatta cctggatgtt    3360 cttttttacga ggtgacaaga gttggggaca gaactcccat tacaactgac caagtttctc   3420
```

```
ttctagatga ttttttgaaa gttaacatta atgcctgctt tttggaaagt cagaatcaga      3480
agatagtctt ggaagctgtt tggaaaagac agtggagatg aggtcagttg tgttttttaa      3540
gatggcaatt actttggtag ctgggaaagc ataaagctca aatgaaatgt atgcattcac      3600
atttagaaaa gtgaattgaa gtttcaagtt ttaaagttca ttgcaattaa acttccaaag      3660
aaagttctac agtgtcctaa gtgctaagtg cttattacat tttattaagc tttttggaat      3720 cttttgtacca aaattttaaa aaggggagtt tttgatagtt gtgtgtatgt gtgtgtgggg      3780 tgggggatg gtaagagaaa agagagaaac actgaaaaga aggaaagatg gttaaacatt       3840
ttcccactca ttctgaatta attaatttgg agcacaaaat tcaaagcatg gacatttaga      3900
agaaagatgt ttggcgtagc agagttaaat ctcaaatagg ctattaaaaa agtctacaac      3960
atagcagatc tgttttgtgg tttggaatat taaaaaactt catgtaattt tattttaaaa      4020
tttcatagct gtacttcttg aatataaaaa atcatgccag tattttaaaa ggcattagag      4080
tcaactacac aaagcaggct tgcccagtac atttaaattt tttggcactt gccattccaa      4140
aatattatgc cccaccaagg ctgagacagt gaatttgggc tgctgtagcc tatttttta       4200 gattgagaaa tgtgtagctg caaaaataat catgaaccaa tctggatgcc tcattatgtc      4260
aaccaggtcc agatgtgcta taatctgttt ttacgtatgt aggcccagtc gtcatcagat      4320
gcttgcggca aaagaaagct gtgtttatat ggaagaaagt aaggtgcttg gagttttacct    4380 ggcttattta atatgcttat aacctagtta agaaaggaa agaaaacaa aaacgaatg         4440 aaaataactg aatttggagg ctggagtaat cagattactg ctttaatcag aaaccctcat      4500
tgtgtttcta ccggagagag aatgtatttg ctgacaacca ttaaagtcag aagttttact     4560
ccaggttatt gcaataaagt ataatgttta ttaaatgctt catttgtatg tcaaagcttt      4620
gactctataa gcaaattgct ttttttccaaa acaaaaagat gtctcaggtt tgttttgtga     4680 atttttctaaa agctttcatg tcccagaact tagcctttac ctgtgaagtg ttactacagc    4740 cttaatatttt tcctagtaga tctatattag atcaaatagt tgcatagcag tatatgttaa    4800
tttgtgtgtt tttagctgtg acacaactgt gtgattaaaa ggtatacttt agtagacatt     4860
tataactcaa ggataccttc ttatttaatc ttttcttatt tttgtacttt atcatgaatg      4920
cttttagtgt gtgcataata gctacagtgc atagttgtag acaaagtaca ttctggggaa     4980
acaacattta tatgtagcct ttactgtttg atataccaaa ttaaaaaaaa attgtatctc      5040
attacttata ctgggacacc attaccaaaa taataaaaat cactttcata atcttgaaaa      5100
aa                                                                     5102

<210> SEQ ID NO 9
<211> LENGTH: 3995
<212> TYPE: DNA
<213> ORGANISM: Homo sapiens

<400> SEQUENCE: 9
ggatccgcgg gacagatgag gaaggggctt aagtcactgc agccagaggg atggaggtgg        60
actgatggga gggcttctcc ggtgggtta gaagggaaaa gtagggaaag agaagtgtaa       120
ggtagatggc agaggcagag acatggaaag acagactcta gggttcctga tgatatctat      180
ctcggccaac acaaagggga gggtacagtg gtggggcac ccaagctagg gtgtgagtac       240
cctaagtgta ttcttctgag atgtaggcca ttcactaact cttggaacag ctacagtttc      300
acagtaggaa gaccccccca gattcactgc ccctccctta gtaaagcctc tgagaccttc      360
ctgaacattc ccttctgtct ttgccctctg ttccttccag agactatgtg cccaggcaga      420
```

-continued

| | |
|---|---|
| tggattcctc ccgggcctga gaggaactgc aggaattctc ctgcctctta cccgtaaaac | 480 |
| cccaacttct ctagccctag ggcaggaagt cccaaacaat tctacccct ttttctgcaa | 540 |
| ttctcattgg ggtgagagga ggcccaggag gagagagagc tgggctcagc ttcttttga | 600 |
| gctgctggag ccctctgtga ggaggccctc tttgctggct tctcaggaga gtgtggctag | 660 |
| gttctgcctg cctatgggaa gagggggcca gggtgtgtgg agcaagatgg tgcggtgctg | 720 |
| gtgccttggg acctggggga atgggacagc tggtcggctc agagacggcc tactttactc | 780 |
| acagctggaa tttagtgggg agaagcagct caactccaat cctggaggat tagggagatt | 840 |
| aaagtgagag aagagagaga tgtcccagag accaagagct cccaggtcag ccctctggct | 900 |
| cctggcaccc ccactgctgc ggtgggcacc ccactcctc acagtgctgc atagcgacct | 960 |
| cttccaggcc ttgctggaca tcctggacta ttatgaggct ccctctcag agagtcagaa | 1020 |
| ataccgctac caagatgaag acacgccccc tctggagcac agcccggccc acctccccaa | 1080 |
| ccaggccaat tctcccccag tgattgtcaa cacagatacc ctagaagccc aggatatga | 1140 |
| gttgcaggtg aacgggaccg agggggagat ggaatacgag gaaatcacat ggaaagggg | 1200 |
| taactcaggt ctgggcttca gcatcgcagg tggcactgac aacccacaca tcggtgacga | 1260 |
| cccatccatt ttcatcacca agatcattcc tggtgggct gcggcccagg atggccgcct | 1320 |
| cagggtcaac gacagcatcc tgtttgtaaa tgaagtggac gtgcgcgagg tgacccactc | 1380 |
| agcggcggtg gaagccctca agaggcagg ctccatcgtt cgcctctatg tcatgcgccg | 1440 |
| gaagcccccg gctgagaagg tcatggagat caagctcatc aagggggccta aaggtcttgg | 1500 |
| cttcagcatc gcagggggcg tagggaacca gcacatccca ggagataata gcatctatgt | 1560 |
| aacaaagatc atcgaagggg gtgctgccca caaggatggg aggttgcaga ttggagacaa | 1620 |
| gatcctggcg gtcaacagtg tgggctaga ggacgtcatg catgaagatg ctgtggcagc | 1680 |
| cctgaagaac acgtatgatg ttgtctacct aaaggtggcc aagcccagca atgcctacct | 1740 |
| gagtgacagc tatgctcccc cagacatcac aacctcttat tcccagcacc tggacaatga | 1800 |
| gatcagtcac agcagctacc tgggcaccga ctaccccaca gccatgaccc ccacttcccc | 1860 |
| tcggcgctac tctccagtgg ccaaggacct gctcgggag gaagacattc cccgagaacc | 1920 |
| gaggcgaatt gtgatccacc ggggctccac gggcctgggc ttcaacatcg tgggtggcga | 1980 |
| ggacggtgaa ggcatcttca tctcctttat cctggccggg ggccctgcag acctcagtgg | 2040 |
| ggagctgcgg aagggggacc agatcctgtc ggtcaacggt gtggacctcc gaaatgccag | 2100 |
| ccatgagcag gctgccattg ccctgaagaa tgcgggtcag acggtcacga tcatcgctca | 2160 |
| gtataaacca gaaagagtaca gccgattcga ggccaagatc cacgaccttc gggaacagct | 2220 |
| catgaacagc agcctgggct cagggactgc gtccttgcgg agcaacccca aaggggttt | 2280 |
| ctacatcagg gccctgtttg attacgacaa gaccaaggac tgcggcttcc tgagccaggc | 2340 |
| cctgagcttc cgctttgggg atgtgctgca tgtcatcgat gctagtgatg aggagtggtg | 2400 |
| gcaggcacgg cgggtccact ctgacagtga gaccgacgac attgggttca tccccagcaa | 2460 |
| acggcgggtt gagcgacgag agtggtcaag gttaaaggcc aaggactggg gctccagctc | 2520 |
| tggatcgcag ggtcgagaag actcggttct gagctacgag acagtgacgc agatggaagt | 2580 |
| gcactatgct cgccccatca tcatccttgg gccaccaag gaccgcgcca acgatgatct | 2640 |
| tctctccgag ttccccgaca gtttggatc ctgtgttccc catacgacac ggcccaagcg | 2700 |
| ggagtatgag atagatggcc gggattacca ctttgtgtcg tcccgggaga aaatggagaa | 2760 |
| ggacattcag gcgcacaagt tcattgaggc cggccagtac aacagccacc tctatgggac | 2820 |

-continued

| | |
|---|---|
| cagcgtccag tccgtgcgag aggtggcaga gcaggggaag cactgcatcc tcgatgtctc | 2880 |
| ggccaatgcc gtgcggcggc tgcaggcggc ccacctgcac cccatcgcca tcttcatccg | 2940 |
| cccccgctcc ctggagaatg tgctagagat taacaagcgg atcacagagg agcaagcccg | 3000 |
| caaagccttc gacagagcca ccaagctgga gcaggagttc acagagtgct tctcagccat | 3060 |
| cgtggagggt gacagctttg aggagatcta ccacaaggtg aagcgtgtca tcgaggacct | 3120 |
| ctcaggcccc tacatctggg ttccagcccg agagagactc tgattcctgc cctggcttgg | 3180 |
| cctggactcg ccctgcctcc atcacctggg cccttggtct ggactgaatt gcccaagccc | 3240 |
| ttggctcccc ccggcctccc tcccacccct tcttatttat ttcctttcta actgatccca | 3300 |
| gcctgttgga gggggacac tcctctgcat gtatccccgc accccagaac tgggctcctg | 3360 |
| aacgccagga acctggggtc tggggggggag ctgggctcct tgttccgagc ccttgctcct | 3420 |
| taggatcccc gccccacct gcccccaatg cacacacaga cccacggggg gccacctgcc | 3480 |
| ctcccccatc ctctcccaca cacattccag aagtcagggc ccctcgagg agcacccgct | 3540 |
| gcagggatgc agggccacag gcctccgctc tctcctaagg cagggtctgg ggtcacccct | 3600 |
| gcctcatcgt aattcccat gttaccttga tttctcattt atttttttcca ctttttttct | 3660 |
| tctcaaaggt ggttttttgg ggggagaagc aggggactcc gcagcgggcc cctgccttcc | 3720 |
| acatgccccc accattttc tttgccggtt tgcatgagtg gaaggtctaa atgtggcttt | 3780 |
| ttttttttt ttcctgggaa ttttttttggg gaaaagggag ggatgggtct agggagtggg | 3840 |
| aaatgcggga gggagggtgg ggcagggggtc ggggtcggg tgtccgggag ccagggaaga | 3900 |
| ctggaaatgc tgccgccttc tgcaatttat ttatttttt cttttgagag agtgaaagga | 3960 |
| agagacagat acttgaaaaa aaaaaaaaaa aaaaa | 3995 |

<210> SEQ ID NO 10
<211> LENGTH: 2000
<212> TYPE: DNA
<213> ORGANISM: Homo sapiens

<400> SEQUENCE: 10

| | |
|---|---|
| tttgggctgt gtgtgcgacg cgggtcggag gggcagtcgg gggaaccgcg aagaagccga | 60 |
| ggagcccgga gccccgcgtg acgctcctct ctcagtccaa aagcggcttt tggttcggcg | 120 |
| cagagagacc cggggggtcta gcttttcctc gaaaagcgcc gccctgccct tggccccgag | 180 |
| aacagacaaa gagcaccgca gggccgatca cgctgggggc gctgaggccg gccatggtca | 240 |
| tggaagtggg caccctggac gctggaggcc tgcgggcgct gctgggggag cgagcggcgc | 300 |
| aatgcctgct gctggactgc cgctccttct tcgctttcaa cgccggccac atcgccggct | 360 |
| ctgtcaacgt gcgcttcagc accatcgtgc ggcgccggga caaggcgcc atgggcctgg | 420 |
| agcacatcgt gcccaacgcc gagctccgcg gccgcctgct ggccggcgcc taccacgccg | 480 |
| tggtgttgct ggacgagcgc agcgccgccc tggacgcgc caagcgcgac ggcaccctgg | 540 |
| ccctggcggc cggcgcgctc tgccgcgagg cgcgcgccgc gcaagtcttc ttcctcaaag | 600 |
| gaggatacga agcgttttcg gcttcctgcc cggagctgtg cagcaaacag tcgacccca | 660 |
| tggggctcag ccttcccctg agtactagcg tccctgacag cgcggaatct gggtgcagtt | 720 |
| cctgcagtac cccactctac gatcagggtg gcccggtgga aatcctgccc tttctgtacc | 780 |
| tgggcagtgc gtatcacgct tccgcaagg acatgctgga tgccttgggc ataactgcct | 840 |
| tgatcaacgt ctcagccaat tgtcccaacc attttgaggg tcactaccag tacaagagca | 900 |
| tccctgtgga ggacaaccac aaggcagaca tcagctcctg gttcaacgag gccattgact | 960 |

```
tcatagactc catcaagaat gctggaggaa gggtgtttgt ccactgccag gcaggcattt    1020
cccggtcagc caccatctgc cttgcttacc ttatgaggac taatcgagtc aagctggacg    1080
aggcctttga gtttgtgaag cagaggcgaa gcatcatctc tcccaacttc agcttcatgg    1140
gccagctgct gcagtttgag tcccaggtgc tggctccgca ctgttcggca gaggctggga    1200
gccccgccat ggctgtgctc gaccgaggca cctccaccac caccgtgttc aacttccccg    1260
tctccatccc tgtccactcc acgaacagtg cgctgagcta ccttcagagc cccattacga    1320
cctctcccag ctgctgaaag gccacgggag gtgaggctct tcacatccca ttgggactcc    1380
atgctccttg agaggagaaa tgcaataact ctggaggggg ctcgagaggg ctggtcctta    1440
tttatttaac ttcacccgag ttcctctggg tttctaagca gttatggtga tgacttagcg    1500
tcaagacatt tgctgaactc agcacattcg ggaccaatat atagtgggta catcaagtcc    1560
atctgacaaa atgggcaga agagaaagga ctcagtgtgt gatccggttt cttttttgctc    1620 gcccctgttt tttgtagaat ctcttcatgc ttgacatacc taccagtatt attcccgacg    1680
acacatatac atatgagaat ataccttatt tattttttgtg taggtgtctg ccttcacaaa    1740
tgtcattgtc tactcctaga agaaccaaat acctcaattt ttgttttttga gtactgtact    1800 atcctgtaaa tatatcttaa gcaggtttgt tttcagcact gatggaaaat accagtgttg    1860 ggttttttttt tagttgccaa cagttgtatg tttgctgatt atttatgacc tgaaataata    1920
tatttcttct tctaagaaga cattttgtta cataaggatg acttttttat acaatggaat    1980
aaattatggc atttctattg                                                2000

<210> SEQ ID NO 11
<211> LENGTH: 1587
<212> TYPE: DNA
<213> ORGANISM: Homo sapiens

<400> SEQUENCE: 11
gcgcggaggc ccggcgtgac aagcggccca gactcccgtg ggcgccgcac acctgttgtt      60
tgcagcagcc agcgacccgc actaccgctc tcggcgggcg gggaagcggc cgcagcggag     120
ccgacccggc aggtggccgc gggcggggcc ggcgagcgaa agtgcgcggg ggcccgacca     180
ccgcggggcc gggacgcgac gcgatggcgc cggcagagcc cgcgagctcg ggccagcagg     240
cgccggcagg gcaggggcag ggccagcggc cgccgccgca gcctccgcag gcgcaagccc     300
cgcagccgcc cccgccgccg cagctcgggg gcgcgggggg cggcagcagc aggcacgaga     360
agagcctggg gctgctcact accaagttcg tgtcgctgct gcaggaggcc aaggacggcg     420
ttctggatct caaagcggct gctgatactt tggctgtgag gcaaaaaagg agaatttatg     480
atatcaccaa tgtcttagag ggaattgact tgattgaaaa aaagtcaaaa aacagtatcc     540
agtggaaagg tgtaggtgct ggctgtaata ctaaagaagt catagataga ttaagatatc     600
ttaaagctga aattgaagat ctagaactga aggaaagaga acttgatcag cagaagttgt     660
ggctacagca aagcatcaaa aatgtgatgg acgattccat taataataga ttttcctatg     720
taactcatga agacatctgt aattgcttta atggtgatac acttttggcc attcaggcac     780
cttctggtac acaactggag gtacccattc cagaaatggg tcagaatgga caaaagaaat     840
accagatcaa tctaaagagt cattcaggac ctatccatgt gctgcttata aataaagagt     900
cgagttcatc taagcccgtg gttttttcctg ttcccccacc tgatgacctc acacagcctt     960
cctcccagtc cttgactcca gtgactccac agaaatccag catggcaact caaaatctgc    1020
ctgagcaaca tgtctctgaa agaagccagg ctctgcagca gacatcagct acagatatat    1080
```

```
cttcaggatc tattagtgga gatatcattg atgagttaat gtcttctgac gtgtttcctc    1140
tcttaaggct ttctcctacc ccggcagatg actacaactt taatttagat gataacgaag    1200
gagtttgtga tctgtttgat gtccagatac taaattatta gattccatgg aaacttggga    1260
ctgttatcta cctctaactg tgtaacattt tagacttctt aataacctaa atatttaaaa    1320
taatgaatgt aacacctttt gttcactgat tctgaagtgt tcttccctaa tacttctttta   1380 cttcacaaaa cttcaaccat aaaaacaaag ggctctgatt gctttagggg ataagtgatt    1440
taatatccac aaacgtcccc actccccaaa agtaactata tctggatttc aacttttctt    1500
ctaattgtga atccttctgt ttttcttctt aaggaggaag taaggacact acaggtcatc    1560
aaaacagtgg ccaaggactc attactg                                        1587

<210> SEQ ID NO 12
<211> LENGTH: 2595
<212> TYPE: DNA
<213> ORGANISM: Homo sapiens

<400> SEQUENCE: 12
gtctgttcct tcccccagtc atgcctctgc tgctgctgtt accagtccaa aagtctgatg      60
acctcggtcc ccatgaacgg aacaagcatc cagtggaaga accacgatca aaacaaccac     120
aacacagacc ggagcagcca taaggacagc atgaactgac cacccttaga agcactcctc     180
ggtactccca taatcctctc ggagaaaaaa atcacaaggc aactgtgact ccgggaatct     240
cttctctgat ccttcttcct taattcactc ccacacccaa gaagaaatgc tttccaaaac     300
cgcaaggtag actggtttat ccacccacaa catctacgaa tcgtacttct ttaattgatc     360
taatttacat attctgcgtg ttgtattcag cactaaaaaa tggtgggagc tgggggagaa     420
tgaagactgt taaatgaaac cagaaggata tttactactt ttgcatgaaa atagagcttt     480
caagtacatg gctagctttt atggcagttc tggtgaatgt tcaatgggaa ctggtcacca     540
tgaaacttta gagattaacg acaagatttt ctacttttt taagtgatt ttttgtccttc      600 agccaaacac aatatgggct caggtcactt ttatttgaaa tgtcatttgg tgccagtatt     660
ttttaactgc ataatagcct aacatgatta tttgaactta tttacacata gtttgaaaaa     720
aaaaagacaa aatagtatt caggtgagca attagattag tattttccac gtcactattt      780
atttttttaa aacacaaatt ctaaagctac aacaaatact acaggcccttt aaagcacagt    840 ctgatgacac atttggcagt ttaatagatg ttactcaaag aattttttaa gaactgtatt     900
ttatttttta aatggtgttt tattacaagg gaccttgaac atgttttgta tgttaaattc     960 aaagtaatg cttcaatcag atagttcttt ttcacaagtt caatctgttt ttcatgtaaa      1020
ttttgtatga aaaatcaatg tcaagtacca aaatgttaat gtatgtgtca tttaactctg     1080
cctgagactt tcagtgcact gtatatagaa gtctaaaaca cacctaagag aaaaagatcg     1140 aattttcag atgattcgga aattttcatt caggtatttg taatagtgac atatatatgt      1200
atatacatat cacctcctat tctcttaatt tttgttaaaa tgttaactgg cagtaagtct     1260
tttttgatca ttcccttttc catataggaa acataatttt gaagtggcca gatgagttta    1320
tcatgtcagt gaaaaataat tacccacaaa tgccaccagt aacttaacga ttcttcactt    1380
cttgggtttt tcagtatgaa cctaactccc caccccaaca tctccctccc acattgtcac   1440
catttcaaag ggcccacagt gactttttgct gggcattttc ccagatgttt acagactgtg   1500
agtacagcag aaaatctttt actagtgtgt gtgtgtatat atataaacaa ttgtaaattt    1560
cttttagccc attttttctag actgtctctg tggaatatat ttgtgtgtgt gatatatgca   1620
```

-continued

| | |
|---|---|
| tgtgtgtgat ggtatgtatg gatttaatct aatctaataa ttgtgccccg cagttgtgcc | 1680 |
| aaagtgcata gtctgagcta aaatctaggt gattgttcat catgacaacc tgcctcagtc | 1740 |
| cattttaacc tgtagcaacc ttctgcattc ataaatcttg taatcatgtt accattacaa | 1800 |
| atgggatata agaggcagcg tgaaagcaga tgagctgtgg actagcaata tagggttttg | 1860 |
| tttggttggt tggtttgata aagcagtatt tgggtcata ttgtttcctg tgctggagca | 1920 |
| aaagtcatta cactttgaag tattatattg ttcttatcct caattcaatg tggtgatgaa | 1980 |
| attgccaggt tgtctgatat ttcttcaga cttcgccaga cagattgctg ataataaatt | 2040 |
| aggtaagata atttgttggg ccatattta ggacaggtaa ataacatca ggttccagtt | 2100 |
| gcttgaattg caaggctaag aagtactgcc cttttgtgtg ttagcagtca aatctattat | 2160 |
| tccactggcg catcatatgc agtgatatat gcctataata taagccatag gttcacacca | 2220 |
| ttttgtttag acaattgtct tttttcaag atgctttgtt tctttcatat gaaaaaatg | 2280 |
| catttttataa attcagaaag tcatagattt ctgaaggcgt caacgtgcat tttatttatg | 2340 |
| gactggtaag taactgtggt ttactagcag gaatatttcc aatttctacc tttactacat | 2400 |
| cttttcaaca gtaactttg tagaaatgag ccagaagcca aggccctgag ttggcagtgg | 2460 |
| cccataagtg taaaataaaa gtttacagaa accttgcaag tgtctcttca tttttatgta | 2520 |
| gttttccata gaaaatgttt gttacataat gcctgttgca aacctctcct tagtaatatc | 2580 |
| ctggaaagca gttta | 2595 |

<210> SEQ ID NO 13
<211> LENGTH: 2727
<212> TYPE: DNA
<213> ORGANISM: Homo sapiens

<400> SEQUENCE: 13

| | |
|---|---|
| cacgagaaga caggaggaag aaagggagag agggccaggc agtcgcactg tgaacagaac | 60 |
| aggagaaggc gaagcggggc aaagttccct gcccaccgac gccagcctgc ttggatgact | 120 |
| tgcctcgttt cataattcac ttactgtctg caccagccgg cctcagcctg gctggaccct | 180 |
| gctgcctgtg tgcccggag ccagaggccc ccacactccc agctgctctt ctacagatgc | 240 |
| catcaacgag caggactctg ggtggctcca ctgtctaagc ctggagagtc accgccgagg | 300 |
| gatgaggacg cgccagcccg ggggaacgcg ccagctgctt tcgcggcccc aagcgcgcag | 360 |
| tgcccagcag ccgcgccgag cctgacacgc tgtcctctcc cctcgcgcac agggctctgc | 420 |
| gagtgacccg gcgggcgagc tccgtgctgc atggaacggc tgcagaagca accacttacc | 480 |
| tccccgggga gcgtgagccc ctcccgagat tccagtgtgc ctggctctcc ctccagcatc | 540 |
| gtggccaaga tggacaatca ggtgctgggc tacaaggacc tggctgccat ccccaaggac | 600 |
| aaggccatcc tggacatcga gcggcccgac ctcatgatct acgagcctca cttcacttat | 660 |
| tccctcctgg aacacgtgga gctgcctcgc cagcgcgagc gctcgctgtc acccaaatcc | 720 |
| acatccccc caccatcccc agaggtgtgg gcggacagcc ggtcgcctgg aatcatctct | 780 |
| caggcctcgg ccccccagaac cactggaacc ccccggacca gcctgcccca tttccaccac | 840 |
| cctgagacct cccgcccaga ttccaacatc tacaagaagc ctcccatcta taagcagaga | 900 |
| gagtccgtgg gaggcagccc tcagaccaag cacctcatcg aggatctcat catcgagtca | 960 |
| tccaagtttc ctgcagccca gccccccgac cccaaccagc cagccaaaat cgaaaccgac | 1020 |
| tactggccat gccccccgtc tctggctgtt gtggagacag aatggaggaa gcggaaggcg | 1080 |

-continued

```
tctcggaggg gagcagagga agaggaggag gaggaagatg acgactctgg agaggagatg    1140
aaggctctca gggagcgtca gagagaggaa ctcagtaagg ttacttccaa cttgggaaag    1200
atgatcttga aagaagagat ggaaaagtca ttgccgatcc gaaggaaaac ccgctctctg    1260
cctgaccgga caccctcca tacctccttg caccagggaa cgtctaaatc ttcctctctc    1320
ccccgctatg gcaggaccac cctgagccgg ctacagtcca cagagttcag cccatcaggg    1380
agtgagactg gaagcccagg cctgcagaac ggagagggcc agaggggag gatggaccgg    1440 gggaactccc tgccctgtgt gctggagcag aagatctatc cctatgaaat gctagtggtg    1500
accaacaagg ggcgaaccaa gctgccaccg ggggtggatc ggatgcggct tgagaggcat    1560
ctgtctgccg aggacttctc aagggtattt gccatgtccc tgaagagtt tggcaagctg    1620 gctctgtgga gcggaatga gctcaagaag aaggcctctc tcttctgatg ccccccacct    1680
gctccgggac ggccccctta cccctgctgc ttcagggttt ttccccggcg ggttgggagg    1740
ggcaggaggt ggggtggaaa tagggtgggc tcctttcctc aggtagagtg gggggccaaa    1800
acctctgcag tccccggcag tgagctatgg actttcttcc ccctcacgag gctggggggcc    1860 tcctgctctc gtccctggcc ctccctgtac agggcaaagc cagtctgggc tctggcacac    1920
agagttcatg tttgccgccc tctccctgcc cctcaccca gaggtgagag gaatgagggg    1980
cattggtggt taggccggtt ggctgtcttg aacagctgga gggaagatgc aggggtggga    2040
agcggccagg cagaaagagc tccaggctct tgtgtcgccc acccagccct cccatactca    2100
ctcctgacag ctttcctgca ctgcagcttc ctgctcctct gactctagtg gaacaggcc    2160 ccagctcagc ctccgcgagg gaggtcaccc ctccacttca gcttgccctg acctccgctc    2220
gcaaaccccg agcttccaag cctttgctc cagcccgcg gcttccccag aagcctgggc    2280
ttagggtgga gatgccgcct acccgatcct ggccctccac ctgcctccag gccacgaaat    2340
gggaattcca gcactaagcc aggcaccggg cagaagctgg gccttccgcc tcccttggat    2400
ggggtcaaga ggccaggcct ggcacatttt ggagtgtcct ggctaccagc tctcacacct    2460
acacccacgc acccccctcac acactatgct ctctcaagaa tgtaatttat tggggccccc    2520
ccagctgctt tcctcacctg cccctgccct accttacacc cccagcttga cttctttcca    2580
gtccacgtgg atataatgat atctatattt ttgcccaggt ctgggtattg ctcctgccca    2640
gaccctgaca tcccttcca ctgtgtgtgt gaccatgctg ggggagggg actctgcttg    2700 gaattaaaag gttgctttgg gtcccta                                      2727
```

<210> SEQ ID NO 14
<211> LENGTH: 3857
<212> TYPE: DNA
<213> ORGANISM: Homo sapiens

<400> SEQUENCE: 14

```
ggaagagctt ccatggagtc agggcagccg gctcgacgga ttgccatggc gccgctgctg     60
gagtacgagc gacagctggt gctggaactg ctcgacactg acgggctagt agtgtgcgcc    120
cgcgggctcg gcgcggaccg gctcctctac cactttctcc agctgcactg ccacccagcc    180
tgcctggtgc tggtgctcaa cacgcagccg gccgaggagg agtatttat caatcagctg    240 aagatagaag gagttgaaca cctccctcgc cgtgtaacaa atgaaatcac aagcaacagt    300
cgctatgaag tttacacaca aggtggtgtt atatttgcga caagtaggat acttgtggtt    360
gacttcttga ctgatagaat accttcagat ttaattactg gcatcttggt gtatagagcc    420
cacagaataa tcgagtcttg tcaagaagca ttcatcttgc gcctctttcg ccagaaaaac    480
```

-continued

```
aaacgtggtt ttattaaagc tttcacagac aatgctgttg cctttgatac tggttttgt     540
catgtggaaa gagtgatgag aaatctttt gtgaggaaac tgtatctgtg gccaaggttc     600
catgtagcag taaactcatt tttagaacag cacaaacctg aagttgtaga atccatgtt     660
tctatgacac ctaccatgct tgctatacag actgctatac tggacatttt aaatgcatgt    720
ctaaaggaac taaaatgcca taacccatcg cttgaagtgg aagatttatc tttagaaaat    780
gctattggaa aaccttttga caagacaatc cgccattatc tggatccttt gtggcaccag    840
cttggagcca agactaaatc cttagttcag gatttgaaga tattcgaac tttgctgcag     900
tatctctctc agtatgattg tgtcacattt cttaatcttc tggaatctct gagagcaacg    960
gaaaagcttt tggtcagaa ttcaggttgg ctgtttcttg actccagcac ctcgatgttt    1020
ataaatgctc gagcaagggt ttatcatctt ccagatgcca aatgagtaa aaagaaaaa    1080
atatctgaaa aaatggaaat taagaaggg gaagaaacaa aaaggaact ggtcctagaa     1140
agcaacccaa agtgggaggc actgactgaa gtattaaaag aaattgaggc agaaaataag   1200
gagagtgaag ctcttggtgg tccaggtcaa gtactgattt gtgcaagtga tgaccgaaca   1260
tgttcccagc tgagagacta tatcactctt ggagcggagg ccttcttatt gaggctctac   1320
aggaaaacct ttgagaagga tagcaaagct gaagaagtct ggatgaaatt taggaaggaa   1380
gacagttcaa agagaattag gaaatctcac aaaagaccta agacccccca aaacaaagaa   1440
cgggcttcta ccaaagaaag aaccctcaaa agaaaaaac ggaagttgac cttaactcaa   1500
atggtaggaa aacctgaaga actggaagag gaaggagatg tcgaggaagg atatcgtcga  1560
gaaataagca gtagcccaga aagctgcccg gaagaaatta agcatgaaga atttgatgta  1620
aatttgtcat cggatgctgc tttcggaatc ctgaaagaac ccctcactat catccatccg  1680
cttctgggtt gcagcgaccc ctatgctctg acaagggtac tacatgaagt ggagccaaga   1740
tacgtggttc tttatgacgc agagctaacc tttgttcggc agcttgaaat ttacagggcg   1800
agtaggcctg ggaaacctct gagggtttac tttcttatat acggaggttc aactgaggaa   1860
caacgctatc tcactgcttt gcggaaagaa aaggaagctt ttgaaaaact cataagggaa  1920
aaagcaagca tggttgtccc tgaagaaaga gaaggcagag atgaaacaaa cttagaccta  1980
gtaagaggca cagcatctgc agatgttttcc actgacactc ggaaagccgg tggccaggaa  2040
cagaatggta cacagcaaag catagttgtg gatatgcgtg aatttcgaag tgagcttcca  2100
tctctgatcc atcgtcgggg cattgacatt gaacccgtga ctttagaggt tggagattac   2160
atcctcactc cagaaatgtg cgtggagcgc aagagtatca gtgatttaat cggctcttta   2220
aataacggcc gcctctacag ccagtgcatc tccatgtccc gctactacaa gcgtcccgtg   2280
cttctgattg agtttgaccc tagcaagcct ttctctctca cttcccgagg tgccttgttt   2340
caggagatct ccagcaatga cattagttcc aaactcactc ttcttacact tcacttcccc   2400
agactacgga ttctctggtg cccctctcct catgcaacgg cggagttgtt tgaggagctg   2460
aaacaaagca agccacagcc tgatgcggcg acagcactgg ccattacagc agattctgaa   2520
acccttcccg agtcagagaa gtataatcct ggtccccaag acttcttgtt aaaaatgcca   2580
ggggtgaatg ccaaaaactg ccgctccttg atgcaccacg ttaagaacat cgcagaatta   2640
gcagccctgt cacaagacga gctcacgagt attctgggga atgctgcaaa tgccaaacag   2700
ctttatgatt tcattcacac ctctttgca gaagtcgtat caaaaggaaa agggaaaaag   2760
tgaacagtga tggctgtttt cttatcccat gcctgtactt ttcagcggct ccttgccaga   2820
catcataggt cattattaat tattggtttg ctatttcatt cttttccaat gctcttaatg  2880
```

```
attgtacggt ggaccagaag ccaggattcc tctctgaact ctgcagttag gcatcacttg      2940
aacttgcctg tgcctgctct ttttcctccc tgcaccgtct atgccgggct tagcatgttt      3000 cttttttaaat gaggtttgtc aggatcaggt aaagttccta caagtgatta cagaaggtag    3060
aaactttacc tgatcctaac agatctcatt tagaaaggaa tatgctaagc ctggcatgga     3120
cggtgcaggg agggaaaaga gcaggcacaa gaaagctacc attttaaca gtccttgtta      3180 tctagtgcaa cataaataac agtcttaatt gcacttatac ccatgtcctg tggctctcca     3240
aatctggtct ttgctgttgt gtctgctgga cgcttgaact gatgtttgtg taggaaatca     3300
tgttctgacc ctttgtctac aaaggagcct tctggaacac tgagaagaaa catctctttg     3360
ccattcctga ccagttctct ctaccacatt ttcttcagct ccatacttct gcctgtctgc     3420
tctaaggaaa tttcatggag ccttcctact actaattcaa gacagtctcc tcaaaaactg    3480
gttgactagt cttctaatga ccctaacata tgtagcatat actataattt cattgttcca    3540
aattagtatt tttaaagcaa aatgaattac ctgtttgcaa aagttaatga tgaaggagct    3600
cttagaattc tcaattttg cacatattca gtctcctaat atcagagatc cctaagtcca    3660
gctggctagt tacagagttt tttcagactt cctcgtttct cagctcttat atcctaagac    3720
accagcatca tatcctctag aaatacaacc taattggcag tgagccgaga tcgcaccact    3780
gcacccctgc ctgggcgaca gagtgagact ttgtctctat tacaaaaaga aaagaaaaga    3840
aatacaacct aagctca                                                   3857

<210> SEQ ID NO 15
<211> LENGTH: 1069
<212> TYPE: DNA
<213> ORGANISM: Homo sapiens

<400> SEQUENCE: 15
gaattcgggg caaaaagcaa tcagcaattg gacaggaaaa gaatggcatt gaagcagatt      60
tccagcaaca agtgctttgg gggattgcag aaagtttttg aacatgacag tgttgaacta     120
aactgcaaaa tgaaatttgc tgtctactta ccaccaaagg cagaaacagg aaagtgccct     180
gcatgtattg gctctccagg tttaacttgc acagagccaa aattttatca tcaaaatctg     240
gttatcatca gtctgcttca gaaccatttg tcttgttgtc attgctccag atacagccct     300
cgtgcgtgca atattaaagg tgaagatgag agctgggact ttgcgactgg tcgtggattt     360
tatgttgatg ccactgaaga tccttggaaa accaactaca gaatgtactc ttatgtcaca     420
gaggagcttc cccaactcat aaatgccaat ttccagtgg atccccaaag gatgtctatt      480
tttggccact ccatgggagg tcatggagct ctgatctgtg cttgaaaaa tcctggaaaa     540 tacaaatctg tgtcagcatt tgctccaatt tgcaaccctg tactctgtcc ctggggcaaa    600
aaagccttta gtggatattt gggaacagat caaagtaaat ggaaggctta tgatgctacc    660
caccttgtga atcctatcc aggatctcag ctggacatac taattgatca agggaaagat      720
gaccagtttc ttttagatgg acagttactc cctgataact tcatagctgc ctgtacagaa     780
aagaaaatcc ccgttgtttt tcgattgcaa gagggttatg atcatagcta ctacttcatt     840 gcaacctta ttactgacca catcagacat catgctaaat acctgaatgc atgaaaaaac      900
tccaaataag agaatctctt caggattata aagttgtaa aatgcaactg tattgctgag     960
caaaaaaaaa aaaattcaa acattggat tttatagtgc taaagggct ttattctata      1020 gttgaatcac ctctgaataa agatataaaa cctaaaaaaa cccgaattc                1069
```

-continued

<210> SEQ ID NO 16
<211> LENGTH: 2570
<212> TYPE: DNA
<213> ORGANISM: Homo sapiens
<220> FEATURE:
<221> NAME/KEY: Unsure
<222> LOCATION: (779)..(779)
<223> OTHER INFORMATION: n = a, c, g or t/u

<400> SEQUENCE: 16

```
acaaagtctt gctctgtcac ccaggctgga gtgcagtggc gcaatcacgg ctctctgcag      60
cctcgacctc cgrggctcaa gctattctcc tgcctcaccc tcctgagtag atgggactac     120
aggtacgtgc ggctatctag ctaattttt aaatcttaag tagagacatt ggtctcactg     180
tgttgcccag actggtcttg aactcctagg ttgaagggat cttccagcct ctgcctcccg     240
aagtgctgta ttacagaaca tatgcagtaa tgtcacctca aaagagagtt aagaacgtcc     300
aggcacaaaa caggacttca caaggtagta gtagttttca gaccacgctt tcagcctgga     360
aagtaaaaca ggatccaagc aactcgaaga acatctcaaa acatggacaa aacaatccag     420
tgggagatta tgaacatgct gatgatcaag ctgaagaaga tgctttgcaa atggcagtgg     480
gatattttga gaaaggtccc attaaagctt cacagaataa agataaaacc ttggaaaaac     540
acttgaaaac tgtggaaaat gtggcttgga agaatgggtt agcttcagaa gaaattgata     600
ttctattaaa tattgcactc agtggcaaat ttggaaatgc tgtaaacaca cggatattga     660
agtgcatgat cccagcaaca gtaatatcag aagattctgt ggttaaggca gtctcctggc     720
tttgtgttgg caagtgttct ggtagcacca aggtactttt ttatcgttgg ctggttgcna     780
tgtttgactt cattgatcgy aaggagcaaa ttaacttgct ctatggcttc ttttttgctt     840
cattgcaaga tgatgcactg tgcccttatg tttgccattt gttatattta cttacgaaaa     900
aagagaatgt caaaccattt cgtgtgagaa aactgcttga tcttcaggcc aaaatgggaa     960
tgcagcctca tctccaggct tgttgtcac tgtataagtt ctttgctcct gctctgattt    1020
cagtatcttt gcctgtaagg aagaagatat atcttcagaa ttcagagaat ctatggaaga    1080
cggctctgct tgccgtgaag caaagaaacc ggggaccttc tccagaacct ctgaagttga    1140
tgttaggtcc agctaatgtt cgtcctctaa aaagaaagtg gaattctctc tcagttatac    1200
cagtgctcaa ttccagtagc tacactaaag aatgtggaaa aaaagagatg agtctttctg    1260
attgtctgaa tagaagtgga tcatttccac tagaacaact tcaaagcttc ccccaacttt    1320
tacagaacat ccattgctta gagctgcctt ctcagatggg ctcagtgcta aacaactctc    1380
tgctgcttca ctacattaac tgtgtcagag atgagccagt cttgctgagg tttcattact    1440
ggttgagtca aacattacaa gaagaatgta tttggtacaa ggtgaataat tatgaacatg    1500
gaaaagaatt taccaacttc ctggatacca tcatcagggc agagtgcttc ttacaagagg    1560
ggtattattc ctgtgaagca ttcctgtata agagccttcc tctctgggat ggccttagtt    1620
gtcggtcaca gttccttcag cttgtgagct ggattccttt tagtagcttc tctgaggtga    1680
aaccacttct ttttgaccat ctagcgcagc tcttctttac atcaaccatt tatttcaagt    1740
gtagtgtgct tcagagtctg aaagagctat tgcagaattg gctgttgtgg cttttctatgg    1800
acattcacat gaaacctgtt acraacagtc ctctagagac aactttgggt ggatccatga    1860
actgtgtgtc taaactgatc cactatgtag ggtggctatc cactactgca atgcgcttgg    1920
agagcaacaa tactttcttg ctgcactttt ttttggattt ctatgagaag gtgtgtgaca    1980
tatatataaa ttatgacctt ccattagtgg tattgtttcc tcctgggatc ttctattctg    2040
```

-continued

```
cactcctcag cctggatacc agcatcctga accagctgtg ttttattatg cacagatatc      2100
gtaaaaattt gactgccgca agaaaaatg agttggtaca aaagacaaaa tcagagttca       2160
atttcagcag caagacttat caagaattta attactattt gacatcaatg gttggttgcc      2220
tgtggacgtc caaacccttt gcgaaaggaa tatatattga ccctgaaatc ctagaaaaaa      2280
ctggagtggc tgaatataaa aacagtttaa atgtagtcca tcatccttct ttcttgagtt      2340
acgctgtttc cttttttgcta caggaaagcc cagaagaaag gacagtaaac gtgagctcta     2400
tycggggaaa gaaatggagc tggtatttgg actatttatt ttcacagggg ttacaaggct      2460
tgaaactttt tataagaagt agtgttcatc attcttccat tcccagagca gagggcataa     2520
actgcaacaa tcaatattaa atgaatgttg acataaactg aaaaaaaaa                 2570
```

<210> SEQ ID NO 17
<211> LENGTH: 2431
<212> TYPE: DNA
<213> ORGANISM: Homo sapiens

<400> SEQUENCE: 17

```
ggcacgaggc cgggagcaga gcgaaccgca ccggcccgag cggagcgccg cacgttccca       60
accgcgaggc cagacatctg actgttggtg tgagaccagt gctcctggtg gtgtgccctg      120
agccatggag gcgcctttgc agacagagat ggtggagctg gtgcccaatg caaacactc       180 agagggctg ctcccggtca tcacccccat ggcaggcaac cagagggtcg aggaccctgc       240
acggagctgt atgagggca agagcttcct acagaaaagt cccagcaagg agccacactt       300
cactgacttc gaggggaaga catcattcgg gatgtcagtg ttcaacctca gcaatgccat      360
catgggcagc ggcatcctgg gactcgccta tgccatggcc aatacgggca ttatccttt      420 cctgttcctg ttgacagctg tcgccttgct ctccagctac tccatccacc tgctactcaa      480
gtcctcaggg gtcgtgggca tccgtgccta tgagcagctg ggctaccgtg cctttgggac      540
cccaggaaag ctggcagcag ccctggccat acgctccag aacatcggag ccatgtccag       600
ctacctgtac atcatcaagt ctgagctgcc acttgtcata cagaccttcc tgaacctgga      660
ggagaaaacc tcggactggt acatgaacgg gaactacctg gtaatccttg tctctgtcac      720
catcattctg cccctggcac tgatgcggca gcttggctac ctgggctact ccagcggctt      780
ctctcttagc tgcatggtgt tcttcctaat tgcagtcatc tacaaaaagt tccacgtgcc      840
ctgcccactg cccccaact tcaacaacac cacaggcaac ttcagccacg tggagatcgt      900
gaaggagaag gtgcagctgc aggtcgagcc tgaggcttca gccttctgca ctcccagcta     960
cttcacgctc aactcacaga cagcatacac catccccatc atggccttcg ccttcgtctg     1020
ccaccccgag gtgctgccca tctatactga gctcaaggac ccctccaaga agaagatgca     1080
gcacatctcc aacctgtcca tcgctgtcat gtacatcatg tacttcctgg ctgccctctt     1140 cggctaccctc accttctaca acgggtgga gtcggagctg ctgcacacct acagcaaggt     1200
ggacccgttt gacgtcctga tcctgtgtgt gcgcgtggcc gtgctgacag cagtcacgct     1260
cacagtgccc atcgttctgt tcccggtgcg ccgcgccatc cagcagatgc tgtttccaaa     1320
ccaggagttc agctggctgc ggcatgtgct tattgccgtt ggcctgctca cttgtatcaa     1380
cctgctggtc atctttgccc ccaacatcct gggcatcttt gggtcatcg gtgccacatc     1440 tgccccattc ctcatcttca tcttccctgc catcttctac ttccgaatca tgcccacgga     1500
gaaggagcct gcaagatcca cccccaaaat cctggccctg tgttttgcta tgcttggctt     1560
cttgctgatg accatgagct tgagcttcat catcattgac tgggccctcag ggaccagccg     1620
```

```
gcatggagga aaccactagg gtgaccctca tcctgttctg tctactcacc ctagcagccc      1680
tgcccagact cttcagcccc tgctcccatc cagtggccag tcgggggagg agaaagacgc      1740
gattaacact gtggcattca gccaggcccc atgtcctctc tgtggaaggt ttttgttcaa      1800
gagccaggac caaggccctt gggccactac cctgctaggc tctggagctg tagaggcttc      1860
ctgaactggg agcagggtag ggctgtcgcc ttagatcccg cccaagcccc tcattccctc      1920
cttgcacaga tgcatacact ggggcccagc agctgcctcc tgaggtgaca cagcctgtag      1980
gaacatacac agctgggatc agcctgcagc catcccccga ccctgctgct aggccacggt      2040
ctgcgccctg gggcctcatc tcccccagcc cacttgtttt ccccctttt attccctagg       2100 cccttttcag actcctgggc ccttggatac tcttctccca tctcccttca caggatgaca      2160
ccctcccata cccatagct ggggccagca ggttctgctg agggtggggc tggtgtaggg       2220 accccccaaga gacccctgtc ctgtcccttc accagtcctg gggaggctgg gactcccccct    2280 gccacaagcc tgggccacag ctcacattcc actgctggga aagaaacag gccgaggccc      2340 agagtggcct gccccgggga gccaaagacc ccagtggcca cactgggata gggtggggag     2400
gctggcagcc ctcttttata aatctcgtgc c                                     2431

<210> SEQ ID NO 18
<211> LENGTH: 6746
<212> TYPE: DNA
<213> ORGANISM: Homo sapiens

<400> SEQUENCE: 18
ctgcagtgtt tggtctcacc aagtttccca caataaagag acatgagtca cctttcaaga      60 cccttttaccc ccaagaatgt ggtcttcaca catgagacca aggtctacaa gtggtcagga    120 gagaggggt ctgctcagat gggggagtag tgcctgagct ggcctcaaga gggttaagtg      180
gccctgcact gaaaacctgg acactgagtt agggtagggc tgggggaaaa cttgggccttt    240 ggagtcgtag ggtctgggtt caaatccaca gaccattccc ttcctagctg tgtgttggtg     300
ggtaattcac tggatctttc tgagtcctgg tttcctcatc tgaggtaaaa cgagtttgcc     360
ggttggtctg agagctgttc taggcatggt ggggagaccc tgacaggcag aggcagccct    420
gctctcaagc agttgattta cagctgggga acaagacag ccacaaatgc aatacctcaa     480
actcaacttc tcaccagaaa gctccttttc ctaattttca cagccagtcc ctcagcctcc    540
tgggccccaa atactagtaa aacctttgcc tcctctctct tctttctttc ttgtaatcat    600
ataggtacaa agtcctacca attcttcctg aaatatgttt ccttatcaaa aagtcctgca    660
aagccgtgcg tggttgctca tgcctataat cccagcactt tggaggctgg gaggatcgct    720
tgagtccagg agttcgagac cagcctggac aacatatgga gacccatctc taccaaaaat    780
tttaaaatca gcaggggtgg tagtggcaag cacctgtggt ctcatctact gggagctg      840 aggtgggggg attgttggag cctgggcggt tgaggctgca gtgatctgtg attgcaccac    900
tgcactctag cctgagggac agagcaagaa cttgtatcag aaaaaaaaa aaaagtcct     960 gcggtactgg acactgccat tgcctatacg attcccactc cctcatcctc cctagcagga    1020
tatcaatttt gttcgaagtg tcaatgaagg ccaggtgcgg tggctgatgc ctgtaatcct    1080
aacactttgg gaggccgagg caggcggatc acctgaggtc aggagttcaa gaccagcctg    1140
gccaacatgg tgaaaccctg tctctactaa aaacacacaa attagcaggg catggtggcg    1200
tgcacctgta atcccagcta ctcaggaggc tgagacagga gaatcacttg aacccggagt    1260
ggaggttgca atcagccaag atcacaccac tgcacttcag cttgggtgac aagagtgaaa    1320
```

```
ctctgtctca aaaagaaaa acaaaacaaa aacaaacaac aacaacaaaa agcaaagtgt      1380
cagtgaaggt ccagcaaaag actcccttcc tattgcccct tgcagccagg gtcatcatgt      1440
gacacagttc agatcaatga gatggaggct gagggtccct gggaaagatg tttttcctat      1500
acaggtacca cctctttcag cttcactctt tccattttcc acgtgaacag gccttgtagc      1560
ctggaggagc tacagctgcc ttttgagat gctgaggcac cctgtctgaa gaaggccctc      1620
acatcactca acttgactac tgggtgagcc cttggagagg cttcccagcc tctgctcttc      1680
aagccgaagt accacagggg acacgagtcc cagagttaca ggaccccagc tatggttcat      1740
gtgtaaaggg aaccattagg caaccagggg aaatgatgaa aagatctac atttacaaat      1800 gtggaaagat gttcgtggta tattgttaaa ttaaaaagct gtttaaaaat agttttgggg      1860
tcaagtgaga tgactcactt atacttttag tataagtatg tcccatgcaa tatctggaac      1920
gtacttgtac taaggggttt ctccctccat cggcacatcc caggcatcct ggcagctgct      1980
ggcctccagc aaccccacat tctagttgtg tgggagtggg ttgtggcatg gaccctgtgg      2040
gctaccactg ccctgacctg cttcttcaca cactggtatt tgtatctgtg gtaaacccag      2100
tgacacgggg gagatgacat acaaaaaggg caggacctga gaaagattaa gctgcaggct      2160
ccctgcccat aaaacagggt gtgaaaggca tctcagcggc tgccccacca tggctacctg      2220
ggccctcctg ctccttgcag ccatgctcct gggcaaccca ggtaaggcct tcccctcggg      2280
atcgatcctg atggcccacc cagcctcgca ctctcaggct ggctgaacct ggagcttgga      2340
ctctgtgggc acccaggtgc ccctgcctcc ccccggcctt ctccccgtc atggaggcct       2400 ggccctcccc tcagagccag gcttagtccg gtgtgctgcc cagcctgtca ctggcctggc      2460
caaggaggag agacaggcca gggattctgg tcctaactct actggccaca ctgtgtggcc      2520
tgagaccccc ctttccctcc aagcccctg cctccgcatc tgcgtggtga aggccattgg       2580
cctcatcggt ggatctgcgt ttcctcgggc ctacactgtc taggattgtg cggggctggt      2640
gagagaacaa gatctcttcc gtgttcaagg cagacttcct gcccctgca cctgctctc        2700 tcccaggcct tgaggtcagt gtgagcccca agggcaagaa cacttctgga agggagagtg      2760
gatttggctg ggccatctgg atggaaggta aaaaagaaa tcccttgaa aggagattga        2820 gggaagtttc tagacaaacc gacccccaaa tctgtgttgc tgggggaaca gaggagaaga     2880
gagagtctcg ccctcctggc tttctagaag gaacgtgaga acacgtgttt gtgctgagag      2940
tgggtcagag cggctccagg gcaaagcatg tggacaggta tcctggcccc ctgcaaggcc      3000
cagctcctgt cctaggccct ggtcacctcc tggactccca ccagcagga gaacgggctt       3060 tccctctcct tccgcctgcg gagggaagc tgaagtctgg tcttcctcag gtctggtctt       3120
ctctcgtctg agccctgagt actacgacct ggcaagagcc cacctgcgtg atgaggagaa     3180
atcctgcccg tgcctggccc aggagggccc ccaggtacgt gttggctctc tgctcacctg      3240
ccacagtccc tctcctttcc ctcctccctg gtggctcctg gggtgaggtc tggagctctc      3300
taatggtcag gaggtgggag tggaggctgg gctgtttctg acgatgctgg ttttgttgaa      3360
ttcatgtctg gccaggaggg ctacaggtat ctggcagact cctccaggag gatcctctgg      3420
ggtctcaccc tccaaggagc ctggggctgc agaacccaaa taggcagact cccctgggag      3480
ttcctcaata ggagagggc aagtgcaggg ctggaaagt actggggttg tgggaggctg        3540
tttctggggt gtctcagagc ctctaagaca agcaaagggg tgggtagggg ccaggcagcc      3600
agttcaggcc ttcagtgtat ccacgctctg ggaagagatc acggacattc ctgccggcct      3660
cagaaacaca aagggcccct ttcctgggca cttttcacgcg ctcccagagt gtctgagaga     3720
```

```
ccatcataag ggctttcttt cctgacaggg tgacctgttg accaaaacac aggagctggg      3780
ccgtgactac aggacctgtc tgacgatagt ccaaaaactg aagaagatgg tggataagcc      3840
cacccaggtg aggccaaggg gctacagagc ctcctgtctg ctgctcaatg gaggggccag      3900
cctgtgacca ggtcggggat cggggagccc gggggcacct tgcacagtga tcctggggga      3960
gggcttccta aagggaatc tgtgagtccc cgtgtgtctg tggatgaatt tcagagaact      4020
tgtgaaattg tgactctctg gaactgtgta agtcagacgg cagagtatac atggttttca      4080
tcatgtatcc tcaaagaggg cttgtcccag agaagttagg aatcttcccc taaagcccta      4140
acatttgtgt ccaaggcaga gttttgagaag ctagttcccc aagaggcctg ggtcaggact      4200
gataaatccc agatctgcta cttccaagct gcatggcctt gggcaagtca cttccacttt      4260
ctgagcccct gttatcttat cttgaaatg tgatggataa tagtccctat cttgcaagtt      4320
gtcaaaccct tttttttttt tttccttgag ataggatctt actctgagac ccaggctgga      4380
gtgcactggt gtgatcttgg ctcactgcaa cctctgcctc cctggcccaa gcaattctcc      4440
tgtctaagcc tcctgagtac ctggggctcc aggtgtgcgc caccatgccc agctaatttt      4500
tgtacttttg tagaaacagg gtctcactgt gttgcccagg ctggtctcca acttctgagc      4560
tgaagcaatc cacctgcctt ggcctcccaa agtgtgggat tataggcatg agccactgca      4620
cctggctgct gaagcttttt aaaagagctg agggctggga tgtgcttagc tccacgtcca      4680
gcactgagta aatgcttaac gaatgactgt gttactacca agaattattg tttcactctc      4740
cctccttccc tctcctctgc tgccccaaac tactcagcat cctggcactg caggctcgca      4800
cttagccctg gatacccaga ttcatcctcc tcccctggga tggcatagaa gagactttaa      4860
aaccaaatga gccaagactc caagctctga ccacacctcc caccccacc agtcttctct      4920 atgcacccc tctatatctg gagcccccag ccaggttctg gaccaaggta gctacatggc      4980
agagcattta atgtgtgcct ggcagccatg ggcaccattc tccacacaga aggcagggac      5040
aggtgcacaa ggggctgaga ccccagcagg gctaactgtc cttgtctcag gagccctacc      5100
tggccagtct tgggccaggc cttggggact gggagtaggg gctgacccgt ctgtacagtc      5160
tctggcccca tggcaccagg tgccagctcc tcgcacccag tactcccatt gctagggctg      5220
ctggaacctg cagggttggc agagctgggc aggactcacc ctataaccat gtccactgtg      5280
gtgctgctgc tgcagagaag tgtttccaat gctgcgaccc gggtgtgtag gacggggagg      5340
tcacgatggc gcgacgtctg cagaaatttc atgaggaggt atcagtctag agttatccag      5400
ggcctcgtgg ccggagaaac tgcccagcag atctgtgagg acctcaggtt gtgtatacct      5460
tctacaggtg agtgcagagg tgacagcagg gatacctcct gagggttgga gacagcttcc      5520
cccaggatat atcaaagctg cctccttact cccccatctc ccagcatggg aaagtgtgga      5580
gaattgagca gatggacttt agctagaaat gtttgagaaa tactgattag agcttgggct      5640
tcagacacag gtggttgtgg agtaaaatct ggtctccatc tctccctggc tgtgtgacct      5700
taagcaaata acttgacctc tctgagcttc agtttcttca tctgtgaagg agagatagca      5760
atcctgattt tgagattgg aatgagaatt gaaggaggtc accgtgtgtg tggacctgac      5820
cctggggaaa tgtcctcaga ctgaggctat tcaaggtcat cagaccctca gtcaaactcc      5880
aacccagccc agcacatggc ccctggggtc gggagctggg gccatatcct cccccacaat      5940
cctgggccct gagatctggg ctagggaacc cttcaggcag gggagcatga ggcctttccc      6000
tccatggctg cccaggctgt gctgagagaa cagatctcgg ctgtaggaaa cggggccaga      6060
aaggggcctc ggtgattggc tctggcagct cagctggcac ttgccaatag ctctgggatt      6120
```

```
ttatgctggc agatcggggg tccccaccat ttcctgtcat tggagcttgt ggcttttcta    6180
ttcaaggccc cacagcctgc tcaggctgcc gactggcttc caggatgtgc ctctgggtgt    6240
gttcagtagg gtcaggtggc tctgggacct taagcaagta acattctgag tgcctgcttc    6300
tccttgagga cccaccacat ctgcccacag ctagctgttc tctccgctcc aggtcccctc    6360
tgagccctct caccttgtcc tgtggaagaa gcacaggctc ctgtcctcag atcccgggaa    6420
cgtcagcaac ctctgccggc tcctcgcttc ctcgatccag aatccactct ccagtctccc    6480 tccccctgact ccctctgctg tcctcccctc tcaggagaat aaagtgtcaa gcaagatttt    6540
agccgcagct gcttcttctt tggtggattt gaggggtggg tgtcagtggc atgctggggt    6600
gagctgtgta gtccttcaat aaatgtctgt cgtgtgtccc atacactgtt gtagatgtta    6660
tggatttagt ggtgaacgag acaaccttaa cagcattcac acagttagtc gtgaaatgct    6720
tactgagcac tcaccacagc catgca                                         6746

<210> SEQ ID NO 19
<211> LENGTH: 915
<212> TYPE: DNA
<213> ORGANISM: Homo sapiens

<400> SEQUENCE: 19
atgtggtcga cgagaagccc caacagcacg gcgtggcctc tcagcctcga gcctgatccg     60
gggatggcct ctgcctccac cacaatgcat actaccacca ttgcagagcc tgatccaggg    120
atgtctggat ggccggatgg cagaatggag acctccaccc ccaccataat ggacattgtc    180
gtcattgcag gtgtgattgc tgctgtggcc atcgtcctag tctccctcct cttcgtcatg    240
ctgcgctaca tgtaccggca caagggcacg taccacacca tgaggccaa gggcacggag     300 tttgctgaga gtgcagatgc agccctgcag ggagaccctg ccctccaaga tgctggtgat    360
agcagcagaa aggagtactt tatttgaggg acaacagact tcacttccct gaatgcctcc    420
cccatctcca tcaggaaaaa tacaccccat cgcccagtat ccccgtcgat accaccagac    480
agagagagag agtacacttg atttcttccc gagatagtta cctagaaaca ctaggtgcct    540
gcccaaggag gaacggagga ggactcgcgc tacaagaggc cactcccagg gacccaggga    600
ggcgatggcc accccagagg ccaccttttg ctccacggag gtgggagaga atctgggcac    660
atggggcccc ctagggcagt gcaggacaac atcagctcac tggcaggaaa gtccttgttg    720
agggtgaggg ggtgctgggg tacccggggg ctggggaagc aaggaaataa gtcatctgta    780
tgctgactgg ggataatggc atcaatgtca gtccttgact ttggggggaa cagcaggtgc    840
cagagctaaa aggtaccttt gtctgccatt gatccagcta agaacgattg gaaataaatt    900
ggaaatgtaa ccgag                                                     915

<210> SEQ ID NO 20
<211> LENGTH: 15164
<212> TYPE: DNA
<213> ORGANISM: Homo sapiens

<400> SEQUENCE: 20
gaattccgcc tctgcggagc cgggctcggg tcgccggagc cgcgccccac cccgccagct     60
ccagagccac gactaatggc tgaaggataa atcaacatgg caactatgat tccaccagtg    120
aagctgaaat ggcttgaaca cttgaacagc tcctggatta cagaggacag tgaatctatt    180
gctacaagag agggagttgc tgttctgtat tctaaactgg ttagcaataa ggaagtagta    240
cctttgcccc aacaagtttt atgcctcaaa ggaccacagt tgccagactt tgaacgtgag    300
```

-continued

| | |
|---|---|
| tctctttcaa gtgatgagca ggaccactat ttggatgccc ttcttagcag ccagctagca | 360 |
| ttggcaaaga tggtatgttc agattcccca tttgccgggg cacttagaaa acgactgctt | 420 |
| gtactccagc gtgtcttttta tgcactttct aataaatacc atgacaaagg caaggtgaag | 480 |
| cagcagcagc attctccgga gagcagttct ggttcagcag atgtccattc tgttagtgaa | 540 |
| cgcccccggt caagcactga tgcacttata gaaatggtg ttcgaactgg tctaagttta | 600 |
| ttatttgcgc ttctaagaca aagttggatg atgcctgtgt caggacctgg tctcagtctt | 660 |
| tgcaacgatg tcattcatac tgcaattgaa gttgtgagct cttttgccacc attatcatta | 720 |
| gcaaatgaaa gcaagattcc tcctatgggc ttggactgct atcgcaagt aacaacattt | 780 |
| cttaaaggag tcactattcc taattctggg gcagacactt taggtcgtag attagcttct | 840 |
| gagttgctgc ttggtttggc agctcaacga ggctcattgc gatatcttct tgaatggata | 900 |
| gaaatggctt tgggggcttc ggcagttgta cacaccatgg agaaaggcaa actactctca | 960 |
| agccaggaag gaatgatcag ctttgactgc tttatgacca tattaatgca gatgaggcgt | 1020 |
| tctttgggtt catctgctga tcggagtcag tggagagaac caaccagaac atcggatggc | 1080 |
| ttgtgctccc tttacgaggc agcattatgt ctctttgaag aggtttgcag aatggcttct | 1140 |
| gattattcga gaacatgtgc tagcccagat agcattcaga ctggtgatgc tcccattgtc | 1200 |
| tccgaaacct gtgaggttta tgtttggggg agcaatagca gccatcagtt ggtagaaggt | 1260 |
| acacaggaga aaatactgca acccaaactg gctcctagtt tctctgatgc acagaccatt | 1320 |
| gaagctggac agtactgcac ttttgtcatt tctacggatg gctcagttag agcttgcggg | 1380 |
| aaaggcagct atgggagact gggccttgga gactccaata atcagtcaac tttaaaaaag | 1440 |
| ttaacattcg agcctcacag atccattaaa aaggtttcat cttctaaagg atctgatggt | 1500 |
| cacactttag cctttacgac agaaggagaa gtcttcagtt ggggagatgg tgattatggg | 1560 |
| aaactggggc atgaaatag ttcaacacag aaatatccca agcttattca gggacctcta | 1620 |
| caaggaaagg tagttgtttg tgtgtcagct ggatacagac atagtgctgc tgtcacagag | 1680 |
| gatggggaat tatacacatg gggtgaagga ctttggaa gattaggtca tggtgacagc | 1740 |
| aatagtcgta acattccaac attagtaaaa gacatcagca atgtaggaga ggtttcttgt | 1800 |
| ggcagttcac atactattgc tctgtctaaa gatgggagaa ctgtatggtc ttttggagga | 1860 |
| ggagacaatg gtaaacttgg tcatggtgat accaacagag tgtataaacc taaagttatt | 1920 |
| gaagctttac aaggaatgtt cattcgcaaa gtttgtgctg ggagccagtc ttcacttgct | 1980 |
| ttgacatcaa caggcaggt ctatgcttgg ggctgtggga cttgtctagg ttgtggttct | 2040 |
| tcagaagcta ctgctttgag acccaagctt attgaagaac tggctgccac aagaatagtt | 2100 |
| gatgtttcta ttgagacag tcattgtttg gctctttctc atgataatga agtttatgcc | 2160 |
| tgggcaata actcaatggg gcaatgtggt cagggaaatt ccacaggtcc tattactaaa | 2220 |
| ccaaagaaag tgagtggctt agatggcata gctattcagc agatttcggc tggaacatca | 2280 |
| catagtctgg catggactgc tcttcctagg acagacaag ttgttgcatg gcaccgacct | 2340 |
| tattgtgtag atcttgaaga gagtaccttc tcacacctgc gttctttttct tgagagatac | 2400 |
| tgtgataaaa taaacagtga gattccccca ctcccttttcc cttcatcaag agaacaccac | 2460 |
| agttttctca gctgtgcct gaagctactt tcaaatcacc ttgctcttgc acttgcggga | 2520 |
| ggggtagcta ccagcattct cgggaggcag gcaggtccac ttcgaaattt gctcttcaga | 2580 |
| ctgatggact caactgtccc agatgaaatc caagagggtgg taattgaaac tttatcagtg | 2640 |
| ggagcaacca tgctgttacc tccattacga gaacggatgg aattacttca ttctctttta | 2700 |

```
cctcaaggac ctgatagatg ggaaagctta tctaaaggac agagaatgca actggatatc       2760
atcctgacaa gtttgcaaga tcatacccac gtagcctccc tacttggcta tagttcaccc       2820
tctgatgctg ctgacctatc ttctgtgtgt actggctacg gaaatctgtc agatcaacct       2880
tacggcactc agagctgcca tccagatacc cacctggctg aaattttgat gaagaccctc       2940
ttaagaaatt taggatttta tacagatcaa gcatttggag agctagaaaa gaatagtgat       3000
aaatttctac ttggaacatc atcatcagaa aacagtcagc ctgctcatct tcatgaactg       3060
ctatgttcac tacagaaaca gctgctggca ttttgccata tcaataacat tagtgagaac       3120
tcaagcagtg tggcattgct tcataaacat cttcagcttt tgttgcctca tgccacagat       3180
atttattcac gttctgcaaa tttgctcaaa gaaagtcctt ggaatggcag tgttggagaa       3240
aaattaagag atgtgatata cgtctcagct gctggcagta tgctctgcca gattgttaac       3300
tccctgctgt tactccctgt gtcagtggct cggcctttat tgagttacct cctcgacttg       3360 ttgccaccte ttgattgcct aatagactc ctgccagctg ctgatctttt agaagaccag       3420
gagttacagt ggcctcttca tggagggcca gaactaattg atcctgctgg tctgccatta       3480
cctcagccag ctcagtcctg ggtatggctt gtggatctag aaagaacaat tgctctcctt       3540
attgggcggt gtcttggtgg catgcttcag ggctcccctg tgtctccaga ggaacaggac       3600
actgcatatt ggatgaaaac gccactgttc agtgacggtg tagaaatgga cactcctcaa       3660
ttggataaat gtatgagttg cctgttagaa gtagcacttt ctggaaatga agaacagaag       3720
ccttttgatt ataaattgcg gcctgaaatt gctgtctatg tagacttggc attgggttgt       3780
tctaaagagc ctgcccgaag cctttggatc agcatgcagg actatgctgt tagtaaagat       3840
tgggacagtg caactttaag taatgagtca ctcttggaca ctgtgtctag atttgttctt       3900
gcagctcttc tgaaacacac aaatttactt agtcaagcat gtggagaaag ccgatatcaa       3960
cctggtaaac acttatcaga agtgtaccgt tgtgtataca agttcgaag tcgtttactt       4020 gcttgcaaga accttgaact tattcaaaca aggtcatcat cacgggacag atggatatca       4080
gaaaaccagg actctgcaga tgttgatcct caggagcatt catttactcg aactattgat       4140
gaagaagctg aaatggaaga acaggctgag agagaccggg aagagggca tccggagcca       4200 gaggatgaag aggaggaacg ggaacatgaa gtgatgacag ctggcaaaat ctttcagtgt       4260
ttcctctcag cccgtgaagt agctcgtagc cgagaccgag atagaatgaa cagtggggca       4320
gggtctgggg ctcgagctga tgatccacct cctcagtctc agcaagagcg aagggtcagc       4380
acagaccttc ctgagggtca ggatgtgtac actgctgcat gcaactccgt gatccatcgg       4440
tgtgccctgt taatattagg agtaagtcct gtgatagatg agcttcagaa gcgaagagaa       4500
gaaggacagt tgcagcaacc ttcaacaagt gcctctgaag ggggtggact tatgaccagg       4560
agtgaaagtc ttactgcaga gagccggcta gtccacacaa gcccaaatta tagactgatc       4620
aaatcgagga gtgaatctga tttgtctcag cctgaatcag atgaagaggg ttacgcactg       4680
agtggcagac aaaatgttga tttggatttg gcagcatctc acagaaagag aggtcctatg       4740
cacagtcaat tggaatccct gagtgactct tgggctcgcc tgaaacatag cagagactgg       4800
ttatgcaact cctcctattc ctttgagtca gattttgatc ttaccaagtc tttgggagtt       4860
cacactttga ttgaaaatgt tgtaagcttt gtgagtggga tgtgggaa tgccccaggt       4920 tttaaagagc cagaggaaag tatgtctaca agtccccagg cctccatcat tgcaatggaa       4980
cagcagcagt taagggcaga acttcgttta gaggcacttc atcagatcct cgttctattg       5040
tctgggatgg aagaaaaagg tagcatctca ctggcaggaa gcagattgag ttcaggcttc       5100
```

```
cagtcctcca cactactcac gtctgtgagg ctgcagttcc tagcagggtg ttttggttta    5160
ggcactgttg gacacacagg agccaaggga gagagtggcc gattgcatca ctatcaggat    5220
gggatcagag cagctaagag aaatattcag attgaaatcc aggtagctgt gcataaaatt    5280
tatcaacagt tgtctgctac cctggaaaga gccctgcaag caaacaagca tcacattgaa    5340
gcccagcaac gtctgcttct ggttacagtt tttgccctaa gtgttcatta tcaaccagta    5400
gatgtttctt tggcaatttc cactggtctg ctaaacgtat tgtcacagtt gtgtggtaca    5460
gacaccatgc taggacagcc cctgcagttt tgccaaaga cgggtgtttc ccagcttagc     5520
acagctttga aagtggccag tacaaggttg ctccagattc tagccatcac tactgggacc    5580
tatgctgata aactgagtcc caaagtagtt caatccttgt tggatctact ctgtagtcag    5640
ttgaagaatt tattgtccca aactggtgta ctacatatgg cctctttcgg agaaggggag    5700
caagaagacg gtgaagaaga agaaaaaaaa gttgactcca gtggagaaac tgagaagaaa    5760
gatttcagag ctgctcttag gaaacaacat gcagccgaac tccatctagg ggattttta    5820 gttttcttc gcagagttgt atcttcaaaa gcaattcaat caaaaatggc ttccccaaag     5880
tggaccgaag tgcttctaaa tatagcatct cagaaatgtt cttcaggtat ccctctggtt    5940
ggtaacttaa gaacaaggct ccttgcactt catgtccttg aagctgtgct gccagcttgt    6000
gaatctggtg tagaagatga tcaaatggcc cagattgttg agcgcttatt ttcccttctc    6060
tctgattgta tgtgggagac acccattgct caggccaaac atgctattca gataaaggaa    6120
aaagaacaag aaataaaact acagaagcag ggcgagttgg aagaagaaga tgagaatctt    6180
cctatccaag aagtatcctt tgacccggag aaagctcagt gttgcctagt ggagaatgga    6240
cagattttaa ctcacggcag tggagggaaa ggatatggat tggcatctac aggagtaact    6300 tctggtgct atcagtggaa gttttatatt gtgaaggaaa acagaggtaa tgaaggcacg      6360
tgtgttggag tttctcgctg gccagtacat gactttaatc accgcactac ctcggatatg    6420
tggctctata gggcctacag tggtaacctc tatcacaatg gagaacagac tctcacattg    6480
tccagcttta ctcaaggaga tttcattacc tgtgtgttag acatggaagc caggaccatt    6540
tcttttggga aaaatggaga ggaacccaaa ttagcttttg aagatgtgga tgcagcagag    6600
ttgtacccat gtgtgatgtt ctatagtagc aatccagggg aaaaggtgaa aatttgtgat    6660
atgcagatgc gtggcacacc ccgagactta cttccaggag acccctattg tagtccagta    6720
gcagcagtgc tggctgaggc cactattcag ctcgtccgta tccttcaccg aacagaccgt    6780
tggacttact gcattaacaa aaaaatgatg gaaaggcttc acaaaattaa gatatgtatt    6840
aaagagtcag gtcagaagct aaagaaaagc cgctcggttc agagccgaga ggaaaatgaa    6900
atgagagagg agaaggagag caaagaggaa gagaaagtaa acatactagg catggcctc    6960 gctgacctct cagagctgca gctgaggact cttttgcatag aggtgtggcc cgtgctggct    7020
gtgataggag gagttgatgc tggtcttaga gttggaggtc ggtgtgttca caagcaaact    7080
gggcgccatg ccacgctgct gggagtggtc aaagagggca gcacgtctgc caaggtccaa    7140
tgggatgaag cagaaattac tatcagcttc ccaacttttt ggtcgcctag tgatactcca    7200
ttgtataatc tggaaccctg tgaaccattg ccgtttgatg tggcgcgatt ccgaggcctg    7260
acggcttctg tgctgctgga cctaacatat ctcactggcg ttcatgaaga catgggcaaa    7320
cagagcacca aacgacatga aaagaaacac cgacatgaat ccgaggagaa agggatgtt    7380 gagcagaaac ctgagagtga atccgcttta gatatgcgaa caggcctaac atctgatgac    7440
gtcaaaagtc agagtaccac aagctccaaa tcagaaaatg aaatcgcttc attttcttta    7500
```

-continued

| | |
|---|---|
| gatccaacac tgccaagtgt ggaatcccaa catcaaataa cagaagggaa aagaaaaaat | 7560 |
| catgaacaca tgtccaaaaa ccatgatgta gcccagtcag aaatcagagc agtccagctg | 7620 |
| tcctatcttt acctcggtgc tatgaagtca cttagtgccc ttcttggctg tagtaaatat | 7680 |
| gctgagctgt tgctgatacc aaaagttctg gctgaaaatg ccacaactc agactgtgca | 7740 |
| agttctccag ttgttcatga agacgtggag atgcgagcag ccctgcagtt cttgatgcga | 7800 |
| cacatggtga agcgagcagt catgcggtca cccataaaga gagcattggg attagctgat | 7860 |
| ctggaacgag cgcaagccat gatctataaa ttagtggttc atgggctttt ggaagaccag | 7920 |
| tttgggggca aaattaagca agagattgat caacaagctg aagaaagtga ccctgcccag | 7980 |
| caggcacaga caccagttac tactagccca tcagcctcaa gcacgacctc ctttatgagc | 8040 |
| agctctctgg aggacaccac aactgccacc actccagtca ctgacacaga aacagtgcct | 8100 |
| gcatccgagt ccccgggagt gatgcctctt agtcttctca ggcaaatgtt ctctagttac | 8160 |
| ccaactacca ctgtacttcc cacacgtcgg gcacagactc ctccaatatc ttcgttacca | 8220 |
| acctctcctt ctgatgaagt aggaaggagg caaagtttaa cttctcctga ttcccagtca | 8280 |
| gcaaggccag ctaaccgcac agccttgtca gacccaagca gtagactttc aacttctcct | 8340 |
| cctcctccag caattgcagt tcccttgctg gaaatggggt tctctcttcg gcagattgcc | 8400 |
| aaagccatgg aagctacagg tgctagggga gaggctgatg cccagaatat cactgtcctt | 8460 |
| gccatgtgga tgatagagca ccctgggcat gaggatgaag aggagcccca gtcgggcagc | 8520 |
| acagcagact ctaggcctgg agcagccgtt ctaggcagtg gcgggaagtc aaatgatccc | 8580 |
| tgttatttgc agtcacctgg agacatacca tcagctgatg ctgctgaaat ggaggaaggt | 8640 |
| tttagtgaaa gccctgataa tttggatcat acagagaatg cagcttctgg aagtggacca | 8700 |
| tcagctagag gtcgctcagc ggtaacaaga agacacaagt ttgacttagc tgctcgcaca | 8760 |
| ctgctagcaa gagcagcggg attataccgc tctgtgcagg cccacaggaa tcaaagtcgg | 8820 |
| agagaaggaa tatctttgca gcaagaccca ggggcgttgt atgactttaa tttagatgag | 8880 |
| gaattggaaa ttgatcttga tgatgaggcg atggaagcta tgtttggaca agacctgacc | 8940 |
| agtgacaatg atattctggg aatgtggatc ccagaggtac tggattggcc tacctggcat | 9000 |
| gtttgtgagt ctgaagacag ggaagaagtg gtggtgtgtg aactgtgtga atgcagcgtc | 9060 |
| gtcagcttca atcagcacat gaagagaaac catccaggct gtgggcgcag tgcaaaccgc | 9120 |
| cagggctatc gcagcaatgg ttcctatgtg gatggctggt ttggcggtga atgtgggagt | 9180 |
| ggaaatccat actacctgtt atgtggcacc tgcaggagaa agtacttagc catgaagacc | 9240 |
| aaatctaagt caacaagttc tgaaaggtac aagggacaag ctccagatct aattggcaag | 9300 |
| caagacagtg tgtatgaaga agactggac atgttggatg ttgatgaaga tgaaaagcta | 9360 |
| actggtgaag aagaatttga attacttgct ggaccgcttg gtttaaatga ccggcgcatt | 9420 |
| gtaccagaac cagttcagtt ccctgacagc gatccactgg gagcatcagt agcaatggtc | 9480 |
| acagccacca acagtatgga agagactctg atgcaaatag gttgccatgg ctccgtagaa | 9540 |
| aagagctcct ctgggagaat aacgttagga gagcaggcag ctgccctagc aaaccctcat | 9600 |
| gaccgtgtgg tggctttaag gagagtgact gctgctgctc aggttcttct ggccagaacc | 9660 |
| atggtcatga gagcgctgtc tcttctctca gtcagtggtt ccagttgtag cctggctgct | 9720 |
| ggtcttgagt ctctggggct aacagatatc cgaacgctag ttcgattaat gtgcttggca | 9780 |
| gcagcaggga gagctggcct ctccaccagc ccttctgcca tggctagcac ctcagaacga | 9840 |
| tcacgaggtg ggcatagcaa ggctaacaag cctatctctt gcctggccta tttgagcaca | 9900 |

```
gcagtgggat gtctggcatc aaatgctcct agtgctgcca aactgcttgt acagttgtgt    9960
acacagaact tgatttctgc tgcaacaggt gtaaatctaa ccacagttga tgactcaatt   10020
cagcgaaagt ttctacccag ctttctccga ggaattgctg aagagaacaa gcttgtgacc   10080
tccccaaact ttgttgtaac acaggccctt gtggcattgc tagcagacaa aggggccaaa   10140
ctaagaccta actatgataa gtcagaagtt gaaaagaaag ccctctggga gttggctaat   10200
gccctggcag cctgctgcct ctcctccagg ctgtcctcac agcatcggca atgggcagct   10260
cagcaactcg tgcgcactct tgctgcacac gaccgtgaca accaaactac tctgcagaca   10320
cttgctgata tgggaggaga tcttagaaaa tgctccttta tcaaattgga ggctcatcag   10380
aacagagtaa tgacatgtgt ttggtgtaat aaaaaaggtc ttttggctac aagtggcaat   10440
gatggcacca tccgcgtatg gaatgttacc aagaagcaat attcactgca acagacctgt   10500
gtgttcaaca gattggaagg ggatgctgag gaaagcctgg gatcacccag tgatccaagt   10560
ttctcaccag tttcctggag tatcagtggc aaatatctag caggcgcttt ggaaaagatg   10620
gtgaatatct ggcaagttaa tggaggaaaa ggattagtag atattcagcc tcattgggta   10680
tctgccctgg cttggccaga agagggtccg gctacagcct ggtcaggaga gtctccagaa   10740
ttgttgttgg tgggacggat ggatggatct ctgggactga ttgaagttgt tgatgtgtcc   10800
accatgcacc gtcgagaatt ggagcattgc tatcgaaagg atgtgtctgt tacttgcatt   10860
gcatggttca gtgaagacag accatttgca gtgggatatt ttgatggaaa actgttactg   10920
ggaacaaagg aaccacttga gaaggaggc attgttctaa ttgatgcaca taaggatact   10980
cttattagca tgaagtggga ccctacaggt catattctta tgacatgtgc caaagaagac   11040
agtgtgaaac tctgggctc tatttcggga tgctggtgct gtctacattc actctgccat   11100
ccatctattg taaatggcat tgcttggtgc cgccttccag ggaaaggatc caagttgcag   11160
ttactgatgg ctactggctg tcagagtggc ttagtatgtg tttggcgcat tcctcaagat   11220
actacacaga ccaatgtgac tagtgcagaa ggatggtggg accaggaatc aaattgccag   11280
gatggatata ggaaatcatc aggagccaag tgtgtttatc agctgcgggg acacatcact   11340
cctgttcgga ctgttgcctt tagttctgat gggttggccc tggtgtctgg tggactaggt   11400
gggctcatga acatttggtc tttaagggat ggctctgtct tgcaaactgt tgtgataggc   11460
tctggagcta ttcagaccac agtatggatt ccagaagttg gagtagctgc ttgctcaaat   11520
agatcaaagg atgttttggt cgtgaattgt acagcagaat gggcagctgc caatcatgtt   11580
ttggcaacct gtaggacagc attgaaacag cagggtgttc tgggattgaa catggctccc   11640
tgcatgagag cattttttgga gcggctcccc atgatgcttc aggagcagta tgcctatgaa   11700
aagcctcatg tggtttgtgg tgaccaactt gttcatagcc cctatatgca atgcttggct   11760
tcccttgctg tgggacttca tctggatcag ctgttgtgta accctccagt gccaccacac   11820
caccagaact gtctgcctga ccctgcatcc tggaatccaa atgaatgggc ctggttagaa   11880
tgtttctcaa ccactataaa agctgccgaa gccctgacca atggagccca gtttccagaa   11940
tcttttaccg ttcagatctc agaacctgtt ccagaggatg aacttgtatt tctaatggat   12000
aacagtaaat ggattaacgg catggatgaa caaattatgt cttgggcaac ttccagacct   12060
gaggactggc acctgggagg taaatgtgat gtctacttat ggggtgctgg taggcatgga   12120
cagctggcag aagctggaag aaatgtaatg gtacctgcag cagctccctc attctcacag   12180
gcccaacagg tcatttgtgg tcagaattgt acctttgtca tccaggccaa tggcacagtg   12240
ttggcttgtg gggaaggaag ttatggcaga ttaggacaag gaaattcaga tgaccttcat   12300
```

```
gtgctgacag ttatttcagc cttacaaggc tttgtggtga cccagctggt gacttcctgt    12360
ggttctgatg ggcactctat ggccctaact gaaagtggtg aggtctttag ctggggagat    12420
ggtgactatg gtaaacttgg ccatgggaac agcgacaggc agcggcggcc caggcagatc    12480
gaggccttac aaggagaaga agtggtgcag atgtcttgtg gcttcaagca ctcagcagtg    12540
gtcacttcag atggcaaact gttcaccttt gggaatggtg actatggtcg tctgggtctt    12600
ggaaatacct ctaacaaaaa acttccagag agagtgactg cactggaggg atatcagatt    12660
ggacaggtgg cctgtggatt aaaccacact ttggcagtgt cagcagatgg ttccatggtg    12720
tgggcttttg gagatggaga ctatggaaaa ctaggcttag gaaattccac tgcaaaatct    12780
tcacctcaga aaattgacgt cctttgtgga attggaataa aaaggttgc ttgtggaact     12840 cagttttctg ttgctttgac caagatggt catgtgtata cctttggtca agatcgcctg     12900
ataggcttgc cagaggggcg tgctcgcaat cacaatcgac cgcaacaaat ccctgtcctg    12960
gctggagtaa tcattgaaga tgtggcagtt ggagctgaac acacacttgc tttggcatca    13020
aatggagatg tgtatgcctg ggggagcaat tcagaagggc agctcggctt aggccatacc    13080
aaccatgttc gagaaccaac cctggtaaca ggtctgcaag ggaaaaatgt tcggcagatc    13140
tcggctggcc gctgccacag tgctgcatgg acagcaccac ctgtcccacc aagagcacca    13200
ggtgtgtcag tacctctgca gctgggcctg cctgacacag tgcccccca gtatggggcg    13260 ctgagagaag tcagcattca cacggtgcgg gccaggctcc ggctgctcta ccacttctct    13320
gacctcatgt actcatcctg gagactgctg aaccttagcc ccaacaacca gaacagcaca    13380
tcccattata atgctggaac ttggggcatt gtacagggac aacttcggcc tttgttagcc    13440
ccaagagtct acactctgcc aatggtgcgc tccataggaa aaaccatggt tcaaggcaaa    13500
aactatggac ctcagataac tgtaaagagg atatcaacca gaggacggaa gtgtaagcct    13560 attttttgtcc aaatagcgag acaagtagtt aagctgaatg cttcagacct ccgcctgcct    13620
tcccgagcgt ggaaggttaa gctggttgga gaagggctg atgatgctgg aggagtgttt     13680
gatgacacca tcacagagat gtgccaggaa cttgaaactg gtattgttga ccttcttata    13740
ccctctccca atgccaccgc agaagtgggt tacaataggg acaggttcct ttttaacct    13800 tctgcctgcc tcgatgaaca cttaatgcag tttaagtttt taggaatttt aatgggggtt    13860
gccattcgca caaagaagcc tctggacctc cacttggccc ctctggtgtg gaagcagctg    13920
tgctgtgtcc cactcaccct agaggacctg gaggaggtgg atctgctcta cgtgcagact    13980
ctcaacagca ttcttcacat tgaagacagt gggattaccg aggagagttt ccatgagatg    14040
attcctcttg attctttgt tggccagagt gctgatggca aaatggttcc tataatccct    14100 ggtggaaaata gtatcccact cacattttcc aacaggaagg aatatgtgga gagggccatt    14160
gaatatcgac ttcatgagat ggacagacag gtggctgcag tccgagaagg gatgtcctgg    14220
attgttcctg tgccgctgct gtccctcctc acagcaaaac aactgcagca gatggtgtgt    14280
gggatgcccg agatctctgt ggaagtcttg aagaaagtgg tgcggtaccg tgaggtggat    14340
gagcagcatc agctggtgca gtggttctgg cacacgctgg aagagttctc caatgaggag    14400
cgggtgcttt tcatgaggtt tgtgtcagga agatctcgac taccagccaa cactgctgac    14460
atttctcaga gatttcaaat catgaaggtt gataggcctt acgacagtct gcctacctca    14520
cagacctgct tcttccagct gaggctgccc ccgtactcca gccagctggt catggccgag    14580
cgcctgcgct atgccatcaa caactgccgc tcaatcgaca tggacaacta catgctctcg    14640
agaaacgtgg acaacgccga gggctccgac actgactact gaccgtgcgg gtgctctcac    14700
```

| | |
|---|---|
| cctcccttct ctccctcaat aatgctcact tctgatttga tgttgatata cttttatggt | 14760 |
| aactacatag atgttataag aacataaacc aacattataa acaatggcca catttagtta | 14820 |
| ctctaaatgt aacaaagaaa ttagatgttt ttattttttct gtgattgtac aaaaacaaca | 14880 |
| aaaacgaagt gctctcagtc aggttttttcc ctccatattt ttggtcactt ttgataagtt | 14940 |
| tgcatgaaac cattttggtg cattttttagt tgggaatggt acattttttgt aaatccaccc | 15000 |
| agtgaacatg aaattgtaca ttgtgtataa ttgttcatta gaaaggacag ttttacatga | 15060 |
| atattcatat atttatttttg ttttaatttg aattgcctgt tcagggttcc ttatgcagag | 15120 |
| aaataaagca gattcaggaa ttggaaaaaa aaaaaaaaaa aaaa | 15164 |

<210> SEQ ID NO 21
<211> LENGTH: 1201
<212> TYPE: DNA
<213> ORGANISM: Homo sapiens

<400> SEQUENCE: 21

| | |
|---|---|
| cctagttaaa acagcagccc atcaaagtct ttaaccctct tagcatttac tcagattact | 60 |
| ttttcattta gcatttatca ccatatattt acttattttt ctctctcctc ctgtactcct | 120 |
| tgaaatatga gctgcacaaa ggacaagatt attattttgt tctattctaa gcatctagtg | 180 |
| tactttctgg cagactgcaa atgaaagaaa gaataaatga aagcatgact tgtgttttat | 240 |
| tgcacaggaa gcagtggctg ggacaagctg tggaaaaagt acggatcacg ctttccccag | 300 |
| gatgacctct gccagtatat cacatcagat gacctcactc agatgctgga caacctaggg | 360 |
| cttaagtatg agtgctatga ccttttgtcc accatggata tatctgactg ctttattgat | 420 |
| ggtaatgaaa atggagacct gctttgggat tttttgactg aaacctgcaa ctttaatgcc | 480 |
| acagcaccac ctgatctcag agcagagctt gggaaagatc tacaagagcc tgaatttagt | 540 |
| gctaagaaag aggggaaggt tctttttaat aatactctga gtttcatagt gattgaggca | 600 |
| taactatcaa tcacaaaagt atattcaaaa attatatttt gaacaactcg aatcactcat | 660 |
| ttgtttccat attaaaatca caaactcatc cattaatgta gataaagcac tgtttggata | 720 |
| tgagatgtag caaattccaa tacattattg gacttccatt tggaatcata tgggatactg | 780 |
| ctggtcttat cctgtccctc ctccaggtag agagaccaca tgcaggctca acataacata | 840 |
| agctagaaaa attagatgac tgaatttcta tggcatattg ataataaaat tcattccatt | 900 |
| tgctgattgt ctgaaatttt ctagaatact aataaaatac atactataga ttcttttatta | 960 |
| gtgaagtatg cactaatcaa tactttgaac acaaagcctg tgttactgat ttggccgttt | 1020 |
| tgtgaagaaa catttatctt tgtacgttct tctattgtgc tttctatcta atttttatta | 1080 |
| atttgtaaga gtaagcacct ttagaatatt aaaaattaat tctttatcac atgttgtcat | 1140 |
| ttcttcccat tgtgttttct cttgtaattt tatctgtgaa ttaatagctt ggggttggtc | 1200 |
| t | 1201 |

<210> SEQ ID NO 22
<211> LENGTH: 1790
<212> TYPE: DNA
<213> ORGANISM: Homo sapiens

<400> SEQUENCE: 22

| | |
|---|---|
| tactaaccat gctgaccact gttcggaacg ggattgaatc acagaaaaac agcaaatggc | 60 |
| tctctcttac agagtgtctg aacttcaaag cacaattcct gagcacattt tgcagagcac | 120 |
| cttttgttcac gttatctctt ctaactggtc tggattacag acagaatcaa taccagagga | 180 |

```
aatgaaacag attgttgagg aacagggaaa taaactgcac tgggcagctc ttctgatact    240
catggtgata atacccacaa ttggtggaaa taccottgtt attctggctg tttcactgga    300
gaagaagctg cagtatgcta ctaattactt tctaatgtcc ttggcggtgg ctgatttgct    360
ggttggattg tttgtgatgc caattgccct cttgacaata atgtttgagg ctatgtggcc    420
cctcccactt gttctatgtc ctgcctggtt atttcttgac gttctctttt caaccgcatc    480
catcatgcat ctctgtgcca tttcagtgga tcgttacata gccatcaaaa agccaatcca    540
ggccaatcaa tataactcac gggctacagc attcatcaag attacagtgg tgtggttaat    600
ttcaataggc attgccattc cagtccctat taaaggata gagactgatg tggacaaccc     660
aaacaatatc acttgtgtgc tgacaaagga acgttttggc gatttcatgc tctttggctc    720
actggctgcc ttcttcacac ctcttgcaat tatgattgtc acctactttc tcactatcca    780
tgctttacag aagaaggctt acttagtcaa aaacaagcca cctcaacgcc taacatggtt    840
gactgtgtct acagttttcc aaagggatga acaccttgc tcgtcaccgg aaaaggtggc     900
aatgctggat ggttctcgaa aggacaaggc tctgcccaac tcaggtgatg aaacacttat    960
gcgaagaaca tccacaattg ggaaaaagtc agtgcagacc atttccaacg aacagagagc   1020
ctcaaaggtc ctagggattg tgttttcct cttttgctt atgtggtgtc ccttctttat     1080
tacaaatata actttagttt tatgtgattc ctgtaaccaa actactctcc aaatgctcct   1140
ggagatattt gtgtggatag ctatgtttc ctcaggagtg aatcctttgg tctacaccct    1200
cttcaataag acatttcggg atgcatttgg ccgatatatc acctgcaatt accgggccac   1260
aaagtcagta aaaactctca gaaaacgctc cagtaagatc tacttccgga atccaatggc   1320
agagaactct aagttttca agaaacatgg aattcgaaat gggattaacc ctgccatgta    1380
ccagagtcca atgaggctcc gaagttcaac cattcagtct tcatcaatca ttctactaga   1440
tacgcttctc ctcactgaaa atgaaggtga caaaactgaa gagcaagtta gttatgtata   1500
gcagaactgg cagttgtcat caaacataat gatgagtaag atgatgaatg agatgtaaat   1560
gtgcccagaa tatattatat aaagaatttt atgtctcata tcaaatcatc tctttaacct   1620
aagatgtaag tattaagaat atctaatttt cctaatttgg acaagattat tccatgagga   1680
aaataatttt atatagctac aaatgaaaac aatccagcac tctggttaaa ttttaaggta   1740
ttcgaatgaa ataaagtcaa atcaataaat ttcaggcttt aaaaaaaaaa               1790
```

<210> SEQ ID NO 23
<211> LENGTH: 985
<212> TYPE: DNA
<213> ORGANISM: Homo sapiens

<400> SEQUENCE: 23

```
acatcccaat ggccctgtcc ttttctttac tgatggccgt gctggtgctc agctacaaat     60
ccatctgttc tctgggctgt gatctgcctc agacccacag cctgggtaat aggagggcct    120
tgatactcct ggcacaaatg ggaagaatct ctcctttctc ctgcctgaag gacagacatg    180
actttggatt cccccaagag gagtttgatg caaccagtt ccagaaggct caagccatct    240
ctgtcctcca tgagatgatc cagcagacct tcaatctctt cagcacaaag gactcatctg    300
ctacttggga cagagcctc ctagaaaaat tttccactga acttaaccag cagctgaatg    360
acatggaagc ctgcgtgata caggaggttg ggtggaaga gactcccctg atgaatgtgg    420
actccatctt ggctgaaag aaatacttcc aaagaatcac tctttatctg acagagaaga    480
aatacagccc ttgtgcttgg gaggttgtca gagcagaaat catgagatcc ttctcttat    540
```

-continued

```
caaaaatttt tcaagaaaga ttaaggagga aggaatgaaa ccgtttcaac atggaaatga      600
tctgtattga ctaatacacc agtccacact tctatgactt ctgccatttc aaagactcat      660
ttctcctata accaccgcat gagttgaatc aaaattttca gatcttttca ggagtgtaag      720
gaaacatcat gtttacctgt gcaggcacta gtcctttaca gatgaccatg ctgatagatc      780
taattatcta tctattgaaa tatttattta tttattagat ttaaattatt tttgtccatg      840 taatatatg tgtacttta cattgtgtta tatcaaaata tgttaatcta atatttagtc       900
aatatattat tttctttta ttaattttta ctattaaaac ttcttatatt atttggttat       960
tctttaataa agaaattcca agccc                                          985

<210> SEQ ID NO 24
<211> LENGTH: 7260
<212> TYPE: DNA
<213> ORGANISM: Homo sapiens

<400> SEQUENCE: 24
tcactgtcac tgctaaattc agagcagatt agagcctgcg caatggaata aagtcctcaa       60
aattgaaatg tgacattgct ctcaacatct cccatctctc tggatttcct tttgcttcat      120
tattcctgct aaccaattca ttttcagact ttgtacttca gaagcaatgg gaaaaatcag      180
cagtcttcca acccaattat ttaagtgctg cttttgtgat ttcttgaagg tgaagatgca      240
caccatgtcc tcctcgcatc tcttctacct ggcgctgtgc ctgctcacct tcaccagctc      300
tgccacggct ggaccggaga cgctctgcgg ggctgagctg gtggatgctc ttcagttcgt      360
gtgtggagac aggggctttt atttcaacaa gcccacaggg tatggctcca gcagtcggag      420
ggcgcctcag acaggcatcg tggatgagtg ctgcttccgg agctgtgatc taaggaggct      480
ggagatgtat tgcgcacccc tcaagcctgc caagtcagct cgctctgtcc gtgcccagcg      540
ccacaccgac atgcccaaga cccagaagga agtacatttg aagaacgcaa gtagagggag      600
tgcaggaaac aagaactaca ggatgtagga agaccctcct gaggagtgaa gagtgacatg      660
ccaccgcagg atcctttgct ctgcacgagt tacctgttaa actttggaac acctaccaaa      720
aaataagttt gataacattt aaaagatggg cgtttccccc aatgaaatac acaagtaaac      780
attccaacat tgtctttagg agtgatttgc accttgcaaa aatggtcctg gagttggtag      840
attgctgttg atcttttatc aataatgttc tatagaaaag aaaaaaaaat atatatat       900 atatatctta gtccctgcct ctcaagagcc acaaatgcat gggtgttgta tagatccagt      960
tgcactaaat tcctctctga atcttggctg ctggagccat tcattcagca accttgtcta     1020
agtggtttat gaattgtttc cttatttgca cttctttcta cacaactcgg gctgtttgtt     1080
ttacagtgtc tgataatctt gttagtctat acccaccacc tcccttcata accttatat      1140 ttgccgaatt tggcctcctc aaaagcagca gcaagtcgtc aagaagcaca ccaattctaa     1200
cccacaagat tccatctgtg gcatttgtac caaatataag ttggatgcat tttattttag    1260
acacaaagct ttattttcc acatcatgct tacaaaaaag aataatgcaa atagttgcaa     1320
ctttgaggcc aatcattttt aggcatatgt tttaaacata gaaagtttct tcaactcaaa    1380
agagttcctt caaatgatga gttaatgtgc aacctaatta gtaactttcc tcttttatt      1440 ttttccatat agagcactat gtaaatttag catatcaatt atacaggata tatcaaacag    1500
tatgtaaaac tctgtttttt agtataatgg tgctattttg tagtttgtta tatgaaagag    1560
tctggccaaa acggtaatac gtgaaagcaa acaatagg gaagcctgga gccaaagatg      1620
acacaagggg aagggtactg aaaacaccat ccatttggga aagaaggcaa agtcccccca    1680
```

```
gttatgcctt ccaagaggaa cttcagacac aaaagtccac tgatgcaaat tggactggcg    1740
agtccagaga ggaaactgtg gaatggaaaa agcagaaggc taggaatttt agcagtcctg    1800
gtttcttttt ctcatggaag aaatgaacat ctgccagctg tgtcatggac tcaccactgt    1860
gtgaccttgg gcaagtcact tcacctctct gtgcctcagt ttcctcatct gcaaaatggg    1920
ggcaatatgt catctaccta cctcaaaggg gtggtataag gtttaaaaag ataaagattc    1980
agattttttt accctgggtt gctgtaaggg tgcaacatca gggcgcttga gttgctgaga    2040
tgcaaggaat tctataaata acccattcat agcatagcta gagattggtg aattgaatgc    2100
tcctgacatc tcagttcttg tcagtgaagc tatccaaata actggccaac tagttgttaa    2160
aagctaacag ctcaatctct taaaacactt ttcaaaatat gtgggaagca tttgattttc    2220
aatttgattt tgaattctgc atttggtttt atgaatacaa agataagtga aaagagagaa    2280
aggaaaagaa aaggagaaa acaaagaga tttctaccag tgaaagggga attaattact    2340
ctttgttagc actcactgac tcttctatgc agttactaca tatctagtaa aaccttgttt    2400
aatactataa ataatattct attcattttg aaaaacacaa tgattccttc ttttctaggc    2460
aatataagga aagtgatcca aaatttgaaa tattaaaata atatctaata aaaagtcaca    2520
aagttatctt ctttaacaaa ctttactctt attcttagct gtatatacat tttttttaaaa    2580 agtttgttaa aatatgcttg actagagttt cagttgaaag gcaaaaactt ccatcacaac    2640
aagaaatttc ccatgcctgc tcagaagggt agcccctagc tctctgtgaa tgtgttttat    2700
ccattcaact gaaaattggt atcaagaaag tccactggtt agtgtactag tccatcatag    2760
cctagaaaat gatccctatc tgcagatcaa gattttctca ttagaacaat gaattatcca    2820
gcattcagat ctttctagtc accttagaac ttttttggtta aaagtaccca ggcttgatta    2880
tttcatgcaa attctatatt ttacattctt ggaaagtcta tatgaaaaac aaaaataaca    2940
tcttcagttt ttctcccact gggtcacctc aaggatcaga ggccaggaaa aaaaaaaaag    3000
actccctgga tctctgaata tatgcaaaaa gaaggcccca tttagtggag ccagcaatcc    3060
tgttcagtca acaagtattt taactctcag tccaacatta tttgaattga gcacctcaag    3120
catgcttagc aatgttctaa tcactatgga cagatgtaaa agaaactata catcattttt    3180
gccctctgcc tgttttccag acatacaggt tctgtggaat aagatactgg actcctcttc    3240
ccaagatggc acttcttttt atttcttgtc cccagtgtgt accttttaaa attattccct    3300
ctcaacaaaa ctttataggc agtcttctgc agacttaaca tgttttctgt catagttaga    3360
tgtgataatt ctaagagtgt ctatgactta tttccttcac ttaattctat ccacagtcaa    3420
aaatccccca aggaggaaag ctgaaagatg caactgccaa tattatcttt cttaactttt    3480
tccaacacat aatcctctcc aactggatta taaataaatt gaaataaact cattataccaa    3540 attcactatt ttattttta atgaattaaa actagaaaac aaattgatgc aaaccctgga    3600
agtcagttga ttactatata ctacagcaga atgactcaga tttcatagaa aggagcaacc    3660
aaaatgtcac aaccaaaact ttacaagctt tgcttcagaa ttagattgct ttataattct    3720
tgaatgaggc aatttcaaga tatttgtaaa agaacagtaa acattggtaa gaatgagctt    3780
tcaactcata ggcttatttc caatttaatt gaccatactg gatacttagg tcaaatttct    3840
gttctctctt gcccaaataa tattaaagta ttatttgaac tttttaagat gaggcagttc    3900
ccctgaaaaa gttaatgcag ctctccatca gaatccactc ttctagggat atgaaaatct    3960
cttaacaccc accctacata cacagacaca cacacacaca cacacacaca cacacacaca    4020
cacacattca ccctaaggat ccaatggaat actgaaaaga aatcacttcc ttgaaaattt    4080
```

-continued

```
tattaaaaaa caaacaaaca aacaaaaagc ctgtccaccc ttgagaatcc ttcctctcct    4140
tggaacgtca atgtttgtgt agatgaaacc atctcatgct ctgtggctcc agggtttctg    4200
ttactatttt atgcacttgg gagaaggctt agaataaaag atgtagcaca ttttgctttc    4260
ccatttattg tttggccagc tatgccaatg tggtgctatt gtttctttaa gaaagtactt    4320
gactaaaaaa aaaagaaaaa aagaaaaaaa agaaagcata gacatatttt tttaaagtat    4380
aaaaacaaca attctataga tagatggctt aataaaatag cattaggtct atctagccac    4440 caccacctt caacttttta tcactcacaa gtagtgtact gttcaccaaa ttgtgaattt    4500
gggggtgcag gggcaggagt tggaaatttt ttaaagttag aaggctccat tgttttgttg    4560
gctctcaaac ttagcaaaat tagcaatata ttatccaatc ttctgaactt gatcaagagc    4620
atggagaata aacgcgggaa aaaagatctt ataggcaaat agaagaattt aaaagataag    4680
taagttcctt attgattttt gtgcactctg ctctaaaaca gatattcagc aagtggagaa    4740
aataagaaca aagagaaaaa atacatagat ttacctgcaa aaaatagctt ctgccaaatc    4800 cccttgggt attctttggc atttactggt ttatagaaga cattctccct tcacccagac    4860
atctcaaaga gcagtagctc tcatgaaaag caatcactga tctcatttgg gaaatgttgg    4920
aaagtatttc cttatgagat gggggttatc tactgataaa gaaagaattt atgagaaatt    4980
gttgaaagag atggctaaca atctgtgaag attttttgtt tcttggtttt gttttttttt    5040
ttttttttac tttatacagt ctttatgaat ttcttaatgt tcaaaatgac ttggttcttt    5100
tcttcttttt tttatatcag aatgaggaat aataagttaa acccacatag actctttaaa    5160
actataggct agatagaaat gtatgtttga cttgttgaag ctataatcag actatttaaa    5220
atgttttgct atttttaatc ttaaaagatt gtgctaattt attagagcag aacctgtttg    5280
gctctcctca gaagaaagaa tctttccatt caaatcacat ggctttccac caatattttc    5340
aaaagataaa tctgatttat gcaatggcat catttatttt aaaacagaag aattgtgaaa    5400
gtttatgccc ctcccttgca aagaccataa agtccagatc tggtagggg gcaacaacaa    5460 aaggaaaatg ttgttgattc ttggttttgg atttgtttt gttttcaatg ctagtgttta    5520
atcctgtagt acatatttgc ttattgctat tttaatattt tataagacct tcctgttagg    5580
tattagaaag tgatacatag atatctttt tgtgtaattt ctatttaaaa aagagagaag    5640
actgtcagaa gctttaagtg catatggtac aggataaaga tatcaattta aataaccaat    5700
tcctatctgg aacaatgctt ttgttttta aagaaacctc tcacagataa gacagaggcc    5760
cagggatttt ttgaagctgt ctttattctg cccccatccc aacccagccc ttattatttt    5820
agtatctgcc tcagaatttt atagagggct gaccaagctg aaactctaga attaaaggaa    5880
cctcactgaa aacatatatt tcacgtgttc cctctctttt ttttccttt tgtgagatgg    5940 ggtctcgcac tgtcccccag gctggagtgc agtggcatga tctcggctca ctgcaacctc    6000
cacctcctgg gtttaagcga ttctcctgcc tcagcctcct gagtagctgg gattacaggc    6060
acccaccact atgcccggct aatttttgg attttaata gagacggggt tttaccatgt    6120
tggccaggtt ggactcaaac tcctgacctt gtgatttgcc cgcctcagcc tcccaaattg    6180
ctgggattac aggcatgagc caccacaccc tgcccatgtg ttccctctta atgtatgatt    6240
acatggatct taaacatgat ccttctctcc tcattcttca actatctttg atgggggctt    6300
tcaaggggaa aaaatccaa gcttttttaa agtaaaaaaa aaaaagaga ggacacaaaa    6360 ccaaatgtta ctgctcaact gaaatatgag ttaagatgga gacagagttt ctcctaataa    6420
ccggagctga attaccttc actttcaaaa acatgacctt ccacaatcct tagaatctgc    6480
```

-continued

| | | | | |
|---|---|---|---|---|
| cttttttttat | attactgagg | cctaaaagta | aacattactc | attttattttt gcccaaaatg | 6540 |
| cactgatgta | aagtaggaaa | aataaaaaca | gagctctaaa | atcccttttca agccacccat | 6600 |
| tgaccccact | caccaactca | tagcaaagtc | acttctgtta | atcccttaat ctgattttgt | 6660 |
| ttggatattt | atcttgtacc | cgctgctaaa | cacactgcag | gagggactct gaaacctcaa | 6720 |
| gctgtctact | tacatctttt | atctgtgtct | gtgtatcatg | aaaatgtcta ttcaaaatat | 6780 |
| caaaacctttt | caaatatcac | gcagcttata | ttcagtttac | ataaaggccc caaataccat | 6840 |
| gtcagatctt | tttggtaaaa | gagttaatga | actatgagaa | ttgggattac atcatgtatt | 6900 |
| ttgcctcatg | tatttttatc | acacttatag | gccaagtgtg | ataaataaac ttacagacac | 6960 |
| tgaattaatt | tcccctgcta | ctttgaaacc | agaaaataat | gactggccat tcgttacatc | 7020 |
| tgtcttagtt | gaaaagcata | tttttttatta | aattaattct | gattgtattt gaaattatta | 7080 |
| ttcaattcac | ttatggcaga | ggaatatcaa | tcctaatgac | ttctaaaaat gtaactaatt | 7140 |
| gaatcattat | cttacattta | ctgtttaata | agcatatttt | gaaaatgtat ggctagagtg | 7200 |
| tcataataaa | atggtatatc | tttctttagt | aattacaaaa | aaaaaaaaaa aaaaaaaaa | 7260 |

<210> SEQ ID NO 25
<211> LENGTH: 2212
<212> TYPE: DNA
<213> ORGANISM: Homo sapiens
<220> FEATURE:
<221> NAME/KEY: Unsure
<222> LOCATION: (625)..(625)
<223> OTHER INFORMATION: n = a, c, g or t/u

<400> SEQUENCE: 25

| | | | | |
|---|---|---|---|---|
| gcatatcctg | gaggtgaagg | taccacctca | tggagacccc | cgcggccgcc gcccccgctg | 60 |
| ggagcttatt | cccctccttc | ctgctcctgg | cctgcgggac | gctggtggcc gccttgctgg | 120 |
| gcgccgctca | ccgcctgggg | ctcttctatc | agctgctgca | caaggtggac aaggcaagcg | 180 |
| tccggcatgg | cggagagaac | gtggccgctg | tgctgagggc | ccatggtgtg cggttcatct | 240 |
| tcacgctggt | cggtgggcac | atttccccgc | tgctggtggc | ctgtgagaaa ctggcatcc | 300 |
| gtgtggtgga | cacacgccat | gaggtcacgg | ccgtctttgc | tgctgatgct atggcccgcc | 360 |
| tgtccgggac | ggtgggcgtg | gcggcagtga | cagcaggccc | tggcctcacc aacacggtga | 420 |
| ctgcggtgaa | gaatgctcag | atggctcagt | ccccaatcct | gcttctgggt ggggctgcca | 480 |
| gcactctgct | gcagaaccgg | ggtgcgctcc | aggctgttga | tcagctgtcc ctttttccggc | 540 |
| cactctgtaa | gttttgtgtg | tctgtgcgga | gggtgcggga | cattgtgccc accctgaggg | 600 |
| ccgcgatggc | tgccgcccag | tcggncaccc | caggtccggt | gtttgtggag ctgcccgttg | 660 |
| acgtgctttta | cccctacttc | atggtccaga | aggagatggt | gccagccaag ccacccaagg | 720 |
| gcctcgtggg | ccgagtggtc | tcctggtatt | tagagaatta | cctggccaac ctctttgcag | 780 |
| gagcctggga | gcctcagccc | gagggaccgc | tgccccctgga | catcccccag gcttccccgc | 840 |
| agcaggttca | gcgctgtgtg | gagatcctga | gccgggccaa | gaggcctctg atggtgctgg | 900 |
| ggagtcaggc | cctgctcacc | ccaacgtctg | ccgacaagct | tcgggctgcc gtggagacct | 960 |
| tgggtgttcc | ctgcttcctt | ggagggatgg | cacgggggct | gttaggccgc aaccacccc | 1020 |
| tccacatccg | ggagaaccgc | agtgcggccc | tgaagaaggc | ggacgtcatt gtcctagcag | 1080 |
| gaactgtgtg | tgacttccgc | ctatcctatg | gccgtgtcct | cagccacagc agcaagatca | 1140 |
| tcatcgtcaa | tcgtaatcgg | gaagagatgt | tgctcaactc | agacatcttc tggaagcccc | 1200 |
| aggaggctgt | gcaggagat | gtggggttcct | tcgtgctgaa | gttagtggag ggccttcagg | 1260 |

```
gccagacctg ggccccagac tgggtggagg agctgcggga agccgaccgg cagaaggagc      1320
agacctttcg ggagaaggca gcgatgcctg tggcccagca cctgaaccca gtgcaggtgc      1380
tgcagctggt ggaggaaacg ctacctgaca actcaattct ggtggtggat ggcggggact      1440
tcgtgggcac tgctgcccat ctggtacagc cccgcgccc cctgcgctgg ctcgatcctg       1500
gggcctttgg gactctggga gttggtgcag gatttgcact tggggccaag ctgtgccggc      1560
cagatgctga ggtctggtgc ctgtttgggg acggagcttt tggctacagc ctcatcgaat      1620
ttgatacatt cgtcagacac aagatcccag tgatggcctt ggtagggaat gatgctggct      1680
ggacacagat ttctcgggag caggtgccct ctctgggcag caacgtggcc tgtggcctgg      1740
cctacactga ttatcacaag gcagccatgg gtctgggggc ccggggcttg ctgctctcac      1800
gggagaacga ggatcaggtg gtcaaggtgc tgcacgatgc ccagcagcag tgccgagacg      1860
gccacccggt tgtggtcaac atcctcattg ggaggacgga cttccgcgat ggctccattg      1920
ctgtataggg ccttgtgggt caggacgctt ggctgccttc ctgcccctgg actgtgtcca      1980
gctggtttgg agtctcatca ttgcttgccc tgggcctatc ccatgaggcc cagtgactcc      2040
acaacctccc tgaggagggg atggagggggt caaatctcag agaggctctc ttgtgagctc      2100
ttggaccctc ctcttcacgg acccaactgt gccgtttgtc ccctctctta tggagactga      2160
ataaaccacc tctggcccat gtaggcccaa gtaaaaaaaa aaaaaaaaaa aa              2212

<210> SEQ ID NO 26
<211> LENGTH: 2144
<212> TYPE: DNA
<213> ORGANISM: Homo sapiens

<400> SEQUENCE: 26
aactgacggg ctttcatttc catttcacac accctagcaa cacttatacc ttgcggaatt      60
gtattggtag cgtgaaaaaa gcacactgag agggcaccat gccggtggaa aggatgcgca      120
tgcgcccgtg gctggaggag cagataaact ccaacacgat cccggggctc aagtggctta      180
acaaggaaaa gaagattttt cagatcccct ggatgcatgc ggctagacat gggtgggatg      240
tggaaaaaga tgcaccactc tttagaaacc gggcaatcca tacaggaaag catcaaccag      300
gagtagataa acctgatccc aaaacatgga aggcgaattt cagatgcgcc atgaattcct      360
tgcctgatat tgaagaagtc aaggataaaa gcataaagaa aggaaataat gccttcaggg      420
tctaccgaat gctgccccta tcagaacggc cttctaagaa aggaaagaaa ccaaagacag      480
aaaaagaaga caaagttaag cacatcaagc aagaaccagt tgagtcatct ctgggggctta      540 gtaatggagt aagtgatctt tctcctgagt atgcggtcct gacttcaact ataaaaaatg      600
aagtggatag tacggtgaac atcatagttg taggacagtc ccatctggac agcaacattg      660
agaatcaaga gattgtcacc aatccgccag acatttgcca agttgtagag gtgaccactg      720
agagcgacga gcagccggtc agcatgagcg agctctaccc tctgcagatc tccccgtgt        780 cttcctatgc agaaagcgaa acgactgata gtgtgcccag cgatgaagag agtgccgagg      840
gcggccacca ctggcggaag aggaatattg aaggcaaaca gtacctcagc aacatggggga    900 ctcgaggctc ctacctgctg cccggcatgg cgtccttcgt cacttccaac aaaccggacc      960
tccaggtcac catcaaagag gagagcaatc cggtgcctta aacagctccc tggcccccctt    1020 ttcaagacct cccccttttct tcctccatga ccccagcatc cagcagcagt cggccagacc     1080
gggagacccg ggccagcgtc atcaagaaaa catcggatat cacccaggcc cgcgtcaaga      1140
gctgttaagc ctctgactct ccgcggtggt tgttggggct tcttggcttt gttttgttgt      1200
```

-continued

```
ttgtttgtat tttatttttt tctctctgac acctattta gacaaatcta agggaaaaag    1260
ccttgacaat agaacattga ttgctgtgtc caactccagt acctggagct tctctttaac    1320
tcaggactcc agcccattgg tagacgtgtg tttctagagc ctgctggatc tcccagggct    1380
actcactcaa gttcaaggac caacaagggc agtggaggtg ctgcattgcc tgcggtcaag    1440
gccagcaagg tggagtggat gcctcagaac ggacgagata atgtgaacta gctggaattt    1500
tttattcttg tgaatatgta cataggcagc actagcgaca ttgcagtctg cttctgcacc    1560
ttatcttaaa gcacttacag ataggccttc ttgtgatctt gctctatctc acagcacact    1620
cagcaccccc ttctctgccc attccccagc ctctcttcct atcccatccc atcccatccc    1680
atcccatccc atcccatccc gctcttttcc tacttttcct tccctcaaag cttccattcc    1740
acatccggag gagaagaagg aaatgaattt ctctacagat gtcccatttt cagactgctt    1800
taaaaaaaat ccttctaatc tgctatgctt gaatgccacg cggtacaaag gaaaaagtat    1860 catgaaata ttatgcaaat tcccagattt gaagacaaaa atactctaat tctaaccaga    1920
gcaagctttt ttattttta tacaggggaa tatttattc aaggtaaaat tctaaataaa    1980
atataattgt ttttatctt ttctacagca aatttataat tttaagattc cttttcttgt    2040
ttatcagcag ttgttattac atccttgtgg cacatttttt tttaattttg taaaggtgaa    2100
aaaagctttt atgagctcat ctagcaatca gattttcctg tgga                    2144
```

<210> SEQ ID NO 27
<211> LENGTH: 2416
<212> TYPE: DNA
<213> ORGANISM: Homo sapiens

<400> SEQUENCE: 27

```
gaacagtgtt accttggagc ctacaatgag aggtatttca aaatgagtga agcatgactc     60
tcacagatga aggcctagac gcaggatctt taatggaaaa acacttgggc cacttcaaga    120
cgacaaacgc tcactgggca aaacaccttc actgaaaaga gacctcatat tatgcaaaaa    180
aaatcttaag aggcctctgc cttcagaagt tacaagatga tcaattcaac ctccacacag    240
cctccagatg aatcctgctc tcagaacctc ctgatcactc agcagatcat tcctgtgctg    300
tactgtatgg tcttcattgc gggaatccta ctcaatggag tgtcaggatg gatattcttt    360
tacgtgccca gctctaagag tttcatcatc tatctcaaga acattgttat tgctgacttt    420
gtgatgagcc tgactttcc tttcaagatc cttggtgact caggccttgg tccctggcag    480
ctgaacgtgt ttgtgtgcag ggtctctgcc gtgctcttct acgtcaacat gtacgtcagc    540
attgtgttct ttgggctcat cagctttgac aggtattata aaattgtaaa gcctcttggg    600
acttctttca tccagtcagt gagttacagc aaacttctgt cagtgatagt atggatgctc    660
atgctcctcc ttgctgttcc aaatattatt ctcaccaacc agagtgttag ggaggttaca    720
caaataaaat gtatagaact gaaaagtgaa ctgggacgga agtggcacaa agcatcaaac    780
tacatcttcg tggccatctt ctggattgtg tttcttttgt taatcgtttt ctatactgct    840
atcacaaaga aaatctttaa gtcccacctt aagtcaagtc ggaattccac ttcggtcaaa    900
aagaaatcta gccgcaacat attcagcatc gtgtttgtgt tttttgtctg ttttgtacct    960
taccatattg ccagaatccc ctacacaaag agtcagaccg aagctcatta cagctgccag   1020
tcaaaagaaa tcttgcggta tatgaaagaa ttcactctgc tactatctgc tgcaaatgta   1080
tgcttggacc ctattattta tttcttttcta tgccagccgt ttagggaaat cttatgtaag   1140
aaattgcaca ttccattaaa agctcagaat gacctagaca tttccagaat caaaagagga   1200
```

| | | | | |
|---|---|---|---|---|
| aatacaacac | ttgaaagcac | agatactttg | tgagttccta | ccctcttcca | aagaaagacc | 1260 |
| acgtgtgcat | gttgtcatct | tcaattacat | aacagaaatc | aataagatat | gtgccctcat | 1320 |
| cataaatatc | atctctagca | ctgccatcca | atttagttca | ataaaattca | aatataagtt | 1380 |
| tccatgcttt | tttgtaacat | caaagaaaac | atacccatca | gtaatttctc | taatactgac | 1440 |
| ctttctattc | tctattaata | aaaaattaat | acatacaatt | attcaattct | attatattaa | 1500 |
| aataagttaa | agtttataac | cactagtctg | gtcagttaat | gtagaaattt | aaatagtaaa | 1560 |
| taaaacacaa | cataatcaaa | gacaactcac | tcaggcatct | tctttctcta | aataccagaa | 1620 |
| tctagtatgt | aattgttttc | aacactgtcc | ttaaagacta | acttgaaagc | aggcacagtt | 1680 |
| tgatgaaggg | ctagagagct | gtttgcaata | aaaagtcagg | ttttttttcct | gatttgaaga | 1740 |
| agcaggaaaa | gctgacaccc | agacaatcac | ttaagaaacc | ccttattgat | gtatttcatg | 1800 |
| gcactgcaaa | ggaagaggaa | tattaattgt | atacttagca | agaaaatttt | ttttttctga | 1860 |
| tagcactttg | aggatattag | atacatgcta | aatatgtttt | ctacaaagac | ttacgtcatt | 1920 |
| taatgagcct | ggggttctgg | tgttagaata | tttttaagta | ggctttactg | agagaaacta | 1980 |
| aatattggca | tacgttatca | gcaacttccc | ctgttcaata | gtatgggaaa | aataagatga | 2040 |
| ctgggaaaaa | gacacaccca | caccgtagaa | catatattaa | tctactggcg | aatgggaaag | 2100 |
| gagaccattt | tcttagaaag | caaataaact | tgatttttttt | aaatctaaaa | tttacattaa | 2160 |
| tgagtgcaaa | ataacacata | aaatgaaaat | tcacacatca | cattttctg | gaaaacagac | 2220 |
| ggattttact | tctggagaca | tggcatacgg | ttactgactt | atgagctacc | aaaactaaat | 2280 |
| tctttctctg | ctattaactg | gctagaagac | attcatctat | ttttcaaatg | ttctttcaaa | 2340 |
| acatttttat | aagtaatgtt | tgtatctatt | tcatgcttta | ctgtctatat | actaataaag | 2400 |
| aaatgtttta | atactg | | | | | 2416 |

<210> SEQ ID NO 28
<211> LENGTH: 756
<212> TYPE: DNA
<213> ORGANISM: Homo sapiens

<400> SEQUENCE: 28

| | | | | |
|---|---|---|---|---|
| ctggagacac | agatcgaggc | tctcaaggag | gagctgctct | tcatgaagaa | gaaccacgaa | 60 |
| gaggaagtaa | aaggcctaca | agcccagatt | gccagctctg | ggttgaccgt | ggaggtagat | 120 |
| gccccgaaat | ctcaggacct | ctccaagatc | atggcagaca | tccgggccca | atatgacgag | 180 |
| ctggctcgga | agaaccgaga | ggagctagac | aagtactggt | ctcagcagat | tgaggagagc | 240 |
| accacagtgg | tcaccacaca | gtctgctgag | gttggagctg | ctgagacgac | gctcacagag | 300 |
| ctgagacgta | cagtccagtc | cttggagatc | cgactggacc | gcatgagaaa | tctgaaggcc | 360 |
| agcttggaga | acagcctgag | ggaggtggag | gcccgttacg | ccctacagat | ggagcagctc | 420 |
| aacgggatcc | tgctgcacct | tgagtcagag | ctggcacaga | cccgggcaga | gggacagcgc | 480 |
| caggcccagg | agtatgaggc | cctgctgaac | atcaaggtca | agctggaggc | tgagatcgcc | 540 |
| acctaccgcc | gcctgctgga | agatggcgag | gactttaatc | ttggtgatgc | cttggacagc | 600 |
| agcaactcca | tgcaaaccat | ccaaaagacc | accacccgcc | ggatagtgga | tggcaaagtg | 660 |
| gtgtctgaga | ccaatgacac | caaagttctg | aggcattaag | ccagcagaag | acgggtacct | 720 |
| ttggggagca | ggaggccaat | aaaaagttca | gagttc | | | 756 |

<210> SEQ ID NO 29
<211> LENGTH: 1752
<212> TYPE: DNA
<213> ORGANISM: Homo sapiens

<400> SEQUENCE: 29

| | | | | | | |
|---|---|---|---|---|---|---|
| ctgctccttc | taggatctcc | gcctggttcg | gcccgcctgc | ctccactcct | gcctccacca | 60 |
| tgtccatcag | ggtgacccag | aagtcctaca | aggtgtccac | ctctggcccc | cgggccttca | 120 |
| gcagccgctc | ctacacgagt | gggcccggtt | cccgcatcag | ctcctcgagc | ttctcccgag | 180 |
| tgggcagcag | caactttcgc | ggtggcctgg | gcggcggcta | tggtggggcc | agcggcatgg | 240 |
| gaggcatcac | cgcagttacg | gtcaaccaga | gcctgctgag | ccccttgtc | ctggaggtgg | 300 |
| accccaacat | ccaggccgtg | cgcacccagg | agaaggagca | gatcaagacc | ctcaacaaca | 360 |
| agtttgcctc | cttcatagac | aaggtacggt | tcctggagca | gcagaacaag | atgctggaga | 420 |
| ccaagtggag | cctcctgcag | cagcagaaga | cggctcgaag | caacatggac | aacatgttcg | 480 |
| agagctacat | caacaacctt | aggcggcagc | tggagactct | gggccaggag | aagctgaagc | 540 |
| tggaggcgga | gcttggcaac | atgcaggggc | tggtggagga | cttcaagaac | aagtatgagg | 600 |
| atgagatcaa | taagcgtaca | gagatggaga | acgaatttgt | cctcatcaag | aaggatgtgg | 660 |
| atgaagctta | catgaacaag | gtagagctgg | agtctcgcct | ggaagggctg | accgacgaga | 720 |
| tcaacttcct | caggcagcta | tatgaagagg | agatccggga | gctgcagtcc | cagatctcgg | 780 |
| acacatctgt | ggtgctgtcc | atggacaaca | gccgctccct | ggacatggac | agcatcattg | 840 |
| ctgaggtcaa | ggcacagtac | gaggatattg | ccaaccgcag | ccgggctgag | ctgagagca | 900 |
| tgtaccagat | caagtatgag | gagctgcaga | gcctggctgg | gaagcacggg | gatgacctgc | 960 |
| ggcgcacaaa | gactgagatc | tctgagatga | accggaacat | cagccggctc | caggctgaga | 1020 |
| ttgagggcct | caaaggccag | agggcttccc | tggaggccgc | cattgcagat | gccgagcagc | 1080 |
| gtggagagct | ggccattaag | gatgccaacg | ccaagttgtc | cgagctggag | gccgccctgc | 1140 |
| agcgggccaa | gcaggacatg | gcgcggcagc | tgcgtgagta | ccaggagctg | atgaacgtca | 1200 |
| agctggccct | ggacatcgag | atcgccacct | acaggaagct | gctggagggc | gaggagagcc | 1260 |
| ggctggagtc | tgggatgcag | aacatgagta | ttcatacgaa | gaccaccagc | ggctatgcag | 1320 |
| gtggtctgag | ctcggcctat | gggggcctca | caagccccgg | cctcagctac | agcctgggct | 1380 |
| ccagctttgg | ctctggcgcg | ggctccagct | ccttcagccg | caccagctcc | tcagggccg | 1440 |
| tggttgtgaa | gaagatcgag | acacgtgatg | ggaagctggt | gtctgagtcc | tctgacgtcc | 1500 |
| tgcccaagtg | aacagctgcg | gcagcccctc | ccagcctacc | cctcctgcgc | tgccccagag | 1560 |
| cctgggaagg | aggccgctat | gcagggtagc | actgggaaca | ggagacccac | ctgaggctca | 1620 |
| gccctagccc | tcagcccacc | tggggagttt | actacctggg | accccccctt | gcccatgcct | 1680 |
| ccagctacaa | aacaattcaa | ttgctttttt | ttttggtcc | aaaataaaac | ctcagctagc | 1740 |
| tctgccaaac | cc | | | | | 1752 |

<210> SEQ ID NO 30
<211> LENGTH: 1744
<212> TYPE: DNA
<213> ORGANISM: Homo sapiens

<400> SEQUENCE: 30

| | | | | | | |
|---|---|---|---|---|---|---|
| tgaggcctga | cttttcaat | aaaacattgt | gtagttctgg | gcctcctgct | gccccggctc | 60 |
| tgtttcccct | ggcgccaaga | gaagaaggcg | gaactgaacc | caggcccaga | gccggctccc | 120 |

-continued

```
tgaggctgtg cccctttccg gcaatctctg gccacaaccc ccactggcca ggccgtccct      180
cccactggcc ctagggcccc tcccactccc acaccagata aggacagccc agtgccgctt      240
tctctggcag taggcaccag ggctggaatg gggccgcccg gctccccatg gcagtgggtg      300
acgctgctgc tggggctgct gctccctcct gccgccccct tctggctcct caatgtgctc      360
ttcccccgc acaccacgcc caaggctgag ctcagtaacc acacgccc cgtcatcctc         420
gtgcccggct gcctggggaa tcagctagaa gccaagctgg acaaaccaga tgtggtgaac      480
tggatgtgct accgcaagac agaggacttc ttcaccatct ggctggatct caacatgttc      540
ctacccccttg gggtagactg ctggatcgat aacaccaggt tgtctacaa ccggagctct      600
gggctcgtgt ccaacgcccc tggtgtccag atccgcgtcc ctggctttgg caagacctac      660
tctgtggagt acctggacag cagcaagctg cagggtacc tgcacacact ggtgcagaac       720
ctggtcaaca atggctacgt gcgggacgag actgtgcgcg ccgcccccta tgactggcgg      780
ctggagcccg ccagcagga ggagtactac cgcaagctcg cagggctggt ggaggagatg       840
cacgctgcct atgggaagcc tgtcttcctc attggccaca gcctcggctg tctacacttg      900
ctctatttcc tgctgcgcca gccccaggcc tggaaggacc gctttattga tggcttcatc      960
tctcttgggg ctccctgggg tggctccatc aagcccatgc tggtcttggc ctcaggtgac     1020
aaccagggca tccccatcat gtccagcatc aagctgaaag aggagcagcg cataaccacc     1080
acctcccct ggatgtttcc ctctcgcatg gcgtggcctg aggaccacgt gttcatttcc      1140
acacccagct tcaactacac aggccgtgac ttccaacgct ctttgcaga cctgcacttt      1200
gaggaaggct ggtacatgtg gctgcagtca cgtgacctcc tggcaggact cccagcacct     1260
ggtgtggaag tatactgtct ttacggcgtg ggcctgccca cgccccgcac ctacatctac     1320
gaccacggct tccctacac ggaccctgtg ggtgtgctct atgaggatgg tgatgacacg      1380
gtggcgaccc gcagcaccga gctctgtggc ctgtggcagg gccgccagcc acagcctgtg     1440
cacctgctgc ccctgcacgg gatacagcat ctcaacatgg tcttcagcaa cctgaccctg     1500
gagcacatca atgccatcct gctgggtgcc taccgccagg gtccccctgc atccccgact     1560
gccagcccag agccccgcc tcctgaataa agaccttcct ttgctaccgt aagccctgat      1620
ggctatgttt caggttgaag ggaggcacta gagtcccaca ctaggtttca ctcctcacca     1680
gccacaggct cagtgctgtg tgcagtgagg caagatgggc tctgctgagg cctgggactg     1740
agct                                                                   1744
```

<210> SEQ ID NO 31
<211> LENGTH: 507
<212> TYPE: DNA
<213> ORGANISM: Homo sapiens

<400> SEQUENCE: 31

```
cttctgacag ctggtgcgcc tgcccgggaa catcctcctg gactcaatca tggcttgtgg       60
tctggtcgcc agcaacctga atctcaaacc tggagagtgc cttcgagtgc gaggcgaggt     120
ggctcctgac gctaagagct tcgtgctgaa cctgggcaaa gacagcaaca acctgtgcct     180
gcacttcaac cctcgcttca cgcccacgg cgacgccaac accatcgtgt gcaacagcaa     240
ggacggcggg gcctggggga ccgagcagcg ggaggctgtc tttcccttcc agcctggaag    300
tgttgcagag gtgtgcatca ccttcgacca ggccaacctg accgtcaagc tgccagatgg     360
atacgaattc aagttccccca accgcctcaa cctggaggcc atcaactaca tggcagctga    420
```

```
cggtgacttc aagatcaaat gtgtggcctt tgactgaaat cagccagccc atggccccca      480
ataaaggcag ctgcctctgc tccctg                                          507
```

<210> SEQ ID NO 32
<211> LENGTH: 672
<212> TYPE: DNA
<213> ORGANISM: Homo sapiens

<400> SEQUENCE: 32

```
aatataactt tttctttttt tatttaaata agtcttataa atgtgggaaa aaattatctt       60
gtgttccttt aatttcattt ttatttaata ctattttcag aatgaacaaa agattgaaaa      120
attatttaga attttttctct gtgcttttc ctgtttcaga taaaggagat gggtgagatg      180
catagggaac tcaatgcata actatataat ttgaagatta tagaagaagg gaaatagcaa      240
atggacacaa attacaaatg tgtgtgcgtg ggacgaagac atctttgaag gtcatgagtt      300
tgttagttta acatcatata tttgtaatag tgaaacctgt actcaaaata taagcagctt      360
gaaactggct ttaccaatct tgaaatttga ccacaagtgt cttatatatg cagatctaat      420
gtaaaatcca gaacttggac tccatcgtta aaattattta tgtgtaacat tcaaatgtgt      480
gcattaaata tgcttccaca gtaaaatctg aaaaactgat ttgtgattga agctgcctt      540 tctatttact tgagtcttgt acatacatac tttttatga gctatgaaat aaaacatttt      600
aaactgaatt tcttaactt gacatttcaa atttcttctt cttttcttt tctttttttt       660 tttttttga ga                                                           672
```

<210> SEQ ID NO 33
<211> LENGTH: 3270
<212> TYPE: DNA
<213> ORGANISM: Homo sapiens
<220> FEATURE:
<221> NAME/KEY: Unsure
<222> LOCATION: (2708)..(2708)
<223> OTHER INFORMATION: n = a, c, g or t/u
<221> NAME/KEY: Unsure
<222> LOCATION: (2746)..(2746)
<223> OTHER INFORMATION: n = a, c, g or t/u

<400> SEQUENCE: 33

```
caaaagtgt gtggaaaggt ggattgaggg agcgggaccc ccgcgggacc cgaggggggcg       60 gcaggcgggg aacgggggagt cagcccgcgc tgtgtctcgg ggccggccgg caggaaggag     120
ccatggctct ggacgggata aggatgccag atggctgcta cgcggacggg acgtgggaac     180
tgagtgtcca tgtgacggac ctgaaccgcg atatcaccct gagagtgacc ggcgaggtgc     240
acattggagg cgtgatgctt aagctggtgg agaaactcga tgtaaaaaaa gattggtctg     300
accatgctct ctggtgggaa aagaagagaa cttggcttct gaagacacat tggaccttag     360
ataagtatgg tattcaggca gatgctaagc ttcagttcac ccctcagcac aaactgctcc     420
gcctgcagct tcccaacatg aagtatgtga aggtgaaagt gaatttctct gatagagtct     480
tcaaagctgt ttctgacatc tgtaagactt ttaatatcag acaccccgaa gaactttctc     540
tcttaaagaa acccagagat ccaacaaaga aaaaaagaa gaagctagat gaccagtctg     600
aagatgaggc acttgaatta gagggggcctc ttatcactcc tggatcagga agtatatatt     660
caagcccagg actgtatagt aaaacaatga ccccccactta tgatgctcat gatggaagcc     720
ccttgtcacc aacttctgct tggtttggtg acagtgcttt gtcagaaggc aatcctggta     780
tacttgctgt cagtcaacca atcacgtcac cagaaatctt ggcaaaaatg ttcaagcctc     840
```

-continued

```
aagctcttct tgataaagca aaaatcaacc aaggatggct tgattcctca agatctctca    900
tggaacaaga tgtgaaggaa aatgaggcct tgctgctccg attcaagtat tacagctttt    960
ttgatttgaa tccaaagtat gatgcaatca gaatcaatca gctttatgag caggccaaat   1020
gggccattct cctggaagag attgaatgca cagaagaaga aatgatgatg tttgcagccc   1080
tgcagtatca tatcaataag ctgtcaatca tgacatcaga gaatcatttg aacaacagtg   1140
acaaagaagt tgatgaagtt gatgctgccc tttcagacct ggagattact ctggaagggg   1200
gtaaaacgtc aacaattttg ggtgacatta cttccattcc tgaacttgct gactacatta   1260
aagttttcaa gccaaaaaag ctgactctga aaggttacaa acaatattgg tgcaccttca   1320
aagacacatc catttcttgt tataagagca aagaagaatc cagtggcaca ccagctcatc   1380
agatgaacct caggggatgt gaagttaccc cagatgtaaa catttcaggc caaaaattta   1440
acattaaact cctgattcca gttgcagaag gcatgaatga aatctggctt cgttgtgaca   1500
atgaaaaaca gtatgcacac tggatggcag cctgcagatt agcctccaaa ggcaagacca   1560
tggcggacag ttcttacaac ttagaagttc agaatattct ttcctttctg aagatgcagc   1620
atttaaaccc agatcctcag ttaataccag agcagatcac gactgatata actcctgaat   1680
gtttggtgtc tccccgctat ctaaaaaagt ataagaacaa gcagataaca gcgagaatct   1740
tggaggccca tcagaatgta gctcagatga gtctaattga agccaagatg agatttattc   1800
aagcttggca gtcactacct gaatttggca tcactcactt cattgcaagg ttccaagggg   1860
gcaaaaaaga agaacttatt ggaattgcat acaacagact gattcggatg gatgccagca   1920
ctggagatgc aattaaaaca tggcgtttca gcaacatgaa acagtggaat gtcaactggg   1980
aaatcaaaat ggtcaccgta gagtttgcag atgaagtacg attgtccttc atttgtactg   2040
aagtagattg caaagtggtt catgaattca ttggtggcta catatttctc tcaacacgtg   2100
caaaagacca aaacgagagt ttagatgaag agatgttcta caaacttacc agtggttggg   2160
tgtgaataga aatactgttt aatgaaactc cacggccata acaatattta actttaaaag   2220
ctgtttgtta tatgctgctt aataaagtaa gcttgaaatt tatcatttta tcatgaaaac   2280
ttctttgcct taccagacca gttaatatgt gcactaaaca agcacgacta ttaatctatc   2340
atgttatgat ataataaact tgaatttggc acacattcct tagggccatg aattgaaaac   2400
tgaaatagtg ggcaaatcag gaacaaacca tcactgattt actgatttaa gctagccaaa   2460
ctgtaagaaa caagccatct attttaaagc tatccagggc ttaacctata tgaactctat   2520
ttatcatgtc taatgcatgt gatttaatgt atgtttaatt tgatatcatg tttttaaaata   2580 tcctacttct ggtagccatt taattcctcc ccctaccccc aaataaatca ggcatgcagg   2640
aggcctgata tttagtaatg tcattgtgtt tgaccttgaa ggaaaatgct attagtccgt   2700
cgtgcttnat ttgttttgt ccttgaataa gcatgttatg tatatngtct cgtgttttta   2760
tttttacacc atattgtatt acacttttag tattcaccag cataancact gtctgcctaa   2820
aatatgcaac tctttgcatt acaatatgaa gtaaagttct atgaagtatg cattttgtgt   2880
aactaatgta aaaacacaaa ttttataaaa ttgtacagtt ttttaaaaac tactcacaac   2940
tagcagatgg cttaaatgta gcaatctctg cgttaattaa atgcctttaa gagatataat   3000
taacgtgcag ttttaatatc tactaaatta agaatgactt cattatgatc atgatttgcc   3060
acaatgtcct taactctaat gcctggactg gccatgttct agtctgttgc gctgttacaa   3120
tctgtattgg tgctagtcag aaaattccta gctcacatag cccaaaaggg tgcgagggag   3180
```

| | |
|---|---|
| aggtggatta ccagtattgt tcaataatcc atggttcaaa gactgtataa atgcatttta | 3240 |
| ttttaaataa aagcaaaact tttatttaaa | 3270 |

<210> SEQ ID NO 34
<211> LENGTH: 3437
<212> TYPE: DNA
<213> ORGANISM: Homo sapiens

<400> SEQUENCE: 34

| | |
|---|---|
| aagttcagtg cctaccgaag acaaaggcgc cccgagggag tggcggtgcg acccagggc | 60 |
| gtgggcccgg ccgcggagcc cacactgccc ggctgacccg gtggtctcgg accatgtctc | 120 |
| ccgccccaag accccccgt tgtctcctgc tcccctgct cacgctcggc accgcgctcg | 180 |
| cctccctcgg ctcggcccaa agcagcagct tcagccccga agcctggcta cagcaatatg | 240 |
| gctacctgcc tcccggggac ctacgtaccc acacacagcg ctcaccccag tcactctcag | 300 |
| cggccatcgc tgccatgcag aagttttacg gcttgcaagt aacaggcaaa gctgatgcag | 360 |
| acaccatgaa ggccatgagg cgcccccgat gtggtgttcc agacaagttt ggggctgaga | 420 |
| tcaaggccaa tgttcgaagg aagcgctacg ccatccaggg tctcaaatgg caacataatg | 480 |
| aaatcacttt ctgcatccag aattacaccc caaggtgggg cgagtatgcc acatacgagg | 540 |
| ccattcgcaa ggcgttccgc gtgtgggaga gtgccacacc actgcgcttc gcgaggtgc | 600 |
| cctatgccta catccgtgag ggccatgaga agcaggccga catcatgatc ttctttgccg | 660 |
| agggcttcca tggcgacagc acgcccttcg atggtgaggg cggcttcctg gcccatgcct | 720 |
| acttcccagg ccccaacatt ggaggagaca cccactttga ctctgccgag ccttggactg | 780 |
| tcaggaatga ggatctgaat ggaaatgaca tcttcctggt ggctgtgcac gagctgggcc | 840 |
| atgccctggg gctcgagcat tccagtgacc cctcggccat catggcaccc ttttaccagt | 900 |
| ggatggacac ggagaatttt gtgctgcccg atgatgaccg ccggggcatc cagcaacttt | 960 |
| atggggtga gtcagggttc cccaccaaga tgccccctca acccaggact acctcccggc | 1020 |
| cttctgttcc tgataaaccc aaaaacccca cctatgggcc caacatctgt gacgggaact | 1080 |
| tgacaccgt ggccatgctc cgaggggaga tgtttgtctt caaggagcgc tggttctggc | 1140 |
| gggtgaggaa taccaagtg atggatggat acccaatgcc cattggccag ttctggcggg | 1200 |
| gcctgcctgc gtccatcaac actgcctacg agaggaagga tggcaaattc gtcttcttca | 1260 |
| aaggagacaa gcattgggtg tttgatgagg cgtccctgga acctggctac cccaagcaca | 1320 |
| ttaaggagct gggccgaggg ctgcctaccg acaagattga tgctgctctc ttctggatgc | 1380 |
| ccaatgaaaa gacctacttc ttccgtggaa acaagtacta ccgtttcaac gaagagctca | 1440 |
| gggcagtgga tagcgagtac cccaagaaca tcaaagtctg ggaagggatc cctgagtctc | 1500 |
| ccagagggtc attcatgggc agcgatgaag tcttcactta cttctacaag gggaacaaat | 1560 |
| actgaaaatt caacaaccag aagctgaagg tagaaccggg ctaccccaag tcagccctga | 1620 |
| ggactggat gggctgccca tcgggaggcc ggccggatga ggggactgag gaggagacgg | 1680 |
| aggtgatcat cattgaggtg acgaggagg gcggcgggc ggtgagcgcg gctgccgtgg | 1740 |
| tgctgcccgt gctgctgctg ctcctggtgc tggcggtggg ccttgcagtc ttcttcttca | 1800 |
| gacgccatgg gaccccagg cgactgctct actgccagcg ttccctgctg acaaggtct | 1860 |
| gacgcccacc gccggcccgc ccactcctac cacaaggact ttgcctctga aggccagtgg | 1920 |
| cagcaggtgg tggtgggtgg gctgctccca tcgtcccgag ccccctcccc gcagcctcct | 1980 |
| tgcttctctc tgtcccctgg ctggcctcct tcaccctgac cgcctccctc cctcctgccc | 2040 |

-continued

```
cggcattgca tcttccctag ataggtcccc tgagggctga gtgggagggc ggcccttttcc    2100
agcctctgcc cctcagggga accctgtagc tttgtgtctg tccagcccca tctgaatgtg    2160
ttggggctc  tgcacttgaa ggcaggaccc tcagacctcg ctggtaaagg tcaaatgggg    2220
tcatctgctc cttttccatc ccctgacata ccttaacctc tgaactctga cctcaggagg    2280
ctctgggcac tccagccctg aaagcccag  gtgtacccaa ttggcagcct ctcactactc    2340
tttctggcta aaaggaatct aatcttgttg agggtagaga ccctgagaca gtgtgagggg    2400
gtggggactg ccaagccacc ctaagacctt ggaggaaaa  ctcagagagg gtcttcgttg    2460
ctcagtcagt caagttcctc ggagatctgc ctctgcctca cctaccccag gaacttcca     2520
aggaaggagc ctgagccact ggggactaag tgggcagaag aaaccccttgg cagccctgtg   2580
cctctcgaat gttagccttg gatgggcctt tcacagttag aagagctgaa accagggtg    2640
cagctgtcag gtagggtggg gccggtggga gaggcccggg tcagagccct gggggtgagc    2700
ctgaaggcca cagagaaaga accttgccca aactcaggca gctggggctg aggcccaaag    2760
gcagaacagc cagagggggc aggaggggac caaaaggaa  atgaggacg  tgcagcagca    2820
ttggaaggct ggggccgggc aggccaggcc aagccaagca gggggccaca gggtgggctg    2880
tggagctctc aggaagggcc ctgaggaagg cacacttgct cctgttggtc cctgtccttg    2940
ctgcccaggc agcgtggagg ggaagggtag ggcagccaga gaaaggagca gagaaggcac    3000
acaaacgagg aatgaggggc ttcacgagag gccacagggc ctggctggcc acgctgtccc    3060
ggcctgctca ccatctcagt gaggggcagg agctggggct cgcttaggct gggtccacgc    3120
ttccctggtg ccagcacccc tcaagcctgt ctcaccagtg gcctgccctc tcgctccccc    3180
acccagccca cccattgaag tctccttggg ccaccaaagg tggtggccat ggtaccgggg    3240
acttgggaga gtgagaccca gtggagggag caagaggaga gggatgtcgg ggggtgggg    3300
cacggggtag gggaaatggg gtgaacggtg ctggcagttc ggctagattt ctgtcttgtt    3360
tgttttttg  ttttgtttaa tgtatatttt tattataatt attatatatg aattccaaaa    3420
aaaaaaaaaa aaaaaaa                                                  3437
```

<210> SEQ ID NO 35
<211> LENGTH: 4898
<212> TYPE: DNA
<213> ORGANISM: Homo sapiens

<400> SEQUENCE: 35

```
gaattccggc tgccaggggc gtccggttac atccccgcct tcctctgtcc tggccgcggg      60
accgggtttg cggaccgca  gttcgggaac atgttggcct cgagcagccg gatccgggct     120
gcgtggacgc gggcgctgct gctgccgctg ctgctggcgg ggcctgtggg ctgcctgagc     180
cgccaggagc tctttccctt cggccccgga caggggggacc tggagctgga ggacggggat    240
gacttcgtct ctcctgccct ggagctgagt ggggcgctcc gcttctacga cagatccgac     300
atcgacgcag tctacgtcac cacaaatggc atcattgcta cgagtgaacc cccggccaaa     360
gaatcccatc ccgggctctt cccaccaaca ttcggtgcag tcgcccccttt cctggcggac    420
ttggacacga ccgatggcct ggggaaggtt tattatcgag aagacttatc cccctccatc     480
actcagcgag cagcagagtg tgtccacaga gggttcccgg agatctcttt ccagcctagt     540
agcgcggtgg ttgtcacttg ggaatccgtg gcccccctacc aagggcccag cagggaccca    600
gaccagaaag gcaagagaaa cacgttccag gctgttctag cctcctctga ttccagctcc     660
tatgccattt tcctttatcc tgaggatggt ctgcagttcc atacgacatt ctcaaagaag     720
```

-continued

| | |
|---|---|
| gaaaacaacc aagttcctgc cgtggttgca ttcagtcaag gttcagtggg attcttatgg | 780 |
| aagagcaacg gagcttataa catatttgct aatgacaggg aatcaattga aaatttggcc | 840 |
| aagagtagta actctgggca gcagggtgtc tgggtgtttg agattgggag tccagccacc | 900 |
| accaatggcg tggtgcctgc agacgtgatc ctcggaactg aagatggggc agagtatgat | 960 |
| gatgaggatg aagattatga cctggcgacc actcgtctgg gcctggagga tgtgggcacc | 1020 |
| acgcccttct cctacaaggc tctgagaagg ggaggtgctg acacatacag tgtgcccagc | 1080 |
| gtcctctccc cgcgccgggc agctaccgaa aggccccttg acctccacag agagaacc | 1140 |
| aggtcttttcc agttggcagt ggagactttt caccagcagc accctcaggt catagatgtg | 1200 |
| gatgaagttg aggaaacagg agttgttttc agctataaca cggattcccg ccagacgtgt | 1260 |
| gctaacaaca gacaccagtg ctcggtgcac gcagagtgca gggactacgc cacgggcttc | 1320 |
| tgctgcagct gtgtcgctgg ctatacgggc aatggcaggc aatgtgttgc agaaggttcc | 1380 |
| ccccagcgag tcaatggcaa ggtgaaagga aggatctttg tggggagcag ccaggtcccc | 1440 |
| attgtctttg agaacactga cctccactct tacgtagtaa tgaaccacgg gcgctcctac | 1500 |
| acagccatca gcaccattcc cgagaccgtt ggatattctc tgcttccact ggccccagtt | 1560 |
| ggaggcatca ttggatggat gtttgcagtg gagcaggacg gattcaagaa tgggttcagc | 1620 |
| atcaccgggg gtgagttcac tcgccaggct gaggtgacct tcgtggggca cccgggcaat | 1680 |
| ctggtcatta agcagcggtt cagcggcatc gatgagcatg ggcacctgac catcgacacg | 1740 |
| gagctggagg gccgcgtgcc gcagattccg ttcggctcct ccgtgcacat tgagccctac | 1800 |
| acggagctgt accactactc cacctcagtg atcacttcct cctccacccg ggagtacacg | 1860 |
| gtgactgagc ccgagcgaga tggggcatct ccttcacgca tctacactta ccagtggcgc | 1920 |
| cagaccatca ccttccagga atgcgtccac gatgactccc ggccagccct gcccagcacc | 1980 |
| cagcagctct cggtggacag cgtgttcgtc ctgtacaacc aggaggagaa gatcttgcgc | 2040 |
| tacgctttca gcaactccat tgggcctgtg agggaaggct cccctgatgc tcttcagaat | 2100 |
| ccctgctaca tcggcactca tgggtgtgac accaacgcgg cctgtcgccc tggtcccagg | 2160 |
| acacagttca cctgcgagtg ctccatcggc ttccgaggag acgggcgaac ctgctatgat | 2220 |
| attgatgaat gttcagaaca accctcagtg tgtgggagcc acacaatctg caataatcac | 2280 |
| ccaggaacct tccgctgcga gtgtgtggag ggctaccagt tttcagatga gggaacgtgt | 2340 |
| gtggctgtcg tggaccagcg ccccatcaac tactgtgaaa ctggccttca taactgcgac | 2400 |
| atacccc agc gggcccagtg tatctacaca ggaggctcct cctacacctg ttcctgcttg | 2460 |
| ccaggcttt ctggggatgg ccaagcctgc caagatgtag atgaatgcca gccaagccga | 2520 |
| tgtcaccctg acgccttctg ctacaacact ccaggtctct tcacgtgcca gtgcaaacct | 2580 |
| ggttatcagg gagacggctt ccgttgcgtg cccggagagg tggagaaaac ccggtgccag | 2640 |
| cacgagcgag aacacattct cggggcagcg ggggcgacag acccacagcg acccattcct | 2700 |
| ccggggctgt tcgttcctga gtgcgatgcg cacgggcact acgcgcccac ccagtgccac | 2760 |
| ggcagcaccg gctactgctg gtgcgtggat cgcgacggcc gcgaggtgga gggcaccagg | 2820 |
| accaggcccg ggatgacgcc cccgtgtctg agtacagtgg ctcccccgat tcaccaagga | 2880 |
| cctgcggtgc ctaccgccgt gatcccttg cctcctggga cccatttact ctttgcccag | 2940 |
| actgggaaga ttgagcgcct gccctggag ggaaatacca tgaggaagac agaagcaaag | 3000 |
| gcgttccttc atgtcccggc taaagtcatc attggactgg cctttgactg cgtggacaag | 3060 |
| atggtttact ggacggacat cactgagcct tccattggga gagctagtct acatggtgga | 3120 |

| | |
|---|---|
| gagccaacca ccatcattag acaagatctt ggaagtccag aaggtatcgc tgttgatcac | 3180 |
| cttggccgca acatcttctg gacagactct aacctggatc gaatagaagt ggcgaagctg | 3240 |
| gacggcacgc agcgccgggt gctctttgag actgacctgg tgaatcccag aggcattgta | 3300 |
| acggattccg tgagagggaa cctttactgg acagactgga acagagataa ccccaagatt | 3360 |
| gaaacttcct acatggacgg cacgaaccgg aggatccttg tgcaggatga cctgggcttg | 3420 |
| cccaatggac tgcacttcga tgcgttctca tctcagctct gctgggtgga tgcaggcacc | 3480 |
| aatcgggcgg aatgcctgaa ccccagtcag cccagcagac gcaaggctct cgaagggctc | 3540 |
| cagtatcctt ttgctgtgac gagctacggg aagaatctgt atttcacaga ctggaagatg | 3600 |
| aattccgtgg ttgctctcga tcttgcaatt tccaaggaga cggatgcttt ccaaccccac | 3660 |
| aagcagaccc ggctgtatgg catcaccacg gccctgtctc agtgtccgca aggccataac | 3720 |
| tactgctcag tgaacaatgg cggctgcacc cacctatgct tggccacccc agggagcagg | 3780 |
| acctgccgtt gccctgacaa caccttggga gttgactgta tcgaacggaa atgaagacaa | 3840 |
| gagtgcctta tttcctttcc aagtatttca cagcaacact ctacttgaag caacttggtc | 3900 |
| cagattgaaa agtgtcctct ggctgagtgg ccactaggcc cagacccagc ccagcctgag | 3960 |
| ccccaacaac aacttttccc tcactgttcc ccaaaacatg caccctggac ttctctaata | 4020 |
| gaaaagtctc caccctaca caaggacaga accctccacc cctaccccca accctcagac | 4080 |
| agacttatac accctgagt gaggattaca tgcccatccc agtgtcctag dacctttttcc | 4140 |
| caatactagc cccccagtgg tgaacagaac ctcccaaatt tgagttgcac ccttccctgt | 4200 |
| ggccttatga gctcagcctc gctttgaggt acccaccgtc ctgtcagctc cttgacctat | 4260 |
| gagctggggc ctgactagga aaagttggga gttaaggagg aaattagcat tccttaatgt | 4320 |
| tttgttttgg tgctctgaat ttcttcttta ttatagtcct atagtttac tcctcagttc | 4380 |
| ctcaccatca tcatcttgtc taagacccc attataatat tcatgcgctg ctttttcatc | 4440 |
| aaaacctacc ctgtcctaga gatctatggg catttggtgg atgataatga gcagccctc | 4500 |
| ccagatagaa tgtcaatatt tgagcagtag gatattggca tttgttagtt aaaggcttaa | 4560 |
| atcaaaagaa tgtccaatgg taggaatttc aaggtgtagg tcagatattt gagaataggg | 4620 |
| gattttttttg atgtgcctta aattatacca aagattacta attattcctc tttgcccaaa | 4680 |
| atacttgcat ccaaggttct agtctctgtt gctgtgctgg tctttagccc cactgctggc | 4740 |
| actgatgtcc ctccttttc acggagacct atctgaggta caggatgggg ctggcaccag | 4800 |
| atgatgtccc accacagtcc ctcacctccg gcctccacat gacagaacca atttacactc | 4860 |
| aaccatgacc tcacccctcc ttggtttctc cctccccg | 4898 |

<210> SEQ ID NO 36
<211> LENGTH: 2511
<212> TYPE: DNA
<213> ORGANISM: Homo sapiens

<400> SEQUENCE: 36

| | |
|---|---|
| cgccgcctgt gccatttctg attttgcaac ttggggaaga agaaaaaagc gagagaaggg | 60 |
| agcttgctcg ccggggggtg gggagggggg aaggagagcg cggcccccc aggaacggag | 120 |
| cgcgggggga gcggcgagg ggagcagggg tgttgggggg ggagcctgag agcctggggg | 180 |
| ggctgcaaaa agagagaaag aaaacagcag gaaccacaac aaaacgccag cagggcgggc | 240 |
| gggcgcgcag cagcagcggg gcggccgagg cagtagcggc ggcagcggcg gcggcggcg | 300 |
| aggcagcggc cggtgtccgg ctcgggctcg gctcctgcga ccccgggggcg cccggcgggc | 360 |

```
ccccgcccc ctccccctcc cccttcccc ttcccctcc cctcccagcg cgcccgcgcg    420 cccgcggcc ctcggcgagc agctcggctc ccccagcgc tccgggcc caaagatatg     480 gcaatggtag ttagcagctg gcagatccg caggacgacg tggccggggg caacccggc   540 ggccccaacc ccgcagcgca ggcggcccgc ggcggcggcg cggcgccgg cgagcagcag  600 cagcaggcgg gctcgggcgc gccgcacacg ccgcagaccc cgggccagcc cggagcgccc 660 gccaccccg gcacggcggg ggacaagggc cagggcccgc ccggttcggg ccagagccag  720
cagcacatcg agtgcgtggt gtgcggggac aagtcgagcg gcaagcacta cggccaattc 780
acctgcgagg gctgcaaaag tttcttcaag aggagcgtcc gcaggaactt aacttacaca 840
tgccgtgcca acaggaactg tcccatcgac cagcaccacc gcaaccagtg ccaatactgc 900
cgcctcaaga agtgcctcaa agtgggcatg aggcgggaag cggttcagcg aggaagaatg  960
cctccaaccc agcccaatcc aggccagtac gcactcacca acggggaccc cctcaacggc  1020
cactgctacc tgtccggcta catctcgctg ctgctgcgcg ccgagcccta ccccacgtcg  1080
cgctacggca gccagtgcat gcagcccaac aacattatgg gcatcgagaa catctgcgag  1140
ctggccgcgc gcctgctctt cagcgccgtc gagtgggccc gcaacatccc cttcttcccg  1200
gatctgcaga tcaccgacca ggtgtccctg ctacgcctca cctggagcga gctgttcgtg  1260
ctcaacgcgg cccagtgctc tatgccgctg cacgtggcgc cgttgctggc cgccgccggc  1320
ctgcatgcct cgcccatgtc tgccgaccgc gtcgtggcct tcatggacca catccgcatc  1380
ttccaggagc aggtggagaa gctcaaggcg ctacacgtcg actcagccga gtacagctgc  1440
ctcaaagcca tcgtgctgtt cacgtcagac gcctgtggcc tgtcggatgc ggcccacatc  1500
gagagcctgc aggagaagtc gcagtgcgca ctggaggagt acgtgaggag ccagtacccc  1560
aaccagccca gccgttttgg caaactgctg ctgcgactgc cctcgctgcg caccgtgtcc  1620
tcctccgtca tcgagcagct cttcttcgtc cgtttggtag gtaaaacccc catcgaaact  1680
ctcatccgcg atatgttact gtctgggagc agcttcaact ggccttacat gtccatccag  1740
tgctcctaga ccttgggcgc ttcccacctg ccccgtcccc ctagagactc agaggaccca  1800
cctgggccaa ggactccaaa gccgcgggga caccgggaag tgcagcgggc caggcaggct  1860
gggtgggagg gaggagggcc gagacaggag cagcccaccc agcagaaata caatccgagc  1920
tacaaagcat gggaaaaaga gactctttta ggatcagatc tgtgagcacg ttggcgagga  1980
aaaacaaaac aaacaaaaaa aagaaccttg tgtctgtctg gtgaaaaaaa gaaaaacaaa  2040
ttggaagaga ggaccatgag aatttttaata aaacagaagg aaactaatgg accttccagg  2100
atttattgtg gacggatgtg gatatattct gtacaggaac aacacatatg gaagtggact  2160
gaagcctatg tagaaacaca cacacactga acattgttat tcattttgta aaatactagt  2220 ctttatttc attttttgta aaatttaaac atcgtatgcg cataaagaaa aggaaacaa   2280 gaattagggg aaaataacat tttccaaata attataaaaa attgtcctgt gtctatgtat  2340
ctatatctgt tttgtatttt tttctggttc caaaccagat ttcctgtgat tctatactaa  2400 taattttga tataacccttt tgcttcttat aatgagtgcg atatatgttg tcgaggctgt  2460
tcttcaagaa ttaaaattga agtgaaaatt taaacaaaaa taaagaatt g            2511
```

<210> SEQ ID NO 37
<211> LENGTH: 2722
<212> TYPE: DNA
<213> ORGANISM: Homo sapiens

<400> SEQUENCE: 37

```
gagcgggctg agggtaggaa gtagccgctc cgagtggagg cgactggggg ctgaagagcg        60
cgccgccctc tcgtcccact ttccaggtgt gtgatcctgt aaaattaaat cttccaagat       120
gatctggtat atattaatta taggaattct gcttccccag tctttggctc atccaggctt       180
ttttacttca attggtcaga tgactgattt gatccatact gagaaagatc tggtgacttc       240
tctgaaagat tatattaagg cagaagagga caagttagaa caaataaaaa aatgggcaga       300
gaagttagat cggctaacta gtacagcgac aaaagatcca aaggatttg ttgggcatcc        360
agtaaatgca ttcaaattaa tgaaacgtct gaatactgag tggagtgagt tggagaatct       420
ggtccttaag gatatgtcag atggctttat ctctaaccta accattcaga gaccagtact       480
ttctaatgat gaagatcagg ttggggcagc caaagctctg ttacgtctcc aggatacccta      540
caatttggat acagatacca tctcaaaggg taatcttcca ggagtgaaac acaaatcttt       600
tctaacggct gaggactgct tgagttggg caaagtggcc tatacagaag cagattatta       660
ccatacggaa ctgtggatgg aacaagccct aaggcaactg gatgaaggcg agatttctac       720
catagataaa gtctctgttc tagattattt gagctatgcg gtatatcagc agggagacct       780
ggataaggca cttttgctca caaagaagct tcttgaacta gatcctgaac atcagagagc       840
taatggtaac ttaaaatatt tgagtatat aatggctaaa gaaaaagatg tcaataagtc        900
tgcttcagat gaccaatctg atcagaaaac tacaccaaag aaaaaggggg ttgctgtgga       960
ttacctgcca gagagacaga agtacgaaat gctgtgccgt ggggagggta tcaaaatgac      1020
ccctcggaga cagaaaaaac tcttttgccg ctaccatgat ggaaaccgta atcctaaatt      1080
tattctggct ccagctaaac aggaggatga atgggacaag cctcgtatta ttcgcttcca      1140
tgatatatt tctgatgcag aaattgaaat cgtcaaagac ctagcaaaac caaggctgag      1200
ccgagctaca gtacatgacc ctgagactgg aaaattgacc acagcacagt acagagtatc      1260
taagagtgcc tggctctctg gctatgaaaa tcctgtggtg tctcgaatta atatgagaat      1320
acaagatcta acaggactag atgtttccac agcagaggaa ttacaggtag caaattatgg      1380
agttggagga cagtatgaac cccattttga ctttgcacgg aaagatgagc cagatgcttt      1440
caaagagctg gggacaggaa atagaattgc tacatggctg ttttatatga gtgatgtgtc      1500
tgcaggagga gccactgttt ttcctgaagt tggagctagt gtttggccca aaaaaggaac      1560
tgctgttttc tggtataatc tgtttgccag tggagaagga gattatagta cacggcatgc      1620
agcctgtcca gtgctagttg gcaacaaatg ggtatccaat aaatggctcc atgaacgtgg      1680
acaagaattt cgaagacctt gtacgttgtc agaattggaa tgacaaacag gcttcccttt      1740
ttctcctatt gttgtactct tatgtgtctg atatacacat ttccatagtc ttaacttcca      1800
ggagtttaca attgactaac actccatgat tgattcagtc atgaacctca tcccatgttt      1860
catctgtgga caattgctta ctttgtgggt tctttttaaaa gtaacacgaa atcatcatat      1920
tgcataaaac cttaaagttc tgttggtatc acagaagaca aggcagagtt taaagtgagg      1980
aatttttat ttaaagaact ttttggttgg ataaaaacat aatttgagca tccagtttta       2040
gtatttcact acatctcagt tggtgggtgt taagctagaa tgggctgtgt gataggaaac      2100
aaatgcctta cagatgtgcc taggtgttct gtttacctag tgtcttactc tgttttctgg      2160
atctgaagac tagtaataaa ctaggacact aactgggttc catgtgattg ccctttcata      2220
tgatcttcta agttgatttt tttcctccca agtcttttt aaagaaagta tactgtattt       2280
taccaacccc ctctctttc ttttagctcc tctgtggtga attaaacgta cttgagttaa       2340
```

-continued

```
aatatttcga tttttttttt tttttttaatg gaaagtcctg cataacaaca ctgggccttc    2400
ttaactaaaa tgctcaccac ttagcctgtt tttttatccc tttttttaaaa tgacagatga    2460 ttttgttcag gaattttgct gtttttctta gtgctaatac cttgcctctt attcctgcta    2520
cagcagggtg gtaatattgg cattctgatt aaatactgtg ccttaggaga ctggaagttt    2580
aaaaatgtac aagtcctttc agtgatgagg gaattgattt tttttaaaag tcttttctt     2640 agaaagccaa aatgtttgtt ttttttaagat tctgaaatgt gttgtgacaa caatgaccta   2700
tttatgatct taaatcttt tt                                              2722
```

<210> SEQ ID NO 38
<211> LENGTH: 811
<212> TYPE: DNA
<213> ORGANISM: Homo sapiens

<400> SEQUENCE: 38

```
catccctctg gctccagagc tcagagccac ccacagccgc agccatgctg tgcctcctgc     60
tcaccctggg cgtggccctg gtctgtggtg tcccggccat ggacatcccc cagaccaagc    120
aggacctgga gctcccaaag ttggcaggga cctggcactc catggccatg gcgaccaaca    180
acatctccct catggcgaca ctgaaggccc ctctgagggt ccacatcacc tcactgttgc    240
ccacccccga ggacaacctg gagatcgttc tgcacagatg ggagaacaac agctgtgttg    300
agaagaaggt ccttggagag aagactggga atccaaagaa gttcaagatc aactatacgg    360
tggcgaacga ggccacgctg ctcgatactg actacgacaa tttcctgttt ctctgcctac    420
aggacaccac cacccccatc cagagcatga tgtgccagta cctggccaga gtcctggtgg    480
aggacgatga gatcatgcag ggattcatca gggctttcag gcccctgccc aggcaccat    540 ggtacttgct ggacttgaaa cagatggaag agccgtgccg tttctagctc acctccgcct    600
ccaggaagac cagactccca cccttccaca cctccagagc agtgggactt cctcctgccc    660
tttcaaagaa taaccacagc tcagaagacg atgacgtggt catctgtgtc gccatcccct    720
tcctgctgca cacctgcacc attgccatgg ggaggctgct ccctgggggc agagtctctg    780
gcagaggtta ttaataaacc cttggagcat g                                   811
```

<210> SEQ ID NO 39
<211> LENGTH: 1480
<212> TYPE: DNA
<213> ORGANISM: Homo sapiens

<400> SEQUENCE: 39

```
ctctgcaaaa ttcagctgct gcctctgtct tgaggacccc agcgcctttc ccccggggcc     60
atgctgcctg cagccacagc ctccctcctg ggcccctcc tcactgcctg cgccctgctg    120
ccttttgccc agggccagac ccccaactac accagacccg tgttcctgtg cggaggggat    180
gtgaaggggg aatcaggtta cgtggcaagt gaggggttcc ccaactccta ccccctaat    240 aaggagtgca tctggaccat aacggtcccc gagggccaga ctgtgtccct ctcattccga    300
gtcttcgacc tggagctgca ccccgcctgc cgctacgatg tctctgaggt cttcgctggg    360
tctgggactt ccggccagcg gctcggacgc ttttgtggga ccttccggcc tgcgccccta    420
gtcgcccccg gcaaccaggt gaccctgagg atgacgacgg atgagggcac aggaggacga    480
ggcttcctgc tctggtacag cgggcgggcc acctcgggct ctgagcacca attttgcggg    540
gggcggctgg agaaggccca gggaaccctg accacgccca actggcccga gtccgattac    600
cccccgggca tcagctgttc ctggcacatc atcgcgcccc cggaccaggt catcgcgctg    660
```

-continued

| | |
|---|---|
| accttcgaga agtttgacct ggagccggac acctactgcc gctatgactc ggtcagcgtc | 720 |
| ttcaacggag ccgtgagcga cgactcccgg aggctgggga agttctgcgg cgacgcagtc | 780 |
| ccgggctcca tctcctccga agggaatgaa ctcctcgtcc agttcgtctc agatctcagt | 840 |
| gtcaccgctg atggcttctc agcctcctac aagaccctgc cgcggggcac tgccaaagaa | 900 |
| gggcaagggc ccggcccaa acggggaact gagcctaaag tcaagctgcc ccccaagtcc | 960 |
| caacctccgg agaaaacaga ggaatctcct tcagcccctg atgcacccac ctgcccaaag | 1020 |
| cagtgccgcc ggacaggcac cttgcagagc aacttctgtg ccagcagcct tgtggtgact | 1080 |
| gcgacagtga agtccatggt tcgggagcca ggggagggcc ttgccgtgac tgtcagtctt | 1140 |
| attggtgctt ataaaactgg aggactggac ctgccaactc cacccactgg tgcctccctg | 1200 |
| aagttttacg tgccttgcaa gcagtgcccc cccatgaaga aggagtcag ttatctgctg | 1260 |
| atgggccagg tagaagagaa cagaggcccc gtccttcctc cagagagctt tgtggttctc | 1320 |
| caccggccca accaggacca gatcctcacc aacctaagca agaggaagtg cccctctcaa | 1380 |
| cctgtgcggg ctgctgcgtc ccaggactga gacgcaggcc agccccggcc cctagccctc | 1440 |
| aggcctctct tcttatccaa ataaatgttt cttaatgaaa | 1480 |

<210> SEQ ID NO 40
<211> LENGTH: 6378
<212> TYPE: DNA
<213> ORGANISM: Homo sapiens

<400> SEQUENCE: 40

| | |
|---|---|
| cccattactg ttggagctac agggagagaa acaggaggag actgcaagag atcatttggg | 60 |
| aaggccgtgg gcacgctctt tactccatgt gtgggacatt cattgcggaa taacatcgga | 120 |
| ggagaagttt cccagagcta tggggacttc ccatccggcg ttcctggtct taggctgtct | 180 |
| tctcacaggg ctgagcctaa tcctctgcca gctttcatta ccctctatcc ttccaaatga | 240 |
| aaatgaaaag gttgtgcagc tgaattcatc cttttctctg agatgctttg gggagagtga | 300 |
| agtgagctgg cagtaccccca tgtctgaaga agagagctcc gatgtggaaa tcagaaatga | 360 |
| agaaaacaac agcggccttt ttgtgacggt cttggaagtg agcagtgcct cggcggccca | 420 |
| cacaggttg tacacttgct attacaacca cactcagaca gaagagaatg agcttgaagg | 480 |
| caggcacatt tacatctatg tgccagaccc agatgtagcc tttgtacctc taggaatgac | 540 |
| ggattattta gtcatcgtgg aggatgatga ttctgccatt ataccttgtc gcacaactga | 600 |
| tcccgagact cctgtaacct tacacaacag tgagggggtg gtacctgcct cctacgacag | 660 |
| cagacagggc tttaatggga ccttcactgt agggccctat atctgtgagg ccaccgtcaa | 720 |
| aggaaagaag ttccagacca tcccatttaa tgtttatgct ttaaaagcaa catcagagct | 780 |
| ggatctagaa atggaagctc ttaaaaccgt gtataagtca ggggaaacga ttgtggtcac | 840 |
| ctgtgctgtt tttaacaatg aggtggttga ccttcaatgg acttaccctg agaagtgaa | 900 |
| aggcaaaggc atcacaatgc tggaagaaat caaagtccca tccatcaaat ggtgtacac | 960 |
| tttgacggtc cccgaggcca cggtgaaaga cagtggagat tacgaatgtg ctgcccgcca | 1020 |
| ggctaccagg gaggtcaaag aaatgaagaa agtcactatt tctgtccatg agaaaggttt | 1080 |
| cattgaaatc aaacccacct tcagccagtt ggaagctgtc aacctgcatg aagtcaaaca | 1140 |
| ttttgttgta gaggtgcggg cctacccacc tcccaggata tcctggctga aaaacaatct | 1200 |
| gactctgatt gaaaatctca ctgagatcac cactgatgtg gaaaagattc aggaaataag | 1260 |
| gtatcgaagc aaattaaagc tgatccgtgc taaggaagaa gacagtggcc attatactat | 1320 |

```
tgtagctcaa aatgaagatg ctgtgaagag ctatactttt gaactgttaa ctcaagttcc    1380
ttcatccatt ctggacttgg tcgatgatca ccatggctca actggggac agacggtgag    1440 gtgcacagct gaaggcacgc cgcttcctga tattgagtgg atgatatgca agatattaa    1500 gaaatgtaat aatgaaactt cctggactat tttggccaac aatgtctcaa acatcatcac    1560
ggagatccac tcccgagaca ggagtaccgt ggagggccgt gtgactttcg ccaaagtgga    1620
ggagaccatc gccgtgcgat gcctggctaa gaatctcctt ggagctgaga accgagagct    1680
gaagctggtg gctcccaccc tgcgttctga actcacggtg gctgctgcag tcctggtgct    1740
gttggtgatt gtgatcatct cacttattgt cctggttgtc atttggaaac agaaaccgag    1800
gtatgaaatt cgctggaggg tcattgaatc aatcagcccg gatggacatg aatatattta    1860
tgtggacccg atgcagctgc cttatgactc aagatgggga tttccaagag atggactagt    1920
gcttggtcgg gtcttggggt ctggagcgtt tgggaaggtg gttgaaggaa cagcctatgg    1980
attaagccgg tcccaacctg tcatgaaagt tgcagtgaag atgctaaaac ccacggccag    2040
atccagtgaa aaacaagctc tcatgtctga actgaagata atgactcacc tggggccaca    2100
tttgaacatt gtaaacttgc tgggagcctg caccaagtca ggccccattt acatcatcac    2160
agagtattgc ttctatggag atttggtcaa ctatttgcat aagaataggg atagcttcct    2220
gagccaccac ccagagaagc caaagaaaga gctggatatc tttggattga accctgctga    2280
tgaaagcaca cggagctatg ttattttatc ttttgaaaac aatggtgact acatggacat    2340
gaagcaggct gatactacac agtatgtccc catgctagaa aggaaagagg tttctaaata    2400
ttccgacatc cagagatcac tctatgatcg tccagcctca tataagaaga atctatgtt    2460 agactcagaa gtcaaaaacc tcctttcaga tgataactca gaaggcctta ctttattgga    2520
tttgttgagc ttcacctatc aagttgcccg aggaatggag ttttggctt caaaaaattg    2580 tgtccaccgt gatctggctg ctcgcaacgt cctcctggca caaggaaaaa ttgtgaagat    2640
ctgtgacttt ggcctggcca gagacatcat gcatgattcg aactatgtgt cgaaaggcag    2700
tacctttctg cccgtgaagt ggatggctcc tgagagcatc tttgacaacc tctacaccac    2760
actgagtgat gtctggtctt atggcattct gctctgggag atcttttccc ttggtggcac    2820
cccttacccc ggcatgatgg tggattctac tttctacaat aagatcaaga gtgggtaccg    2880
gatggccaag cctgaccacg ctaccagtga agtctacgag atcatggtga atgctggaa    2940 cagtgagccg gagaagagac cctccttta ccacctgagt gagattgtgg agaatctgct    3000
gcctggacaa tataaaaaga gttatgaaaa aattcacctg gacttcctga agagtgacca    3060
tcctgctgtg gcacgcatgc gtgtggactc agacaatgca tacattggtg tcacctacaa    3120
aaacgaggaa gacaagctga aggactggga gggtggtctg gatgagcaga gactgagcgc    3180
tgacagtggc tacatcattc ctctgcctga cattgaccct gtccctgagg aggaggacct    3240
gggcaagagg aacagacaca gctcgcagac ctctgaagag agtgccattg agacgggttc    3300
cagcagttcc accttcatca agagagagga cgagaccatt gaagacatcg acatgatgga    3360
cgacatcggc atagactctt cagacctggt ggaagacagc ttcctgtaac tggcggattc    3420
gaggggttcc ttccacttct ggggccacct ctggatcccg ttcagaaaac cactttattg    3480
caatgcggag gttgagagga ggacttggtt gatgtttaaa gagaagttcc cagccaaggg    3540
cctcggggag cgttctaaat atgaatgaat gggatatttt gaaatgaact tgtcagtgt    3600 tgcctctcgc aatgcctcag tagcatctca gtggtgtgtg aagtttggag atagatggat    3660
aagggaataa taggccacag aaggtgaact ttgtgcttca aggacattgg tgagagtcca    3720
```

```
acagacacaa tttatactgc gacagaactt cagcattgta attatgtaaa taactctaac    3780
caaggctgtg tttagattgt attaactatc ttctttggac ttctgaagag accactcaat    3840
ccatccatgt acttccctct tgaaacctga tgtcagctgc tgttgaactt tttaaagaag    3900
tgcatgaaaa accattttg aaccttaaaa ggtactggta ctatagcatt ttgctatctt    3960
ttttagtgtt aagagataaa gaataataat taaccaacct tgtttaatag atttgggtca    4020
tttagaagcc tgacaactca ttttcatatt gtaatctatg tttataatac tactactgtt    4080
atcagtaatg ctaaatgtgt aataatgtaa catgatttcc ctccagagaa agcacaattt    4140
aaaacaatcc ttactaagta ggtgatgagt ttgacagttt ttgacattta tattaaataa    4200
catgtttctc tataaagtat ggtaatagct ttagtgaatt aaatttagtt gagcatagag    4260
aacaaagtaa aagtagtgtt gtccaggaag tcagaatttt taactgtact gaataggttc    4320
cccaatccat cgtattaaaa aacaattaac tgccctctga ataatgggga ttagaaacaa    4380
acaaaactct taagtcctaa aagttctcaa tgtagaggca taaacctgtg ctgaacataa    4440
cttctcatgt atattaccca atggaaaata taatgatcag caaaaagact ggatttgcag    4500
aagttttttt tttttttctt catgcctgat gaaagctttg caaccccaa tatatgtatt    4560 ttttgaatct atgaacctga aaagggtcag aaggatgccc agacatcagc ctccttcttt    4620 cacccccttac cccaaagaga aagagtttga aactcgagac cataaagata ttctttagtg    4680
gaggctggat gtgcattagc ctggatcctc agttctcaaa tgtgtgtggc agccaggatg    4740
actagatcct gggtttccat ccttgagatt ctgaagtatg aagtctgagg gaaaccagag    4800
tctgtatttt tctaaactcc ctggctgttc tgatcggcca gttttcggaa acactgactt    4860
aggtttcagg aagttgccat gggaaacaaa taatttgaac tttggaacag ggttggaatt    4920
caaccacgca ggaagcctac tatttaaatc cttggcttca ggttagtgac atttaatgcc    4980
atctagctag caattgcgac cttaatttaa cttttccagtc ttagctgagg ctgagaaagc    5040
taaagtttgg ttttgacagg ttttccaaaa gtaaagatgc tacttcccac tgtatgggggg    5100 agattgaact ttcccccgtct cccgtcttct gcctcccact ccatacccccg ccaaggaaag    5160 gcatgtacaa aaattatgca attcagtgtt ccaagtctct gtgtaaccag ctcagtgttt    5220
tggtggaaaa aacattttaa gttttactga taatttgagg ttagatggga ggatgaattg    5280
tcacatctat ccacactgtc aaacaggttg gtgtgggttc attggcattc tttgcaatac    5340
tgcttaattg ctgataccat atgaatgaaa catgggctgt gattactgca atcactgtgc    5400
tatcggcaga tgatgctttg gaagatgcag aagcaataat aaagtacttg actacctact    5460
ggtgtaatct caatgcaagc cccaactttc ttatccaact ttttcatagt aagtgcgaag    5520
actgagccag attggccaat taaaaacgaa aacctgacta ggttctgtag agccaattag    5580
acttgaaata cgtttgtgtt tctagaatca cagctcaagc attctgttta tcgctcactc    5640
tcccttgtac agccttattt tgttggtgct ttgcattttg atattgctgt gagccttgca    5700
tgacatcatg aggccggatg aaacttctca gtccagcagt ttccagtcct aacaaatgct    5760
cccacctgaa tttgtatatg actgcatttg tgggtgtgtg tgtgttttca gcaaattcca    5820
gatttgtttc cttttggcct cctgcaaagt ctccagaaga aaatttgcca atctttccta    5880 cttttctattt ttatgatgac aatcaaagcc ggcctgagaa acactatttg tgactttta    5940 aacgattagt gatgtcctta aaatgtggtc tgccaatctg tacaaaatgg tcctattttt    6000
gtgaagaggg acataagata aaatgatgtt atacatcaat atgtatatat gtatttctat    6060
atagacttgg agaatactgc caaaacattt atgacaagct gtatcactgc cttcgtttat    6120
```

-continued

| | |
|---|---|
| attttttttaa ctgtgataat ccccacaggc acattaactg ttgcactttt gaatgtccaa | 6180 |
| aatttatatt ttagaaataa taaaaagaaa gatacttaca tgttcccaaa acaatggtgt | 6240 |
| ggtgaatgtg tgagaaaaac taacttgata gggtctacca atacaaaatg tattacgaat | 6300 |
| gccctgttc atgtttttgt tttaaaacgt gtaaatgaag atctttatat ttcaataaat | 6360 |
| gatatataat ttaaagtt | 6378 |

<210> SEQ ID NO 41
<211> LENGTH: 2075
<212> TYPE: DNA
<213> ORGANISM: Homo sapiens

<400> SEQUENCE: 41

| | |
|---|---|
| gggaatgtaa gatggcggag tagcaacgca aagcgcttgg tattgagtct gtggccgact | 60 |
| tcggttccgg tctctgcagc agccgtgatc gcttagtgga gtgcttaggg tagttggcca | 120 |
| ggatgccgaa tatcaaaatc ttcagcggca gctcccacca ggacttatct cagaaaattg | 180 |
| ctgaccgcct gggcctggag ctaggcaagg tggtgactaa gaaattcagc aaccaggaga | 240 |
| cctgtgtgga aattggtgaa agtgtacgtg gagaggatgt ctacattgtt cagagtggtt | 300 |
| gtggcgaaat caatgacaat ttaatggagc ttttgatcat gattaatgcc tgcaagattg | 360 |
| cttcagccag ccgggttact gcagtcatcc atgcttccc ttatgcccgg caggataaga | 420 |
| aagataagag ccgggcgcca atctcagcca agcttgttgc aaatatgcta tctgtagcag | 480 |
| gtgcagatca tattatcacc atggacctac atgcttctca aattcaggc ttttttgata | 540 |
| tcccagtaga caatttgtat gcagagccgg ctgtcctaaa gtggataagg gagaatatct | 600 |
| ctgagtggag gaactgcact attgtctcac ctgatgctgg tggagctaag agagtgacct | 660 |
| ccattgcaga caggctgaat gtggactttg ccttgattca caagaacgg aagaaggcca | 720 |
| atgaagtgga ccgcatggtg cttgtgggag atgtgaagga tcgggtggcc atccttgtgg | 780 |
| atgacatggc tgacacttgt ggcacaatct gccatgcagc tgacaaactt ctctcagctg | 840 |
| gcgccaccag agtttatgcc atcttgactc atggaatctt ctccggtcct gctatttctc | 900 |
| gcatcaacaa cgcatgcttt gaggcagtag tagtcaccaa taccatacct caggaggaca | 960 |
| agatgaagca ttgctccaaa atacaggtga ttgacatctc tatgatcctt gcagaagcca | 1020 |
| tcaggagaac tcacaatgga gaatccgttt cttacctatt cagccatgtc cctttataat | 1080 |
| agagtaactt ctgaggcttt tgagaataa aatccacccc accttgtttt ccccttggta | 1140 |
| tttgatgaca aattcagcag aagacccggc ttgctccagt gtagctttct acatcccaca | 1200 |
| tcaggtatat tagagcttat ccgaactggg gaaagacgga ttgagattaa ctgctgggac | 1260 |
| ctcctacctg cattatctca ttctggcttc cttgataatt ctgtgggcct tgcagcttta | 1320 |
| actatagctc agctgctgca agatttcaga cttttgagga tgttgtgtga gggtgtttga | 1380 |
| ctgtgactgg ggaagctcag actactttgt atgtgaatgc ttcagggttt ctttgttga | 1440 |
| gaacaactag caacaaaggc aacccatgtg tgaccagttc tccccaaggt ctatgctaaa | 1500 |
| ttatagcaag agccctgggc aaccccaaac ctagtcctgg tagctgagca ccctgtaagg | 1560 |
| caggagcagg cagctcagct tgagcagaca ttgggtgggg ggtggggggt ggttgagggg | 1620 |
| ggaggcagca cagtgcagca aatgtttctt gggaggaaga agcctgatcc atcaccatct | 1680 |
| gcttgactat gtagcttgga ttctcctttg tacctatccc tttcgatttg gctttacctt | 1740 |
| catctatctt gatcctttcc tggccaaata tcctcttggg cccaaatgaa cattgtacca | 1800 |
| tagtcttctg gaaagcaaac atgcttcctg ctatgtaatt gctaacattc atattagatg | 1860 |

-continued

| atgtgctgta gcttgatctt ccttagccta ctgccactga ggcagtaggt tttaggtggt | 1920 |
| atcgtagtgc cttttgatta atttaagtat ttaattttca tcttccttct ttggatctat | 1980 |
| ttggcctctc aaatgaactg agattcctgt taaaaaagat tgatgttatt gtctcttgta | 2040 |
| gaggaaacta ataaagtgtg tgtacctgtg tgaat | 2075 |

<210> SEQ ID NO 42
<211> LENGTH: 2457
<212> TYPE: DNA
<213> ORGANISM: Homo sapiens

<400> SEQUENCE: 42

| cgctgttgcc tccgccacct cctccgccgc cgcgcgcccc tcggagttcc gcgccccacc | 60 |
| atgcccaaca tcgtgctgtt cagcggcagc tcgcatcagg acctatccca gcgcgtggcc | 120 |
| gaccgcctgg gcctggagct gggcaaggtg gtcacgaaga agttcagcaa ccaggagacc | 180 |
| agcgtggaga ttggtgaaag cgtgagaggg aagatgtctc acatcatcca gagcggctgc | 240 |
| ggggaaatta acgacaacct gatggaactc ctcatcatga tcaatgcctg caagattgcg | 300 |
| tcatcatcca gagtaactgc cgtgatcccg tgtttcccat acgccgacaa agataaaaag | 360 |
| gacaagagtc gtgccccaat ttctgcaaaa cttgtggcca atatgctgtc ggtggctggg | 420 |
| gcggatcaca tcatcaccat ggacctgcat gcttctcaga tacagggatt ctttgatatt | 480 |
| cctgtggata atttgtatgc ggagcccgca gtcctgcagt ggattcggga aacattgcc | 540 |
| gagtggaaga actgtatcat tgtttcacct gacgcagggg gagccaaaag ggttacatca | 600 |
| attgcagaca ggttgaatgt ggaatttgct tgatccaca agagaggaa gaaggcgaat | 660 |
| gaagtggacc ggatggtcct ggtgggcgac gtgaaggacc gtgtggccat cctcgtggat | 720 |
| gacatggctg acacttgcgg caccatctgc catgctgcgg acaagctgct gtcagctgga | 780 |
| gccaccaaag tgtatgctat ccttacccat gggatcttct ctggaccagc tatttccaga | 840 |
| ataaataatg ccgcctttga ggctgttgtc gtcacaaaca caattccgca agaggacaaa | 900 |
| atgaaacact gcaccaagat tcaggtcatt gacatttcca tgatcttggc cgaagcaatc | 960 |
| cgaaggacac acaatgggga atccgtgtcc tacctgttca gccatgtccc gctataaatc | 1020 |
| cagaatggga agtgtccagc aagcctactc tgacttctga cttgtttttg ttttctggat | 1080 |
| ttttagctgt aggtattcag caatgatagg ttaatcactg gcaaaagcat cagatctttg | 1140 |
| tatatgctaa gatttattgt ttcccttct aaagctcaag atcatttctt tccagttttt | 1200 |
| ggggaaatgg tggtggttat ttggtcttta agtgaactgt cttaaatgag aaacgttttt | 1260 |
| gtcattttga cttttaacag gtacaggtga tctcttcctt tgttctttca gtactttgag | 1320 |
| gcgacaactt tcaagtatat aatttcattg tggaagtcat agtttatata tttcgaggtt | 1380 |
| gccaaaggtg acttcacatt aaagccttct gtgtaaatat atactgataa tgcctatgga | 1440 |
| catttgggta aaaccctgta tagaattaat tatccttta cttggagtg aaccttggaa | 1500 |
| aatttataat tataataacca tggattttga atttttcttt ttttttttt ttttttggata | 1560 |
| actcagtttc agataaaacca tcttggttac tgtgcttaat ttggaccaaa ttttatttag | 1620 |
| cttaatatgg acactgacac attttggggg gtatacatta gacatatcag agcagtgtat | 1680 |
| ttctggatca tttttttaaat gacctcttct aaaacataac tgtcacttac ctgaaatgct | 1740 |
| gcatcctaaa attccaaaat tatattgagc aatcgccaag gcctaaagcc aactgactta | 1800 |
| aagtaatca tttcagctaa gattaaattt aaagcctaag aatgtataga gctagttta | 1860 |
| aaataatgat ctcagatttt taaaaaggat ataggaacct gcattgtcat tctctgaatt | 1920 |

```
aagaactgat ggtttctatc attatttagc cccacctttg tatttttaaaa tccttcagaa   1980 tacatttatg aaccaatgcg actggactta gccacacaca atggaaattc agaccttgac   2040
tatttggtgt ttccagttca caaaggtgat gaagactgtc ttgggagcag cttaatccca   2100
aaatttgtac atttcttgct gctcctggcg tggaaactta agtgagacca ccaaatacat   2160
tggtcctgtc caattctact gaatgggggt ggacctggca tttatctggc caaaaacagg   2220
agccagagaa atatgaatat accaaagttg tttgtttagc ctccaactta aattacatta   2280
gtcaacttat agatactcat atgatcactt ttcttttag atactacatc aactagattc   2340
aggagtatat catttgcagt gcttgtattg gtttaaaatg taagatttta agatcctcta   2400
acactgtact aaaacatttc aataaaatca ttctgactgc gttcaaaaaa aaaaaaa     2457
```

<210> SEQ ID NO 43
<211> LENGTH: 1550
<212> TYPE: DNA
<213> ORGANISM: Homo sapiens

<400> SEQUENCE: 43

```
gtggcctacc atggtttcaa cgggtaacgg ggaataaggg ttcgattcgg agctgcggga     60
gccgggctgg caggagcagg atggcggcgg cggcggctgc aggcgaggcg cgccgggtgc    120
tggtgtacgg cggcaggggc gctctgggtt ctcgatgcgt gcaggctttt cgggcccgca    180
actggtgggt tgccagcgtt gatgtggtgg agaatgaaga ggccagcgct acgatcattg    240
ttaaaatgac agactcgttc actgagcagg ctgaccaggt gactgctgag gttggaaagc    300
tcttgggtga agagaaggtg gatgcaattc tttgcgttgc tggaggatgg gccggggggca   360 atgccaaatc caagtctctc tttaagaact gtgacctgat gtggaagcag agcatatgga   420
catcgaccat ctccagccat ctggctacca agcatctcaa ggaaggaggc ctcctgacct   480
tggctggcgc aaaggctgcc ctggatggga ctcctggtat gatcgggtac ggcatggcca   540
agggtgctgt tcaccagctc tgccagagcc tggctgggaa gaacagcggc atgccgcccg   600
gggcagccgc catcgctgtg ctcccggtta ccctggatac cccgatgaac aggaaatcaa   660
tgcctgaggc tgacttcagc tcctggacac ccttagaatt cctagttgaa actttccatg   720
actggatcac agggaaaaac cgaccgagct caggaagcct aatccaggtg gtaaccacag   780
aaggaaggac ggaactcacc ccagcatatt tttaggcctc atctcagtgc ctatgagggg   840
cctgccagaa aagtcactaa cctgtctcag tgtggccttg tccagccttg tgttttctgt   900
aacccctgtt tgtggtacga gataatgagt cctattttttc tctcacataa tatgcatttg   960
ctctcctagg gacaagtgta atacattat gtgaagtaag acaatgcgag actggtggcc    1020
gtcaaatagc atccgtcaat ctgtgttaac tgcataggag gctctcgata gcacctgcta   1080
tagcggtgtc atgttggatc gctttgtgac tgttcatctg tccttgacag tggctgtcat   1140
cttgactact ttgttgattt gttggtattg gggcattttt aaaggctgag ttattttttga  1200 atgtcatgtt tatgtcatag acgtagaaaa cgcatccttg aattaaactg ccttaactcc   1260
ttttgtggta taagcaaact acatggactc tgtccctggt atcctttttcc tgtgtggttg   1320 cccctgtgcc tgtggtctgg cctaggttaa gtgtgcaaga taactactcg tgagttattc   1380
agaatgttgt tcctaataaa tgcacttgtt gtctgtcttc tttaatcaaa tcacatctta   1440
tatacagcag tcagagatga gtatactaga atcatggatt gctggaggtc ttttaatctg   1500
atgttctcag aaggggggtgg attaaatcc tgaaataaat atttcaacac                1550
```

<210> SEQ ID NO 44
<211> LENGTH: 1179
<212> TYPE: DNA
<213> ORGANISM: Homo sapiens

<400> SEQUENCE: 44

| | | | | | |
|---|---|---|---|---|---|
| gaattcggca | cgaggcggtt | agacatgggc | actccacaga | aggatgttat | tatcaagtca | 60 |
| gatgcaccgg | acactttgtt | attggagaaa | catgcagatt | atatcgcatc | ctatggctca | 120 |
| aagaaagatg | attatgaata | ctgtatgtct | gagtatttga | aatgagtgg | catctattgg | 180 |
| ggtctgacag | taatggatct | catgggacaa | cttcatcgca | tgaatagaga | agagattctg | 240 |
| gcatttatta | agtcttgcca | acatgaatgt | ggtggaataa | gtgctagtat | cggacatgat | 300 |
| cctcatcttt | tatacactct | tagtgctgtc | cagattctta | cgctgtatga | cagtattaat | 360 |
| gttattgacg | taaataaagt | tgtggaatat | gttaaaggtc | tacagaaaga | agatggttct | 420 |
| tttgctggag | atatttgggg | agaaattgac | acaagattct | cttttttgtgc | ggtggcaact | 480 |
| ttggctttgt | tggggaagct | tgatgctatt | aatgtggaaa | aggcaatcga | atttgtttta | 540 |
| tcctgtatga | actttgacgg | tggatttggt | tgcagaccag | ttctgaatc | ccatgctggg | 600 |
| cagatctatt | gttgcacagg | atttctggct | attacaagtc | agttgcatca | agtaaattct | 660 |
| gatttacttg | gctggtggct | ttgtgaacga | caattaccct | caggcgggct | caatggaagg | 720 |
| ccggagaagt | taccagatgt | atgctactca | tggtgggtcc | tggcttccct | aaagataatt | 780 |
| ggaagacttc | attggattga | tagagagaaa | ctgcgtaatt | tcattttagc | atgtcaagat | 840 |
| gaagaaacgg | ggggatttgc | agacaggcca | ggagatatgg | tggatccttt | tcatacctta | 900 |
| tttggaattg | ctggattgtc | acttttggga | gaagaacaga | ttaaacctgt | taatcctgtc | 960 |
| ttttgcatgc | ctgaagaagt | gcttcagaga | gtgaatgttc | agcctgagct | agtgagctag | 1020 |
| attcattgaa | ttgaaagttg | catagtatag | ttttgccatt | taacatttc | tgtatttgaa | 1080 |
| gtgcttatcg | aatctaaaag | tgactactgt | taatattttg | tatattgtgt | taaattaatt | 1140 |
| ttaataaatt | atataattat | gcatattgta | aaataaaaa | | | 1179 |

<210> SEQ ID NO 45
<211> LENGTH: 3524
<212> TYPE: DNA
<213> ORGANISM: Homo sapiens

<400> SEQUENCE: 45

| | | | | | |
|---|---|---|---|---|---|
| tctccgtcag | ccgcattgcc | cgctcggcgt | ccggcccccg | acccgtgctc | gtccgcccgc | 60 |
| ccgcccgccc | gcccgcgcca | tgaacgccaa | ggtcgtggtc | gtgctggtcc | tcgtgctgac | 120 |
| cgcgctctgc | ctcagcgacg | ggaagccgt | cagcctgagc | tacagatgcc | catgccgatt | 180 |
| cttcgaaagc | catgttgcca | gagccaacgt | caagcatctc | aaaattctca | acactccaaa | 240 |
| ctgtgccctt | cagattgtag | cccggctgaa | gaacaacaac | agacaagtgt | gcattgaccc | 300 |
| gaagctaaag | tggattcagg | agtacctgga | gaaagcttta | aacaagaggt | tcaagatgtg | 360 |
| agagggtcag | acgcctgagg | aacccttaca | gtaggagccc | agctctgaaa | ccagtgttag | 420 |
| ggaagggcct | gccacagcct | cccctgccag | ggcagggccc | caggcattgc | caagggcttt | 480 |
| gttttgcaca | ctttgccata | ttttcaccat | ttgattatgt | agcaaaatac | atgcacattta | 540 |
| tttttcattt | agtttgatta | ttcagtgtca | ctggcgacac | gtagcagctt | agactaaggc | 600 |
| cattattgta | cttgccttat | tagagtgtct | ttccacggag | ccactcctct | gactcagggc | 660 |
| tcctgggttt | tgtattctct | gagctgtgca | ggtggggaga | ctgggctgag | ggagcctggc | 720 |

```
cccatggtca gccctagggt ggagagccac caagagggac gcctgggggt gccaggacca      780
gtcaacctgg gcaaagccta gtgaaggctt ctctctgtgg gatgggatgg tggagggcca      840
catgggaggc tcaccccctt ctccatccac atgggagccg ggtctgcctc ttctggagg       900 gcagcagggc taccctgagc tgaggcagca gtgtgaggcc agggcagagt gagacccagc      960
cctcatcccg agcacctcca catcctccac gttctgctca tcattctctg tctcatccat     1020
catcatgtgt gtccacgact gtctccatgg ccccgcaaaa ggactctcag gaccaaagct     1080
ttcatgtaaa ctgtgcacca agcaggaaat gaaaatgtct tgtgttacct gaaaacactg     1140
tgcacatctg tgtcttgtgt ggaatattgt ccattgtcca atcctatgtt tttgttcaaa     1200
gccagcgtcc tcctctgtga ccaatgtctt gatgcatgca ctgttccccc tgtgcagccg     1260
ctgagcgagg agatgctcct tgggcccttt gagtgcagtc ctgatcagag ccgtggtcct     1320
ttggggtgaa ctaccttggt tcccccactg atcacaaaaa catggtgggt ccatgggcag     1380
agcccaaggg aattcggtgt gcaccagggt tgacccagga ggattgctgc cccatcagtg     1440
ctccctcaca tgtcagtacc ttcaaactag gccaagccc agcactgctt gaggaaaaca      1500
agcattcaca acttgttttt ggttttaaa acccagtcca caaataacc aatcctggac       1560 atgaagattc tttcccaatt cacatctaac ctcatcttct tcaccatttg gcaatgccat     1620
catctcctgc cttcctcctg ggccctctct gctctgcgtg tcacctgtgc ttcgggccct     1680
tcccacagga catttctcta agagaacaat gtgctatgtg aagagtaagt caacctgcct     1740
gacatttgga gtgttcccct cccactgagg gcagtcgata gagctgtatt aagccactta     1800
aaatgttcac ttttgacaaa ggcaagcact tgtgggtttt tgttttgttt ttcattcagt     1860
cttacgaata cttttgccct ttgattaaag actccagtta aaaaaatttt taatgaagaa     1920
agtggaaaac aaggaagtca aagcaaggaa actatgtaac atgtaggaag taggaagtaa     1980
attatagtga tgtaatcttg aattgtaact gttcgtgaat ttaataatct gtagggtaat     2040
tagtaacatg tgttaagtat tttcataagt atttcaaatt ggagcttcat ggcagaaggc     2100
aaacccatca acaaaaattg tcccttaaac aaaaattaaa atcctcaatc cagctatgtt     2160
atattgaaaa aatagagcct gagggatctt tactagttat aaagatacag aactctttca     2220
aaaccttttg aaattaacct ctcactatac cagtataatt gagttttcag tggggcagtc     2280
attatccagg taatccaaga tatttttaaaa tctgtcacgt agaacttgga tgtacctgcc     2340
cccaatccat gaaccaagac cattgaattc ttggttgagg aaacaaacat gaccctaaat     2400
cttgactaca gtcaggaaag gaatcatttc tatttctcct ccatgggaga aaatagataa     2460
gagtagaaac tgcagggaaa attatttgca taacaattcc tctactaaca atcagctcct     2520
tcctggagac tgcccagcta aagcaatatg catttaaata cagtcttcca tttgcaaggg     2580
aaaagtctct tgtaatccga atctcttttt gctttcgaac tgctagtcaa gtgcgtccac     2640
gagctgttta ctagggatcc ctcatctgtc cctccgggac ctggtgctgc ctctacctga     2700
cactcccttg ggctccctgt aacctcttca gaggccctcg ctgccagctc tgtatcagga     2760
cccagaggaa ggggccagag gctcgttgac tggctgtgtg ttgggattga gtctgtgcca     2820
cgtgtatgtg ctgtggtgtg tcccctctg tccaggcact gagataccag cgaggaggct      2880
ccagagggca ctctgcttgt tattagagat tacctcctga gaaaaagct tccgcttgga      2940 gcagagggc tgaatagcag aaggttgcac ctcccccaac cttagatgtt ctaagtcttt      3000
ccattggatc tcattggacc cttccatggt gtgatcgtct gactggtgtt atcaccgtgg     3060
gctccctgac tgggagttga tcgcctttcc caggtgctac accctttccc agctggatga    3120
```

-continued

| | |
|---|---|
| gaatttgagt gctctgatcc ctctacagag cttccctgac tcattctgaa ggagccccat | 3180 |
| tcctgggaaa tattccctag aaacttccaa atccccctaag cagaccactg ataaaaccat | 3240 |
| gtagaaaatt tgttattttg caacctcgct ggactctcag tctctgagca gtgaatgatt | 3300 |
| cagtgttaaa tgtgatgaat actgtatttt gtattgtttc aagtgcatct cccagataat | 3360 |
| gtgaaaatgg tccaggagaa ggccaattcc tatacgcagc gtgctttaaa aaataaataa | 3420 |
| gaaacaactc tttgagaaac aacaatttct actttgaagt cataccaatg aaaaaatgta | 3480 |
| tatgcactta aattttcct aataaagttc tgtactcaaa tgta | 3524 |

<210> SEQ ID NO 46
<211> LENGTH: 2038
<212> TYPE: DNA
<213> ORGANISM: Homo sapiens

<400> SEQUENCE: 46

| | |
|---|---|
| gcaggcccgt tggaagtggt tgtgacaacc ccagcaatgt ggagaagcct ggggcttgcc | 60 |
| ctggctctct gtctcctccc atcgggagga acagagagcc aggaccaaag ctccttatgt | 120 |
| aagcaacccc cagcctggag cataagagat caagatccaa tgctaaactc caatggttca | 180 |
| gtgactgtgg ttgctcttct tcaagccagc tgatacctgt gcatcatcga ggcatctaaa | 240 |
| ttagaagacc tgcgagtaaa actgaagaaa gaaggatatt ctaatatttc ttatattgtt | 300 |
| gttaatcatc aaggaatctc ttctcgatta aaatacacac atcttaagaa taaggtttca | 360 |
| gagcatattc ctgtttatca acaagaagaa aaccaaacag atgtctggac tcttttaaat | 420 |
| ggaagcaaag atgacttcct catatatgat agatgtggcc gtcttgtata tcatcttggt | 480 |
| ttgcctttt ccttcctaac tttcccatat gtagaagaag ccattaagat tgcttactgt | 540 |
| gaaaagaaat gtggaaactg ctctctcacg actctcaaag atgaagactt ttgtaaacgt | 600 |
| gtatctttgg ctactgtgga taaaacagtt gaaactccat cgcctcatta ccatcatgag | 660 |
| catcatcaca atcatggaca tcagcacctt ggcagcagtg agctttcaga gaatcagcaa | 720 |
| ccaggagcac caaatgctcc tactcatcct gctcctccag gccttcatca ccaccataag | 780 |
| cacaagggtc agcataggca gggtcaccca gagaaccgag atatgccagc aagtgaagat | 840 |
| ttacaagatt tacaaaagaa gctctgtcga aagagatgta taaatcaatt actctgtaaa | 900 |
| ttgcccacag attcagagtt ggctcctagg agctgatgct gccattgtcg acatctgata | 960 |
| tttgaaaaaa cagggtctgc aatcacctga cagtgtaaag aaaacctccc atctttatgt | 1020 |
| agctgacagg gacttcgggc agaggagaac ataactgaat cttgtcagtg acgtttgcct | 1080 |
| ccagctgcct gacaaataag tcagcagctt atacccacag aagccagtgc cagttgacgc | 1140 |
| tgaaagaatc aggcaaaaaa gtgagaatga ccttcaaact aaatatttaa aataggacat | 1200 |
| actccccaat ttagtctaga cacaatttca tttccagcat tttataaaac taccaaatta | 1260 |
| gtgaaccaaa aatagaaatt agatttgtgc aaacatggag aaatctactg aattggcttc | 1320 |
| cagattttaa attttatgtc atagaaatat tgactcaaac catatttttt atgatggagc | 1380 |
| aactgaaagg tgattgcagc ttttggttaa tatgtctttt tttttctttt tccagtgttc | 1440 |
| tatttgcttt aatgagaata gaaacgtaaa ctatgaccta ggggttttct gttggataat | 1500 |
| tagcagttta gaatggagga agaacaacaa agacatgctt tccattttt cctttactta | 1560 |
| tctctcaaaa caatattact ttgtcttttc aatcttctac ttttaactaa taaaataagt | 1620 |
| ggatttgta ttttaagatc cagaaatact taacacgtga atatttgct aaaaaagcat | 1680 |
| atataactat tttaaatatc catttatctt ttgtatatct aagactcatc ctgattttta | 1740 |

-continued

| | |
|---|---|
| ctatcacaca tgaataaagg cctttgtatc tttctttctc taatgttgta tcatactctt | 1800 |
| ctaaaacttg agtggctgtc ttaaaagata taaggggaaa gataatattg tctgtctcta | 1860 |
| tattgcttag taagtatttc catagtcaat gatggtttaa taggtaaacc aaaccctata | 1920 |
| aacctgacct cctttatggt taatactatt aagcaagaat gcagtacaga attggataca | 1980 |
| gtacggattt gtccaaataa attcaataaa aaccttaaaa aaaaaaaaa aaaaaaaa | 2038 |

<210> SEQ ID NO 47
<211> LENGTH: 2588
<212> TYPE: DNA
<213> ORGANISM: Homo sapiens

<400> SEQUENCE: 47

| | |
|---|---|
| gaattcgccg gtccagcctc ctctgggagc gggcagttgg cgaccctgca ctgacccgcg | 60 |
| tccctccgtc ccgagcccgc gcgccctcag agggtgcccg gacagactga agccatggcg | 120 |
| attcttttg ctgttgttgc caggggggacc actatccttg ccaaacatgc ttggtgtgga | 180 |
| ggaaacttcc tggaggtgac agagcagatt ctggctaaga taccttctga aaataacaaa | 240 |
| ctaacgtact cacatggcaa ttatttgttt cattacatct gccaagacag gattgtatat | 300 |
| cttttgtatca ctgatgatga ttttgaacgt tcccgagcct ttaattttct gaatgagata | 360 |
| aagaagaggt tccagactac ttacggttca agagcacaga cagcacttcc atatgccatg | 420 |
| aatagcgagt tctcaagtgt cttagctgca cagctgaagc atcactctga gaataagggc | 480 |
| ctagacaaag tgatggagac tcaagcccaa gtggatgaac tgaaaggaat catggtcaga | 540 |
| aacatagatc tggtagctca gcgaggagaa agattggaat tattgattga caaaacagaa | 600 |
| aatcttgtgg attcttctgt caccttcaaa actaccagca gaaatcttgc tcgagccatg | 660 |
| tgtatgaaga acctcaagct cactattatc atcatcatcg tatcaattgt gttcatctat | 720 |
| atcattgttt cacctctctg tggtggattt acatggccaa gctgtgtgaa gaaataggaa | 780 |
| agaagaagtt accattaacc aaggatatga gagaacaagg agttaaaagc aatccatgtg | 840 |
| actcaagcct ttcacatact gacagatggt atctgccagt ctcttcaacc ctcttctcac | 900 |
| ttttttaaaat cttgttccat gcctccaggt ttatctttgt cttatctacc agtttattcc | 960 |
| tgtgaacttc agattgaacc attcattgca gcagtagcct taaaaaggct tttgtttatt | 1020 |
| tctttggtttt gttaactagt gtcatctatt tagagaaaca ttttgttttt taattgctca | 1080 |
| aagctgtcgc cgctagtctt atgagctatc tactaaaact atggagaaac tttgtatgtg | 1140 |
| cacacaaaag tattcaagag acagtattgc taacatctca tcttaatgtc ttttgttatt | 1200 |
| gagaagtttt aggtgcttca aaacaatata aatggataat agttgttatt tggggaattg | 1260 |
| taatgatgtt ggtgctgctt ccttctaaga gctcagacaa gtaaagtatg aaacattctt | 1320 |
| atttcagtta gatggggaac attttgctag cccattagaa gcacacagaa ttatccttgt | 1380 |
| cctcctaata ttgactttca ggaataaagt tcagtgtgct gatcattcac aatacagtgg | 1440 |
| atagcttgat atcttctgtt tcccattgc agttgatttg agaagatgaa ggtttaaata | 1500 |
| ttgttgaaag ttgcagtttt ttaaatgtgt tccttttct tctgtgaata tttagggcaa | 1560 |
| tcgtgtcgct aatagaatat gtagtagagg gggtggggag gtaaattcct ctgacttgcc | 1620 |
| aaagaaaaag aagggaacca cagtggatat gctagcattt tagctgtgca aagggaggta | 1680 |
| gtgtgggaaa agtgtttcca ttctgggaaa agcccaaacc gaatacggtc agcagtcaac | 1740 |
| tccagggttt gggcttgatt cctgttgaat aatagttttg agcattcttt gtggttaaat | 1800 |
| aaattcttaa atctgcctag ttttgatgaa ttcttttgtg aaacttgaaa gagaatagac | 1860 |

-continued

| | |
|---|---|
| agtatgacat atagaattaa tacaaaacag tttaacaacc atttaactgc agtgtaagaa | 1920 |
| aattggactg taatcatatc gctactggca tctgttatct agtatgcatt tctggtgtgt | 1980 |
| atctgaaagg aagacatttt ctaccctaga tccaattgca tttatttatc aataagtgcc | 2040 |
| attaaattga aattatatta cattttacac tttctcaatg aatgaacaaa ttagtctgta | 2100 |
| gaatctagcc acctgtttag cctagtcatg tgccttgaac atatatgtgt cccataatct | 2160 |
| ggctcatggt acctgttctt ctatccaaac ctttcaattc atgctacctg attcatttat | 2220 |
| ttgacataga tcttaggccc acttgaactc ttttcttgtt tatctagcat agcacaaacg | 2280 |
| tttttccagt cttctttatc aacactaatg cctcttaatt gcatcagtat ttcctattgg | 2340 |
| aaaatacatc tgttccagaa aaacatttgg cattcctgaa taatttccaa atgttttttaa | 2400 |
| tccaaagaaa aaggttttaaa gcttatttcc ctttcttata cacacctgaa taaaattgat | 2460 |
| gtgcatgttt tagggatcaa ttacctaact gttccttggt ctatttatgt ataagaatgc | 2520 |
| ttttttaaagc acatgtctca ttttaaatga cgcacaaact gaagatgtta ataaaattta | 2580 |
| aggaattc | 2588 |

<210> SEQ ID NO 48
<211> LENGTH: 7888
<212> TYPE: DNA
<213> ORGANISM: Homo sapiens

<400> SEQUENCE: 48

| | |
|---|---|
| tccgggtatg gatgtcaatc ttttgtctac aatgtgaata catttatcct tcggggacca | 60 |
| tcaagacttt caggaaaggc cccgcctgtc tctgcgcggc cactttgctg ggacaaaggt | 120 |
| caactgaaga agtgggcagg cccgaggcag gagagatgct gaggagtcca tgtgcagggg | 180 |
| agggaaaggg agaggcagtc agggagagga ggaggaggta ccgccagaag gggatcctcc | 240 |
| cgctccgaaa accagacacc gggtcttgcc ctgtggtcca ggcaggagtg cagtggtgca | 300 |
| acctcagctc actgcagcct tgacctcccc gggctcaagc gatcctccgg ccacagcact | 360 |
| tggctgttca gcggctggag gagcagggcc ccaggtcctc cccaccctca cctgctgctc | 420 |
| ccaggtcgtg gccgtcttgc tcttccaggt ccttctctag ggatgcaata ttcacattgc | 480 |
| taagatgcag gtctaacgca gaacctgtca acagagcccc ccatcatcca cagcccaccc | 540 |
| agcgctgcag agctcaggaa gcctagctga ggaggacgac cgtcccacct gggcttagag | 600 |
| tgagaccaag ggcagaaggc gtgggagttc tgggcagc cagggaagga cccccccagc | 660 |
| ccgtcctcgc agcccccac aggcagtggg aggcttggct gttcctccgg caaaacgggc | 720 |
| atgctcagtg ggccgggccg gcaggtttgc gtggccgctg agttgccggc gccggctgag | 780 |
| ccagcggacg ccgcgttcct tggcggccgc cggttcccgg gaagttacgt ggcgaagccg | 840 |
| gcttccgagg agacgccggg aggccacggg tgctgctgac gggcgggcga ccgggcgagg | 900 |
| ccgacgtggc cgggctgcga aagctgcggg aggccgagtg ggtgaccgcg ctcggaggga | 960 |
| ggtgccggtc gggcgcgccc cgtggagaag acccgggcgg ggcgggcgct tcccggactt | 1020 |
| ttgtccgagt tgaattccct cccctgggc cgggccttc cgtccgcccc cgcccgtgcc | 1080 |
| ccgctcgctc tcgggagatg tttatttggg ctgtggcgtg aggagcgggc gggccagcgc | 1140 |
| cgcggagttt cgggtccgag gagcctcgcg cggcgctgga gagagacaag atgtccgcca | 1200 |
| gagctgcggc cgccaagagc acagcaatgg aggaaacagc tatatgggaa caacatacag | 1260 |
| tgacgcttca cagggctcct ggatttggat ttggaattgc aatatctggt ggacgagata | 1320 |
| atcctcattt tcagagtggg gaaacgtcaa tagtgatttc agatgtgctg aaaggaggac | 1380 |

-continued

```
cagctgaagg acagctacag gaaaatgacc gagttgcaat ggttaacgga gtttcaatgg   1440
ataatgttga acatgctttt gctgttcagc aactaaggaa aagtgggaaa aatgcaaaaa   1500
ttacaattag aaggaagaag aaagttcaaa taccagtaag tcgtcctgat cctgaaccag   1560
tatctgataa tgaagaagat agttatgatg aggaaataca tgatccaaga agtggccgga   1620
gtggtgtggt taacagaagg agtgagaaga tttggccgag ggatagaagt gcaagtagag   1680
agaggagctt gtccccgcgg tcagacaggc ggtcagtggc ttccagccag cctgctaaac   1740
ctactaaagt cacactggtg aaatcccgga aaaatgaaga atatggtctt cgattggcaa   1800
gccatatatt tgttaaggaa atttcacaag atagtttggc agcaagagat ggcaatattc   1860
aagaaggtga tgttgtattg aagataaatg gtactgtgac agaaaatatg tcattgacag   1920
atgcaaagac attgatagaa aggtctaaag gcaaattaaa aatggtagtt caaagagatg   1980
aacgggctac gctattgaat gtccctgatc tttctgacag catccactct gctaatgcct   2040
ctgagagaga cgacatttca gaaattcagt cactggcatc agatcattct ggtcgatcac   2100
acgataggcc tccccgccgc agccggtcac gatctcctga ccagcggtca gagccttctg   2160
atcattccag gcactcgccg cagcagccaa gcaatggcag tctccggagt agagatgaag   2220
agagaatttc taaacctggg gctgtctcaa ctcctgtaaa gcatgctgat gatcacacac   2280
ctaaaacagt ggaagaagtt acagttgaaa gaaatgagaa acaaacacct tctcttccag   2340
aaccaaagcc tgtgtatgcc caagttggca accagatgtg gatttacctg tcagtccatc   2400
tgatggtgtc ctacctaatt caactcatga agatgggatt tcttcggccc agcatgaaat   2460
tggtaaaatt cagaaaagga gatagtgtgg gtttgcggct ggctggtgga aatgatgttg   2520
gaatatttgt agctggcgtt ctagaagata gccctgcagc caaggaaggc ttagaggaag   2580
gtgatcaaat tctcagggta aacaacgtag attttacaaa tatcataaga gaagaagccg   2640
tccttttcct gcttgacctc cctaaaggag aagaagtgac catattggct cagaagaaga   2700
aggatgttta tcgtcgcatt gtagaatcag atgtaggaga ttctttctat attagaaccc   2760
attttgaata tgaaaaggaa tctccctatg gacttagttt taacaaagga gaggtgttcc   2820
gtgctgtgga taccttgtac aatggaaaac tgggctcttg gcttgctatt cgaattggta   2880
aaaatcataa ggaggtagaa cgaggcatca tccctaataa gaacagagct gagcagctag   2940
ccagtgtaca gtatacactt ccaaaaacag caggcggaga ccgtgctgac ttctggagat   3000
tcagaggtct tcgcagctcc aagagaaatc ttcgaaaaag cagagaggat ttgtccgctc   3060
agcctgttca aacaaagttt ccagcttatg aaagagtggt tcttcgagaa gctggatttc   3120
tgaggcctgt aaccattttt ggaccaatag ctgatgttgc cagagaaaag ctggcaagag   3180
aagaaccaga tatttatcaa attgcaaaga gtgaaccacg agacgctgga actgaccaac   3240
gtagctctgg ctatattcgc ctgcatacaa taaagcaaat catagatcaa gacaaacatg   3300
ctttattaga gtgtaacacca aatgcagttg atcgtcttaa ctatgcccag tggtatccaa   3360
ttgttgtatt tcttaaccct gattctaagc aaggagtaaa acaatgagaa atgaggttat   3420
gtccagaatc tcggaaaagt gccaggaagt tatacgagcg atctcataaa cttgctaaaa   3480
ataatcacca tctttttaca actacaatta acttaaattc aatgaatgat ggttggtatg   3540
gtgcgctgaa agaagcagtt caacaacagc aaaaccagct ggtatgggtt ccgagggaa   3600 aggcggatgg tgctacaagt gatgaccttg atttgcatga tgatcgtctg tcctacctgt   3660
cagctccagg tagtgaatac tcaatgtata gcacggacta gacacacact tctgactatg   3720
aagacacaga cacagaaggc ggggcctaca ctgatcaaga actagatgaa actcttaatg   3780
```

```
atgaggttgg gactccaccg gagtctgcca ttacacggtc ctctgagcct gtaagagagg   3840
actcctctgg aatgcatcat gaaaaccaaa catatcctcc ttactcacca caagcgcagc   3900
cacaaccaat tcatagaata gactcccctg gatttaagcc agcctctcaa cagaaagcag   3960
aagcttcatc tccagtccct tacctttcgc ctgaaacaaa cccagcatca tcaacctctg   4020
ctgttaatca taatgtaaat ttaactaatg tcagactgga ggagcccacc ccagctcctt   4080
ccacctctta ctcaccacaa gctgattctt taagaacacc aagtactgag gcagctcaca   4140
taatgctaag agatcaagaa ccatcattgt cgtcgcatgt agatccaaca aaggtgtata   4200
gaaaggatcc atatcccgag gaaatgatga ggcagaacca tgttttgaaa cagccagccg   4260
ttagtcaccc agggcacagg ccagacaaag agcctaatct gacctatgaa ccccaactcc   4320
catacgtaga gaaacaagcc agcagagacc tcgagcagcc cacatacaga tacgagtcct   4380
caagctatac ggaccagttt tctcgaaact atgaacatcg tctgcgatac gaagatcgcg   4440
tccccatgta tgaagaacag tggtcatatt atgatgacaa acagccctac ccatctcggc   4500
caccttttga taatcagcac tctcaagacc ttgactccag acagcatccc gaagagtcct   4560
cagaacgagg gtactttcca cgttttgaag agccagcccc tctgtcttac gacagcagac   4620
cacgttacga acaggcacct agagcatccg ccctgcggca cgaagagcag ccagctcctg   4680
ggtatgacac acatggtaga ctcagaccgg aagcccagcc ccaccttca gcagggccca    4740 agcctgcaga gtccaagcag tattttgagc aatattcacg cagttacgag caagtaccac   4800
cccaaggatt tacctctaga gcaggtcatt ttgagcctct ccatggtgct gcagctgtcc   4860
ctccgctgat accttcatct cagcataagc cagaagctct gccttcaaac accaaaccac   4920
tgcctccacc cccaactcaa accgaagaag aggaagatcc agcaatgaag ccacagtctg   4980 tactccaccag agttaagatg tttgaaaaca aagatctgc atccttagag accaagaagg    5040
atgtaaatga cactggcagt tttaagcctc cagaagtagc atctaaacct tcaggtgctc   5100
ccatcattgg tcccaaaccc acttctcaga atcaattcag tgaacatgac aaaactctgt   5160
acaggatccc agaacctcaa aaacctcaac tgaagccacc tgaagatatt gttcggtcca   5220
atcattatga ccctgaagaa gatgaagaat attatcgaaa acagctgtca tactttgacc   5280
gaagaagttt tgagaataag cctcctgcac acattgctgc cagccatctc tccgagcctg   5340
caaagccagc tcattctcag aatcaatcaa atttttctag ttattcttca aagggaaagc   5400
ctcctgaagc tgatggtgtg gatagatcat ttggcgagaa acgctatgaa cccatccagg   5460
ccactccccc tcctcctcca ttgccctcgc agtatgccca gccatctcag cctgtcacca   5520
gcgcgtctct ccacatacat tctaagggag cacatggtga aggtaattca gtgtcattgg   5580
attttcagaa ttccttagtg tccaaaccag acccacctcc atctcagaat aagccagcaa   5640
ctttcagacc accaaaccga gaagatactg ctcaggcagc tttctatccc cagaaaagtt   5700
ttccagataa agcccagtt aatggaactg aacagactca gaaaacagtc actccagcat    5760
acaatcgatt cacaccaaaa ccatatacaa gttctgcccg accatttgaa cgcaagtttg   5820
aaagtcctaa attcaatcac aatcttctgc caagtgaaac tgcacataaa cctgacttgt   5880
cttcaaaaac tcccacttct ccaaaaactc ttgtgaaatc gcacagtttg gcacagcctc   5940
ctgagtttga cagtggagtt gaaactttct ctatccatgc agagaagcct aaatatcaaa   6000
taaataatat cagcacagtg cctaaagcta ttcctgtgag tccttcagct gtggaagagg   6060
atgaagatga agatggtcat actgtggtgg ccacagcccg aggcatattt aacagcaatg   6120
ggggcgtgct gagttccata gaaactggtg ttagtataat tatccctcaa ggagccattc   6180
```

-continued

```
ccgaaggagt tgagcaggaa atctatttca aggtctgccg ggacaacagc atccttccac    6240
ctttagataa agagaaaggt gaaacactgc tgagtccttt ggtgatgtgt ggtccccatg    6300
gcctcaagtt cctgaagcct gtggagctgc gcttaccaca ctgtgatcct aaaacctggc    6360
aaaacaagtg tcttcccgga gatccaaatt atctcgttgg agcaaactgt gtttctgtcc    6420
ttattgacca cttttaactc ttgaaatata ggaacttaaa taatgtgaaa ctggattaaa    6480
cttaatctaa atgaaccac tctatcaagt attataccttt ttagagtt gatactacag     6540 tttgttagta tgaggcattt gtttgaactg ataaagatga gtgagcatgc ccctgaacca    6600
tggtcggaaa acatgctaca cactgcatgt ttgtgattga cgggactgtt ggtattggct    6660
agaggttcaa agatattttg ctttgtgatt tttgtaattt ttttatcgtc actgcttaac    6720
ttcacatatt gatttccgtt aaaataccag ccagtaaatg ggggtgcatt tgaggtctgt    6780
tctttccaaa gtacactgtt tcaaacttta ctatggccct ggcctagcat acgtacacat    6840
tttattttat tatgcatgaa gtaatatgca cacattttt aaatgcacct ggaatatata    6900
accagtgttg tggatttaac agaaatgtac agcaaggaga tttacaactg ggggagggtg    6960
aagtgaagac aatgacttac tgtacatgaa aacacatttt tcttagggaa ggatacaaaa    7020
gcatgtgaga ctggttccat ggcctcttca gatctctaac ttcaccatat taccacagac    7080
atactaacca gcagaaatgc cttaccctca tgttcttaat tcttagctca ttctccttgt    7140
gttactaagt ttttatggct tttgtgcatt atctagatac tgtatcatga caaagactga    7200
gtacgttgtg catttggtgg tttcagaaat gtgttatcac ccagaagaaa atagtggtgt    7260
gatttgggga tattttttc ttttcttttc tttctttttt tttttttttt tgacaagggg     7320
cagtggtggt tttctgttct ttctggctat gcatttgaaa atttttgatgt tttaaggatg    7380 cttgtacata atgcgtgcat accacttttg ttcttggttt gtaaattaac ttttataaac    7440
tttacctttt ttatacataa acaagaccac gtttctaaag gctaccttg tattctctcc     7500 tgtacctctt gagccttgaa ctttgacctc tgcagcaata aagcagcgtt tctatgacac    7560
atgcaaggtc attttttta agaaaaagga tgcacagagt tgttacattt ttaagtgctg     7620
catttaaaag atacagttac tcagaattct ctagtttgat taaattcttg caaagtatcc    7680
ctactgtaat ttgtgataca atgctgtgcc ctaaagtgta ttttttttact aatagacaat   7740 ttattatgac acatcagcac gatttctgtt taaataatac accactacat tctgttaatc    7800
attaggtgtg actgaatttc ttttgccgtt attaaaaatc tcaaatttct aaatctccaa    7860
aataaaactt tttaaaataa aaaaaaat                                       7888
```

<210> SEQ ID NO 49
<211> LENGTH: 5503
<212> TYPE: DNA
<213> ORGANISM: Homo sapiens
<220> FEATURE:
<221> NAME/KEY: Unsure
<222> LOCATION: (2083)..(2083)
<223> OTHER INFORMATION: n = a, c, g or t/u

<400> SEQUENCE: 49

```
ggtgcgctca ggactggaag caactctcag ttcatcaatt tcatgggcct acgtatctgc      60
tctggccacg gcctggcctc catccccact gtggcattaa tgcagaacaa attgagacat     120
atcctctata taattagttc cagaatttaa aaagatttac ggtataataa tagaggcagt     180
gccgcggaat cctttcactg aggactctcg gggagctcgg ggaccatctc gcggtggcat     240
cagaacagac gagtaacccc agcggctcca ggcactgcga actgggggag agggggaaat    300
```

-continued

```
tttgcaccgc attcggcagt acctaacggt tccgggctcc cagataggt cagcgaggag      360
agttaggaca gtaagtgggg actggttaaa aaaaatcgac ttaattttga aatgatcaga      420
agaagctggg agtagttatc acaaagcccc tcccttgccc cccctttttt ttaattgaag      480
gaatgacgtt gaaattttca ccgccagcgc ggggctggga accatcctaa acacttgccc      540
tgcagccccg agtgggcaga ttccgaagag ttggagtcgg cggggagggg aggaacagct      600
gttgggctgt cttgcgcgtg gggctcgggg cgcgggcccc ggggagaggc gctagtcgaa      660
agcttgttcc tctcccgcga caggcagcag cgaggtcgag ccactcttta ttacggcctg      720
cgggccccgc gcgcagtgtg gctgtccccg cccttgaccg accgcagcgc tttggggtgt      780
ttattcagtt gtccgcggcc gctgggtgac tcccggaggc ggcccaggcg tgcgcactgg      840
tccctggggt tgcggctgta gcagcccagc tccgcgctct gtcagatgca gtggacagcg      900
ccggggtgaa agtaagggtt gagaaatcct cactgccctg ctcctaccca gcctcgattt      960
tttcatattg caataattat gccacttcga ggccgggatg cctgcgcttt gccagtgtat     1020
caacgccaca tggttttcca ggggctgtcc tcgcctctgc atcccattag ctctgaagag     1080
gtagagggg ggtgggtaaa acctccaact ggacgttgag agacccgggt ttcagctcgg      1140
cgttgccact aacttgtttc ctgtccttaa acagtagtag taacaaaaac tgtaaagttg     1200
attgagtcaa aggcccacac tgctctccta tctaatcctc agaacaactc tatgaggtgg     1260
gcgctagtat cccattatcc cgtttgacca gtaaggaaac tgaggctcag agagactgcg     1320
gaactcgtct agggtcacac agctgttggt tacctggcag agctgaggtt ccattctggg     1380
gccaccaacc ccttgctctt tacgtgcgct ccatagactg cctctccttc ggctgtctgg     1440
gcctcagttt ccttctctgt aaaacgagaa gtttaatctg cagcttcttt tgccaatcgg     1500
tggttcagac caggaacctc tgctacagat ctcggcgctg acagggtaa gaaggtgggt      1560
gaaagaaggg ggcgcccagt tttccacagc ctgctttct ctgggacctc gcgaagggcg      1620
ggcctcgcga gctaaaggag gtacaggaga gcgcctatcg tccgcggcgg gtgaaggtgc     1680
tacctgcctt cgtgctaggc tgtgagtcct ggtgcttagc tcaggcgcc aaggccagtg      1740
tagctggcat gtcccccttg gaaaacctca ggtctcccgc agagaacgtt acccacaaca     1800
aagaagagga cagagaggca tggagcgccc tgcgactgca ggagtacgtc agttccccag     1860
cgctggctta gtgtcgcctg gcttccggg catgtggatc cgttgggtc gtacggagac       1920
ttcctgtcgg gtccctgggg tcctccgact gcggctcctc agcttagcac tttcttcttg     1980
gccccgcagg ctgcagggaa ctcctcccac ctctttagtc ggagaagtcc aagtcgggcg     2040
aggggggcacc ccgggggttcg caccggtgct cttcccctcc ccnccccccac aaggattctg   2100
agaaaataaa tggcagagga gagaggagtt ctacatttgc ttggctctcc tttcctccta     2160
tccacccta catccctcac cccggnncaa aaacttatttt ttgaaaaatg ttggcagaga     2220
tttacgtgtc tttgccttac ctgggtttca caaacacaac gactcacatt caagccagcc     2280
tcccttcaga taacctcctc tcccccgct aaaagtgcca aggatggtaa agaagaaac       2340
aatctcaatc ttttcgtttg gaaatgaaag tccccggctt ttcataaagg ctcctcgcc     2400
cctcacagtt gagtcctagt taagaaaaac gacttccaag tagaaataat aggcggggag    2460
aaggaaggga gatacaggga tctgggngnt tcttagggca actggcagtg aattttgtct    2520
cgagagtcct ttctccactc aaaaaaaccaa acgcgcgagc cccgcgaaag gtttagggat    2580
agatcgtgtg ggagaggact gagcagagag cgtggggca gtgtcttgta gaatcttct      2640
tttcttaata ataattttaa aagcttctga gtggagacga cgcaaagtca agcagcaaag    2700
```

-continued

```
gtggcctggg aggcaagcgg agggctcaag tgccgcatct ttacccctcag ggtctcctgc    2760
gcctacggga tgcgcattcc caagaagtgc gcccttcgag taagtcctgg gcccgcacac    2820
acttcgggtc cgcagccaga atttaatggc gacaacgttt atgcaatgca agctaaaaac    2880
caaagcgtaa aaaattacta tgtcatttat tgaaacgcca ttctttgtca aactgcaact    2940
actttgcttc acataagttt ggctggaaag cttgcagccc cagcccgggc cagccaggta    3000
caggaggccg gactgcaacc ggttgcttcc ctcccgtcgc cctggccgt cccacgctgc    3060
gccgtcgctg ctgcctcctg cgcccctggg gattttatac gcacctctga aacacgctcc    3120
gctccggccc ccggttcttc tccttgccta ggggttgttt cccaatagat actgactcct    3180
ttagaagatc caaaaaccaa accaaaacac cccctacccg ccccaaacac ctgctctggg    3240
gcgcggggc tgccaaacag agactagacg aagggagtca gatttagcga agctcttcga    3300
gctcccaaag attcgaacac taactcgcgc ccgtgggccg atggaggttc tccctactcc    3360
actccttggt cccctaact ggcttncgcc tcctggtcaa tcactgagca accagaatgg    3420
tatcctcgac cagggccaca ggcagtgctc ggcggagtgg ctccaggagt tacccgctcc    3480
ctgccgggct tcgtatccaa acctccct tcacccctcc tccccaaact gggcgccagg    3540
atgctccggc cggaatatac gcaggctttg ggcgtttgcc caagggtttt cttccctcct    3600
aaactagccg ctgttttccc ggcttaaccg tagaagaatt agatattcct cactggaaag    3660
ggaaactaag tgctgctgac tccaatttta ggtaggcggc aaccgccttc cgcctggngn    3720
aaacctcacc aagtaaacaa ctactagccg atcgaaatac gcccggctta taactggtgc    3780
aactcccggc cacccaactg agggacgttc gctttcagtc ccgacctctg gaacccacaa    3840
agggccacct ctttccccag tgaccccaag atcatggcca ctcccctacc cgacagttct    3900
agaagcaaga gccagactca agggtgcaaa gcaagggnat acgcttcttt gaagcttgac    3960
tgagttcttt ctgcgctttc ctgaagttcc cgccctcttg gagcctacct gcccctccct    4020
ccaaaccact cttttagatt aacaacccca tctctactcc caccgcattc gaccctgccc    4080
ggactcactg cttacctgaa cgactctcca gtgagacgag gctcccacac tggcgaaggc    4140
caagaagggg aggtggggg agggttgtgc cacaccggcc agctgagagc gcgtgttggg    4200
ttgaagagga gggtgtctcc gagagggacg ctccctcgga cccgcccctca ccccagctgc    4260
gagggcgccc ccaaggagca gcgcgcgctg cctggccggg cttgggctgc tgagtgaatg    4320
gagcggccga gcctcctggc tcctcctctt ccccgcgccg ccggcccctc ttatttgagc    4380
tttgggaagc tgagggcagc caggcagctg gggtaaggag ttcaaggcag cgcccacacc    4440
cgggggctct ccgcaacccg accgcctgtc cgctcccca cttcccgccc tccctcccac    4500
ctactcattc acccacccac ccacccagag ccgggacggc agcccaggcg cccgggcccc    4560
gccgtctcct cgccgcgatc ctggacttcc tcttgctgca ggacccggct tccacgtgtg    4620
tcccggagcc ggcgtctcag cacacgctcc gctccgggct tgggtgccta cagcagccag    4680
agcagcaggg agtccgggac ccggcggca tctgggccaa gttaggcgcc gccgaggcca    4740
gcgctgaacg tctccaggggc cggaggagcc gcggggcgtc cgggtctgag cctcagcaaa    4800
tgggctccga cgtgcgggac ctgaacgcgc tgctgcccgc cgtcccctcc ctgggtggcg    4860
gcggcggctg tgcctgcct gtgagcggcg cggcgcagtg ggcgccggtg ctggactttg    4920
cgccccgg cgcttcggct tacgggtcgt tgggcggccc cgcgccgcca ccggctccgc    4980
cgccacccc gccgccgccg cctcactcct tcatcaaaca ggagccgagc tgggcggcg    5040
cggagccgca cgaggagcag tgcctgagcg ccttcactgt ccacttttcc ggccagttca    5100
```

-continued

| | |
|---|---|
| ctggcacagc cggagcctgt cgctacgggc ccttcggtcc tcctccgccc agccaggcgt | 5160 |
| catccggcca ggccaggatg tttcctaacg cgccctacct gcccagctgc ctcgagagcc | 5220 |
| agcccgctat tcgcaatcag ggtaagtagg ccggggagcg ccccctacgc gcggggcagt | 5280 |
| ggcgccaggg actctccgct ctaggacacc cccctctcct accccttttg accgcagctc | 5340 |
| ttacccagct gcttcccaag ggccgtgagg atagcggaag cggcggctgg ggaggaggcc | 5400 |
| ggagagtggg agtgcacgca ggcactggcc cccgacatcc tccaaagcca ggcagagcta | 5460 |
| ggagcctgac tgttcgcaag agccgggagg gcgtctgggg ccc | 5503 |

<210> SEQ ID NO 50
<211> LENGTH: 1860
<212> TYPE: DNA
<213> ORGANISM: Homo sapiens

<400> SEQUENCE: 50

| | |
|---|---|
| gggacgtgag ccgctgcgcc caccgggcta gacccggcgc catcatgctg cttctgccaa | 60 |
| gcgccgcgga cggccggggc accgccatca cccacgctct gacctctgcc tctacactct | 120 |
| gtcaagttga acctgtggga agatggtttg aagcttttgt taagaggaga aacagaaatg | 180 |
| cttctgcctc ttttcaggaa ctggaggata agaaagagtt atccgaggaa tcagaagatg | 240 |
| aagaattgca gttggaagag tttcccatgc tgaaaacact tgatcccaaa gactggaaga | 300 |
| accaagatca ttatgcagtt cttggacttg ccatgtgaga tacaaggct acacagagac | 360 |
| agatcaaagc agctcataaa gcaatggttt taaaacatca cccagacaaa cggaaagcag | 420 |
| ctggtgaacc aataaaagaa ggagataatg actacttcac ttgcataact aaagcttatg | 480 |
| aaatgttatc tgatccagtg aaaagacgag catttaacag tgtagatcct acttttgata | 540 |
| actcagttcc ttctaaaagt gaagcaaagg ataatttctt cgaagtgttt accccagtgt | 600 |
| ttgaaaggaa ttccagatgg tcaaataaaa aaaatgttcc taaacttggt gatatgaatt | 660 |
| catcatttga agatgtagat atattttatt ctttctggta aattttgat tcttggagag | 720 |
| aattttctta tttagatgaa gaagaaaaag aaaaagcaga atgtcgtgat gagaggagat | 780 |
| ggattgaaaa gcagaacgga gcaacaagag cacaaagaaa aaagaagaa atgaacagaa | 840 |
| taagaacatt agttgacaat gcatacagct gtgatccaag gataaaaaag ttcaaggaag | 900 |
| aagaaaaagc caagaaagaa gcagaaaaga agcaaaaagc agaagctaaa cggaaggagc | 960 |
| aagaagctaa agaaaaacaa agacaagctg aattagaagc tgctcggtta gctaaggaga | 1020 |
| aagaagagga ggaagtcaga cagcaagcat tgctggcaaa gaaggaaaaa gatatccaga | 1080 |
| aaaaagccat taagaaggaa aggcaaaaac ttcgaaactc atgcaagata gaagaaataa | 1140 |
| atgagcaaat cagaaaagag aaagaggaag ctgaggctcg tatgcgacaa gcatctaaga | 1200 |
| acacagagaa atcaactggt ggaggtggaa atggaagtaa aaattggtca gaagatgatc | 1260 |
| tacaattact aattaaagct gtgaatctgt tccctgctaa aacaaattca agatgggaag | 1320 |
| ttattgctaa ttacatgaac atacattctt cctctggagt caaagaact gccaaagatg | 1380 |
| ttattggcaa agcaaagagt ctccaaaaac ttgaccctca tcaaaagat gacataaata | 1440 |
| aaaaggcatt tgataagttc aaaaaagaac atggagtggt acctcaagca gacaacgcaa | 1500 |
| cgccttcaga acgatttgaa ggtccatata cagacttcac cccttggaca acagaagaac | 1560 |
| agaagctttt ggaacaagct ttgaaaacat acccagtaaa tacacctgaa agatgggaaa | 1620 |
| aaatagcaga agcggtgcct ggcaggacaa agaaggactg catgaaacga tacaaggaac | 1680 |
| ttgtcgagat ggtaaaagca agaaaagctg ctcaagaaca agtgctgaat gcaagtagag | 1740 |

-continued

```
ccaagaaatg acaatctttg ttgtgtgtgc atttttataa taaaactgaa aatactgtaa     1800
acatttcat tcttaaaatt atactcatgg taataatttg aaagtaaaaa aaaaaaaaa       1860
```

<210> SEQ ID NO 51
<211> LENGTH: 729
<212> TYPE: PRT
<213> ORGANISM: Homo sapiens

<400> SEQUENCE: 51

```
Met His Leu Lys Ile Val Leu Ala Phe Leu Ala Leu Ser Leu Ile Thr
1               5                   10                  15

Ile Phe Ala Leu Ala Tyr Val Leu Leu Thr Ser Pro Gly Gly Ser Ser
            20                  25                  30

Gln Pro Pro His Cys Pro Ser Val Ser His Arg Ala Gln Pro Trp Pro
        35                  40                  45

His Pro Gly Gln Ser Gln Leu Phe Ala Asp Leu Ser Arg Glu Glu Leu
    50                  55                  60

Thr Ala Val Met Arg Phe Leu Thr Gln Arg Leu Gly Pro Gly Leu Val
65                  70                  75                  80

Asp Ala Ala Gln Ala Gln Pro Ser Asp Asn Cys Ile Phe Ser Val Glu
                85                  90                  95

Leu Gln Leu Pro Pro Lys Ala Ala Leu Ala His Leu Asp Arg Gly
            100                 105                 110

Ser Pro Pro Pro Ala Arg Glu Ala Leu Ala Ile Val Leu Phe Gly Gly
        115                 120                 125

Gln Pro Gln Pro Asn Val Ser Glu Leu Val Val Gly Pro Leu Pro His
    130                 135                 140

Pro Ser Tyr Met Arg Asp Val Thr Val Glu Arg His Gly Gly Pro Leu
145                 150                 155                 160

Pro Tyr His Arg Arg Pro Val Leu Arg Ala Glu Phe Thr Gln Met Trp
                165                 170                 175

Arg His Leu Lys Asp Val Glu Leu Pro Lys Ala Pro Ile Phe Leu Ser
            180                 185                 190

Ser Thr Phe Asn Tyr Asn Gly Ser Thr Leu Ala Ala Val His Ala Thr
        195                 200                 205

Pro Arg Gly Leu Arg Ser Arg Glu Arg Thr Thr Trp Ile Gly Leu Tyr
    210                 215                 220

His Asn Ile Ser Gly Val Gly Leu Phe Leu His Pro Val Gly Leu Glu
225                 230                 235                 240

Leu Leu Leu Asp His Arg Ala Leu Asp Pro Ala His Trp Thr Val Gln
                245                 250                 255

Gln Val Phe Tyr Leu Gly His Tyr Tyr Ala Asp Leu Gly Gln Leu Glu
            260                 265                 270

Arg Glu Phe Lys Ser Gly Arg Leu Glu Val Val Arg Val Pro Leu Pro
        275                 280                 285

Pro Pro Asn Gly Ala Ser Ser Leu Arg Ser Arg Asn Ser Pro Gly Pro
    290                 295                 300

Leu Pro Pro Leu Gln Phe Ser Pro Gln Gly Ser Gln Tyr Ser Val Gln
305                 310                 315                 320

Gly Asn Leu Val Val Ser Ser Leu Trp Ser Phe Thr Phe Gly His Gly
                325                 330                 335

Val Phe Ser Gly Leu Arg Ile Phe Asp Val Arg Phe Gln Gly Glu Arg
            340                 345                 350
```

```
Ile Ala Tyr Glu Val Ser Val Gln Glu Cys Val Ser Ile Tyr Gly Ala
            355                 360                 365

Asp Ser Pro Lys Thr Met Leu Thr Arg Tyr Leu Asp Ser Ser Phe Gly
        370                 375                 380

Leu Gly Arg Asn Ser Arg Gly Leu Val Arg Gly Val Asp Cys Pro Tyr
385                 390                 395                 400

Gln Ala Thr Met Val Asp Ile His Ile Leu Val Gly Lys Gly Ala Val
                405                 410                 415

Gln Leu Leu Pro Gly Ala Val Cys Val Phe Glu Glu Ala Gln Gly Leu
            420                 425                 430

Pro Leu Arg Arg His His Asn Tyr Leu Gln Asn His Phe Tyr Gly Gly
        435                 440                 445

Leu Ala Ser Ser Ala Leu Val Val Arg Ser Val Ser Ser Val Gly Asn
450                 455                 460

Tyr Asp Tyr Ile Trp Asp Phe Val Leu Tyr Pro Asn Gly Ala Leu Glu
465                 470                 475                 480

Gly Arg Val His Ala Thr Gly Tyr Ile Asn Thr Ala Phe Leu Lys Gly
                485                 490                 495

Gly Glu Glu Gly Leu Leu Phe Gly Asn Arg Val Gly Glu Arg Val Leu
            500                 505                 510

Gly Thr Val His Thr His Ala Phe His Phe Lys Leu Asp Leu Asp Val
        515                 520                 525

Ala Gly Leu Lys Asn Trp Val Ala Glu Asp Val Val Phe Lys Pro
            530                 535                 540

Val Ala Ala Pro Trp Asn Pro Glu His Trp Leu Gln Arg Pro Gln Leu
545                 550                 555                 560

Thr Arg Gln Val Leu Gly Lys Glu Asp Leu Thr Ala Phe Ser Leu Gly
                565                 570                 575

Ser Pro Leu Pro Arg Tyr Leu Tyr Leu Ala Ser Asn Gln Thr Asn Ala
            580                 585                 590

Trp Gly His Gln Arg Gly Tyr Gln Leu Val Val Thr Gln Arg Lys Glu
        595                 600                 605

Glu Glu Ser Gln Ser Ser Ile Tyr His Gln Asn Asp Ile Trp Thr
            610                 615                 620

Pro Thr Val Thr Phe Ala Asp Phe Ile Asn Asn Glu Thr Leu Leu Gly
625                 630                 635                 640

Glu Asp Leu Val Ala Trp Val Thr Ala Ser Phe Leu His Ile Pro His
                645                 650                 655

Ala Glu Asp Ile Pro Asn Thr Val Thr Leu Gly Asn Arg Val Gly Phe
            660                 665                 670

Leu Leu Arg Pro Tyr Asn Phe Phe Asp Glu Asp Pro Ser Ile Phe Ser
        675                 680                 685

Pro Gly Ser Val Tyr Phe Glu Lys Gly Gln Asp Ala Gly Leu Cys Ser
            690                 695                 700

Ile Asn Pro Val Ala Cys Leu Pro Asp Leu Ala Ala Cys Val Pro Asp
705                 710                 715                 720

Leu Pro Pro Phe Ser Tyr His Gly Phe
                725

<210> SEQ ID NO 52
<211> LENGTH: 885
<212> TYPE: PRT
<213> ORGANISM: Homo sapiens
```

-continued

<400> SEQUENCE: 52

```
Met Ala Trp Arg Cys Pro Arg Met Gly Arg Val Pro Leu Ala Trp Cys
 1               5                  10                  15

Leu Ala Leu Cys Gly Trp Ala Cys Met Ala Pro Arg Gly Thr Gln Ala
             20                  25                  30

Glu Glu Ser Pro Phe Val Gly Asn Pro Gly Asn Ile Thr Gly Ala Arg
         35                  40                  45

Gly Leu Thr Gly Thr Leu Arg Cys Gln Leu Gln Val Gln Gly Glu Pro
     50                  55                  60

Pro Glu Val His Trp Leu Arg Asp Gly Gln Ile Leu Glu Leu Ala Asp
 65                  70                  75                  80

Ser Thr Gln Thr Gln Val Pro Leu Gly Glu Asp Glu Gln Asp Asp Trp
                 85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Lys Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415
```

-continued

```
Trp Ser Leu Pro Val Pro Leu Glu Ala Trp Arg Pro Val Lys Glu Pro
            420                 425                 430

Ser Thr Pro Ala Phe Ser Trp Pro Trp Trp Tyr Val Leu Leu Gly Ala
            435                 440                 445

Val Val Ala Ala Ala Cys Val Leu Ile Leu Ala Leu Phe Leu Val His
        450                 455                 460

Arg Arg Lys Lys Glu Thr Arg Tyr Gly Glu Val Phe Glu Pro Thr Val
465                 470                 475                 480

Glu Arg Gly Glu Leu Val Val Arg Tyr Arg Val Arg Lys Ser Tyr Ser
                485                 490                 495

Arg Arg Thr Thr Glu Ala Thr Leu Asn Ser Leu Gly Ile Ser Glu Glu
                500                 505                 510

Leu Lys Glu Lys Leu Arg Asp Val Met Val Asp Arg His Lys Val Ala
        515                 520                 525

Leu Gly Lys Thr Leu Gly Glu Gly Glu Phe Gly Ala Val Met Glu Gly
        530                 535                 540

Gln Leu Asn Gln Asp Asp Ser Ile Leu Lys Val Ala Val Lys Thr Met
545                 550                 555                 560

Lys Ile Ala Ile Cys Thr Arg Ser Glu Leu Glu Asp Phe Leu Ser Glu
                565                 570                 575

Ala Val Cys Met Lys Glu Phe Asp His Pro Asn Val Met Arg Leu Ile
            580                 585                 590

Gly Val Cys Phe Gln Gly Ser Glu Arg Glu Ser Phe Pro Ala Pro Val
        595                 600                 605

Val Ile Leu Pro Phe Met Lys His Gly Asp Leu His Ser Phe Leu Leu
        610                 615                 620

Tyr Ser Arg Leu Gly Asp Gln Pro Val Tyr Leu Pro Thr Gln Met Leu
625                 630                 635                 640

Val Lys Phe Met Ala Asp Ile Ala Ser Gly Met Glu Tyr Leu Ser Thr
                645                 650                 655

Lys Arg Phe Ile His Arg Asp Leu Ala Ala Arg Asn Cys Met Leu Asn
                660                 665                 670

Glu Asn Met Ser Val Cys Val Ala Asp Phe Gly Leu Ser Lys Lys Ile
            675                 680                 685

Tyr Asn Gly Asp Tyr Tyr Arg Gln Gly Arg Ile Ala Lys Met Pro Val
        690                 695                 700

Lys Trp Ile Ala Ile Glu Ser Leu Ala Asp Arg Val Tyr Thr Ser Lys
705                 710                 715                 720

Ser Asp Val Trp Ser Phe Gly Val Thr Met Trp Glu Ile Ala Thr Arg
                725                 730                 735

Gly Gln Thr Pro Tyr Pro Gly Val Glu Asn Ser Glu Ile Tyr Asp Tyr
                740                 745                 750

Leu Arg Gln Gly Asn Arg Leu Lys Gln Pro Ala Asp Cys Leu Asp Gly
        755                 760                 765

Leu Tyr Ala Leu Met Ser Arg Cys Trp Glu Leu Asn Pro Gln Asp Arg
        770                 775                 780

Pro Ser Phe Thr Glu Leu Arg Glu Asp Leu Glu Asn Thr Leu Lys Ala
785                 790                 795                 800

Leu Pro Pro Ala Gln Glu Pro Asp Glu Ile Leu Tyr Val Asn Met Asp
                805                 810                 815

Glu Gly Gly Gly Tyr Pro Glu Pro Pro Gly Ala Ala Gly Gly Ala Asp
            820                 825                 830
```

```
Pro Pro Thr Gln Pro Asp Pro Lys Asp Ser Cys Ser Cys Leu Thr Ala
        835                 840                 845

Ala Glu Val His Pro Ala Gly Arg Tyr Val Leu Cys Pro Ser Thr Thr
    850                 855                 860

Pro Ser Pro Ala Gln Pro Ala Asp Arg Gly Ser Pro Ala Ala Pro Gly
865                 870                 875                 880

Gln Glu Asp Gly Ala
            885

<210> SEQ ID NO 53
<211> LENGTH: 373
<212> TYPE: PRT
<213> ORGANISM: Homo sapiens

<400> SEQUENCE: 53

Met Leu Leu Gly Leu Ala Ala Met Glu Leu Lys Val Trp Val Asp Gly
1               5                   10                  15

Ile Gln Arg Val Val Cys Gly Val Ser Glu Gln Thr Thr Cys Gln Glu
            20                  25                  30

Val Val Ile Ala Leu Ala Gln Ala Ile Gly Gln Thr Gly Arg Phe Val
        35                  40                  45

Leu Val Gln Arg Leu Arg Glu Lys Glu Arg Gln Leu Leu Pro Gln Glu
    50                  55                  60

Cys Pro Val Gly Ala Gln Ala Thr Cys Gly Gln Phe Ala Ser Asp Val
65                  70                  75                  80

Gln Phe Val Leu Arg Arg Thr Gly Pro Ser Leu Ala Gly Arg Pro Ser
                85                  90                  95

Ser Asp Ser Cys Pro Pro Glu Arg Cys Leu Ile Arg Ala Ser Leu
            100                 105                 110

Pro Val Lys Pro Arg Ala Ala Leu Gly Cys Glu Pro Arg Lys Thr Leu
            115                 120                 125

Thr Pro Glu Pro Ala Pro Ser Leu Ser Arg Pro Gly Pro Ala Ala Pro
    130                 135                 140

Val Thr Pro Thr Pro Gly Cys Cys Thr Asp Leu Arg Gly Leu Glu Leu
145                 150                 155                 160

Arg Val Gln Arg Asn Ala Glu Glu Leu Gly His Glu Ala Phe Trp Glu
                165                 170                 175

Gln Glu Leu Arg Arg Glu Gln Ala Arg Glu Arg Glu Gly Gln Ala Arg
            180                 185                 190

Leu Gln Ala Leu Ser Ala Ala Thr Ala Glu His Ala Ala Arg Leu Gln
        195                 200                 205

Ala Leu Asp Ala Gln Ala Arg Ala Leu Glu Ala Glu Leu Gln Leu Ala
    210                 215                 220

Ala Glu Ala Pro Gly Pro Pro Ser Pro Met Ala Ser Ala Thr Glu Arg
225                 230                 235                 240

Leu His Gln Asp Leu Ala Val Gln Glu Arg Gln Ser Ala Glu Val Gln
                245                 250                 255

Gly Ser Leu Ala Leu Val Ser Arg Ala Leu Glu Ala Ala Glu Arg Ala
            260                 265                 270

Leu Gln Ala Gln Ala Gln Glu Leu Glu Glu Leu Asn Arg Glu Leu Arg
        275                 280                 285

Gln Cys Asn Leu Gln Gln Phe Ile Gln Gln Thr Gly Ala Ala Leu Pro
    290                 295                 300

Pro Pro Pro Arg Pro Asp Arg Gly Pro Pro Gly Thr Gln Gly Pro Leu
305                 310                 315                 320
```

```
Pro Pro Ala Arg Glu Glu Ser Leu Leu Gly Ala Pro Ser Glu Ser His
            325                 330                 335

Ala Gly Ala Gln Pro Arg Pro Arg Gly Gly Pro His Asp Ala Glu Leu
        340                 345                 350

Leu Glu Val Ala Ala Pro Ala Pro Glu Trp Cys Pro Leu Ala Ala
    355                 360                 365

Gln Pro Gln Ala Leu
    370

<210> SEQ ID NO 54
<211> LENGTH: 289
<212> TYPE: PRT
<213> ORGANISM: Homo sapiens

<400> SEQUENCE: 54

Met Glu Leu Leu Cys His Glu Val Asp Pro Val Arg Arg Ala Val Arg
1               5                   10                  15

Asp Arg Asn Leu Leu Arg Asp Asp Arg Val Leu Gln Asn Leu Leu Thr
            20                  25                  30

Ile Glu Glu Arg Tyr Leu Pro Gln Cys Ser Tyr Phe Lys Cys Val Gln
        35                  40                  45

Lys Asp Ile Gln Pro Tyr Met Arg Arg Met Val Ala Thr Trp Met Leu
    50                  55                  60

Glu Val Cys Glu Glu Gln Lys Cys Glu Glu Val Phe Pro Leu Ala
65                  70                  75                  80

Met Asn Tyr Leu Asp Arg Phe Leu Ala Gly Val Pro Thr Pro Lys Ser
                85                  90                  95

His Leu Gln Leu Leu Gly Ala Val Cys Met Phe Leu Ala Ser Lys Leu
            100                 105                 110

Lys Glu Thr Ser Pro Leu Thr Ala Glu Lys Leu Cys Ile Tyr Thr Asp
        115                 120                 125

Asn Ser Ile Lys Pro Gln Glu Leu Leu Glu Trp Glu Leu Val Val Leu
    130                 135                 140

Gly Lys Leu Lys Trp Asn Leu Ala Ala Val Thr Pro His Asp Phe Ile
145                 150                 155                 160

Glu His Ile Leu Arg Lys Leu Pro Gln Gln Arg Glu Lys Leu Ser Leu
                165                 170                 175

Ile Arg Lys His Ala Gln Thr Phe Ile Ala Leu Cys Ala Thr Asp Phe
            180                 185                 190

Lys Phe Ala Met Tyr Pro Pro Ser Met Ile Ala Thr Gly Ser Val Gly
        195                 200                 205

Ala Ala Ile Cys Gly Leu Gln Gln Asp Glu Glu Val Ser Ser Leu Thr
    210                 215                 220

Cys Asp Ala Leu Thr Glu Leu Leu Ala Lys Ile Thr Asn Thr Asp Val
225                 230                 235                 240

Asp Cys Leu Lys Ala Cys Gln Glu Gln Ile Glu Ala Val Leu Leu Asn
                245                 250                 255

Ser Leu Gln Gln Tyr Arg Gln Asp Gln Arg Asp Gly Ser Lys Ser Glu
            260                 265                 270

Asp Glu Leu Asp Gln Ala Ser Thr Pro Thr Asp Val Arg Asp Ile Asp
        275                 280                 285

Leu
```

<210> SEQ ID NO 55
<211> LENGTH: 693
<212> TYPE: PRT
<213> ORGANISM: Homo sapiens

<400> SEQUENCE: 55

| Met | Lys | Glu | Asn | Tyr | Cys | Leu | Gln | Ala | Ala | Leu | Val | Cys | Leu | Gly | Met |
|---|---|---|---|---|---|---|---|---|---|---|---|---|---|---|---|
| 1 | | | | 5 | | | | | 10 | | | | | 15 | |

| Leu | Cys | His | Ser | His | Ala | Phe | Ala | Pro | Glu | Arg | Arg | Gly | His | Leu | Arg |
|---|---|---|---|---|---|---|---|---|---|---|---|---|---|---|---|
| | | | 20 | | | | | 25 | | | | | 30 | | |

| Pro | Ser | Phe | His | Gly | His | His | Glu | Lys | Gly | Lys | Glu | Gly | Gln | Val | Leu |
|---|---|---|---|---|---|---|---|---|---|---|---|---|---|---|---|
| | | | 35 | | | | | 40 | | | | | 45 | | |

| Gln | Arg | Ser | Lys | Arg | Gly | Trp | Val | Trp | Asn | Gln | Phe | Phe | Val | Ile | Glu |
|---|---|---|---|---|---|---|---|---|---|---|---|---|---|---|---|
| | 50 | | | | | 55 | | | | | 60 | | | | |

| Glu | Tyr | Thr | Gly | Pro | Asp | Pro | Val | Leu | Val | Gly | Arg | Leu | His | Ser | Asp |
|---|---|---|---|---|---|---|---|---|---|---|---|---|---|---|---|
| 65 | | | | | 70 | | | | | 75 | | | | | 80 |

| Ile | Asp | Ser | Gly | Asp | Gly | Asn | Ile | Lys | Tyr | Ile | Leu | Ser | Gly | Glu | Gly |
|---|---|---|---|---|---|---|---|---|---|---|---|---|---|---|---|
| | | | | 85 | | | | | 90 | | | | | 95 | |

| Ala | Gly | Thr | Ile | Phe | Val | Ile | Asp | Asp | Lys | Ser | Gly | Asn | Ile | His | Ala |
|---|---|---|---|---|---|---|---|---|---|---|---|---|---|---|---|
| | | | 100 | | | | | 105 | | | | | 110 | | |

| Thr | Lys | Thr | Leu | Asp | Arg | Glu | Glu | Arg | Ala | Gln | Tyr | Thr | Leu | Met | Ala |
|---|---|---|---|---|---|---|---|---|---|---|---|---|---|---|---|
| | | | 115 | | | | | 120 | | | | | 125 | | |

| Gln | Ala | Val | Asp | Arg | Asp | Thr | Asn | Arg | Pro | Leu | Glu | Pro | Pro | Ser | Glu |
|---|---|---|---|---|---|---|---|---|---|---|---|---|---|---|---|
| | 130 | | | | | 135 | | | | | 140 | | | | |

| Phe | Ile | Val | Lys | Val | Gln | Asp | Ile | Asn | Asp | Asn | Pro | Pro | Glu | Phe | Leu |
|---|---|---|---|---|---|---|---|---|---|---|---|---|---|---|---|
| 145 | | | | | 150 | | | | | 155 | | | | | 160 |

| His | Glu | Thr | Tyr | His | Ala | Asn | Val | Pro | Glu | Arg | Ser | Asn | Val | Gly | Thr |
|---|---|---|---|---|---|---|---|---|---|---|---|---|---|---|---|
| | | | | 165 | | | | | 170 | | | | | 175 | |

| Ser | Val | Ile | Gln | Val | Thr | Ala | Ser | Asp | Ala | Asp | Asp | Pro | Thr | Tyr | Gly |
|---|---|---|---|---|---|---|---|---|---|---|---|---|---|---|---|
| | | | 180 | | | | | 185 | | | | | 190 | | |

| Asn | Ser | Ala | Lys | Leu | Val | Tyr | Ser | Ile | Leu | Glu | Gly | Gln | Pro | Tyr | Phe |
|---|---|---|---|---|---|---|---|---|---|---|---|---|---|---|---|
| | | | 195 | | | | | 200 | | | | | 205 | | |

| Ser | Val | Glu | Ala | Gln | Thr | Gly | Ile | Ile | Arg | Thr | Ala | Leu | Pro | Asn | Met |
|---|---|---|---|---|---|---|---|---|---|---|---|---|---|---|---|
| | 210 | | | | | 215 | | | | | 220 | | | | |

| Asp | Arg | Glu | Ala | Lys | Glu | Glu | Tyr | His | Val | Val | Ile | Gln | Ala | Lys | Asp |
|---|---|---|---|---|---|---|---|---|---|---|---|---|---|---|---|
| 225 | | | | | 230 | | | | | 235 | | | | | 240 |

| Met | Gly | Gly | His | Met | Gly | Gly | Leu | Ser | Gly | Thr | Thr | Lys | Val | Thr | Ile |
|---|---|---|---|---|---|---|---|---|---|---|---|---|---|---|---|
| | | | | 245 | | | | | 250 | | | | | 255 | |

| Thr | Leu | Thr | Asp | Val | Asn | Asp | Asn | Pro | Pro | Lys | Phe | Pro | Gln | Ser | Val |
|---|---|---|---|---|---|---|---|---|---|---|---|---|---|---|---|
| | | | 260 | | | | | 265 | | | | | 270 | | |

| Tyr | Gln | Ile | Ser | Val | Ser | Glu | Ala | Ala | Val | Pro | Gly | Glu | Glu | Val | Gly |
|---|---|---|---|---|---|---|---|---|---|---|---|---|---|---|---|
| | | | 275 | | | | | 280 | | | | | 285 | | |

| Arg | Val | Lys | Ala | Lys | Asp | Pro | Asp | Ile | Gly | Glu | Asn | Gly | Leu | Val | Thr |
|---|---|---|---|---|---|---|---|---|---|---|---|---|---|---|---|
| | 290 | | | | | 295 | | | | | 300 | | | | |

| Tyr | Asn | Ile | Val | Asp | Gly | Asp | Gly | Met | Glu | Ser | Phe | Glu | Ile | Thr | Thr |
|---|---|---|---|---|---|---|---|---|---|---|---|---|---|---|---|
| 305 | | | | | 310 | | | | | 315 | | | | | 320 |

| Asp | Tyr | Glu | Thr | Gln | Glu | Gly | Val | Ile | Lys | Leu | Lys | Lys | Pro | Val | Asp |
|---|---|---|---|---|---|---|---|---|---|---|---|---|---|---|---|
| | | | | 325 | | | | | 330 | | | | | 335 | |

| Phe | Glu | Thr | Lys | Arg | Ala | Tyr | Ser | Leu | Lys | Val | Glu | Ala | Ala | Asn | Val |
|---|---|---|---|---|---|---|---|---|---|---|---|---|---|---|---|
| | | | 340 | | | | | 345 | | | | | 350 | | |

| His | Ile | Asp | Pro | Lys | Phe | Ile | Ser | Asn | Gly | Pro | Phe | Lys | Asp | Thr | Val |
|---|---|---|---|---|---|---|---|---|---|---|---|---|---|---|---|
| | | | 355 | | | | | 360 | | | | | 365 | | |

| Thr | Val | Lys | Ile | Ala | Val | Glu | Asp | Ala | Asp | Glu | Pro | Pro | Met | Phe | Leu |
|---|---|---|---|---|---|---|---|---|---|---|---|---|---|---|---|
| | 370 | | | | | 375 | | | | | 380 | | | | |

-continued

```
Ala Pro Ser Tyr Ile His Glu Val Gln Glu Asn Ala Ala Gly Thr
385                 390                 395                 400

Val Val Gly Arg Val His Ala Lys Asp Pro Asp Ala Ala Asn Ser Pro
            405                 410                 415

Ile Arg Tyr Ser Ile Asp Arg His Thr Asp Leu Asp Arg Phe Phe Thr
            420                 425                 430

Ile Asn Pro Glu Asp Gly Phe Ile Lys Thr Thr Lys Pro Leu Asp Arg
        435                 440                 445

Glu Glu Thr Ala Trp Leu Asn Ile Thr Val Phe Ala Ala Glu Ile His
    450                 455                 460

Asn Arg His Gln Glu Ala Lys Val Pro Val Ala Ile Arg Val Leu Asp
465                 470                 475                 480

Val Asn Asp Asn Ala Pro Lys Phe Ala Ala Pro Tyr Glu Gly Phe Ile
                485                 490                 495

Cys Glu Ser Asp Gln Thr Lys Pro Leu Ser Asn Gln Pro Ile Val Thr
            500                 505                 510

Ile Ser Ala Asp Asp Lys Asp Asp Thr Ala Asn Gly Pro Arg Phe Ile
        515                 520                 525

Phe Ser Leu Pro Pro Glu Ile Ile His Asn Pro Asn Phe Thr Val Arg
    530                 535                 540

Asp Asn Arg Asp Asn Thr Ala Gly Val Tyr Ala Arg Arg Gly Gly Phe
545                 550                 555                 560

Ser Arg Gln Lys Gln Asp Leu Tyr Leu Leu Pro Ile Val Ile Ser Asp
                565                 570                 575

Gly Gly Ile Pro Pro Met Ser Ser Thr Asn Thr Leu Thr Ile Lys Val
            580                 585                 590

Cys Gly Cys Asp Val Asn Gly Ala Leu Leu Ser Cys Asn Ala Glu Ala
        595                 600                 605

Tyr Ile Leu Asn Ala Gly Leu Ser Thr Gly Ala Leu Ile Ala Ile Leu
    610                 615                 620

Ala Cys Ile Val Ile Leu Leu Gly Cys Pro Ser Leu Met Glu Pro Pro
625                 630                 635                 640

Ser Pro Arg Glu Asp Met Arg Leu Leu Tyr Leu Gly Phe Gln Leu Met
                645                 650                 655

Leu Phe Ser Tyr Val Lys Val Asn Arg Arg Phe Cys Leu Leu Gly Val
            660                 665                 670

Phe Ile Lys Leu Pro Phe Leu Tyr Val Val Ala Thr Glu Ser Pro Thr
        675                 680                 685

Thr Leu Thr Ser Leu
    690

<210> SEQ ID NO 56
<211> LENGTH: 1806
<212> TYPE: PRT
<213> ORGANISM: Homo sapiens
<220> FEATURE:
<221> NAME/KEY: UNSURE
<222> LOCATION: (758)..(758)
<223> OTHER INFORMATION: Xaa = any amino acid
<221> NAME/KEY: UNSURE
<222> LOCATION: (809)..(809)
<223> OTHER INFORMATION: Xaa = any amino acid

<400> SEQUENCE: 56

Met Glu Pro Trp Ser Ser Arg Trp Lys Thr Lys Arg Trp Leu Trp Asp
1               5                   10                  15
```

```
Phe Thr Val Thr Thr Leu Ala Leu Thr Phe Leu Phe Gln Ala Arg Glu
            20                  25                  30

Val Arg Gly Ala Ala Pro Val Asp Val Leu Lys Ala Leu Asp Phe His
            35                  40                  45

Asn Ser Pro Glu Gly Ile Ser Lys Thr Thr Gly Phe Cys Thr Asn Arg
 50                      55                  60

Lys Asn Ser Lys Gly Ser Asp Thr Ala Tyr Arg Val Ser Lys Gln Ala
 65                  70                  75                  80

Gln Leu Ser Ala Pro Thr Lys Gln Leu Phe Pro Gly Gly Thr Phe Pro
                 85                  90                  95

Glu Asp Phe Ser Ile Leu Phe Thr Val Lys Pro Lys Lys Gly Ile Gln
            100                 105                 110

Ser Phe Leu Leu Ser Ile Tyr Asn Glu His Gly Ile Gln Gln Ile Gly
            115                 120                 125

Val Glu Val Gly Arg Ser Pro Val Phe Leu Phe Glu Asp His Thr Gly
 130                     135                 140

Lys Pro Ala Pro Glu Asp Tyr Pro Leu Phe Arg Thr Val Asn Ile Ala
 145                 150                 155                 160

Asp Gly Lys Trp His Arg Val Ala Ile Ser Val Glu Lys Lys Thr Val
                 165                 170                 175

Thr Met Ile Val Asp Cys Lys Lys Thr Thr Lys Pro Leu Asp Arg
                 180                 185                 190

Ser Glu Arg Ala Ile Val Asp Thr Asn Gly Ile Thr Val Phe Gly Thr
                 195                 200                 205

Arg Ile Leu Asp Glu Glu Val Phe Glu Gly Asp Ile Gln Gln Phe Leu
 210                     215                 220

Ile Thr Gly Asp Pro Lys Ala Ala Tyr Asp Tyr Cys Glu His Tyr Ser
225                     230                 235                 240

Pro Asp Cys Asp Ser Ser Ala Pro Lys Ala Ala Gln Ala Gln Glu Pro
                 245                 250                 255

Gln Ile Asp Glu Tyr Ala Pro Glu Asp Ile Ile Glu Tyr Asp Tyr Glu
                 260                 265                 270

Tyr Gly Glu Ala Glu Tyr Lys Glu Ala Glu Ser Val Thr Glu Gly Pro
                 275                 280                 285

Thr Val Thr Glu Glu Thr Ile Ala Gln Thr Glu Ala Asn Ile Val Asp
 290                     295                 300

Asp Phe Gln Glu Tyr Asn Tyr Gly Thr Met Glu Ser Tyr Gln Thr Glu
305                     310                 315                 320

Ala Pro Arg His Val Ser Gly Thr Asn Glu Pro Asn Pro Val Glu Glu
                 325                 330                 335

Ile Phe Thr Glu Glu Tyr Leu Thr Gly Glu Asp Tyr Asp Ser Gln Arg
                 340                 345                 350

Lys Asn Ser Glu Asp Thr Leu Tyr Glu Asn Lys Glu Ile Asp Gly Arg
                 355                 360                 365

Asp Ser Asp Leu Leu Val Asp Gly Asp Leu Gly Glu Tyr Asp Phe Tyr
                 370                 375                 380

Glu Tyr Lys Glu Tyr Glu Asp Lys Pro Thr Ser Pro Asn Glu Glu
385                     390                 395                 400

Phe Gly Pro Gly Val Pro Ala Glu Thr Asp Ile Thr Glu Thr Ser Ile
                 405                 410                 415

Asn Gly His Gly Ala Tyr Gly Glu Lys Gly Gln Lys Gly Glu Pro Ala
                 420                 425                 430
```

-continued

```
Val Val Glu Pro Gly Met Leu Val Glu Gly Pro Pro Gly Pro Ala Gly
        435                 440                 445
Pro Ala Gly Ile Met Gly Pro Pro Gly Leu Gln Gly Pro Thr Gly Pro
        450                 455                 460
Pro Gly Asp Pro Gly Asp Arg Gly Pro Gly Arg Pro Gly Leu Pro
465                 470                 475                 480
Gly Ala Asp Gly Leu Pro Gly Pro Pro Gly Thr Met Leu Met Leu Pro
                485                 490                 495
Phe Arg Tyr Gly Gly Asp Gly Ser Lys Gly Pro Thr Ile Ser Ala Gln
            500                 505                 510
Glu Ala Gln Ala Gln Ala Ile Leu Gln Gln Ala Arg Ile Ala Leu Arg
            515                 520                 525
Gly Pro Pro Gly Pro Met Gly Leu Thr Gly Arg Pro Gly Pro Val Gly
        530                 535                 540
Gly Pro Gly Ser Ser Gly Ala Lys Gly Glu Ser Gly Asp Pro Gly Pro
545                 550                 555                 560
Gln Gly Pro Arg Gly Val Gln Gly Pro Pro Gly Pro Thr Gly Lys Pro
                565                 570                 575
Gly Lys Arg Gly Arg Pro Gly Ala Asp Gly Gly Arg Gly Met Pro Gly
            580                 585                 590
Glu Pro Gly Ala Lys Gly Asp Arg Gly Phe Asp Gly Leu Pro Gly Leu
            595                 600                 605
Pro Gly Asp Lys Gly His Arg Gly Glu Arg Gly Pro Gln Gly Pro Pro
        610                 615                 620
Gly Pro Pro Gly Asp Asp Gly Met Arg Gly Glu Asp Gly Glu Ile Gly
625                 630                 635                 640
Pro Arg Gly Leu Pro Gly Glu Ala Gly Pro Arg Gly Leu Leu Gly Pro
                645                 650                 655
Arg Gly Thr Pro Gly Ala Pro Gly Gln Pro Gly Met Ala Gly Val Asp
            660                 665                 670
Gly Pro Pro Gly Pro Lys Gly Asn Met Gly Pro Gln Gly Glu Pro Gly
        675                 680                 685
Pro Pro Gly Gln Gln Gly Asn Pro Gly Pro Gln Gly Leu Pro Gly Pro
        690                 695                 700
Gln Gly Pro Ile Gly Pro Pro Gly Glu Lys Gly Pro Gln Gly Lys Pro
705                 710                 715                 720
Gly Leu Ala Gly Leu Pro Gly Ala Asp Gly Pro Pro Gly His Pro Gly
                725                 730                 735
Lys Glu Gly Gln Ser Gly Glu Lys Gly Ala Leu Gly Pro Pro Gly Pro
            740                 745                 750
Gln Gly Pro Ile Gly Xaa Pro Gly Pro Arg Gly Val Lys Gly Ala Asp
            755                 760                 765
Gly Val Arg Gly Leu Lys Gly Ser Lys Gly Glu Lys Gly Glu Asp Gly
        770                 775                 780
Phe Pro Gly Phe Lys Gly Asp Met Gly Leu Lys Gly Asp Arg Gly Glu
785                 790                 795                 800
Val Gly Gln Ile Gly Pro Arg Gly Xaa Asp Gly Pro Glu Gly Pro Lys
                805                 810                 815
Gly Arg Ala Gly Pro Thr Gly Asp Pro Gly Pro Ser Gly Gln Ala Gly
            820                 825                 830
Glu Lys Gly Lys Leu Gly Val Pro Gly Leu Pro Gly Tyr Pro Gly Arg
            835                 840                 845
```

-continued

```
Gln Gly Pro Lys Gly Ser Thr Gly Phe Pro Gly Phe Pro Gly Ala Asn
    850                 855                 860

Gly Glu Lys Gly Ala Arg Gly Val Ala Gly Lys Pro Gly Pro Arg Gly
865                 870                 875                 880

Gln Arg Gly Pro Thr Gly Pro Arg Gly Ser Arg Gly Ala Arg Gly Pro
                885                 890                 895

Thr Gly Lys Pro Gly Pro Lys Gly Thr Ser Gly Gly Asp Gly Pro Pro
            900                 905                 910

Gly Pro Pro Gly Glu Arg Gly Pro Gln Gly Pro Gln Gly Pro Val Gly
        915                 920                 925

Phe Pro Gly Pro Lys Gly Pro Pro Gly Pro Pro Gly Arg Met Gly Cys
930                 935                 940

Pro Gly His Pro Gly Gln Arg Gly Glu Thr Gly Phe Gln Gly Lys Thr
945                 950                 955                 960

Gly Pro Pro Gly Pro Gly Gly Val Val Gly Pro Gln Gly Pro Thr Gly
                965                 970                 975

Glu Thr Gly Pro Ile Gly Glu Arg Gly Tyr Pro Gly Pro Pro Gly Pro
            980                 985                 990

Pro Gly Glu Gln Gly Leu Pro Gly  Ala Ala Gly Lys Glu  Gly Ala Lys
        995                 1000                1005

Gly Asp  Pro Gly Pro Gln Gly  Ile Ser Gly Lys Asp  Gly Pro Ala
    1010                1015                1020

Gly Leu  Arg Gly Phe Pro Gly  Glu Arg Gly Leu Pro   Gly Ala Gln
    1025                1030                1035

Gly Ala  Pro Gly Leu Lys Gly  Gly Glu Gly Pro Gln  Gly Pro Pro
    1040                1045                1050

Gly Pro  Val Gly Ser Pro Gly  Glu Arg Gly Ser Ala  Gly Thr Ala
    1055                1060                1065

Gly Pro  Ile Gly Leu Arg Gly  Arg Pro Gly Pro Gln  Gly Pro Pro
    1070                1075                1080

Gly Pro  Ala Gly Glu Lys Gly  Ala Pro Gly Glu Lys  Gly Pro Gln
    1085                1090                1095

Gly Pro  Ala Gly Arg Asp Gly  Val Gln Gly Pro Val  Gly Leu Pro
    1100                1105                1110

Gly Pro  Ala Gly Pro Ala Gly  Ser Pro Gly Glu Asp  Gly Asp Lys
    1115                1120                1125

Gly Glu  Ile Gly Glu Pro Gly  Gln Lys Gly Ser Lys  Gly Gly Lys
    1130                1135                1140

Gly Glu  Asn Gly Pro Pro Gly  Pro Pro Gly Leu Gln  Gly Pro Val
    1145                1150                1155

Gly Ala  Pro Gly Ile Ala Gly  Gly Asp Gly Glu Pro  Gly Pro Arg
    1160                1165                1170

Gly Gln  Gln Gly Met Phe Gly  Gln Lys Gly Asp Glu  Gly Ala Arg
    1175                1180                1185

Gly Phe  Pro Gly Pro Pro Gly  Pro Ile Gly Leu Gln  Gly Leu Pro
    1190                1195                1200

Gly Pro  Pro Gly Glu Lys Gly  Glu Asn Gly Asp Val  Gly Pro Trp
    1205                1210                1215

Gly Pro  Pro Gly Pro Pro Gly  Pro Arg Gly Pro Gln  Gly Pro Asn
    1220                1225                1230

Gly Ala  Asp Gly Pro Gln Gly  Pro Pro Gly Ser Val  Gly Ser Val
    1235                1240                1245
```

-continued

```
Gly Gly Val Gly Glu Lys Gly Glu Pro Gly Glu Ala Gly Asn Pro
        1250                1255                1260

Gly Pro Pro Gly Glu Ala Gly Val Gly Gly Pro Lys Gly Glu Arg
        1265                1270                1275

Gly Glu Lys Gly Glu Ala Gly Pro Pro Gly Ala Ala Gly Pro Pro
        1280                1285                1290

Gly Ala Lys Gly Pro Pro Gly Asp Asp Gly Pro Lys Gly Asn Pro
        1295                1300                1305

Gly Pro Val Gly Phe Pro Gly Asp Pro Gly Pro Gly Glu Leu
        1310                1315                1320

Gly Pro Ala Gly Gln Asp Gly Val Gly Gly Asp Lys Gly Glu Asp
        1325                1330                1335

Gly Asp Pro Gly Gln Pro Gly Pro Pro Gly Pro Ser Gly Glu Ala
        1340                1345                1350

Gly Pro Pro Gly Pro Pro Gly Lys Arg Gly Pro Pro Gly Ala Ala
        1355                1360                1365

Gly Ala Glu Gly Arg Gln Gly Glu Lys Gly Ala Lys Gly Glu Ala
        1370                1375                1380

Gly Ala Glu Gly Pro Pro Gly Lys Thr Gly Pro Val Gly Pro Gln
        1385                1390                1395

Gly Pro Ala Gly Lys Pro Gly Pro Glu Gly Leu Arg Gly Ile Pro
        1400                1405                1410

Gly Pro Val Gly Glu Gln Gly Leu Pro Gly Ala Ala Gly Gln Asp
        1415                1420                1425

Gly Pro Pro Gly Pro Met Gly Pro Pro Gly Leu Pro Gly Leu Lys
        1430                1435                1440

Gly Asp Pro Gly Ser Lys Gly Glu Lys Gly His Pro Gly Leu Ile
        1445                1450                1455

Gly Leu Ile Gly Pro Pro Gly Glu Gln Gly Glu Lys Gly Asp Arg
        1460                1465                1470

Gly Leu Pro Gly Thr Gln Gly Ser Pro Gly Ala Lys Gly Asp Gly
        1475                1480                1485

Gly Ile Pro Gly Pro Ala Gly Pro Leu Gly Pro Pro Gly Pro Pro
        1490                1495                1500

Gly Leu Pro Gly Pro Gln Gly Pro Lys Gly Asn Lys Gly Ser Thr
        1505                1510                1515

Gly Pro Ala Gly Gln Lys Gly Asp Ser Gly Leu Pro Gly Pro Pro
        1520                1525                1530

Gly Pro Pro Gly Pro Pro Gly Glu Val Ile Gln Pro Leu Pro Ile
        1535                1540                1545

Leu Ser Ser Lys Lys Thr Arg Arg His Thr Glu Gly Met Gln Ala
        1550                1555                1560

Asp Ala Asp Asp Asn Ile Leu Asp Tyr Ser Asp Gly Met Glu Glu
        1565                1570                1575

Ile Phe Gly Ser Leu Asn Ser Leu Lys Gln Asp Ile Glu His Met
        1580                1585                1590

Lys Phe Pro Met Gly Thr Gln Thr Asn Pro Ala Arg Thr Cys Lys
        1595                1600                1605

Asp Leu Gln Leu Ser His Pro Asp Phe Pro Asp Gly Glu Tyr Trp
        1610                1615                1620

Ile Asp Pro Asn Gln Gly Cys Ser Gly Asp Ser Phe Lys Val Tyr
        1625                1630                1635
```

```
Cys Asn Phe Thr Ser Gly Gly Glu Thr Cys Ile Tyr Pro Asp Lys
1640                1645                1650

Lys Ser Glu Gly Val Arg Ile Ser Ser Trp Pro Lys Glu Lys Pro
1655                1660                1665

Gly Ser Trp Phe Ser Glu Phe Lys Arg Gly Lys Leu Leu Ser Tyr
1670                1675                1680

Leu Asp Val Glu Gly Asn Ser Ile Asn Met Val Gln Met Thr Phe
1685                1690                1695

Leu Lys Leu Leu Thr Ala Ser Ala Arg Gln Asn Phe Thr Tyr His
1700                1705                1710

Cys His Gln Ser Ala Ala Trp Tyr Asp Val Ser Ser Gly Ser Tyr
1715                1720                1725

Asp Lys Ala Leu Arg Phe Leu Gly Ser Asn Asp Glu Glu Met Ser
1730                1735                1740

Tyr Asp Asn Asn Pro Phe Ile Lys Thr Leu Tyr Asp Gly Cys Thr
1745                1750                1755

Ser Arg Lys Gly Tyr Glu Lys Thr Val Ile Glu Ile Asn Thr Pro
1760                1765                1770

Lys Ile Asp Gln Val Pro Ile Val Asp Val Met Ile Ser Asp Phe
1775                1780                1785

Gly Asp Gln Asn Gln Lys Phe Gly Phe Glu Val Gly Pro Val Cys
1790                1795                1800

Phe Leu Gly
1805

<210> SEQ ID NO 57
<211> LENGTH: 755
<212> TYPE: PRT
<213> ORGANISM: Homo sapiens

<400> SEQUENCE: 57

Cys Lys Ala Ala Lys Ala Asp Leu Val Phe Met Val Asp Gly Ser Trp
1               5                   10                  15

Ser Ile Gly Asp Glu Asn Phe Asn Lys Ile Ile Ser Phe Leu Tyr Ser
                20                  25                  30

Thr Val Gly Ala Leu Asn Lys Ile Gly Thr Asp Gly Thr Gln Val Ala
            35                  40                  45

Met Val Gln Phe Thr Asp Asp Pro Arg Thr Glu Phe Lys Leu Asn Ala
        50                  55                  60

Tyr Lys Thr Lys Glu Thr Leu Leu Asp Ala Ile Lys His Ile Ser Tyr
65                  70                  75                  80

Lys Gly Gly Asn Thr Lys Thr Gly Lys Ala Ile Lys Tyr Val Arg Asp
                85                  90                  95

Thr Leu Phe Thr Ala Glu Ser Gly Thr Arg Arg Gly Ile Pro Lys Val
            100                 105                 110

Ile Val Val Ile Thr Asp Gly Arg Ser Gln Asp Asp Val Asn Lys Ile
        115                 120                 125

Ser Arg Glu Met Gln Leu Asp Gly Tyr Ser Ile Phe Ala Ile Gly Val
    130                 135                 140

Ala Asp Ala Asp Tyr Ser Glu Leu Val Ser Ile Gly Ser Lys Pro Ser
145                 150                 155                 160

Ala Arg His Val Phe Phe Val Asp Asp Phe Asp Ala Phe Lys Lys Ile
                165                 170                 175

Glu Asp Glu Leu Ile Thr Phe Val Cys Glu Thr Ala Ser Ala Thr Cys
            180                 185                 190
```

-continued

```
Pro Val His Lys Asp Gly Ile Asp Leu Ala Gly Phe Lys Met Met
    195                 200                 205
Glu Met Phe Gly Leu Val Glu Lys Asp Phe Ser Ser Val Glu Gly Val
    210                 215                 220
Ser Met Glu Pro Gly Thr Phe Asn Val Phe Pro Cys Tyr Gln Leu His
225                 230                 235                 240
Lys Asp Ala Leu Val Ser Gln Pro Thr Arg Tyr Leu His Pro Glu Gly
                245                 250                 255
Leu Pro Ser Asp Tyr Thr Ile Ser Phe Leu Phe Arg Ile Leu Pro Asp
                260                 265                 270
Thr Pro Gln Glu Pro Phe Ala Leu Trp Glu Ile Leu Asn Lys Asn Ser
                275                 280                 285
Asp Pro Leu Val Gly Val Ile Leu Asp Asn Gly Gly Lys Thr Leu Thr
    290                 295                 300
Tyr Phe Asn Tyr Asp Gln Ser Gly Asp Phe Gln Thr Val Thr Phe Glu
305                 310                 315                 320
Gly Pro Glu Ile Arg Lys Ile Phe Tyr Gly Ser Phe His Lys Leu His
                325                 330                 335
Ile Val Val Ser Glu Thr Leu Val Lys Val Val Ile Asp Cys Lys Gln
                340                 345                 350
Val Gly Glu Lys Ala Met Asn Ala Ser Ala Asn Ile Thr Ser Asp Gly
                355                 360                 365
Val Glu Val Leu Gly Lys Met Val Arg Ser Arg Gly Pro Gly Gly Asn
    370                 375                 380
Ser Ala Pro Phe Gln Leu Gln Met Phe Asp Ile Val Cys Ser Thr Ser
385                 390                 395                 400
Trp Ala Asn Thr Asp Lys Cys Cys Glu Leu Pro Gly Leu Arg Asp Asp
                405                 410                 415
Glu Ser Cys Pro Asp Leu Pro His Ser Cys Ser Cys Ser Glu Thr Asn
                420                 425                 430
Glu Val Ala Leu Gly Pro Ala Gly Pro Pro Gly Pro Gly Leu Arg
    435                 440                 445
Gly Pro Lys Gly Gln Gln Gly Glu Pro Gly Pro Lys Gly Pro Asp Gly
    450                 455                 460
Pro Arg Gly Glu Ile Gly Leu Pro Gly Pro Gln Gly Pro Pro Gly Pro
465                 470                 475                 480
Gln Gly Pro Ser Gly Leu Ser Ile Gln Gly Met Pro Gly Met Pro Gly
                485                 490                 495
Glu Lys Gly Glu Lys Gly Asp Thr Gly Leu Pro Gly Pro Gln Gly Ile
                500                 505                 510
Pro Gly Val Gly Ser Pro Gly Arg Asp Gly Ser Pro Gly Gln Arg
    515                 520                 525
Gly Leu Pro Gly Lys Asp Gly Ser Ser Gly Pro Pro Gly Pro Pro Gly
    530                 535                 540
Pro Ile Gly Ile Pro Gly Thr Pro Gly Val Pro Gly Ile Thr Gly Ser
545                 550                 555                 560
Met Gly Pro Gln Gly Ala Leu Gly Pro Pro Gly Val Pro Gly Ala Lys
                565                 570                 575
Gly Glu Arg Gly Glu Arg Gly Asp Leu Gln Ser Gln Ala Met Val Arg
                580                 585                 590
Ser Val Ala Arg Gln Val Cys Glu Gln Leu Ile Gln Ser His Met Ala
                595                 600                 605
```

```
Arg Tyr Thr Ala Ile Leu Asn Gln Ile Pro Ser His Ser Ser Ser Ile
    610                 615                 620

Arg Thr Val Gln Gly Pro Pro Gly Glu Pro Gly Arg Pro Gly Ser Pro
625                 630                 635                 640

Gly Ala Pro Gly Glu Gln Gly Pro Pro Gly Thr Pro Gly Phe Pro Gly
                645                 650                 655

Asn Ala Gly Val Pro Gly Thr Pro Gly Glu Arg Gly Leu Thr Gly Ile
            660                 665                 670

Lys Gly Glu Lys Gly Asn Pro Gly Val Gly Thr Gln Gly Pro Arg Gly
        675                 680                 685

Pro Pro Gly Pro Ala Gly Pro Ser Gly Glu Ser Arg Pro Gly Ser Pro
    690                 695                 700

Gly Pro Pro Gly Ser Pro Gly Pro Arg Gly Pro Pro Gly His Leu Gly
705                 710                 715                 720

Val Pro Gly Pro Gln Gly Pro Ser Gly Gln Pro Gly Tyr Cys Asp Pro
                725                 730                 735

Ser Ser Cys Ser Ala Tyr Gly Val Arg Asp Leu Ile Pro Tyr Asn Asp
            740                 745                 750

Tyr Gln His
        755

<210> SEQ ID NO 58
<211> LENGTH: 543
<212> TYPE: PRT
<213> ORGANISM: Homo sapiens

<400> SEQUENCE: 58

Met Gly Thr Ser Leu Ser Pro Asn Asp Pro Trp Pro Leu Asn Pro Leu
1               5                   10                  15

Ser Ile Gln Gln Thr Thr Leu Leu Leu Leu Ser Val Leu Ala Thr
            20                  25                  30

Val His Val Gly Gln Arg Leu Leu Arg Gln Arg Arg Gln Leu Arg
        35                  40                  45

Ser Ala Pro Pro Gly Pro Phe Ala Trp Pro Leu Ile Gly Asn Ala Ala
    50                  55                  60

Ala Val Gly Gln Ala Ala His Leu Ser Phe Ala Arg Leu Ala Arg Arg
65                  70                  75                  80

Tyr Gly Asp Val Phe Gln Ile Arg Leu Gly Ser Cys Pro Ile Val Val
                85                  90                  95

Leu Asn Gly Glu Arg Ala Ile His Gln Ala Leu Val Gln Gln Gly Ser
            100                 105                 110

Ala Phe Ala Asp Arg Pro Ala Phe Ala Ser Phe Arg Val Val Ser Gly
        115                 120                 125

Gly Arg Ser Met Ala Phe Gly His Tyr Ser Glu His Trp Lys Val Gln
    130                 135                 140

Arg Arg Ala Ala His Ser Met Met Arg Asn Phe Thr Arg Gln Pro
145                 150                 155                 160

Arg Ser Arg Gln Val Leu Glu Gly His Val Leu Ser Glu Ala Arg Glu
                165                 170                 175

Leu Val Ala Leu Leu Val Arg Gly Ser Ala Asp Gly Ala Phe Leu Asp
            180                 185                 190

Pro Arg Pro Leu Thr Val Val Ala Val Ala Asn Val Met Ser Ala Val
        195                 200                 205

Cys Phe Gly Cys Arg Tyr Ser His Asp Asp Pro Glu Phe Arg Glu Leu
    210                 215                 220
```

```
Leu Ser His Asn Glu Glu Phe Gly Arg Thr Val Gly Ala Gly Ser Leu
225                 230                 235                 240

Val Asp Val Met Pro Trp Leu Gln Tyr Phe Pro Asn Pro Val Arg Thr
            245                 250                 255

Val Phe Arg Glu Phe Glu Gln Leu Asn Arg Asn Phe Ser Asn Phe Ile
        260                 265                 270

Leu Asp Lys Phe Leu Arg His Cys Glu Ser Leu Arg Pro Gly Ala Ala
    275                 280                 285

Pro Arg Asp Met Met Asp Ala Phe Ile Leu Ser Ala Glu Lys Lys Ala
290                 295                 300

Ala Gly Asp Ser His Gly Gly Ala Arg Leu Asp Leu Glu Asn Val
305                 310                 315                 320

Pro Ala Thr Ile Thr Asp Ile Phe Gly Ala Ser Gln Asp Thr Leu Ser
            325                 330                 335

Thr Ala Leu Gln Trp Leu Leu Leu Phe Thr Arg Tyr Pro Asp Val
        340                 345                 350

Gln Thr Arg Val Gln Ala Glu Leu Asp Gln Val Val Gly Arg Asp Arg
        355                 360                 365

Leu Pro Cys Met Gly Asp Gln Pro Asn Leu Pro Tyr Val Leu Ala Phe
    370                 375                 380

Leu Tyr Glu Ala Met Arg Phe Ser Ser Phe Val Pro Val Thr Ile Pro
385                 390                 395                 400

His Ala Thr Thr Ala Asn Thr Ser Val Leu Gly Tyr His Ile Pro Lys
            405                 410                 415

Asp Thr Val Val Phe Val Asn Gln Trp Ser Val Asn His Asp Pro Val
        420                 425                 430

Lys Trp Pro Asn Pro Glu Asn Phe Asp Pro Ala Arg Phe Leu Asp Lys
    435                 440                 445

Asp Gly Leu Ile Asn Lys Asp Leu Thr Ser Arg Val Met Ile Phe Ser
450                 455                 460

Val Gly Lys Arg Arg Cys Ile Gly Glu Glu Leu Ser Lys Met Gln Leu
465                 470                 475                 480

Phe Leu Phe Ile Ser Ile Leu Ala His Gln Cys Asp Phe Arg Ala Asn
            485                 490                 495

Pro Asn Glu Pro Ala Lys Met Asn Phe Ser Tyr Gly Leu Thr Ile Lys
        500                 505                 510

Pro Lys Ser Phe Lys Val Asn Val Thr Leu Arg Glu Ser Met Glu Leu
        515                 520                 525

Leu Asp Ser Ala Val Gln Asn Leu Gln Ala Lys Glu Thr Cys Gln
    530                 535                 540

<210> SEQ ID NO 59
<211> LENGTH: 767
<212> TYPE: PRT
<213> ORGANISM: Homo sapiens

<400> SEQUENCE: 59

Met Ser Gln Arg Pro Arg Ala Pro Arg Ser Ala Leu Trp Leu Leu Ala
1               5                   10                  15

Pro Pro Leu Leu Arg Trp Ala Pro Pro Leu Leu Thr Val Leu His Ser
            20                  25                  30

Asp Leu Phe Gln Ala Leu Leu Asp Ile Leu Asp Tyr Tyr Glu Ala Ser
        35                  40                  45

Leu Ser Glu Ser Gln Lys Tyr Arg Tyr Gln Asp Glu Asp Thr Pro Pro
    50                  55                  60
```

-continued

```
Leu Glu His Ser Pro Ala His Leu Pro Asn Gln Ala Asn Ser Pro Pro
 65                  70                  75                  80

Val Ile Val Asn Thr Asp Thr Leu Glu Ala Pro Gly Tyr Glu Leu Gln
                 85                  90                  95

Val Asn Gly Thr Glu Gly Glu Met Glu Tyr Glu Ile Thr Leu Glu
             100                 105                 110

Arg Gly Asn Ser Gly Leu Gly Phe Ser Ile Ala Gly Thr Asp Asn
             115                 120                 125

Pro His Ile Gly Asp Asp Pro Ser Ile Phe Ile Thr Lys Ile Ile Pro
130                 135                 140

Gly Gly Ala Ala Ala Gln Asp Gly Arg Leu Arg Val Asn Asp Ser Ile
145                 150                 155                 160

Leu Phe Val Asn Glu Val Asp Val Arg Glu Val Thr His Ser Ala Ala
                165                 170                 175

Val Glu Ala Leu Lys Glu Ala Gly Ser Ile Val Arg Leu Tyr Val Met
            180                 185                 190

Arg Arg Lys Pro Pro Ala Glu Lys Val Met Glu Ile Lys Leu Ile Lys
            195                 200                 205

Gly Pro Lys Gly Leu Gly Phe Ser Ile Ala Gly Val Gly Asn Gln
210                 215                 220

His Ile Pro Gly Asp Asn Ser Ile Tyr Val Thr Lys Ile Ile Glu Gly
225                 230                 235                 240

Gly Ala Ala His Lys Asp Gly Arg Leu Gln Ile Gly Asp Lys Ile Leu
                245                 250                 255

Ala Val Asn Ser Val Gly Leu Glu Asp Val Met His Glu Asp Ala Val
            260                 265                 270

Ala Ala Leu Lys Asn Thr Tyr Asp Val Val Tyr Leu Lys Val Ala Lys
            275                 280                 285

Pro Ser Asn Ala Tyr Leu Ser Asp Ser Tyr Ala Pro Pro Asp Ile Thr
290                 295                 300

Thr Ser Tyr Ser Gln His Leu Asp Asn Glu Ile Ser His Ser Ser Tyr
305                 310                 315                 320

Leu Gly Thr Asp Tyr Pro Thr Ala Met Thr Pro Thr Ser Pro Arg Arg
                325                 330                 335

Tyr Ser Pro Val Ala Lys Asp Leu Leu Gly Glu Glu Asp Ile Pro Arg
            340                 345                 350

Glu Pro Arg Arg Ile Val Ile His Arg Gly Ser Thr Gly Leu Gly Phe
            355                 360                 365

Asn Ile Val Gly Gly Glu Asp Gly Glu Gly Ile Phe Ile Ser Phe Ile
370                 375                 380

Leu Ala Gly Gly Pro Ala Asp Leu Ser Gly Glu Leu Arg Lys Gly Asp
385                 390                 395                 400

Gln Ile Leu Ser Val Asn Gly Val Asp Leu Arg Asn Ala Ser His Glu
                405                 410                 415

Gln Ala Ala Ile Ala Leu Lys Asn Ala Gly Gln Thr Val Thr Ile Ile
            420                 425                 430

Ala Gln Tyr Lys Pro Glu Glu Tyr Ser Arg Phe Glu Ala Lys Ile His
            435                 440                 445

Asp Leu Arg Glu Gln Leu Met Asn Ser Ser Leu Gly Ser Gly Thr Ala
450                 455                 460

Ser Leu Arg Ser Asn Pro Lys Arg Gly Phe Tyr Ile Arg Ala Leu Phe
465                 470                 475                 480
```

-continued

Asp Tyr Asp Lys Thr Lys Asp Cys Gly Phe Leu Ser Gln Ala Leu Ser
            485                 490                 495

Phe Arg Phe Gly Asp Val Leu His Val Ile Asp Ala Ser Asp Glu Glu
        500                 505                 510

Trp Trp Gln Ala Arg Arg Val His Ser Asp Ser Glu Thr Asp Asp Ile
        515                 520                 525

Gly Phe Ile Pro Ser Lys Arg Val Glu Arg Glu Trp Ser Arg
    530                 535                 540

Leu Lys Ala Lys Asp Trp Gly Ser Ser Gly Ser Gln Gly Arg Glu
545                 550                 555                 560

Asp Ser Val Leu Ser Tyr Glu Thr Val Thr Gln Met Glu Val His Tyr
            565                 570                 575

Ala Arg Pro Ile Ile Ile Leu Gly Pro Thr Lys Asp Arg Ala Asn Asp
        580                 585                 590

Asp Leu Leu Ser Glu Phe Pro Asp Lys Phe Gly Ser Cys Val Pro His
        595                 600                 605

Thr Thr Arg Pro Lys Arg Glu Tyr Glu Ile Asp Gly Arg Asp Tyr His
    610                 615                 620

Phe Val Ser Ser Arg Glu Lys Met Glu Lys Asp Ile Gln Ala His Lys
625                 630                 635                 640

Phe Ile Glu Ala Gly Gln Tyr Asn Ser His Leu Tyr Gly Thr Ser Val
            645                 650                 655

Gln Ser Val Arg Glu Val Ala Glu Gln Gly Lys His Cys Ile Leu Asp
        660                 665                 670

Val Ser Ala Asn Ala Val Arg Leu Gln Ala Ala His Leu His Pro
        675                 680                 685

Ile Ala Ile Phe Ile Arg Pro Arg Ser Leu Glu Asn Val Leu Glu Ile
    690                 695                 700

Asn Lys Arg Ile Thr Glu Glu Gln Ala Arg Lys Ala Phe Asp Arg Ala
705                 710                 715                 720

Thr Lys Leu Glu Gln Glu Phe Thr Glu Cys Phe Ser Ala Ile Val Glu
            725                 730                 735

Gly Asp Ser Phe Glu Glu Ile Tyr His Lys Val Lys Arg Val Ile Glu
        740                 745                 750

Asp Leu Ser Gly Pro Tyr Ile Trp Val Pro Ala Arg Glu Arg Leu
        755                 760                 765

<210> SEQ ID NO 60
<211> LENGTH: 367
<212> TYPE: PRT
<213> ORGANISM: Homo sapiens

<400> SEQUENCE: 60

Met Val Met Glu Val Gly Thr Leu Asp Ala Gly Gly Leu Arg Ala Leu
1               5                   10                  15

Leu Gly Glu Arg Ala Ala Gln Cys Leu Leu Asp Cys Arg Ser Phe
            20                  25                  30

Phe Ala Phe Asn Ala Gly His Ile Ala Gly Ser Val Asn Val Arg Phe
        35                  40                  45

Ser Thr Ile Val Arg Arg Ala Lys Gly Ala Met Gly Leu Glu His
    50                  55                  60

Ile Val Pro Asn Ala Glu Leu Arg Gly Arg Leu Leu Ala Gly Ala Tyr
65                  70                  75                  80

His Ala Val Val Leu Leu Asp Glu Arg Ser Ala Ala Leu Asp Gly Ala
            85                  90                  95

```
Lys Arg Asp Gly Thr Leu Ala Leu Ala Ala Gly Ala Leu Cys Arg Glu
                100                 105                 110

Ala Arg Ala Ala Gln Val Phe Phe Leu Lys Gly Gly Tyr Glu Ala Phe
            115                 120                 125

Ser Ala Ser Cys Pro Glu Leu Cys Ser Lys Gln Ser Thr Pro Met Gly
        130                 135                 140

Leu Ser Leu Pro Leu Ser Thr Ser Val Pro Asp Ser Ala Glu Ser Gly
145                 150                 155                 160

Cys Ser Ser Cys Ser Thr Pro Leu Tyr Asp Gln Gly Gly Pro Val Glu
                165                 170                 175

Ile Leu Pro Phe Leu Tyr Leu Gly Ser Ala Tyr His Ala Ser Arg Lys
            180                 185                 190

Asp Met Leu Asp Ala Leu Gly Ile Thr Ala Leu Ile Asn Val Ser Ala
        195                 200                 205

Asn Cys Pro Asn His Phe Glu Gly His Tyr Gln Tyr Lys Ser Ile Pro
    210                 215                 220

Val Glu Asp Asn His Lys Ala Asp Ile Ser Ser Trp Phe Asn Glu Ala
225                 230                 235                 240

Ile Asp Phe Ile Asp Ser Ile Lys Asn Ala Gly Gly Arg Val Phe Val
                245                 250                 255

His Cys Gln Ala Gly Ile Ser Arg Ser Ala Thr Ile Cys Leu Ala Tyr
            260                 265                 270

Leu Met Arg Thr Asn Arg Val Lys Leu Asp Glu Ala Phe Glu Phe Val
        275                 280                 285

Lys Gln Arg Arg Ser Ile Ile Ser Pro Asn Phe Ser Phe Met Gly Gln
    290                 295                 300

Leu Leu Gln Phe Glu Ser Gln Val Leu Ala Pro His Cys Ser Ala Glu
305                 310                 315                 320

Ala Gly Ser Pro Ala Met Ala Val Leu Asp Arg Gly Thr Ser Thr Thr
                325                 330                 335

Thr Val Phe Asn Phe Pro Val Ser Ile Pro Val His Ser Thr Asn Ser
            340                 345                 350

Ala Leu Ser Tyr Leu Gln Ser Pro Ile Thr Thr Ser Pro Ser Cys
        355                 360                 365

<210> SEQ ID NO 61
<211> LENGTH: 345
<212> TYPE: PRT
<213> ORGANISM: Homo sapiens

<400> SEQUENCE: 61

Met Ala Ala Ala Glu Pro Ala Ser Ser Gly Gln Gln Ala Pro Ala Gly
1               5                   10                  15

Gln Gly Gln Gly Gln Arg Pro Pro Gln Pro Pro Gln Ala Gln Ala
            20                  25                  30

Pro Gln Pro Pro Pro Pro Gln Leu Gly Gly Ala Gly Gly Gly Ser
        35                  40                  45

Ser Arg His Glu Lys Ser Leu Gly Leu Leu Thr Thr Lys Phe Val Ser
    50                  55                  60

Leu Leu Gln Glu Ala Lys Asp Gly Val Leu Asp Leu Lys Ala Ala Ala
65                  70                  75                  80

Asp Thr Leu Ala Val Arg Gln Lys Arg Arg Ile Tyr Asp Ile Thr Asn
                85                  90                  95

Val Leu Glu Gly Ile Asp Leu Ile Glu Lys Lys Ser Lys Asn Ser Ile
            100                 105                 110
```

-continued

```
Gln Trp Lys Gly Val Gly Ala Gly Cys Asn Thr Lys Glu Val Ile Asp
            115                 120                 125

Arg Leu Arg Tyr Leu Lys Ala Glu Ile Glu Asp Leu Glu Leu Lys Glu
        130                 135                 140

Arg Glu Leu Asp Gln Gln Lys Leu Trp Leu Gln Gln Ser Ile Lys Asn
145                 150                 155                 160

Val Met Asp Asp Ser Ile Asn Asn Arg Phe Ser Tyr Val Thr His Glu
                165                 170                 175

Asp Ile Cys Asn Cys Phe Asn Gly Asp Thr Leu Leu Ala Ile Gln Ala
            180                 185                 190

Pro Ser Gly Thr Gln Leu Glu Val Pro Ile Pro Glu Met Gly Gln Asn
        195                 200                 205

Gly Gln Lys Lys Tyr Gln Ile Asn Leu Lys Ser His Ser Gly Pro Ile
        210                 215                 220

His Val Leu Leu Ile Asn Lys Glu Ser Ser Ser Lys Pro Val Val
225                 230                 235                 240

Phe Pro Val Pro Pro Asp Asp Leu Thr Gln Pro Ser Ser Gln Ser
                245                 250                 255

Leu Thr Pro Val Thr Pro Gln Lys Ser Ser Met Ala Thr Gln Asn Leu
            260                 265                 270

Pro Glu Gln His Val Ser Glu Arg Ser Gln Ala Leu Gln Gln Thr Ser
        275                 280                 285

Ala Thr Asp Ile Ser Ser Gly Ser Ile Ser Gly Asp Ile Ile Asp Glu
    290                 295                 300

Leu Met Ser Ser Asp Val Phe Pro Leu Leu Arg Leu Ser Pro Thr Pro
305                 310                 315                 320

Ala Asp Asp Tyr Asn Phe Asn Leu Asp Asp Asn Glu Gly Val Cys Asp
                325                 330                 335

Leu Phe Asp Val Gln Ile Leu Asn Tyr
            340                 345

<210> SEQ ID NO 62
<211> LENGTH: 427
<212> TYPE: PRT
<213> ORGANISM: Homo sapiens

<400> SEQUENCE: 62

Met Glu Thr Leu Cys Leu Arg Ala Ser Phe Trp Leu Ala Leu Val Gly
1               5                   10                  15

Cys Val Ile Ser Asp Asn Pro Glu Arg Tyr Ser Thr Asn Leu Ser Asn
            20                  25                  30

His Val Asp Asp Phe Thr Thr Phe Arg Gly Thr Glu Leu Ser Phe Leu
        35                  40                  45

Val Thr Thr His Gln Pro Thr Asn Leu Val Leu Pro Ser Asn Gly Ser
    50                  55                  60

Met His Asn Tyr Cys Pro Gln Gln Thr Lys Ile Thr Ser Ala Phe Lys
65                  70                  75                  80

Tyr Ile Asn Thr Val Ile Ser Cys Thr Ile Phe Ile Val Gly Met Val
                85                  90                  95

Gly Asn Ala Thr Leu Leu Arg Ile Ile Tyr Gln Asn Lys Cys Met Arg
            100                 105                 110

Asn Gly Pro Asn Ala Leu Ile Ala Ser Leu Ala Leu Gly Asp Leu Ile
        115                 120                 125

Tyr Val Val Ile Asp Leu Pro Ile Asn Val Phe Lys Leu Leu Ala Gly
    130                 135                 140
```

-continued

```
Arg Trp Pro Phe Asp His Asn Asp Phe Gly Val Phe Leu Cys Lys Leu
145                 150                 155                 160

Phe Pro Phe Leu Gln Lys Ser Ser Val Gly Ile Thr Val Leu Asn Leu
                165                 170                 175

Cys Ala Leu Ser Val Asp Arg Tyr Arg Ala Val Ala Ser Trp Ser Arg
            180                 185                 190

Val Gln Gly Ile Gly Ile Pro Leu Val Thr Ala Ile Glu Ile Val Ser
        195                 200                 205

Ile Trp Ile Leu Ser Phe Ile Leu Ala Ile Pro Glu Ala Ile Gly Phe
    210                 215                 220

Val Met Val Pro Phe Glu Tyr Arg Gly Glu Gln His Lys Thr Cys Met
225                 230                 235                 240

Leu Asn Ala Thr Ser Lys Phe Met Glu Phe Tyr Gln Asp Val Lys Asp
                245                 250                 255

Trp Trp Leu Phe Gly Phe Tyr Phe Cys Met Pro Leu Val Cys Thr Ala
            260                 265                 270

Ile Phe Tyr Thr Leu Met Thr Cys Glu Met Leu Asn Arg Arg Asn Gly
        275                 280                 285

Ser Leu Arg Ile Ala Leu Ser Glu His Leu Lys Gln Arg Arg Glu Val
    290                 295                 300

Ala Lys Thr Val Phe Cys Leu Val Val Ile Phe Ala Leu Cys Trp Phe
305                 310                 315                 320

Pro Leu His Leu Ser Arg Ile Leu Lys Lys Thr Val Tyr Asn Glu Met
                325                 330                 335

Asp Lys Asn Arg Cys Glu Leu Leu Ser Phe Leu Leu Leu Met Asp Tyr
            340                 345                 350

Ile Gly Ile Asn Leu Ala Thr Met Asn Ser Cys Ile Asn Pro Ile Ala
        355                 360                 365

Leu Tyr Phe Val Ser Lys Lys Phe Lys Asn Cys Phe Gln Ser Cys Leu
    370                 375                 380

Cys Cys Cys Cys Tyr Gln Ser Lys Ser Leu Met Thr Ser Val Pro Met
385                 390                 395                 400

Asn Gly Thr Ser Ile Gln Trp Lys Asn His Asp Gln Asn Asn His Asn
                405                 410                 415

Thr Asp Arg Ser Ser His Lys Asp Ser Met Asn
            420                 425

<210> SEQ ID NO 63
<211> LENGTH: 405
<212> TYPE: PRT
<213> ORGANISM: Homo sapiens

<400> SEQUENCE: 63

Met Glu Arg Leu Gln Lys Gln Pro Leu Thr Ser Pro Gly Ser Val Ser
1               5                   10                  15

Pro Ser Arg Asp Ser Ser Val Pro Gly Ser Pro Ser Ser Ile Val Ala
                20                  25                  30

Lys Met Asp Asn Gln Val Leu Gly Tyr Lys Asp Leu Ala Ala Ile Pro
            35                  40                  45

Lys Asp Lys Ala Ile Leu Asp Ile Glu Arg Pro Asp Leu Met Ile Tyr
        50                  55                  60

Glu Pro His Phe Thr Tyr Ser Leu Leu Glu His Val Glu Leu Pro Arg
65                  70                  75                  80

Gln Arg Glu Arg Ser Leu Ser Pro Lys Ser Thr Ser Pro Pro Pro Ser
                85                  90                  95
```

-continued

```
Pro Glu Val Trp Ala Asp Ser Arg Ser Pro Gly Ile Ile Ser Gln Ala
                100                 105                 110

Ser Ala Pro Arg Thr Thr Gly Thr Pro Arg Thr Ser Leu Pro His Phe
            115                 120                 125

His His Pro Glu Thr Ser Arg Pro Asp Ser Asn Ile Tyr Lys Lys Pro
        130                 135                 140

Pro Ile Tyr Lys Gln Arg Glu Ser Val Gly Gly Ser Pro Gln Thr Lys
145                 150                 155                 160

His Leu Ile Glu Asp Leu Ile Ile Glu Ser Ser Lys Phe Pro Ala Ala
                165                 170                 175

Gln Pro Pro Asp Pro Asn Gln Pro Ala Lys Ile Glu Thr Asp Tyr Trp
            180                 185                 190

Pro Cys Pro Pro Ser Leu Ala Val Val Glu Thr Glu Trp Arg Lys Arg
        195                 200                 205

Lys Ala Ser Arg Arg Gly Ala Glu Glu Glu Glu Glu Glu Asp Asp
210                 215                 220

Asp Ser Gly Glu Glu Met Lys Ala Leu Arg Glu Arg Gln Arg Glu Glu
225                 230                 235                 240

Leu Ser Lys Val Thr Ser Asn Leu Gly Lys Met Ile Leu Lys Glu Glu
                245                 250                 255

Met Glu Lys Ser Leu Pro Ile Arg Arg Lys Thr Arg Ser Leu Pro Asp
            260                 265                 270

Arg Thr Pro Phe His Thr Ser Leu His Gln Gly Thr Ser Lys Ser Ser
        275                 280                 285

Ser Leu Pro Arg Tyr Gly Arg Thr Thr Leu Ser Arg Leu Gln Ser Thr
290                 295                 300

Glu Phe Ser Pro Ser Gly Ser Glu Thr Gly Ser Pro Gly Leu Gln Asn
305                 310                 315                 320

Gly Glu Gly Gln Arg Gly Arg Met Asp Arg Gly Asn Ser Leu Pro Cys
                325                 330                 335

Val Leu Glu Gln Lys Ile Tyr Pro Tyr Glu Met Leu Val Val Thr Asn
            340                 345                 350

Lys Gly Arg Thr Lys Leu Pro Pro Gly Val Asp Arg Met Arg Leu Glu
        355                 360                 365

Arg His Leu Ser Ala Glu Asp Phe Ser Arg Val Phe Ala Met Ser Pro
370                 375                 380

Glu Glu Phe Gly Lys Leu Ala Leu Trp Lys Arg Asn Glu Leu Lys Lys
385                 390                 395                 400

Lys Ala Ser Leu Phe
                405
```

<210> SEQ ID NO 64
<211> LENGTH: 916
<212> TYPE: PRT
<213> ORGANISM: Homo sapiens

<400> SEQUENCE: 64

```
Met Glu Ser Gly Gln Pro Ala Arg Arg Ile Ala Met Ala Pro Leu Leu
1               5                   10                  15

Glu Tyr Glu Arg Gln Leu Val Leu Glu Leu Leu Asp Thr Asp Gly Leu
            20                  25                  30

Val Val Cys Ala Arg Gly Leu Gly Ala Asp Arg Leu Leu Tyr His Phe
        35                  40                  45

Leu Gln Leu His Cys His Pro Ala Cys Leu Val Leu Val Leu Asn Thr
    50                  55                  60
```

-continued

```
Gln Pro Ala Glu Glu Tyr Phe Ile Asn Gln Leu Lys Ile Glu Gly
 65                  70                  75                  80

Val Glu His Leu Pro Arg Arg Val Thr Asn Glu Ile Thr Ser Asn Ser
                 85                  90                  95

Arg Tyr Glu Val Tyr Thr Gln Gly Gly Val Ile Phe Ala Thr Ser Arg
            100                 105                 110

Ile Leu Val Val Asp Phe Leu Thr Asp Arg Ile Pro Ser Asp Leu Ile
        115                 120                 125

Thr Gly Ile Leu Val Tyr Arg Ala His Arg Ile Ile Glu Ser Cys Gln
    130                 135                 140

Glu Ala Phe Ile Leu Arg Leu Phe Arg Gln Lys Asn Lys Arg Gly Phe
145                 150                 155                 160

Ile Lys Ala Phe Thr Asp Asn Ala Val Ala Phe Asp Thr Gly Phe Cys
                165                 170                 175

His Val Glu Arg Val Met Arg Asn Leu Phe Val Arg Lys Leu Tyr Leu
            180                 185                 190

Trp Pro Arg Phe His Val Ala Val Asn Ser Phe Leu Glu Gln His Lys
        195                 200                 205

Pro Glu Val Val Glu Ile His Val Ser Met Thr Pro Thr Met Leu Ala
    210                 215                 220

Ile Gln Thr Ala Ile Leu Asp Ile Leu Asn Ala Cys Leu Lys Glu Leu
225                 230                 235                 240

Lys Cys His Asn Pro Ser Leu Glu Val Glu Asp Leu Ser Leu Glu Asn
                245                 250                 255

Ala Ile Gly Lys Pro Phe Asp Lys Thr Ile Arg His Tyr Leu Asp Pro
            260                 265                 270

Leu Trp His Gln Leu Gly Ala Lys Thr Lys Ser Leu Val Gln Asp Leu
        275                 280                 285

Lys Ile Leu Arg Thr Leu Leu Gln Tyr Leu Ser Gln Tyr Asp Cys Val
    290                 295                 300

Thr Phe Leu Asn Leu Leu Glu Ser Leu Arg Ala Thr Glu Lys Ala Phe
305                 310                 315                 320

Gly Gln Asn Ser Gly Trp Leu Phe Leu Asp Ser Ser Thr Ser Met Phe
                325                 330                 335

Ile Asn Ala Arg Ala Arg Val Tyr His Leu Pro Asp Ala Lys Met Ser
            340                 345                 350

Lys Lys Glu Lys Ile Ser Glu Lys Met Glu Ile Lys Glu Gly Glu Glu
        355                 360                 365

Thr Lys Lys Glu Leu Val Leu Glu Ser Asn Pro Lys Trp Glu Ala Leu
    370                 375                 380

Thr Glu Val Leu Lys Glu Ile Glu Ala Glu Asn Lys Glu Ser Glu Ala
385                 390                 395                 400

Leu Gly Gly Pro Gly Gln Val Leu Ile Cys Ala Ser Asp Asp Arg Thr
                405                 410                 415

Cys Ser Gln Leu Arg Asp Tyr Ile Thr Leu Gly Ala Glu Ala Phe Leu
            420                 425                 430

Leu Arg Leu Tyr Arg Lys Thr Phe Glu Lys Asp Ser Lys Ala Glu Glu
        435                 440                 445

Val Trp Met Lys Phe Arg Lys Glu Asp Ser Ser Lys Arg Ile Arg Lys
    450                 455                 460

Ser His Lys Arg Pro Lys Asp Pro Gln Asn Lys Glu Arg Ala Ser Thr
465                 470                 475                 480
```

-continued

```
Lys Glu Arg Thr Leu Lys Lys Lys Arg Lys Leu Thr Leu Thr Gln
                485                 490                 495

Met Val Gly Lys Pro Glu Leu Glu Glu Gly Asp Val Glu Glu
                500             505             510

Gly Tyr Arg Arg Glu Ile Ser Ser Pro Glu Ser Cys Pro Glu Glu
                515             520             525

Ile Lys His Glu Glu Phe Asp Val Asn Leu Ser Ser Asp Ala Ala Phe
                530             535             540

Gly Ile Leu Lys Glu Pro Leu Thr Ile Ile His Pro Leu Leu Gly Cys
545                 550             555                 560

Ser Asp Pro Tyr Ala Leu Thr Arg Val Leu His Glu Val Glu Pro Arg
                565             570                 575

Tyr Val Val Leu Tyr Asp Ala Glu Leu Thr Phe Val Arg Gln Leu Glu
                580             585             590

Ile Tyr Arg Ala Ser Arg Pro Gly Lys Pro Leu Arg Val Tyr Phe Leu
                595             600             605

Ile Tyr Gly Gly Ser Thr Glu Glu Gln Arg Tyr Leu Thr Ala Leu Arg
                610             615             620

Lys Glu Lys Glu Ala Phe Glu Lys Leu Ile Arg Glu Lys Ala Ser Met
625                 630             635                 640

Val Val Pro Glu Glu Arg Glu Gly Arg Asp Glu Thr Asn Leu Asp Leu
                645             650             655

Val Arg Gly Thr Ala Ser Ala Asp Val Ser Thr Asp Thr Arg Lys Ala
                660             665             670

Gly Gly Gln Glu Gln Asn Gly Thr Gln Gln Ser Ile Val Val Asp Met
                675             680             685

Arg Glu Phe Arg Ser Glu Leu Pro Ser Leu Ile His Arg Arg Gly Ile
                690             695             700

Asp Ile Glu Pro Val Thr Leu Glu Val Gly Asp Tyr Ile Leu Thr Pro
705                 710             715                 720

Glu Met Cys Val Glu Arg Lys Ser Ile Ser Asp Leu Ile Gly Ser Leu
                725             730             735

Asn Asn Gly Arg Leu Tyr Ser Gln Cys Ile Ser Met Ser Arg Tyr Tyr
                740             745             750

Lys Arg Pro Val Leu Leu Ile Glu Phe Asp Pro Ser Lys Pro Phe Ser
                755             760             765

Leu Thr Ser Arg Gly Ala Leu Phe Gln Glu Ile Ser Ser Asn Asp Ile
                770             775             780

Ser Ser Lys Leu Thr Leu Leu Thr Leu His Phe Pro Arg Leu Arg Ile
785                 790             795                 800

Leu Trp Cys Pro Ser Pro His Ala Thr Ala Glu Leu Phe Glu Glu Leu
                805             810             815

Lys Gln Ser Lys Pro Gln Pro Asp Ala Ala Thr Ala Leu Ala Ile Thr
                820             825             830

Ala Asp Ser Glu Thr Leu Pro Glu Ser Glu Lys Tyr Asn Pro Gly Pro
                835             840             845

Gln Asp Phe Leu Leu Lys Met Pro Gly Val Asn Ala Lys Asn Cys Arg
                850             855             860

Ser Leu Met His His Val Lys Asn Ile Ala Glu Leu Ala Ala Leu Ser
865                 870             875                 880

Gln Asp Glu Leu Thr Ser Ile Leu Gly Asn Ala Ala Asn Ala Lys Gln
                885             890             895
```

-continued

Leu Tyr Asp Phe Ile His Thr Ser Phe Ala Glu Val Val Ser Lys Gly
            900                 905                 910

Lys Gly Lys Lys
        915

<210> SEQ ID NO 65
<211> LENGTH: 297
<212> TYPE: PRT
<213> ORGANISM: Homo sapiens

<400> SEQUENCE: 65

Glu Phe Gly Ala Lys Ser Asn Gln Gln Leu Asp Arg Lys Arg Met Ala
1               5                   10                  15

Leu Lys Gln Ile Ser Ser Asn Lys Cys Phe Gly Gly Leu Gln Lys Val
            20                  25                  30

Phe Glu His Asp Ser Val Glu Leu Asn Cys Lys Met Lys Phe Ala Val
        35                  40                  45

Tyr Leu Pro Pro Lys Ala Glu Thr Gly Lys Cys Pro Ala Cys Ile Gly
    50                  55                  60

Ser Pro Gly Leu Thr Cys Thr Glu Pro Lys Phe Tyr His Gln Asn Leu
65                  70                  75                  80

Val Ile Ile Ser Leu Leu Gln Asn His Leu Ser Cys Cys His Cys Ser
                85                  90                  95

Arg Tyr Ser Pro Arg Ala Cys Asn Ile Lys Gly Glu Asp Glu Ser Trp
            100                 105                 110

Asp Phe Ala Thr Gly Arg Gly Phe Tyr Val Asp Ala Thr Glu Asp Pro
        115                 120                 125

Trp Lys Thr Asn Tyr Arg Met Tyr Ser Tyr Val Thr Glu Glu Leu Pro
    130                 135                 140

Gln Leu Ile Asn Ala Asn Phe Pro Val Asp Pro Gln Arg Met Ser Ile
145                 150                 155                 160

Phe Gly His Ser Met Gly Gly His Gly Ala Leu Ile Cys Ala Leu Lys
                165                 170                 175

Asn Pro Gly Lys Tyr Lys Ser Val Ser Ala Phe Ala Pro Ile Cys Asn
            180                 185                 190

Pro Val Leu Cys Pro Trp Gly Lys Lys Ala Phe Ser Gly Tyr Leu Gly
        195                 200                 205

Thr Asp Gln Ser Lys Trp Lys Ala Tyr Asp Ala Thr His Leu Val Lys
    210                 215                 220

Ser Tyr Pro Gly Ser Gln Leu Asp Ile Leu Ile Asp Gln Gly Lys Asp
225                 230                 235                 240

Asp Gln Phe Leu Leu Asp Gly Gln Leu Leu Pro Asp Asn Phe Ile Ala
                245                 250                 255

Ala Cys Thr Glu Lys Lys Ile Pro Val Val Phe Arg Leu Gln Glu Gly
            260                 265                 270

Tyr Asp His Ser Tyr Tyr Phe Ile Ala Thr Phe Ile Thr Asp His Ile
        275                 280                 285

Arg His His Ala Lys Tyr Leu Asn Ala
    290                 295

<210> SEQ ID NO 66
<211> LENGTH: 756
<212> TYPE: PRT
<213> ORGANISM: Homo sapiens -continued

```
<400> SEQUENCE: 66

Met Ser Pro Gln Lys Arg Val Lys Asn Val Gln Ala Gln Asn Arg Thr
 1               5                  10                  15

Ser Gln Gly Ser Ser Ser Phe Gln Thr Thr Leu Ser Ala Trp Lys Val
             20                  25                  30

Lys Gln Asp Pro Ser Asn Ser Lys Asn Ile Ser Lys His Gly Gln Asn
         35                  40                  45

Asn Pro Val Gly Asp Tyr Glu His Ala Asp Asp Gln Ala Glu Glu Asp
     50                  55                  60

Ala Leu Gln Met Ala Val Gly Tyr Phe Glu Lys Gly Pro Ile Lys Ala
 65                  70                  75                  80

Ser Gln Asn Lys Asp Lys Thr Leu Glu Lys His Leu Lys Thr Val Glu
                 85                  90                  95

Asn Val Ala Trp Lys Asn Gly Leu Ala Ser Glu Ile Asp Ile Leu
             100                 105                 110

Leu Asn Ile Ala Leu Ser Gly Lys Phe Gly Asn Ala Val Asn Thr Arg
            115                 120                 125

Ile Leu Lys Cys Met Ile Pro Ala Thr Val Ile Ser Glu Asp Ser Val
130                 135                 140

Val Lys Ala Val Ser Trp Leu Cys Val Gly Lys Cys Ser Gly Ser Thr
145                 150                 155                 160

Lys Val Leu Phe Tyr Arg Trp Leu Val Ala Met Phe Asp Phe Ile Asp
                165                 170                 175

Arg Lys Glu Gln Ile Asn Leu Leu Tyr Gly Phe Phe Ala Ser Leu
            180                 185                 190

Gln Asp Asp Ala Leu Cys Pro Tyr Val Cys His Leu Leu Tyr Leu Leu
            195                 200                 205

Thr Lys Lys Glu Asn Val Lys Pro Phe Arg Val Arg Lys Leu Leu Asp
    210                 215                 220

Leu Gln Ala Lys Met Gly Met Gln Pro His Leu Gln Ala Leu Leu Ser
225                 230                 235                 240

Leu Tyr Lys Phe Phe Ala Pro Ala Leu Ile Ser Val Ser Leu Pro Val
                245                 250                 255

Arg Lys Lys Ile Tyr Leu Gln Asn Ser Glu Asn Leu Trp Lys Thr Ala
            260                 265                 270

Leu Leu Ala Val Lys Gln Arg Asn Arg Gly Pro Ser Pro Glu Pro Leu
        275                 280                 285

Lys Leu Met Leu Gly Pro Ala Asn Val Arg Pro Leu Arg Lys Trp
    290                 295                 300

Asn Ser Leu Ser Val Ile Pro Val Leu Asn Ser Ser Tyr Thr Lys
305                 310                 315                 320

Glu Cys Gly Lys Lys Glu Met Ser Leu Ser Asp Cys Leu Asn Arg Ser
                325                 330                 335

Gly Ser Phe Pro Leu Glu Gln Leu Gln Ser Phe Pro Gln Leu Leu Gln
            340                 345                 350

Asn Ile His Cys Leu Glu Leu Pro Ser Gln Met Gly Ser Val Leu Asn
        355                 360                 365

Asn Ser Leu Leu Leu His Tyr Ile Asn Cys Val Arg Asp Glu Pro Val
    370                 375                 380

Leu Leu Arg Phe His Tyr Trp Leu Ser Gln Thr Leu Gln Glu Glu Cys
385                 390                 395                 400

Ile Trp Tyr Lys Val Asn Asn Tyr Glu His Gly Lys Glu Phe Thr Asn
                405                 410                 415
```

-continued

Phe Leu Asp Thr Ile Ile Arg Ala Glu Cys Phe Leu Gln Glu Gly Tyr
            420                 425                 430

Tyr Ser Cys Glu Ala Phe Leu Tyr Lys Ser Leu Pro Leu Trp Asp Gly
            435                 440                 445

Leu Ser Cys Arg Ser Gln Phe Leu Gln Leu Val Ser Trp Ile Pro Phe
            450                 455                 460

Ser Ser Phe Ser Glu Val Lys Pro Leu Leu Phe Asp His Leu Ala Gln
465                 470                 475                 480

Leu Phe Phe Thr Ser Thr Ile Tyr Phe Lys Cys Ser Val Leu Gln Ser
            485                 490                 495

Leu Lys Glu Leu Leu Gln Asn Trp Leu Leu Trp Leu Ser Met Asp Ile
            500                 505                 510

His Met Lys Pro Val Thr Asn Ser Pro Leu Glu Thr Thr Leu Gly Gly
            515                 520                 525

Ser Met Asn Cys Val Ser Lys Leu Ile His Tyr Val Gly Trp Leu Ser
            530                 535                 540

Thr Thr Ala Met Arg Leu Glu Ser Asn Asn Thr Phe Leu Leu His Phe
545                 550                 555                 560

Ile Leu Asp Phe Tyr Glu Lys Val Cys Asp Ile Tyr Ile Asn Tyr Asp
            565                 570                 575

Leu Pro Leu Val Val Leu Phe Pro Pro Gly Ile Phe Tyr Ser Ala Leu
            580                 585                 590

Leu Ser Leu Asp Thr Ser Ile Leu Asn Gln Leu Cys Phe Ile Met His
            595                 600                 605

Arg Tyr Arg Lys Asn Leu Thr Ala Ala Lys Lys Asn Glu Leu Val Gln
            610                 615                 620

Lys Thr Lys Ser Glu Phe Asn Phe Ser Ser Lys Thr Tyr Gln Glu Phe
625                 630                 635                 640

Asn Tyr Tyr Leu Thr Ser Met Val Gly Cys Leu Trp Thr Ser Lys Pro
            645                 650                 655

Phe Ala Lys Gly Ile Tyr Ile Asp Pro Glu Ile Leu Glu Lys Thr Gly
            660                 665                 670

Val Ala Glu Tyr Lys Asn Ser Leu Asn Val Val His His Pro Ser Phe
            675                 680                 685

Leu Ser Tyr Ala Val Ser Phe Leu Leu Gln Glu Ser Pro Glu Glu Arg
            690                 695                 700

Thr Val Asn Val Ser Ser Ile Arg Gly Lys Lys Trp Ser Trp Tyr Leu
705                 710                 715                 720

Asp Tyr Leu Phe Ser Gln Gly Leu Gln Gly Leu Lys Leu Phe Ile Arg
            725                 730                 735

Ser Ser Val His His Ser Ser Ile Pro Arg Ala Glu Gly Ile Asn Cys
            740                 745                 750

Asn Asn Gln Tyr
        755

<210> SEQ ID NO 67
<211> LENGTH: 504
<212> TYPE: PRT
<213> ORGANISM: Homo sapiens

<400> SEQUENCE: 67

Met Glu Ala Pro Leu Gln Thr Glu Met Val Glu Leu Val Pro Asn Gly
1               5                   10                  15

Lys His Ser Glu Gly Leu Leu Pro Val Ile Thr Pro Met Ala Gly Asn
            20                  25                  30

-continued

```
Gln Arg Val Glu Asp Pro Ala Arg Ser Cys Met Glu Gly Lys Ser Phe
         35                  40                  45

Leu Gln Lys Ser Pro Ser Lys Glu Pro His Phe Thr Asp Phe Glu Gly
         50                  55                  60

Lys Thr Ser Phe Gly Met Ser Val Phe Asn Leu Ser Asn Ala Ile Met
 65                  70                  75                  80

Gly Ser Gly Ile Leu Gly Leu Ala Tyr Ala Met Ala Asn Thr Gly Ile
                 85                  90                  95

Ile Leu Phe Leu Phe Leu Leu Thr Ala Val Ala Leu Leu Ser Ser Tyr
             100                 105                 110

Ser Ile His Leu Leu Leu Lys Ser Ser Gly Val Val Gly Ile Arg Ala
             115                 120                 125

Tyr Glu Gln Leu Gly Tyr Arg Ala Phe Gly Thr Pro Gly Lys Leu Ala
         130                 135                 140

Ala Ala Leu Ala Ile Thr Leu Gln Asn Ile Gly Ala Met Ser Ser Tyr
145                 150                 155                 160

Leu Tyr Ile Ile Lys Ser Glu Leu Pro Leu Val Ile Gln Thr Phe Leu
                 165                 170                 175

Asn Leu Glu Glu Lys Thr Ser Asp Trp Tyr Met Asn Gly Asn Tyr Leu
             180                 185                 190

Val Ile Leu Val Ser Val Thr Ile Ile Leu Pro Leu Ala Leu Met Arg
             195                 200                 205

Gln Leu Gly Tyr Leu Gly Tyr Ser Ser Gly Phe Ser Leu Ser Cys Met
         210                 215                 220

Val Phe Phe Leu Ile Ala Val Ile Tyr Lys Lys Phe His Val Pro Cys
225                 230                 235                 240

Pro Leu Pro Pro Asn Phe Asn Asn Thr Thr Gly Asn Phe Ser His Val
                 245                 250                 255

Glu Ile Val Lys Glu Lys Val Gln Leu Gln Val Glu Pro Glu Ala Ser
             260                 265                 270

Ala Phe Cys Thr Pro Ser Tyr Phe Thr Leu Asn Ser Gln Thr Ala Tyr
         275                 280                 285

Thr Ile Pro Ile Met Ala Phe Ala Phe Val Cys His Pro Glu Val Leu
         290                 295                 300

Pro Ile Tyr Thr Glu Leu Lys Asp Pro Ser Lys Lys Met Gln His
305                 310                 315                 320

Ile Ser Asn Leu Ser Ile Ala Val Met Tyr Ile Met Tyr Phe Leu Ala
                 325                 330                 335

Ala Leu Phe Gly Tyr Leu Thr Phe Tyr Asn Gly Val Glu Ser Glu Leu
             340                 345                 350

Leu His Thr Tyr Ser Lys Val Asp Pro Phe Asp Val Leu Ile Leu Cys
             355                 360                 365

Val Arg Val Ala Val Leu Thr Ala Val Thr Leu Thr Val Pro Ile Val
         370                 375                 380

Leu Phe Pro Val Arg Arg Ala Ile Gln Gln Met Leu Phe Pro Asn Gln
385                 390                 395                 400

Glu Phe Ser Trp Leu Arg His Val Leu Ile Ala Val Gly Leu Leu Thr
                 405                 410                 415

Cys Ile Asn Leu Leu Val Ile Phe Ala Pro Asn Ile Leu Gly Ile Phe
             420                 425                 430

Gly Val Ile Gly Ala Thr Ser Ala Pro Phe Leu Ile Phe Ile Phe Pro
         435                 440                 445
```

-continued

```
Ala Ile Phe Tyr Phe Arg Ile Met Pro Thr Glu Lys Glu Pro Ala Arg
    450                 455                 460

Ser Thr Pro Lys Ile Leu Ala Leu Cys Phe Ala Met Leu Gly Phe Leu
465                 470                 475                 480

Leu Met Thr Met Ser Leu Ser Phe Ile Ile Ile Asp Trp Ala Ser Gly
                485                 490                 495

Thr Ser Arg His Gly Gly Asn His
            500

<210> SEQ ID NO 68
<211> LENGTH: 145
<212> TYPE: PRT
<213> ORGANISM: Homo sapiens

<400> SEQUENCE: 68

Met Ala Thr Trp Ala Leu Leu Leu Ala Met Leu Leu Gly Asn
1               5                   10                  15

Pro Gly Leu Val Phe Ser Arg Leu Ser Pro Glu Tyr Tyr Asp Leu Ala
                20                  25                  30

Arg Ala His Leu Arg Asp Glu Glu Lys Ser Cys Pro Cys Leu Ala Gln
            35                  40                  45

Glu Gly Pro Gln Gly Asp Leu Leu Thr Lys Thr Gln Glu Leu Gly Arg
    50                  55                  60

Asp Tyr Arg Thr Cys Leu Thr Ile Val Gln Lys Leu Lys Lys Met Val
65                  70                  75                  80

Asp Lys Pro Thr Gln Arg Ser Val Ser Asn Ala Ala Thr Arg Val Cys
                85                  90                  95

Arg Thr Gly Arg Ser Arg Trp Arg Asp Val Cys Arg Asn Phe Met Arg
            100                 105                 110

Arg Tyr Gln Ser Arg Val Ile Gln Gly Leu Val Ala Gly Glu Thr Ala
        115                 120                 125

Gln Gln Ile Cys Glu Asp Leu Arg Leu Cys Ile Pro Ser Thr Gly Pro
    130                 135                 140

Leu
145

<210> SEQ ID NO 69
<211> LENGTH: 128
<212> TYPE: PRT
<213> ORGANISM: Homo sapiens

<400> SEQUENCE: 69

Met Trp Ser Thr Arg Ser Pro Asn Ser Thr Ala Trp Pro Leu Ser Leu
1               5                   10                  15

Glu Pro Asp Pro Gly Met Ala Ser Ala Ser Thr Thr Met His Thr Thr
                20                  25                  30

Thr Ile Ala Glu Pro Asp Pro Gly Met Ser Gly Trp Pro Asp Gly Arg
            35                  40                  45

Met Glu Thr Ser Thr Pro Thr Ile Met Asp Ile Val Val Ile Ala Gly
    50                  55                  60

Val Ile Ala Ala Val Ala Ile Val Leu Val Ser Leu Leu Phe Val Met
65                  70                  75                  80

Leu Arg Tyr Met Tyr Arg His Lys Gly Thr Tyr His Thr Asn Glu Ala
                85                  90                  95

Lys Gly Thr Glu Phe Ala Glu Ser Ala Asp Ala Ala Leu Gln Gly Asp
            100                 105                 110
```

Pro Ala Leu Gln Asp Ala Gly Asp Ser Ser Arg Lys Glu Tyr Phe Ile
        115                 120                 125

<210> SEQ ID NO 70
<211> LENGTH: 4861
<212> TYPE: PRT
<213> ORGANISM: Homo sapiens

<400> SEQUENCE: 70

Met Ala Thr Met Ile Pro Pro Val Lys Leu Lys Trp Leu Glu His Leu
1               5                   10                  15

Asn Ser Ser Trp Ile Thr Glu Asp Ser Glu Ser Ile Ala Thr Arg Glu
            20                  25                  30

Gly Val Ala Val Leu Tyr Ser Lys Leu Val Ser Asn Lys Glu Val Val
        35                  40                  45

Pro Leu Pro Gln Gln Val Leu Cys Leu Lys Gly Pro Gln Leu Pro Asp
    50                  55                  60

Phe Glu Arg Glu Ser Leu Ser Ser Asp Glu Gln Asp His Tyr Leu Asp
65                  70                  75                  80

Ala Leu Leu Ser Ser Gln Leu Ala Leu Ala Lys Met Val Cys Ser Asp
                85                  90                  95

Ser Pro Phe Ala Gly Ala Leu Arg Lys Arg Leu Leu Val Leu Gln Arg
            100                 105                 110

Val Phe Tyr Ala Leu Ser Asn Lys Tyr His Asp Lys Gly Lys Val Lys
        115                 120                 125

Gln Gln Gln His Ser Pro Glu Ser Ser Gly Ser Ala Asp Val His
    130                 135                 140

Ser Val Ser Glu Arg Pro Arg Ser Ser Thr Asp Ala Leu Ile Glu Met
145                 150                 155                 160

Gly Val Arg Thr Gly Leu Ser Leu Leu Phe Ala Leu Leu Arg Gln Ser
                165                 170                 175

Trp Met Met Pro Val Ser Gly Pro Gly Leu Ser Leu Cys Asn Asp Val
            180                 185                 190

Ile His Thr Ala Ile Glu Val Val Ser Ser Leu Pro Pro Leu Ser Leu
        195                 200                 205

Ala Asn Glu Ser Lys Ile Pro Pro Met Gly Leu Asp Cys Leu Ser Gln
    210                 215                 220

Val Thr Thr Phe Leu Lys Gly Val Thr Ile Pro Asn Ser Gly Ala Asp
225                 230                 235                 240

Thr Leu Gly Arg Arg Leu Ala Ser Glu Leu Leu Leu Gly Leu Ala Ala
                245                 250                 255

Gln Arg Gly Ser Leu Arg Tyr Leu Leu Glu Trp Ile Glu Met Ala Leu
            260                 265                 270

Gly Ala Ser Ala Val Val His Thr Met Glu Lys Gly Lys Leu Leu Ser
        275                 280                 285

Ser Gln Glu Gly Met Ile Ser Phe Asp Cys Phe Met Thr Ile Leu Met
    290                 295                 300

Gln Met Arg Arg Ser Leu Gly Ser Ser Ala Asp Arg Ser Gln Trp Arg
305                 310                 315                 320

Glu Pro Thr Arg Thr Ser Asp Gly Leu Cys Ser Leu Tyr Glu Ala Ala
                325                 330                 335

Leu Cys Leu Phe Glu Glu Val Cys Arg Met Ala Ser Asp Tyr Ser Arg
            340                 345                 350

Thr Cys Ala Ser Pro Asp Ser Ile Gln Thr Gly Asp Ala Pro Ile Val
        355                 360                 365

-continued

```
Ser Glu Thr Cys Glu Val Tyr Val Trp Gly Ser Asn Ser Ser His Gln
    370                 375                 380

Leu Val Glu Gly Thr Gln Glu Lys Ile Leu Gln Pro Lys Leu Ala Pro
385                 390                 395                 400

Ser Phe Ser Asp Ala Gln Thr Ile Glu Ala Gly Gln Tyr Cys Thr Phe
                405                 410                 415

Val Ile Ser Thr Asp Gly Ser Val Arg Ala Cys Gly Lys Gly Ser Tyr
            420                 425                 430

Gly Arg Leu Gly Leu Gly Asp Ser Asn Asn Gln Ser Thr Leu Lys Lys
        435                 440                 445

Leu Thr Phe Glu Pro His Arg Ser Ile Lys Lys Val Ser Ser Ser Lys
    450                 455                 460

Gly Ser Asp Gly His Thr Leu Ala Phe Thr Thr Glu Gly Glu Val Phe
465                 470                 475                 480

Ser Trp Gly Asp Gly Asp Tyr Gly Lys Leu Gly His Gly Asn Ser Ser
                485                 490                 495

Thr Gln Lys Tyr Pro Lys Leu Ile Gln Gly Pro Leu Gln Gly Lys Val
            500                 505                 510

Val Val Cys Val Ser Ala Gly Tyr Arg His Ser Ala Ala Val Thr Glu
        515                 520                 525

Asp Gly Glu Leu Tyr Thr Trp Gly Glu Gly Asp Phe Gly Arg Leu Gly
    530                 535                 540

His Gly Asp Ser Asn Ser Arg Asn Ile Pro Thr Leu Val Lys Asp Ile
545                 550                 555                 560

Ser Asn Val Gly Glu Val Ser Cys Gly Ser Ser His Thr Ile Ala Leu
                565                 570                 575

Ser Lys Asp Gly Arg Thr Val Trp Ser Phe Gly Gly Gly Asp Asn Gly
            580                 585                 590

Lys Leu Gly His Gly Asp Thr Asn Arg Val Tyr Lys Pro Lys Val Ile
        595                 600                 605

Glu Ala Leu Gln Gly Met Phe Ile Arg Lys Val Cys Ala Gly Ser Gln
    610                 615                 620

Ser Ser Leu Ala Leu Thr Ser Thr Gly Gln Val Tyr Ala Trp Gly Cys
625                 630                 635                 640

Gly Ala Cys Leu Gly Cys Gly Ser Ser Glu Ala Thr Ala Leu Arg Pro
                645                 650                 655

Lys Leu Ile Glu Glu Leu Ala Ala Thr Arg Ile Val Asp Val Ser Ile
            660                 665                 670

Gly Asp Ser His Cys Leu Ala Leu Ser His Asp Asn Glu Val Tyr Ala
        675                 680                 685

Trp Gly Asn Asn Ser Met Gly Gln Cys Gly Gln Gly Asn Ser Thr Gly
    690                 695                 700

Pro Ile Thr Lys Pro Lys Lys Val Ser Gly Leu Asp Gly Ile Ala Ile
705                 710                 715                 720

Gln Gln Ile Ser Ala Gly Thr Ser His Ser Leu Ala Trp Thr Ala Leu
                725                 730                 735

Pro Arg Asp Arg Gln Val Val Ala Trp His Arg Pro Tyr Cys Val Asp
            740                 745                 750

Leu Glu Glu Ser Thr Phe Ser His Leu Arg Ser Phe Leu Glu Arg Tyr
        755                 760                 765

Cys Asp Lys Ile Asn Ser Glu Ile Pro Pro Leu Pro Phe Pro Ser Ser
    770                 775                 780
```

-continued

```
Arg Glu His His Ser Phe Leu Lys Leu Cys Leu Lys Leu Leu Ser Asn
785                 790                 795                 800

His Leu Ala Leu Ala Leu Ala Gly Gly Val Ala Thr Ser Ile Leu Gly
            805                 810                 815

Arg Gln Ala Gly Pro Leu Arg Asn Leu Leu Phe Arg Leu Met Asp Ser
        820                 825                 830

Thr Val Pro Asp Glu Ile Gln Glu Val Val Ile Glu Thr Leu Ser Val
    835                 840                 845

Gly Ala Thr Met Leu Leu Pro Pro Leu Arg Glu Arg Met Glu Leu Leu
850                 855                 860

His Ser Leu Leu Pro Gln Gly Pro Asp Arg Trp Glu Ser Leu Ser Lys
865                 870                 875                 880

Gly Gln Arg Met Gln Leu Asp Ile Ile Leu Thr Ser Leu Gln Asp His
            885                 890                 895

Thr His Val Ala Ser Leu Leu Gly Tyr Ser Ser Pro Ser Asp Ala Ala
        900                 905                 910

Asp Leu Ser Ser Val Cys Thr Gly Tyr Gly Asn Leu Ser Asp Gln Pro
    915                 920                 925

Tyr Gly Thr Gln Ser Cys His Pro Asp Thr His Leu Ala Glu Ile Leu
930                 935                 940

Met Lys Thr Leu Leu Arg Asn Leu Gly Phe Tyr Thr Asp Gln Ala Phe
945                 950                 955                 960

Gly Glu Leu Glu Lys Asn Ser Asp Lys Phe Leu Leu Gly Thr Ser Ser
            965                 970                 975

Ser Glu Asn Ser Gln Pro Ala His Leu His Glu Leu Leu Cys Ser Leu
        980                 985                 990

Gln Lys Gln Leu Leu Ala Phe Cys His Ile Asn Asn Ile Ser Glu Asn
    995                 1000                1005

Ser Ser Ser Val Ala Leu Leu His Lys His Leu Gln Leu Leu Leu
    1010                1015                1020

Pro His Ala Thr Asp Ile Tyr Ser Arg Ser Ala Asn Leu Leu Lys
    1025                1030                1035

Glu Ser Pro Trp Asn Gly Ser Val Gly Glu Lys Leu Arg Asp Val
    1040                1045                1050

Ile Tyr Val Ser Ala Ala Gly Ser Met Leu Cys Gln Ile Val Asn
    1055                1060                1065

Ser Leu Leu Leu Leu Pro Val Ser Val Ala Arg Pro Leu Leu Ser
    1070                1075                1080

Tyr Leu Leu Asp Leu Leu Pro Pro Leu Asp Cys Leu Asn Arg Leu
    1085                1090                1095

Leu Pro Ala Ala Asp Leu Leu Glu Asp Gln Glu Leu Gln Trp Pro
    1100                1105                1110

Leu His Gly Gly Pro Glu Leu Ile Asp Pro Ala Gly Leu Pro Leu
    1115                1120                1125

Pro Gln Pro Ala Gln Ser Trp Val Trp Leu Val Asp Leu Glu Arg
    1130                1135                1140

Thr Ile Ala Leu Leu Ile Gly Arg Cys Leu Gly Gly Met Leu Gln
    1145                1150                1155

Gly Ser Pro Val Ser Pro Glu Glu Gln Asp Thr Ala Tyr Trp Met
    1160                1165                1170

Lys Thr Pro Leu Phe Ser Asp Gly Val Glu Met Asp Thr Pro Gln
    1175                1180                1185
```

-continued

```
Leu Asp Lys Cys Met Ser Cys Leu Leu Glu Val Ala Leu Ser Gly
    1190                1195                1200

Asn Glu Glu Gln Lys Pro Phe Asp Tyr Lys Leu Arg Pro Glu Ile
    1205                1210                1215

Ala Val Tyr Val Asp Leu Ala Leu Gly Cys Ser Lys Glu Pro Ala
    1220                1225                1230

Arg Ser Leu Trp Ile Ser Met Gln Asp Tyr Ala Val Ser Lys Asp
    1235                1240                1245

Trp Asp Ser Ala Thr Leu Ser Asn Glu Ser Leu Leu Asp Thr Val
    1250                1255                1260

Ser Arg Phe Val Leu Ala Ala Leu Leu Lys His Thr Asn Leu Leu
    1265                1270                1275

Ser Gln Ala Cys Gly Glu Ser Arg Tyr Gln Pro Gly Lys His Leu
    1280                1285                1290

Ser Glu Val Tyr Arg Cys Val Tyr Lys Val Arg Ser Arg Leu Leu
    1295                1300                1305

Ala Cys Lys Asn Leu Glu Leu Ile Gln Thr Arg Ser Ser Ser Arg
    1310                1315                1320

Asp Arg Trp Ile Ser Glu Asn Gln Asp Ser Ala Asp Val Asp Pro
    1325                1330                1335

Gln Glu His Ser Phe Thr Arg Thr Ile Asp Glu Glu Ala Glu Met
    1340                1345                1350

Glu Glu Gln Ala Glu Arg Asp Arg Glu Glu Gly His Pro Glu Pro
    1355                1360                1365

Glu Asp Glu Glu Glu Glu Arg Glu His Glu Val Met Thr Ala Gly
    1370                1375                1380

Lys Ile Phe Gln Cys Phe Leu Ser Ala Arg Glu Val Ala Arg Ser
    1385                1390                1395

Arg Asp Arg Asp Arg Met Asn Ser Gly Ala Gly Ser Gly Ala Arg
    1400                1405                1410

Ala Asp Asp Pro Pro Pro Gln Ser Gln Gln Glu Arg Arg Val Ser
    1415                1420                1425

Thr Asp Leu Pro Glu Gly Gln Asp Val Tyr Thr Ala Ala Cys Asn
    1430                1435                1440

Ser Val Ile His Arg Cys Ala Leu Leu Ile Leu Gly Val Ser Pro
    1445                1450                1455

Val Ile Asp Glu Leu Gln Lys Arg Arg Glu Glu Gly Gln Leu Gln
    1460                1465                1470

Gln Pro Ser Thr Ser Ala Ser Glu Gly Gly Gly Leu Met Thr Arg
    1475                1480                1485

Ser Glu Ser Leu Thr Ala Glu Ser Arg Leu Val His Thr Ser Pro
    1490                1495                1500

Asn Tyr Arg Leu Ile Lys Ser Arg Ser Glu Ser Asp Leu Ser Gln
    1505                1510                1515

Pro Glu Ser Asp Glu Glu Gly Tyr Ala Leu Ser Gly Arg Gln Asn
    1520                1525                1530

Val Asp Leu Asp Leu Ala Ala Ser His Arg Lys Arg Gly Pro Met
    1535                1540                1545

His Ser Gln Leu Glu Ser Leu Ser Asp Ser Trp Ala Arg Leu Lys
    1550                1555                1560

His Ser Arg Asp Trp Leu Cys Asn Ser Ser Tyr Ser Phe Glu Ser
    1565                1570                1575
```

-continued

```
Asp Phe Asp Leu Thr Lys Ser Leu Gly Val His Thr Leu Ile Glu
    1580                1585                1590
Asn Val Val Ser Phe Val Ser Gly Asp Val Gly Asn Ala Pro Gly
    1595                1600                1605
Phe Lys Glu Pro Glu Glu Ser Met Ser Thr Ser Pro Gln Ala Ser
    1610                1615                1620
Ile Ile Ala Met Glu Gln Gln Gln Leu Arg Ala Glu Leu Arg Leu
    1625                1630                1635
Glu Ala Leu His Gln Ile Leu Val Leu Leu Ser Gly Met Glu Glu
    1640                1645                1650
Lys Gly Ser Ile Ser Leu Ala Gly Ser Arg Leu Ser Ser Gly Phe
    1655                1660                1665
Gln Ser Ser Thr Leu Leu Thr Ser Val Arg Leu Gln Phe Leu Ala
    1670                1675                1680
Gly Cys Phe Gly Leu Gly Thr Val Gly His Thr Gly Ala Lys Gly
    1685                1690                1695
Glu Ser Gly Arg Leu His His Tyr Gln Asp Gly Ile Arg Ala Ala
    1700                1705                1710
Lys Arg Asn Ile Gln Ile Glu Ile Gln Val Ala Val His Lys Ile
    1715                1720                1725
Tyr Gln Gln Leu Ser Ala Thr Leu Glu Arg Ala Leu Gln Ala Asn
    1730                1735                1740
Lys His His Ile Glu Ala Gln Gln Arg Leu Leu Leu Val Thr Val
    1745                1750                1755
Phe Ala Leu Ser Val His Tyr Gln Pro Val Asp Val Ser Leu Ala
    1760                1765                1770
Ile Ser Thr Gly Leu Leu Asn Val Leu Ser Gln Leu Cys Gly Thr
    1775                1780                1785
Asp Thr Met Leu Gly Gln Pro Leu Gln Leu Leu Pro Lys Thr Gly
    1790                1795                1800
Val Ser Gln Leu Ser Thr Ala Leu Lys Val Ala Ser Thr Arg Leu
    1805                1810                1815
Leu Gln Ile Leu Ala Ile Thr Thr Gly Thr Tyr Ala Asp Lys Leu
    1820                1825                1830
Ser Pro Lys Val Val Gln Ser Leu Leu Asp Leu Leu Cys Ser Gln
    1835                1840                1845
Leu Lys Asn Leu Leu Ser Gln Thr Gly Val Leu His Met Ala Ser
    1850                1855                1860
Phe Gly Glu Gly Glu Gln Glu Asp Gly Glu Glu Glu Lys Lys
    1865                1870                1875
Val Asp Ser Ser Gly Glu Thr Glu Lys Lys Asp Phe Arg Ala Ala
    1880                1885                1890
Leu Arg Lys Gln His Ala Ala Glu Leu His Leu Gly Asp Phe Leu
    1895                1900                1905
Val Phe Leu Arg Arg Val Val Ser Ser Lys Ala Ile Gln Ser Lys
    1910                1915                1920
Met Ala Ser Pro Lys Trp Thr Glu Val Leu Leu Asn Ile Ala Ser
    1925                1930                1935
Gln Lys Cys Ser Ser Gly Ile Pro Leu Val Gly Asn Leu Arg Thr
    1940                1945                1950
Arg Leu Leu Ala Leu His Val Leu Glu Ala Val Leu Pro Ala Cys
    1955                1960                1965
```

-continued

```
Glu Ser Gly Val Glu Asp Asp Gln Met Ala Gln Ile Val Glu Arg
    1970            1975                1980

Leu Phe Ser Leu Leu Ser Asp Cys Met Trp Glu Thr Pro Ile Ala
    1985            1990                1995

Gln Ala Lys His Ala Ile Gln Ile Lys Glu Lys Glu Gln Glu Ile
    2000            2005                2010

Lys Leu Gln Lys Gln Gly Glu Leu Glu Glu Glu Asp Glu Asn Leu
    2015            2020                2025

Pro Ile Gln Glu Val Ser Phe Asp Pro Glu Lys Ala Gln Cys Cys
    2030            2035                2040

Leu Val Glu Asn Gly Gln Ile Leu Thr His Gly Ser Gly Gly Lys
    2045            2050                2055

Gly Tyr Gly Leu Ala Ser Thr Gly Val Thr Ser Gly Cys Tyr Gln
    2060            2065                2070

Trp Lys Phe Tyr Ile Val Lys Glu Asn Arg Gly Asn Glu Gly Thr
    2075            2080                2085

Cys Val Gly Val Ser Arg Trp Pro Val His Asp Phe Asn His Arg
    2090            2095                2100

Thr Thr Ser Asp Met Trp Leu Tyr Arg Ala Tyr Ser Gly Asn Leu
    2105            2110                2115

Tyr His Asn Gly Glu Gln Thr Leu Thr Leu Ser Ser Phe Thr Gln
    2120            2125                2130

Gly Asp Phe Ile Thr Cys Val Leu Asp Met Glu Ala Arg Thr Ile
    2135            2140                2145

Ser Phe Gly Lys Asn Gly Glu Glu Pro Lys Leu Ala Phe Glu Asp
    2150            2155                2160

Val Asp Ala Ala Glu Leu Tyr Pro Cys Val Met Phe Tyr Ser Ser
    2165            2170                2175

Asn Pro Gly Glu Lys Val Lys Ile Cys Asp Met Gln Met Arg Gly
    2180            2185                2190

Thr Pro Arg Asp Leu Leu Pro Gly Asp Pro Ile Cys Ser Pro Val
    2195            2200                2205

Ala Ala Val Leu Ala Glu Ala Thr Ile Gln Leu Val Arg Ile Leu
    2210            2215                2220

His Arg Thr Asp Arg Trp Thr Tyr Cys Ile Asn Lys Lys Met Met
    2225            2230                2235

Glu Arg Leu His Lys Ile Lys Ile Cys Ile Lys Glu Ser Gly Gln
    2240            2245                2250

Lys Leu Lys Lys Ser Arg Ser Val Gln Ser Arg Glu Glu Asn Glu
    2255            2260                2265

Met Arg Glu Glu Lys Glu Ser Lys Glu Glu Glu Lys Gly Lys His
    2270            2275                2280

Thr Arg His Gly Leu Ala Asp Leu Ser Glu Leu Gln Leu Arg Thr
    2285            2290                2295

Leu Cys Ile Glu Val Trp Pro Val Leu Ala Val Ile Gly Gly Val
    2300            2305                2310

Asp Ala Gly Leu Arg Val Gly Gly Arg Cys Val His Lys Gln Thr
    2315            2320                2325

Gly Arg His Ala Thr Leu Leu Gly Val Val Lys Glu Gly Ser Thr
    2330            2335                2340

Ser Ala Lys Val Gln Trp Asp Glu Ala Glu Ile Thr Ile Ser Phe
    2345            2350                2355
```

```
Pro Thr Phe Trp Ser Pro Ser Asp Thr Pro Leu Tyr Asn Leu Glu
    2360            2365            2370

Pro Cys Glu Pro Leu Pro Phe Asp Val Ala Arg Phe Arg Gly Leu
    2375            2380            2385

Thr Ala Ser Val Leu Leu Asp Leu Thr Tyr Leu Thr Gly Val His
    2390            2395            2400

Glu Asp Met Gly Lys Gln Ser Thr Lys Arg His Glu Lys Lys His
    2405            2410            2415

Arg His Glu Ser Glu Glu Lys Gly Asp Val Glu Gln Lys Pro Glu
    2420            2425            2430

Ser Glu Ser Ala Leu Asp Met Arg Thr Gly Leu Thr Ser Asp Asp
    2435            2440            2445

Val Lys Ser Gln Ser Thr Thr Ser Ser Lys Ser Glu Asn Glu Ile
    2450            2455            2460

Ala Ser Phe Ser Leu Asp Pro Thr Leu Pro Ser Val Glu Ser Gln
    2465            2470            2475

His Gln Ile Thr Glu Gly Lys Arg Lys Asn His Glu His Met Ser
    2480            2485            2490

Lys Asn His Asp Val Ala Gln Ser Glu Ile Arg Ala Val Gln Leu
    2495            2500            2505

Ser Tyr Leu Tyr Leu Gly Ala Met Lys Ser Leu Ser Ala Leu Leu
    2510            2515            2520

Gly Cys Ser Lys Tyr Ala Glu Leu Leu Leu Ile Pro Lys Val Leu
    2525            2530            2535

Ala Glu Asn Gly His Asn Ser Asp Cys Ala Ser Ser Pro Val Val
    2540            2545            2550

His Glu Asp Val Glu Met Arg Ala Ala Leu Gln Phe Leu Met Arg
    2555            2560            2565

His Met Val Lys Arg Ala Val Met Arg Ser Pro Ile Lys Arg Ala
    2570            2575            2580

Leu Gly Leu Ala Asp Leu Glu Arg Ala Gln Ala Met Ile Tyr Lys
    2585            2590            2595

Leu Val Val His Gly Leu Leu Glu Asp Gln Phe Gly Gly Lys Ile
    2600            2605            2610

Lys Gln Glu Ile Asp Gln Gln Ala Glu Glu Ser Asp Pro Ala Gln
    2615            2620            2625

Gln Ala Gln Thr Pro Val Thr Thr Ser Pro Ser Ala Ser Ser Thr
    2630            2635            2640

Thr Ser Phe Met Ser Ser Ser Leu Glu Asp Thr Thr Thr Ala Thr
    2645            2650            2655

Thr Pro Val Thr Asp Thr Glu Thr Val Pro Ala Ser Glu Ser Pro
    2660            2665            2670

Gly Val Met Pro Leu Ser Leu Leu Arg Gln Met Phe Ser Ser Tyr
    2675            2680            2685

Pro Thr Thr Thr Val Leu Pro Thr Arg Arg Ala Gln Thr Pro Pro
    2690            2695            2700

Ile Ser Ser Leu Pro Thr Ser Pro Ser Asp Glu Val Gly Arg Arg
    2705            2710            2715

Gln Ser Leu Thr Ser Pro Asp Ser Gln Ser Ala Arg Pro Ala Asn
    2720            2725            2730

Arg Thr Ala Leu Ser Asp Pro Ser Ser Arg Leu Ser Thr Ser Pro
    2735            2740            2745
```

```
Pro Pro Pro Ala Ile Ala Val Pro Leu Leu Glu Met Gly Phe Ser
    2750             2755             2760

Leu Arg Gln Ile Ala Lys Ala Met Glu Ala Thr Gly Ala Arg Gly
    2765             2770             2775

Glu Ala Asp Ala Gln Asn Ile Thr Val Leu Ala Met Trp Met Ile
    2780             2785             2790

Glu His Pro Gly His Glu Asp Glu Glu Glu Pro Gln Ser Gly Ser
    2795             2800             2805

Thr Ala Asp Ser Arg Pro Gly Ala Ala Val Leu Gly Ser Gly Gly
    2810             2815             2820

Lys Ser Asn Asp Pro Cys Tyr Leu Gln Ser Pro Gly Asp Ile Pro
    2825             2830             2835

Ser Ala Asp Ala Ala Glu Met Glu Glu Gly Phe Ser Glu Ser Pro
    2840             2845             2850

Asp Asn Leu Asp His Thr Glu Asn Ala Ala Ser Gly Ser Gly Pro
    2855             2860             2865

Ser Ala Arg Gly Arg Ser Ala Val Thr Arg Arg His Lys Phe Asp
    2870             2875             2880

Leu Ala Ala Arg Thr Leu Leu Ala Arg Ala Ala Gly Leu Tyr Arg
    2885             2890             2895

Ser Val Gln Ala His Arg Asn Gln Ser Arg Arg Glu Gly Ile Ser
    2900             2905             2910

Leu Gln Gln Asp Pro Gly Ala Leu Tyr Asp Phe Asn Leu Asp Glu
    2915             2920             2925

Glu Leu Glu Ile Asp Leu Asp Asp Glu Ala Met Glu Ala Met Phe
    2930             2935             2940

Gly Gln Asp Leu Thr Ser Asp Asn Asp Ile Leu Gly Met Trp Ile
    2945             2950             2955

Pro Glu Val Leu Asp Trp Pro Thr Trp His Val Cys Glu Ser Glu
    2960             2965             2970

Asp Arg Glu Glu Val Val Val Cys Glu Leu Cys Glu Cys Ser Val
    2975             2980             2985

Val Ser Phe Asn Gln His Met Lys Arg Asn His Pro Gly Cys Gly
    2990             2995             3000

Arg Ser Ala Asn Arg Gln Gly Tyr Arg Ser Asn Gly Ser Tyr Val
    3005             3010             3015

Asp Gly Trp Phe Gly Gly Glu Cys Gly Ser Gly Asn Pro Tyr Tyr
    3020             3025             3030

Leu Leu Cys Gly Thr Cys Arg Glu Lys Tyr Leu Ala Met Lys Thr
    3035             3040             3045

Lys Ser Lys Ser Thr Ser Ser Glu Arg Tyr Lys Gly Gln Ala Pro
    3050             3055             3060

Asp Leu Ile Gly Lys Gln Asp Ser Val Tyr Glu Glu Asp Trp Asp
    3065             3070             3075

Met Leu Asp Val Asp Glu Asp Glu Lys Leu Thr Gly Glu Glu Glu
    3080             3085             3090

Phe Glu Leu Leu Ala Gly Pro Leu Gly Leu Asn Asp Arg Arg Ile
    3095             3100             3105

Val Pro Glu Pro Val Gln Phe Pro Asp Ser Asp Pro Leu Gly Ala
    3110             3115             3120

Ser Val Ala Met Val Thr Ala Thr Asn Ser Met Glu Glu Thr Leu
    3125             3130             3135
```

-continued

| | | | | | | | | | | | |
|---|---|---|---|---|---|---|---|---|---|---|---|
| Met | Gln | Ile | Gly | Cys | His | Gly | Ser | Val | Glu | Lys | Ser | Ser | Ser | Gly |
| | 3140 | | | | 3145 | | | | 3150 | | | | | |
| Arg | Ile | Thr | Leu | Gly | Glu | Gln | Ala | Ala | Ala | Leu | Ala | Asn | Pro | His |
| 3155 | | | | | 3160 | | | | | 3165 | | | | |
| Asp | Arg | Val | Val | Ala | Leu | Arg | Arg | Val | Thr | Ala | Ala | Ala | Gln | Val |
| 3170 | | | | | 3175 | | | | | 3180 | | | | |
| Leu | Leu | Ala | Arg | Thr | Met | Val | Met | Arg | Ala | Leu | Ser | Leu | Leu | Ser |
| 3185 | | | | | 3190 | | | | | 3195 | | | | |
| Val | Ser | Gly | Ser | Ser | Cys | Ser | Leu | Ala | Ala | Gly | Leu | Glu | Ser | Leu |
| 3200 | | | | | 3205 | | | | | 3210 | | | | |
| Gly | Leu | Thr | Asp | Ile | Arg | Thr | Leu | Val | Arg | Leu | Met | Cys | Leu | Ala |
| 3215 | | | | | 3220 | | | | | 3225 | | | | |
| Ala | Ala | Gly | Arg | Ala | Gly | Leu | Ser | Thr | Ser | Pro | Ser | Ala | Met | Ala |
| 3230 | | | | | 3235 | | | | | 3240 | | | | |
| Ser | Thr | Ser | Glu | Arg | Ser | Arg | Gly | Gly | His | Ser | Lys | Ala | Asn | Lys |
| 3245 | | | | | 3250 | | | | | 3255 | | | | |
| Pro | Ile | Ser | Cys | Leu | Ala | Tyr | Leu | Ser | Thr | Ala | Val | Gly | Cys | Leu |
| 3260 | | | | | 3265 | | | | | 3270 | | | | |
| Ala | Ser | Asn | Ala | Pro | Ser | Ala | Ala | Lys | Leu | Leu | Val | Gln | Leu | Cys |
| 3275 | | | | | 3280 | | | | | 3285 | | | | |
| Thr | Gln | Asn | Leu | Ile | Ser | Ala | Ala | Thr | Gly | Val | Asn | Leu | Thr | Thr |
| 3290 | | | | | 3295 | | | | | 3300 | | | | |
| Val | Asp | Asp | Ser | Ile | Gln | Arg | Lys | Phe | Leu | Pro | Ser | Phe | Leu | Arg |
| 3305 | | | | | 3310 | | | | | 3315 | | | | |
| Gly | Ile | Ala | Glu | Glu | Asn | Lys | Leu | Val | Thr | Ser | Pro | Asn | Phe | Val |
| 3320 | | | | | 3325 | | | | | 3330 | | | | |
| Val | Thr | Gln | Ala | Leu | Val | Ala | Leu | Leu | Ala | Asp | Lys | Gly | Ala | Lys |
| 3335 | | | | | 3340 | | | | | 3345 | | | | |
| Leu | Arg | Pro | Asn | Tyr | Asp | Lys | Ser | Glu | Val | Glu | Lys | Lys | Gly | Pro |
| 3350 | | | | | 3355 | | | | | 3360 | | | | |
| Leu | Glu | Leu | Ala | Asn | Ala | Leu | Ala | Ala | Cys | Cys | Leu | Ser | Ser | Arg |
| 3365 | | | | | 3370 | | | | | 3375 | | | | |
| Leu | Ser | Ser | Gln | His | Arg | Gln | Trp | Ala | Ala | Gln | Leu | Val | Arg |
| 3380 | | | | | 3385 | | | | | 3390 | | | | |
| Thr | Leu | Ala | Ala | His | Asp | Arg | Asp | Asn | Gln | Thr | Thr | Leu | Gln | Thr |
| 3395 | | | | | 3400 | | | | | 3405 | | | | |
| Leu | Ala | Asp | Met | Gly | Gly | Asp | Leu | Arg | Lys | Cys | Ser | Phe | Ile | Lys |
| 3410 | | | | | 3415 | | | | | 3420 | | | | |
| Leu | Glu | Ala | His | Gln | Asn | Arg | Val | Met | Thr | Cys | Val | Trp | Cys | Asn |
| 3425 | | | | | 3430 | | | | | 3435 | | | | |
| Lys | Lys | Gly | Leu | Leu | Ala | Thr | Ser | Gly | Asn | Asp | Gly | Thr | Ile | Arg |
| 3440 | | | | | 3445 | | | | | 3450 | | | | |
| Val | Trp | Asn | Val | Thr | Lys | Lys | Gln | Tyr | Ser | Leu | Gln | Gln | Thr | Cys |
| 3455 | | | | | 3460 | | | | | 3465 | | | | |
| Val | Phe | Asn | Arg | Leu | Glu | Gly | Asp | Ala | Glu | Glu | Ser | Leu | Gly | Ser |
| 3470 | | | | | 3475 | | | | | 3480 | | | | |
| Pro | Ser | Asp | Pro | Ser | Phe | Ser | Pro | Val | Ser | Trp | Ser | Ile | Ser | Gly |
| 3485 | | | | | 3490 | | | | | 3495 | | | | |
| Lys | Tyr | Leu | Ala | Gly | Ala | Leu | Glu | Lys | Met | Val | Asn | Ile | Trp | Gln |
| 3500 | | | | | 3505 | | | | | 3510 | | | | |
| Val | Asn | Gly | Gly | Lys | Gly | Leu | Val | Asp | Ile | Gln | Pro | His | Trp | Val |
| 3515 | | | | | 3520 | | | | | 3525 | | | | |

-continued

```
Ser Ala Leu Ala Trp Pro Glu Glu Gly Pro Ala Thr Ala Trp Ser
3530                3535                3540

Gly Glu Ser Pro Glu Leu Leu Val Gly Arg Met Asp Gly Ser
3545                3550                3555

Leu Gly Leu Ile Glu Val Val Asp Val Ser Thr Met His Arg Arg
3560                3565                3570

Glu Leu Glu His Cys Tyr Arg Lys Asp Val Ser Val Thr Cys Ile
3575                3580                3585

Ala Trp Phe Ser Glu Asp Arg Pro Phe Ala Val Gly Tyr Phe Asp
3590                3595                3600

Gly Lys Leu Leu Leu Gly Thr Lys Glu Pro Leu Glu Lys Gly Gly
3605                3610                3615

Ile Val Leu Ile Asp Ala His Lys Asp Thr Leu Ile Ser Met Lys
3620                3625                3630

Trp Asp Pro Thr Gly His Ile Leu Met Thr Cys Ala Lys Glu Asp
3635                3640                3645

Ser Val Lys Leu Trp Gly Ser Ile Ser Gly Cys Trp Cys Cys Leu
3650                3655                3660

His Ser Leu Cys His Pro Ser Ile Val Asn Gly Ile Ala Trp Cys
3665                3670                3675

Arg Leu Pro Gly Lys Gly Ser Lys Leu Gln Leu Leu Met Ala Thr
3680                3685                3690

Gly Cys Gln Ser Gly Leu Val Cys Val Trp Arg Ile Pro Gln Asp
3695                3700                3705

Thr Thr Gln Thr Asn Val Thr Ser Ala Glu Gly Trp Trp Asp Gln
3710                3715                3720

Glu Ser Asn Cys Gln Asp Gly Tyr Arg Lys Ser Ser Gly Ala Lys
3725                3730                3735

Cys Val Tyr Gln Leu Arg Gly His Ile Thr Pro Val Arg Thr Val
3740                3745                3750

Ala Phe Ser Ser Asp Gly Leu Ala Leu Val Ser Gly Gly Leu Gly
3755                3760                3765

Gly Leu Met Asn Ile Trp Ser Leu Arg Asp Gly Ser Val Leu Gln
3770                3775                3780

Thr Val Val Ile Gly Ser Gly Ala Ile Gln Thr Thr Val Trp Ile
3785                3790                3795

Pro Glu Val Gly Val Ala Ala Cys Ser Asn Arg Ser Lys Asp Val
3800                3805                3810

Leu Val Val Asn Cys Thr Ala Glu Trp Ala Ala Ala Asn His Val
3815                3820                3825

Leu Ala Thr Cys Arg Thr Ala Leu Lys Gln Gln Gly Val Leu Gly
3830                3835                3840

Leu Asn Met Ala Pro Cys Met Arg Ala Phe Leu Glu Arg Leu Pro
3845                3850                3855

Met Met Leu Gln Glu Gln Tyr Ala Tyr Glu Lys Pro His Val Val
3860                3865                3870

Cys Gly Asp Gln Leu Val His Ser Pro Tyr Met Gln Cys Leu Ala
3875                3880                3885

Ser Leu Ala Val Gly Leu His Leu Asp Gln Leu Leu Cys Asn Pro
3890                3895                3900

Pro Val Pro Pro His His Gln Asn Cys Leu Pro Asp Pro Ala Ser
3905                3910                3915
```

-continued

| | | | | | | | | | | | |
|---|---|---|---|---|---|---|---|---|---|---|---|
| Trp | Asn | Pro | Asn | Glu | Trp | Ala | Trp | Leu | Glu | Cys | Phe | Ser | Thr | Thr |
| 3920 | | | | 3925 | | | | 3930 | | | |

Trp Asn Pro Asn Glu Trp Ala Trp Leu Glu Cys Phe Ser Thr Thr
3920              3925              3930

Ile Lys Ala Ala Glu Ala Leu Thr Asn Gly Ala Gln Phe Pro Glu
3935              3940              3945

Ser Phe Thr Val Pro Asp Leu Glu Pro Val Pro Glu Asp Glu Leu
3950              3955              3960

Val Phe Leu Met Asp Asn Ser Lys Trp Ile Asn Gly Met Asp Glu
3965              3970              3975

Gln Ile Met Ser Trp Ala Thr Ser Arg Pro Glu Asp Trp His Leu
3980              3985              3990

Gly Gly Lys Cys Asp Val Tyr Leu Trp Gly Ala Gly Arg His Gly
3995              4000              4005

Gln Leu Ala Glu Ala Gly Arg Asn Val Met Val Pro Ala Ala Ala
4010              4015              4020

Pro Ser Phe Ser Gln Ala Gln Gln Val Ile Cys Gly Gln Asn Cys
4025              4030              4035

Thr Phe Val Ile Gln Ala Asn Gly Thr Val Leu Ala Cys Gly Glu
4040              4045              4050

Gly Ser Tyr Gly Arg Leu Gly Gln Gly Asn Ser Asp Asp Leu His
4055              4060              4065

Val Leu Thr Val Ile Ser Ala Leu Gln Gly Phe Val Val Thr Gln
4070              4075              4080

Leu Val Thr Ser Cys Gly Ser Asp Gly His Ser Met Ala Leu Thr
4085              4090              4095

Glu Ser Gly Glu Val Phe Ser Trp Gly Asp Gly Asp Tyr Gly Lys
4100              4105              4110

Leu Gly His Gly Asn Ser Asp Arg Gln Arg Arg Pro Arg Gln Ile
4115              4120              4125

Glu Ala Leu Gln Gly Glu Glu Val Val Gln Met Ser Cys Gly Phe
4130              4135              4140

Lys His Ser Ala Val Val Thr Ser Asp Gly Lys Leu Phe Thr Phe
4145              4150              4155

Gly Asn Gly Asp Tyr Gly Arg Leu Gly Leu Gly Asn Thr Ser Asn
4160              4165              4170

Lys Lys Leu Pro Glu Arg Val Thr Ala Leu Glu Gly Tyr Gln Ile
4175              4180              4185

Gly Gln Val Ala Cys Gly Leu Asn His Thr Leu Ala Val Ser Ala
4190              4195              4200

Asp Gly Ser Met Val Trp Ala Phe Gly Asp Gly Asp Tyr Gly Lys
4205              4210              4215

Leu Gly Leu Gly Asn Ser Thr Ala Lys Ser Ser Pro Gln Lys Ile
4220              4225              4230

Asp Val Leu Cys Gly Ile Gly Ile Lys Lys Val Ala Cys Gly Thr
4235              4240              4245

Gln Phe Ser Val Ala Leu Thr Lys Asp Gly His Val Tyr Thr Phe
4250              4255              4260

Gly Gln Asp Arg Leu Ile Gly Leu Pro Glu Gly Arg Ala Arg Asn
4265              4270              4275

His Asn Arg Pro Gln Gln Ile Pro Val Leu Ala Gly Val Ile Ile
4280              4285              4290

Glu Asp Val Ala Val Gly Ala Glu His Thr Leu Ala Leu Ala Ser
4295              4300              4305

```
Asn Gly Asp Val Tyr Ala Trp Gly Ser Asn Ser Glu Gly Gln Leu
    4310            4315            4320

Gly Leu Gly His Thr Asn His Val Arg Glu Pro Thr Leu Val Thr
    4325            4330            4335

Gly Leu Gln Gly Lys Asn Val Arg Gln Ile Ser Ala Gly Arg Cys
    4340            4345            4350

His Ser Ala Ala Trp Thr Ala Pro Pro Val Pro Pro Arg Ala Pro
    4355            4360            4365

Gly Val Ser Val Pro Leu Gln Leu Gly Leu Pro Asp Thr Val Pro
    4370            4375            4380

Pro Gln Tyr Gly Ala Leu Arg Glu Val Ser Ile His Thr Val Arg
    4385            4390            4395

Ala Arg Leu Arg Leu Leu Tyr His Phe Ser Asp Leu Met Tyr Ser
    4400            4405            4410

Ser Trp Arg Leu Leu Asn Leu Ser Pro Asn Asn Gln Asn Ser Thr
    4415            4420            4425

Ser His Tyr Asn Ala Gly Thr Trp Gly Ile Val Gln Gly Gln Leu
    4430            4435            4440

Arg Pro Leu Leu Ala Pro Arg Val Tyr Thr Leu Pro Met Val Arg
    4445            4450            4455

Ser Ile Gly Lys Thr Met Val Gln Gly Lys Asn Tyr Gly Pro Gln
    4460            4465            4470

Ile Thr Val Lys Arg Ile Ser Thr Arg Gly Arg Lys Cys Lys Pro
    4475            4480            4485

Ile Phe Val Gln Ile Ala Arg Gln Val Val Lys Leu Asn Ala Ser
    4490            4495            4500

Asp Leu Arg Leu Pro Ser Arg Ala Trp Lys Val Lys Leu Val Gly
    4505            4510            4515

Glu Gly Ala Asp Asp Ala Gly Gly Val Phe Asp Thr Ile Thr
    4520            4525            4530

Glu Met Cys Gln Glu Leu Glu Thr Gly Ile Val Asp Leu Leu Ile
    4535            4540            4545

Pro Ser Pro Asn Ala Thr Ala Glu Val Gly Tyr Asn Arg Asp Arg
    4550            4555            4560

Phe Leu Phe Asn Pro Ser Ala Cys Leu Asp Glu His Leu Met Gln
    4565            4570            4575

Phe Lys Phe Leu Gly Ile Leu Met Gly Val Ala Ile Arg Thr Lys
    4580            4585            4590

Lys Pro Leu Asp Leu His Leu Ala Pro Leu Val Trp Lys Gln Leu
    4595            4600            4605

Cys Cys Val Pro Leu Thr Leu Glu Asp Leu Glu Glu Val Asp Leu
    4610            4615            4620

Leu Tyr Val Gln Thr Leu Asn Ser Ile Leu His Ile Glu Asp Ser
    4625            4630            4635

Gly Ile Thr Glu Glu Ser Phe His Glu Met Ile Pro Leu Asp Ser
    4640            4645            4650

Phe Val Gly Gln Ser Ala Asp Gly Lys Met Val Pro Ile Ile Pro
    4655            4660            4665

Gly Gly Asn Ser Ile Pro Leu Thr Phe Ser Asn Arg Lys Glu Tyr
    4670            4675            4680

Val Glu Arg Ala Ile Glu Tyr Arg Leu His Glu Met Asp Arg Gln
    4685            4690            4695
```

-continued

```
Val Ala Ala Val Arg Glu Gly Met Ser Trp Ile Val Pro Val Pro
    4700                4705                4710
Leu Leu Ser Leu Leu Thr Ala Lys Gln Leu Glu Gln Met Val Cys
    4715                4720                4725
Gly Met Pro Glu Ile Ser Val Glu Val Leu Lys Lys Val Val Arg
    4730                4735                4740
Tyr Arg Glu Val Asp Glu Gln His Gln Leu Val Gln Trp Phe Trp
    4745                4750                4755
His Thr Leu Glu Glu Phe Ser Asn Glu Arg Val Leu Phe Met
    4760                4765                4770
Arg Phe Val Ser Gly Arg Ser Arg Leu Pro Ala Asn Thr Ala Asp
    4775                4780                4785
Ile Ser Gln Arg Phe Gln Ile Met Lys Val Asp Arg Pro Tyr Asp
    4790                4795                4800
Ser Leu Pro Thr Ser Gln Thr Cys Phe Phe Gln Leu Arg Leu Pro
    4805                4810                4815
Pro Tyr Ser Ser Gln Leu Val Met Ala Glu Arg Leu Arg Tyr Ala
    4820                4825                4830
Ile Asn Asn Cys Arg Ser Ile Asp Met Asp Asn Tyr Met Leu Ser
    4835                4840                4845
Arg Asn Val Asp Asn Ala Glu Gly Ser Asp Thr Asp Tyr
    4850                4855                4860

<210> SEQ ID NO 71
<211> LENGTH: 292
<212> TYPE: PRT
<213> ORGANISM: Homo sapiens

<400> SEQUENCE: 71

Met Ala Ser Ser Met Arg Ser Leu Phe Ser Asp His Gly Lys Tyr Val
1               5                   10                  15
Glu Ser Phe Arg Arg Phe Leu Asn His Ser Thr Glu His Gln Cys Met
                20                  25                  30
Gln Glu Phe Met Asp Lys Lys Leu Pro Gly Ile Ile Gly Arg Ile Gly
            35                  40                  45
Asp Thr Lys Ser Glu Ile Lys Ile Leu Ser Gly Gly Gly Ala Gly
        50                  55                  60
Glu Ile Asp Leu Gln Ile Leu Ser Lys Val Gln Ala Gln Tyr Pro Gly
65                  70                  75                  80
Val Cys Ile Asn Asn Glu Val Val Glu Pro Ser Ala Glu Gln Ile Ala
                85                  90                  95
Lys Tyr Lys Glu Leu Val Ala Lys Thr Ser Asn Leu Glu Asn Val Lys
                100                 105                 110
Phe Ala Trp His Lys Glu Thr Ser Ser Glu Tyr Gln Ser Arg Met Leu
            115                 120                 125
Glu Lys Lys Glu Leu Gln Lys Trp Asp Phe Ile His Met Ile Gln Met
        130                 135                 140
Leu Tyr Tyr Val Lys Asp Ile Pro Ala Thr Leu Lys Phe Phe His Ser
145                 150                 155                 160
Leu Leu Gly Thr Asn Ala Lys Met Leu Ile Ile Val Val Ser Gly Ser
                165                 170                 175
Ser Gly Trp Asp Lys Leu Trp Lys Lys Tyr Gly Ser Arg Phe Pro Gln
                180                 185                 190
```

```
Asp Asp Leu Cys Gln Tyr Ile Thr Ser Asp Leu Thr Gln Met Leu
        195                 200                 205

Asp Asn Leu Gly Leu Lys Tyr Glu Cys Tyr Asp Leu Leu Ser Thr Met
    210                 215                 220

Asp Ile Ser Asp Cys Phe Ile Asp Gly Asn Glu Asn Gly Asp Leu Leu
225                 230                 235                 240

Trp Asp Phe Leu Thr Glu Thr Cys Asn Phe Asn Ala Thr Ala Pro Pro
                245                 250                 255

Asp Leu Arg Ala Glu Leu Gly Lys Asp Leu Gln Glu Pro Glu Phe Ser
            260                 265                 270

Ala Lys Lys Glu Gly Lys Val Leu Phe Asn Asn Thr Leu Ser Phe Ile
        275                 280                 285

Val Ile Glu Ala
        290

<210> SEQ ID NO 72
<211> LENGTH: 481
<212> TYPE: PRT
<213> ORGANISM: Homo sapiens

<400> SEQUENCE: 72

Met Ala Leu Ser Tyr Arg Val Ser Glu Leu Gln Ser Thr Ile Pro Glu
1               5                   10                  15

His Ile Leu Gln Ser Thr Phe Val His Val Ile Ser Ser Asn Trp Ser
                20                  25                  30

Gly Leu Gln Thr Glu Ser Ile Pro Glu Glu Met Lys Gln Ile Val Glu
            35                  40                  45

Glu Gln Gly Asn Lys Leu His Trp Ala Ala Leu Leu Ile Leu Met Val
        50                  55                  60

Ile Ile Pro Thr Ile Gly Gly Asn Thr Leu Val Ile Leu Ala Val Ser
65                  70                  75                  80

Leu Glu Lys Lys Leu Gln Tyr Ala Thr Asn Tyr Phe Leu Met Ser Leu
                85                  90                  95

Ala Val Ala Asp Leu Leu Val Gly Leu Phe Val Met Pro Ile Ala Leu
            100                 105                 110

Leu Thr Ile Met Phe Glu Ala Met Trp Pro Leu Pro Leu Val Leu Cys
        115                 120                 125

Pro Ala Trp Leu Phe Leu Asp Val Leu Phe Ser Thr Ala Ser Ile Met
    130                 135                 140

His Leu Cys Ala Ile Ser Val Asp Arg Tyr Ile Ala Ile Lys Lys Pro
145                 150                 155                 160

Ile Gln Ala Asn Gln Tyr Asn Ser Arg Ala Thr Ala Phe Ile Lys Ile
                165                 170                 175

Thr Val Val Trp Leu Ile Ser Ile Gly Ile Ala Ile Pro Val Pro Ile
            180                 185                 190

Lys Gly Ile Glu Thr Asp Val Asp Asn Pro Asn Asn Ile Thr Cys Val
        195                 200                 205

Leu Thr Lys Glu Arg Phe Gly Asp Phe Met Leu Phe Gly Ser Leu Ala
    210                 215                 220

Ala Phe Phe Thr Pro Leu Ala Ile Met Ile Val Thr Tyr Phe Leu Thr
225                 230                 235                 240

Ile His Ala Leu Gln Lys Lys Ala Tyr Leu Val Lys Asn Lys Pro Pro
                245                 250                 255

Gln Arg Leu Thr Trp Leu Thr Val Ser Thr Val Phe Gln Arg Asp Glu
            260                 265                 270
```

```
Thr Pro Cys Ser Ser Pro Glu Lys Val Ala Met Leu Asp Gly Ser Arg
        275                 280                 285

Lys Asp Lys Ala Leu Pro Asn Ser Gly Asp Glu Thr Leu Met Arg Arg
290                 295                 300

Thr Ser Thr Ile Gly Lys Lys Ser Val Gln Thr Ile Ser Asn Glu Gln
305                 310                 315                 320

Arg Ala Ser Lys Val Leu Gly Ile Val Phe Leu Phe Leu Leu Met
        325                 330                 335

Trp Cys Pro Phe Phe Ile Thr Asn Ile Thr Leu Val Leu Cys Asp Ser
        340                 345                 350

Cys Asn Gln Thr Thr Leu Gln Met Leu Leu Glu Ile Phe Val Trp Ile
        355                 360                 365

Gly Tyr Val Ser Ser Gly Val Asn Pro Leu Val Tyr Thr Leu Phe Asn
370                 375                 380

Lys Thr Phe Arg Asp Ala Phe Gly Arg Tyr Ile Thr Cys Asn Tyr Arg
385                 390                 395                 400

Ala Thr Lys Ser Val Lys Thr Leu Arg Lys Arg Ser Lys Ile Tyr
        405                 410                 415

Phe Arg Asn Pro Met Ala Glu Asn Ser Lys Phe Phe Lys Lys His Gly
        420                 425                 430

Ile Arg Asn Gly Ile Asn Pro Ala Met Tyr Gln Ser Pro Met Arg Leu
        435                 440                 445

Arg Ser Ser Thr Ile Gln Ser Ser Ile Ile Leu Leu Asp Thr Leu
450                 455                 460

Leu Leu Thr Glu Asn Glu Gly Asp Lys Thr Glu Gln Val Ser Tyr
465                 470                 475                 480

Val

<210> SEQ ID NO 73
<211> LENGTH: 189
<212> TYPE: PRT
<213> ORGANISM: Homo sapiens

<400> SEQUENCE: 73

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

Pro Phe Ser Cys Leu Lys Asp Arg His Asp Phe Gly Phe Pro Gln Glu
    50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Thr Trp Glu Gln Ser Leu Leu Glu Lys Phe Ser Thr Glu Leu
            100                 105                 110

Asn Gln Gln Leu Asn Asp Met Glu Ala Cys Val Ile Gln Glu Val Gly
        115                 120                 125

Val Glu Glu Thr Pro Leu Met Asn Val Asp Ser Ile Leu Ala Val Lys
    130                 135                 140

Lys Tyr Phe Gln Arg Ile Thr Leu Tyr Leu Thr Glu Lys Lys Tyr Ser
145                 150                 155                 160
```

```
Pro Cys Ala Trp Glu Val Val Arg Ala Glu Ile Met Arg Ser Phe Ser
                165                 170                 175

Leu Ser Lys Ile Phe Gln Glu Arg Leu Arg Arg Lys Glu
            180                 185

<210> SEQ ID NO 74
<211> LENGTH: 153
<212> TYPE: PRT
<213> ORGANISM: Homo sapiens

<400> SEQUENCE: 74

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150

<210> SEQ ID NO 75
<211> LENGTH: 632
<212> TYPE: PRT
<213> ORGANISM: Homo sapiens
<220> FEATURE:
<221> NAME/KEY: UNSURE
<222> LOCATION: (199)..(199)
<223> OTHER INFORMATION: Xaa = any amino acid

<400> SEQUENCE: 75

Met Glu Thr Pro Ala Ala Ala Pro Ala Gly Ser Leu Phe Pro Ser
1               5                   10                  15

Phe Leu Leu Leu Ala Cys Gly Thr Leu Val Ala Ala Leu Leu Gly Ala
            20                  25                  30

Ala His Arg Leu Gly Leu Phe Tyr Gln Leu Leu His Lys Val Asp Lys
        35                  40                  45

Ala Ser Val Arg His Gly Gly Glu Asn Val Ala Val Leu Arg Ala
    50                  55                  60

His Gly Val Arg Phe Ile Phe Thr Leu Val Gly Gly His Ile Ser Pro
65                  70                  75                  80

Leu Leu Val Ala Cys Glu Lys Leu Gly Ile Arg Val Val Asp Thr Arg
                85                  90                  95

His Glu Val Thr Ala Val Phe Ala Ala Asp Ala Met Ala Arg Leu Ser
            100                 105                 110

Gly Thr Val Gly Val Ala Ala Val Thr Ala Gly Pro Gly Leu Thr Asn
        115                 120                 125
```

-continued

```
Thr Val Thr Ala Val Lys Asn Ala Gln Met Ala Gln Ser Pro Ile Leu
130                 135                 140

Leu Leu Gly Gly Ala Ala Ser Thr Leu Leu Gln Asn Arg Gly Ala Leu
145                 150                 155                 160

Gln Ala Val Asp Gln Leu Ser Leu Phe Arg Pro Leu Cys Lys Phe Cys
                165                 170                 175

Val Ser Val Arg Arg Val Arg Asp Ile Val Pro Thr Leu Arg Ala Ala
            180                 185                 190

Met Ala Ala Gln Ser Xaa Thr Pro Gly Pro Val Phe Val Glu Leu
        195                 200                 205

Pro Val Asp Val Leu Tyr Pro Tyr Phe Met Val Gln Lys Glu Met Val
    210                 215                 220

Pro Ala Lys Pro Pro Lys Gly Leu Val Gly Arg Val Val Ser Trp Tyr
225                 230                 235                 240

Leu Glu Asn Tyr Leu Ala Asn Leu Phe Ala Gly Ala Trp Glu Pro Gln
                245                 250                 255

Pro Glu Gly Pro Leu Pro Leu Asp Ile Pro Gln Ala Ser Pro Gln Gln
            260                 265                 270

Val Gln Arg Cys Val Glu Ile Leu Ser Arg Ala Lys Arg Pro Leu Met
        275                 280                 285

Val Leu Gly Ser Gln Ala Leu Leu Thr Pro Thr Ser Ala Asp Lys Leu
    290                 295                 300

Arg Ala Ala Val Glu Thr Leu Gly Val Pro Cys Phe Leu Gly Gly Met
305                 310                 315                 320

Ala Arg Gly Leu Leu Gly Arg Asn His Pro Leu His Ile Arg Glu Asn
                325                 330                 335

Arg Ser Ala Ala Leu Lys Lys Ala Asp Val Ile Val Leu Ala Gly Thr
            340                 345                 350

Val Cys Asp Phe Arg Leu Ser Tyr Gly Arg Val Leu Ser His Ser Ser
        355                 360                 365

Lys Ile Ile Ile Val Asn Arg Asn Arg Glu Glu Met Leu Leu Asn Ser
    370                 375                 380

Asp Ile Phe Trp Lys Pro Gln Glu Ala Val Gln Gly Asp Val Gly Ser
385                 390                 395                 400

Phe Val Leu Lys Leu Val Glu Gly Leu Gln Gly Gln Thr Trp Ala Pro
                405                 410                 415

Asp Trp Val Glu Glu Leu Arg Glu Ala Asp Arg Gln Lys Glu Gln Thr
            420                 425                 430

Phe Arg Glu Lys Ala Ala Met Pro Val Ala Gln His Leu Asn Pro Val
        435                 440                 445

Gln Val Leu Gln Leu Val Glu Glu Thr Leu Pro Asp Asn Ser Ile Leu
    450                 455                 460

Val Val Asp Gly Gly Asp Phe Val Gly Thr Ala Ala His Leu Val Gln
465                 470                 475                 480

Pro Arg Gly Pro Leu Arg Trp Leu Asp Pro Gly Ala Phe Gly Thr Leu
                485                 490                 495

Gly Val Gly Ala Gly Phe Ala Leu Gly Ala Lys Leu Cys Arg Pro Asp
            500                 505                 510

Ala Glu Val Trp Cys Leu Phe Asp Gly Asp Gly Ala Phe Gly Tyr Ser Leu
        515                 520                 525

Ile Glu Phe Asp Thr Phe Val Arg His Lys Ile Pro Val Met Ala Leu
    530                 535                 540
```

Val Gly Asn Asp Ala Gly Trp Thr Gln Ile Ser Arg Glu Gln Val Pro
545                 550                 555                 560

Ser Leu Gly Ser Asn Val Ala Cys Gly Leu Ala Tyr Thr Asp Tyr His
            565                 570                 575

Lys Ala Ala Met Gly Leu Gly Ala Arg Gly Leu Leu Leu Ser Arg Glu
        580                 585                 590

Asn Glu Asp Gln Val Val Lys Val Leu His Asp Ala Gln Gln Gln Cys
        595                 600                 605

Arg Asp Gly His Pro Val Val Val Asn Ile Leu Ile Gly Arg Thr Asp
        610                 615                 620

Phe Arg Asp Gly Ser Ile Ala Val
625                 630

<210> SEQ ID NO 76
<211> LENGTH: 349
<212> TYPE: PRT
<213> ORGANISM: Homo sapiens

<400> SEQUENCE: 76

Met Pro Val Glu Arg Met Arg Met Arg Pro Trp Leu Glu Glu Gln Ile
1               5                   10                  15

Asn Ser Asn Thr Ile Pro Gly Leu Lys Trp Leu Asn Lys Glu Lys Lys
            20                  25                  30

Ile Phe Gln Ile Pro Trp Met His Ala Ala Arg His Gly Trp Asp Val
        35                  40                  45

Glu Lys Asp Ala Pro Leu Phe Arg Asn Arg Ala Ile His Thr Gly Lys
    50                  55                  60

His Gln Pro Gly Val Asp Lys Pro Asp Pro Lys Thr Trp Lys Ala Asn
65                  70                  75                  80

Phe Arg Cys Ala Met Asn Ser Leu Pro Asp Ile Glu Glu Val Lys Asp
                85                  90                  95

Lys Ser Ile Lys Lys Gly Asn Asn Ala Phe Arg Val Tyr Arg Met Leu
            100                 105                 110

Pro Leu Ser Glu Arg Pro Ser Lys Lys Gly Lys Lys Pro Lys Thr Glu
        115                 120                 125

Lys Glu Asp Lys Val Lys His Ile Lys Gln Glu Pro Val Glu Ser Ser
    130                 135                 140

Leu Gly Leu Ser Asn Gly Val Ser Asp Leu Ser Pro Glu Tyr Ala Val
145                 150                 155                 160

Leu Thr Ser Thr Ile Lys Asn Glu Val Asp Ser Thr Val Asn Ile Ile
                165                 170                 175

Val Val Gly Gln Ser His Leu Asp Ser Asn Ile Glu Asn Gln Glu Ile
            180                 185                 190

Val Thr Asn Pro Pro Asp Ile Cys Gln Val Val Glu Val Thr Thr Glu
        195                 200                 205

Ser Asp Glu Gln Pro Val Ser Met Ser Glu Leu Tyr Pro Leu Gln Ile
    210                 215                 220

Ser Pro Val Ser Ser Tyr Ala Glu Ser Glu Thr Thr Asp Ser Val Pro
225                 230                 235                 240

Ser Asp Glu Glu Ser Ala Glu Gly Arg Pro His Trp Arg Lys Arg Asn
                245                 250                 255

Ile Glu Gly Lys Gln Tyr Leu Ser Asn Met Gly Thr Arg Gly Ser Tyr
            260                 265                 270

Leu Leu Pro Gly Met Ala Ser Phe Val Thr Ser Asn Lys Pro Asp Leu
        275                 280                 285

```
Gln Val Thr Ile Lys Glu Ser Asn Pro Val Pro Tyr Asn Ser Ser
    290             295             300

Trp Pro Pro Phe Gln Asp Leu Pro Leu Ser Ser Met Thr Pro Ala
305             310             315             320

Ser Ser Ser Ser Arg Pro Asp Arg Glu Thr Arg Ala Ser Val Ile Lys
                325             330             335

Lys Thr Ser Asp Ile Thr Gln Ala Arg Val Lys Ser Cys
            340             345

<210> SEQ ID NO 77
<211> LENGTH: 338
<212> TYPE: PRT
<213> ORGANISM: Homo sapiens

<400> SEQUENCE: 77

Met Ile Asn Ser Thr Ser Thr Gln Pro Pro Asp Glu Ser Cys Ser Gln
1               5                   10                  15

Asn Leu Leu Ile Thr Gln Gln Ile Ile Pro Val Leu Tyr Cys Met Val
                20                  25                  30

Phe Ile Ala Gly Ile Leu Leu Asn Gly Val Ser Gly Trp Ile Phe Phe
            35                  40                  45

Tyr Val Pro Ser Ser Lys Ser Phe Ile Ile Tyr Leu Lys Asn Ile Val
    50                  55                  60

Ile Ala Asp Phe Val Met Ser Leu Thr Phe Pro Phe Lys Ile Leu Gly
65                  70                  75                  80

Asp Ser Gly Leu Gly Pro Trp Gln Leu Asn Val Phe Val Cys Arg Val
                85                  90                  95

Ser Ala Val Leu Phe Tyr Val Asn Met Tyr Val Ser Ile Val Phe Phe
                100                 105                 110

Gly Leu Ile Ser Phe Asp Arg Tyr Tyr Lys Ile Val Lys Pro Leu Trp
            115                 120                 125

Thr Ser Phe Ile Gln Ser Val Ser Tyr Ser Lys Leu Leu Ser Val Ile
    130                 135                 140

Val Trp Met Leu Met Leu Leu Leu Ala Val Pro Asn Ile Ile Leu Thr
145                 150                 155                 160

Asn Gln Ser Val Arg Glu Val Thr Gln Ile Lys Cys Ile Glu Leu Lys
                165                 170                 175

Ser Glu Leu Gly Arg Lys Trp His Lys Ala Ser Asn Tyr Ile Phe Val
            180                 185                 190

Ala Ile Phe Trp Ile Val Phe Leu Leu Leu Ile Val Phe Tyr Thr Ala
    195                 200                 205

Ile Thr Lys Lys Ile Phe Lys Ser His Leu Lys Ser Ser Arg Asn Ser
210                 215                 220

Thr Ser Val Lys Lys Ser Ser Arg Asn Ile Phe Ser Ile Val Phe
225                 230                 235                 240

Val Phe Phe Val Cys Phe Val Pro Tyr His Ile Ala Arg Ile Pro Tyr
                245                 250                 255

Thr Lys Ser Gln Thr Glu Ala His Tyr Ser Cys Gln Ser Lys Glu Ile
            260                 265                 270

Leu Arg Tyr Met Lys Glu Phe Thr Leu Leu Leu Ser Ala Ala Asn Val
    275                 280                 285

Cys Leu Asp Pro Ile Ile Tyr Phe Phe Leu Cys Gln Pro Phe Arg Glu
290                 295                 300

Ile Leu Cys Lys Lys Leu His Ile Pro Leu Lys Ala Gln Asn Asp Leu
305                 310                 315                 320
```

```
Asp Ile Ser Arg Ile Lys Arg Gly Asn Thr Thr Leu Glu Ser Thr Asp
                325                 330                 335

Thr Leu

<210> SEQ ID NO 78
<211> LENGTH: 232
<212> TYPE: PRT
<213> ORGANISM: Homo sapiens

<400> SEQUENCE: 78

Leu Glu Thr Gln Ile Glu Ala Leu Lys Glu Leu Leu Phe Met Lys
1               5                  10                  15

Lys Asn His Glu Glu Val Lys Gly Leu Gln Ala Gln Ile Ala Ser
                20                  25                  30

Ser Gly Leu Thr Val Glu Val Asp Ala Pro Lys Ser Gln Asp Leu Ser
                35                  40                  45

Lys Ile Met Ala Asp Ile Arg Ala Gln Tyr Asp Glu Leu Ala Arg Lys
    50                  55                  60

Asn Arg Glu Glu Leu Asp Lys Tyr Trp Ser Gln Gln Ile Glu Glu Ser
65                  70                  75                  80

Thr Thr Val Val Thr Thr Gln Ser Ala Glu Val Gly Ala Ala Glu Thr
                85                  90                  95

Thr Leu Thr Glu Leu Arg Arg Thr Val Gln Ser Leu Glu Ile Arg Leu
                100                 105                 110

Asp Arg Met Arg Asn Leu Lys Ala Ser Leu Glu Asn Ser Leu Arg Glu
                115                 120                 125

Val Glu Ala Arg Tyr Ala Leu Gln Met Glu Gln Leu Asn Gly Ile Leu
    130                 135                 140

Leu His Leu Glu Ser Glu Leu Ala Gln Thr Arg Ala Glu Gly Gln Arg
145                 150                 155                 160

Gln Ala Gln Glu Tyr Glu Ala Leu Leu Asn Ile Lys Val Lys Leu Glu
                165                 170                 175

Ala Glu Ile Ala Thr Tyr Arg Arg Leu Leu Glu Asp Gly Glu Asp Phe
            180                 185                 190

Asn Leu Gly Asp Ala Leu Asp Ser Ser Asn Ser Met Gln Thr Ile Gln
                195                 200                 205

Lys Thr Thr Thr Arg Arg Ile Val Asp Gly Lys Val Val Ser Glu Thr
    210                 215                 220

Asn Asp Thr Lys Val Leu Arg His
225                 230

<210> SEQ ID NO 79
<211> LENGTH: 483
<212> TYPE: PRT
<213> ORGANISM: Homo sapiens

<400> SEQUENCE: 79

Met Ser Ile Arg Val Thr Gln Lys Ser Tyr Lys Val Ser Thr Ser Gly
1               5                   10                  15

Pro Arg Ala Phe Ser Ser Arg Ser Tyr Thr Ser Gly Pro Gly Ser Arg
                20                  25                  30

Ile Ser Ser Ser Ser Phe Ser Arg Val Gly Ser Ser Asn Phe Arg Gly
                35                  40                  45

Gly Leu Gly Gly Gly Tyr Gly Gly Ala Ser Gly Met Gly Gly Ile Thr
    50                  55                  60
```

-continued

```
Ala Val Thr Val Asn Gln Ser Leu Leu Ser Pro Leu Val Leu Glu Val
 65                  70                  75                  80

Asp Pro Asn Ile Gln Ala Val Arg Thr Gln Glu Lys Glu Gln Ile Lys
                 85                  90                  95

Thr Leu Asn Asn Lys Phe Ala Ser Phe Ile Asp Lys Val Arg Phe Leu
            100                 105                 110

Glu Gln Gln Asn Lys Met Leu Glu Thr Lys Trp Ser Leu Leu Gln Gln
        115                 120                 125

Gln Lys Thr Ala Arg Ser Asn Met Asp Asn Met Phe Glu Ser Tyr Ile
    130                 135                 140

Asn Asn Leu Arg Arg Gln Leu Glu Thr Leu Gly Gln Glu Lys Leu Lys
145                 150                 155                 160

Leu Glu Ala Glu Leu Gly Asn Met Gln Gly Leu Val Glu Asp Phe Lys
                165                 170                 175

Asn Lys Tyr Glu Asp Glu Ile Asn Lys Arg Thr Glu Met Glu Asn Glu
            180                 185                 190

Phe Val Leu Ile Lys Lys Asp Val Asp Glu Ala Tyr Met Asn Lys Val
        195                 200                 205

Glu Leu Glu Ser Arg Leu Glu Gly Leu Thr Asp Glu Ile Asn Phe Leu
    210                 215                 220

Arg Gln Leu Tyr Glu Glu Ile Arg Glu Leu Gln Ser Gln Ile Ser
225                 230                 235                 240

Asp Thr Ser Val Val Leu Ser Met Asp Asn Ser Arg Ser Leu Asp Met
                245                 250                 255

Asp Ser Ile Ile Ala Glu Val Lys Ala Gln Tyr Glu Asp Ile Ala Asn
            260                 265                 270

Arg Ser Arg Ala Glu Ala Glu Ser Met Tyr Gln Ile Lys Tyr Glu Glu
        275                 280                 285

Leu Gln Ser Leu Ala Gly Lys His Gly Asp Asp Leu Arg Arg Thr Lys
    290                 295                 300

Thr Glu Ile Ser Glu Met Asn Arg Asn Ile Ser Arg Leu Gln Ala Glu
305                 310                 315                 320

Ile Glu Gly Leu Lys Gly Gln Arg Ala Ser Leu Glu Ala Ala Ile Ala
                325                 330                 335

Asp Ala Glu Gln Arg Gly Glu Leu Ala Ile Lys Asp Ala Asn Ala Lys
            340                 345                 350

Leu Ser Glu Leu Glu Ala Ala Leu Gln Arg Ala Lys Gln Asp Met Ala
        355                 360                 365

Arg Gln Leu Arg Glu Tyr Gln Glu Leu Met Asn Val Lys Leu Ala Leu
    370                 375                 380

Asp Ile Glu Ile Ala Thr Tyr Arg Lys Leu Leu Glu Gly Glu Glu Ser
385                 390                 395                 400

Arg Leu Glu Ser Gly Met Gln Asn Met Ser Ile His Thr Lys Thr Thr
                405                 410                 415

Ser Gly Tyr Ala Gly Gly Leu Ser Ser Ala Tyr Gly Gly Leu Thr Ser
            420                 425                 430

Pro Gly Leu Ser Tyr Ser Leu Gly Ser Ser Phe Gly Ser Gly Ala Gly
        435                 440                 445

Ser Ser Ser Phe Ser Arg Thr Ser Ser Arg Ala Val Val Val Lys
    450                 455                 460

Lys Ile Glu Thr Arg Asp Gly Lys Leu Val Ser Glu Ser Ser Asp Val
465                 470                 475                 480

Leu Pro Lys
```

<210> SEQ ID NO 80
<211> LENGTH: 440
<212> TYPE: PRT
<213> ORGANISM: Homo sapiens

<400> SEQUENCE: 80

```
Met Gly Pro Pro Gly Ser Pro Trp Gln Trp Val Thr Leu Leu Leu Gly
  1               5                  10                  15

Leu Leu Leu Pro Pro Ala Ala Pro Phe Trp Leu Leu Asn Val Leu Phe
             20                  25                  30

Pro Pro His Thr Thr Pro Lys Ala Glu Leu Ser Asn His Thr Arg Pro
         35                  40                  45

Val Ile Leu Val Pro Gly Cys Leu Gly Asn Gln Leu Glu Ala Lys Leu
 50                  55                  60

Asp Lys Pro Asp Val Val Asn Trp Met Cys Tyr Arg Lys Thr Glu Asp
 65                  70                  75                  80

Phe Phe Thr Ile Trp Leu Asp Leu Asn Met Phe Leu Pro Leu Gly Val
                 85                  90                  95

Asp Cys Trp Ile Asp Asn Thr Arg Val Val Tyr Asn Arg Ser Ser Gly
            100                 105                 110

Leu Val Ser Asn Ala Pro Gly Val Gln Ile Arg Val Pro Gly Phe Gly
            115                 120                 125

Lys Thr Tyr Ser Val Glu Tyr Leu Asp Ser Ser Lys Leu Ala Gly Tyr
130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
            195                 200                 205

Leu His Leu Leu Tyr Phe Leu Leu Arg Gln Pro Gln Ala Trp Lys Asp
210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
            275                 280                 285

Phe Ile Ser Thr Pro Ser Phe Asn Tyr Thr Gly Arg Asp Phe Gln Arg
290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly
            355                 360                 365

Asp Asp Thr Val Ala Thr Arg Ser Thr Glu Leu Cys Gly Leu Trp Gln
370                 375                 380
```

```
Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
            405                 410                 415

Ile Leu Leu Gly Ala Tyr Arg Gln Gly Pro Pro Ala Ser Pro Thr Ala
            420                 425                 430

Ser Pro Glu Pro Pro Pro Glu
        435                 440

<210> SEQ ID NO 81
<211> LENGTH: 135
<212> TYPE: PRT
<213> ORGANISM: Homo sapiens

<400> SEQUENCE: 81

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
        130                 135

<210> SEQ ID NO 82
<211> LENGTH: 314
<212> TYPE: PRT
<213> ORGANISM: Homo sapiens

<400> SEQUENCE: 82

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Asn Arg Gln Cys Gln Cys
        35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Thr Cys Trp Cys Val Asn Thr Ala Gly Val Arg Arg Thr Asp
        115                 120                 125
```

-continued

```
Lys Asp Thr Glu Ile Thr Cys Ser Glu Arg Val Arg Thr Tyr Trp Ile
130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270

Val Val Val Ile Ala Val Val Ala Gly Ile Val Leu Val Ile
        275                 280                 285

Ser Arg Lys Lys Arg Met Ala Lys Tyr Glu Lys Ala Glu Ile Lys Glu
290                 295                 300

Met Gly Glu Met His Arg Glu Leu Asn Ala
305                 310

<210> SEQ ID NO 83
<211> LENGTH: 720
<212> TYPE: PRT
<213> ORGANISM: Homo sapiens

<400> SEQUENCE: 83

Lys Ser Val Trp Lys Gly Gly Leu Arg Glu Arg Asp Pro Arg Gly Thr
1               5                   10                  15

Arg Gly Gly Gly Arg Arg Gly Thr Gly Ser Gln Pro Ala Leu Cys Leu
            20                  25                  30

Gly Ala Gly Arg Gln Glu Gly Ala Met Ala Leu Asp Gly Ile Arg Met
        35                  40                  45

Pro Asp Gly Cys Tyr Ala Asp Gly Thr Trp Glu Leu Ser Val His Val
50                  55                  60

Thr Asp Leu Asn Arg Asp Ile Thr Leu Arg Val Thr Gly Glu Val His
65                  70                  75                  80

Ile Gly Gly Val Met Leu Lys Leu Val Glu Lys Leu Asp Val Lys Lys
                85                  90                  95

Asp Trp Ser Asp His Ala Leu Trp Trp Glu Lys Lys Arg Thr Trp Leu
            100                 105                 110

Leu Lys Thr His Trp Thr Leu Asp Lys Tyr Gly Ile Gln Ala Asp Ala
        115                 120                 125

Lys Leu Gln Phe Thr Pro Gln His Lys Leu Leu Arg Leu Gln Leu Pro
130                 135                 140

Asn Met Lys Tyr Val Lys Val Lys Val Asn Phe Ser Asp Arg Val Phe
145                 150                 155                 160

Lys Ala Val Ser Asp Ile Cys Lys Thr Phe Asn Ile Arg His Pro Glu
                165                 170                 175

Glu Leu Ser Leu Leu Lys Lys Pro Arg Asp Pro Thr Lys Lys Lys Lys
            180                 185                 190
```

-continued

```
Lys Lys Leu Asp Asp Gln Ser Glu Asp Glu Ala Leu Glu Leu Glu Gly
        195                 200                 205

Pro Leu Ile Thr Pro Gly Ser Gly Ser Ile Tyr Ser Ser Pro Gly Leu
210                 215                 220

Tyr Ser Lys Thr Met Thr Pro Thr Tyr Asp Ala His Asp Gly Ser Pro
225                 230                 235                 240

Leu Ser Pro Thr Ser Ala Trp Phe Gly Asp Ser Ala Leu Ser Glu Gly
        245                 250                 255

Asn Pro Gly Ile Leu Ala Val Ser Gln Pro Ile Thr Ser Pro Glu Ile
        260                 265                 270

Leu Ala Lys Met Phe Lys Pro Gln Ala Leu Leu Asp Lys Ala Lys Ile
        275                 280                 285

Asn Gln Gly Trp Leu Asp Ser Ser Arg Ser Leu Met Glu Gln Asp Val
        290                 295                 300

Lys Glu Asn Glu Ala Leu Leu Leu Arg Phe Lys Tyr Tyr Ser Phe Phe
305                 310                 315                 320

Asp Leu Asn Pro Lys Tyr Asp Ala Ile Arg Ile Asn Gln Leu Tyr Glu
                325                 330                 335

Gln Ala Lys Trp Ala Ile Leu Leu Glu Glu Ile Glu Cys Thr Glu Glu
        340                 345                 350

Glu Met Met Met Phe Ala Ala Leu Gln Tyr His Ile Asn Lys Leu Ser
        355                 360                 365

Ile Met Thr Ser Glu Asn His Leu Asn Asn Ser Asp Lys Glu Val Asp
        370                 375                 380

Glu Val Asp Ala Ala Leu Ser Asp Leu Glu Ile Thr Leu Glu Gly Gly
385                 390                 395                 400

Lys Thr Ser Thr Ile Leu Gly Asp Ile Thr Ser Ile Pro Glu Leu Ala
                405                 410                 415

Asp Tyr Ile Lys Val Phe Lys Pro Lys Lys Leu Thr Leu Lys Gly Tyr
                420                 425                 430

Lys Gln Tyr Trp Cys Thr Phe Lys Asp Thr Ser Ile Ser Cys Tyr Lys
        435                 440                 445

Ser Lys Glu Glu Ser Ser Gly Thr Pro Ala His Gln Met Asn Leu Arg
        450                 455                 460

Gly Cys Glu Val Thr Pro Asp Val Asn Ile Ser Gly Gln Lys Phe Asn
465                 470                 475                 480

Ile Lys Leu Leu Ile Pro Val Ala Glu Gly Met Asn Glu Ile Trp Leu
                485                 490                 495

Arg Cys Asp Asn Glu Lys Gln Tyr Ala His Trp Met Ala Ala Cys Arg
                500                 505                 510

Leu Ala Ser Lys Gly Lys Thr Met Ala Asp Ser Ser Tyr Asn Leu Glu
        515                 520                 525

Val Gln Asn Ile Leu Ser Phe Leu Lys Met Gln His Leu Asn Pro Asp
        530                 535                 540

Pro Gln Leu Ile Pro Glu Gln Ile Thr Thr Asp Ile Thr Pro Glu Cys
545                 550                 555                 560

Leu Val Ser Pro Arg Tyr Leu Lys Tyr Lys Asn Lys Gln Ile Thr
                565                 570                 575

Ala Arg Ile Leu Glu Ala His Gln Asn Val Ala Gln Met Ser Leu Ile
        580                 585                 590

Glu Ala Lys Met Arg Phe Ile Gln Ala Trp Gln Ser Leu Pro Glu Phe
        595                 600                 605
```

```
Gly Ile Thr His Phe Ile Ala Arg Phe Gln Gly Gly Lys Lys Glu Glu
    610                 615                 620

Leu Ile Gly Ile Ala Tyr Asn Arg Leu Ile Arg Met Asp Ala Ser Thr
625                 630                 635                 640

Gly Asp Ala Ile Lys Thr Trp Arg Phe Ser Asn Met Lys Gln Trp Asn
                645                 650                 655

Val Asn Trp Glu Ile Lys Met Val Thr Val Glu Phe Ala Asp Glu Val
                660                 665                 670

Arg Leu Ser Phe Ile Cys Thr Glu Val Asp Cys Lys Val Val His Glu
                675                 680                 685

Phe Ile Gly Gly Tyr Ile Phe Leu Ser Thr Arg Ala Lys Asp Gln Asn
690                 695                 700

Glu Ser Leu Asp Glu Glu Met Phe Tyr Lys Leu Thr Ser Gly Trp Val
705                 710                 715                 720

<210> SEQ ID NO 84
<211> LENGTH: 582
<212> TYPE: PRT
<213> ORGANISM: Homo sapiens

<400> SEQUENCE: 84

Met Ser Pro Ala Pro Arg Pro Pro Arg Cys Leu Leu Leu Pro Leu Leu
1               5                   10                  15

Thr Leu Gly Thr Ala Leu Ala Ser Leu Gly Ser Ala Gln Ser Ser Ser
                20                  25                  30

Phe Ser Pro Glu Ala Trp Leu Gln Gln Tyr Gly Tyr Leu Pro Pro Gly
            35                  40                  45

Asp Leu Arg Thr His Thr Gln Arg Ser Pro Gln Ser Leu Ser Ala Ala
        50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
                245                 250                 255

Met Ala Pro Phe Tyr Gln Trp Met Asp Thr Glu Asn Phe Val Leu Pro
            260                 265                 270
```

-continued

```
Asp Asp Asp Arg Arg Gly Ile Gln Gln Leu Tyr Gly Gly Glu Ser Gly
        275                 280                 285
Phe Pro Thr Lys Met Pro Pro Gln Pro Arg Thr Thr Ser Arg Pro Ser
    290                 295                 300
Val Pro Asp Lys Pro Lys Asn Pro Thr Tyr Gly Pro Asn Ile Cys Asp
305                 310                 315                 320
Gly Asn Phe Asp Thr Val Ala Met Leu Arg Gly Glu Met Phe Val Phe
                325                 330                 335
Lys Glu Arg Trp Phe Trp Arg Val Arg Asn Asn Gln Val Met Asp Gly
            340                 345                 350
Tyr Pro Met Pro Ile Gly Gln Phe Trp Arg Gly Leu Pro Ala Ser Ile
        355                 360                 365
Asn Thr Ala Tyr Glu Arg Lys Asp Gly Lys Phe Val Phe Phe Lys Gly
    370                 375                 380
Asp Lys His Trp Val Phe Asp Glu Ala Ser Leu Glu Pro Gly Tyr Pro
385                 390                 395                 400
Lys His Ile Lys Glu Leu Gly Arg Gly Leu Pro Thr Asp Lys Ile Asp
                405                 410                 415
Ala Ala Leu Phe Trp Met Pro Asn Gly Lys Thr Tyr Phe Phe Arg Gly
            420                 425                 430
Asn Lys Tyr Tyr Arg Phe Asn Glu Glu Leu Arg Ala Val Asp Ser Glu
        435                 440                 445
Tyr Pro Lys Asn Ile Lys Val Trp Glu Gly Ile Pro Glu Ser Pro Arg
    450                 455                 460
Gly Ser Phe Met Gly Ser Asp Glu Val Phe Thr Tyr Phe Tyr Lys Gly
465                 470                 475                 480
Asn Lys Tyr Trp Lys Phe Asn Asn Gln Lys Leu Lys Val Glu Pro Gly
                485                 490                 495
Tyr Pro Lys Ser Ala Leu Arg Asp Trp Met Gly Cys Pro Ser Gly Gly
            500                 505                 510
Arg Pro Asp Glu Gly Thr Glu Glu Thr Glu Val Ile Ile Ile Glu
        515                 520                 525
Val Asp Glu Glu Gly Gly Ala Val Ser Ala Ala Val Val Leu
    530                 535                 540
Pro Val Leu Leu Leu Leu Val Leu Ala Val Gly Leu Ala Val Phe
545                 550                 555                 560
Phe Phe Arg Arg His Gly Thr Pro Arg Leu Leu Tyr Cys Gln Arg
                565                 570                 575
Ser Leu Leu Asp Lys Val
        580

<210> SEQ ID NO 85
<211> LENGTH: 1246
<212> TYPE: PRT
<213> ORGANISM: Homo sapiens

<400> SEQUENCE: 85

Met Leu Ala Ser Ser Arg Ile Arg Ala Ala Trp Thr Arg Ala Leu
1               5                   10                  15
Leu Leu Pro Leu Leu Leu Ala Gly Pro Val Gly Cys Leu Ser Arg Gln
            20                  25                  30
Glu Leu Phe Pro Phe Gly Pro Gly Gln Gly Asp Leu Glu Leu Glu Asp
        35                  40                  45
Gly Asp Asp Phe Val Ser Pro Ala Leu Glu Leu Ser Gly Ala Leu Arg
    50                  55                  60
```

-continued

```
Phe Tyr Asp Arg Ser Asp Ile Asp Ala Val Tyr Val Thr Thr Asn Gly
 65                  70                  75                  80

Ile Ile Ala Thr Ser Glu Pro Pro Ala Lys Glu Ser His Pro Gly Leu
                 85                  90                  95

Phe Pro Pro Thr Phe Gly Ala Val Ala Pro Phe Leu Ala Asp Leu Asp
            100                 105                 110

Thr Thr Asp Gly Leu Gly Lys Val Tyr Tyr Arg Glu Asp Leu Ser Pro
            115                 120                 125

Ser Ile Thr Gln Arg Ala Ala Glu Cys Val His Arg Gly Phe Pro Glu
        130                 135                 140

Ile Ser Phe Gln Pro Ser Ser Ala Val Val Thr Trp Glu Ser Val
145                 150                 155                 160

Ala Pro Tyr Gln Gly Pro Ser Arg Asp Pro Asp Gln Lys Gly Lys Arg
                165                 170                 175

Asn Thr Phe Gln Ala Val Leu Ala Ser Ser Asp Ser Ser Tyr Ala
            180                 185                 190

Ile Phe Leu Tyr Pro Glu Asp Gly Leu Gln Phe His Thr Thr Phe Ser
            195                 200                 205

Lys Lys Glu Asn Asn Gln Val Pro Ala Val Val Ala Phe Ser Gln Gly
        210                 215                 220

Ser Val Gly Phe Leu Trp Lys Ser Asn Gly Ala Tyr Asn Ile Phe Ala
225                 230                 235                 240

Asn Asp Arg Glu Ser Ile Glu Asn Leu Ala Lys Ser Asn Ser Gly
                245                 250                 255

Gln Gln Gly Val Trp Val Phe Glu Ile Gly Ser Pro Ala Thr Thr Asn
            260                 265                 270

Gly Val Val Pro Ala Asp Val Ile Leu Gly Thr Glu Asp Gly Ala Glu
            275                 280                 285

Tyr Asp Asp Glu Asp Glu Asp Tyr Asp Leu Ala Thr Thr Arg Leu Gly
        290                 295                 300

Leu Glu Asp Val Gly Thr Thr Pro Phe Ser Tyr Lys Ala Leu Arg Arg
305                 310                 315                 320

Gly Gly Ala Asp Thr Tyr Ser Val Pro Ser Val Leu Ser Pro Arg Arg
                325                 330                 335

Ala Ala Thr Glu Arg Pro Leu Gly Pro Pro Thr Glu Arg Thr Arg Ser
            340                 345                 350

Phe Gln Leu Ala Val Glu Thr Phe His Gln Gln His Pro Gln Val Ile
            355                 360                 365

Asp Val Asp Glu Val Glu Glu Thr Gly Val Val Phe Ser Tyr Asn Thr
        370                 375                 380

Asp Ser Arg Gln Thr Cys Ala Asn Asn Arg His Gln Cys Ser Val His
385                 390                 395                 400

Ala Glu Cys Arg Asp Tyr Ala Thr Gly Phe Cys Ser Cys Val Ala
                405                 410                 415

Gly Tyr Thr Gly Asn Gly Arg Gln Cys Val Ala Glu Gly Ser Pro Gln
            420                 425                 430

Arg Val Asn Gly Lys Val Lys Gly Arg Ile Phe Val Gly Ser Ser Gln
            435                 440                 445

Val Pro Ile Val Phe Glu Asn Thr Asp Leu His Ser Tyr Val Val Met
        450                 455                 460

Asn His Gly Arg Ser Tyr Thr Ala Ile Ser Thr Ile Pro Glu Thr Val
465                 470                 475                 480
```

```
Gly Tyr Ser Leu Leu Pro Leu Ala Pro Val Gly Gly Ile Ile Gly Trp
                485                 490                 495

Met Phe Ala Val Glu Gln Asp Gly Phe Lys Asn Gly Phe Ser Ile Thr
            500                 505                 510

Gly Gly Glu Phe Thr Arg Gln Ala Glu Val Thr Phe Val Gly His Pro
            515                 520                 525

Gly Asn Leu Val Ile Lys Gln Arg Phe Ser Gly Ile Asp Glu His Gly
            530                 535                 540

His Leu Thr Ile Asp Thr Glu Leu Glu Gly Arg Val Pro Gln Ile Pro
545                 550                 555                 560

Phe Gly Ser Ser Val His Ile Glu Pro Tyr Thr Glu Leu Tyr His Tyr
                565                 570                 575

Ser Thr Ser Val Ile Thr Ser Ser Thr Arg Glu Tyr Thr Val Thr
            580                 585                 590

Glu Pro Glu Arg Asp Gly Ala Ser Pro Ser Arg Ile Tyr Thr Tyr Gln
            595                 600                 605

Trp Arg Gln Thr Ile Thr Phe Gln Glu Cys Val His Asp Asp Ser Arg
            610                 615                 620

Pro Ala Leu Pro Ser Thr Gln Gln Leu Ser Val Asp Ser Val Phe Val
625                 630                 635                 640

Leu Tyr Asn Gln Glu Glu Lys Ile Leu Arg Tyr Ala Phe Ser Asn Ser
                645                 650                 655

Ile Gly Pro Val Arg Glu Gly Ser Pro Asp Ala Leu Gln Asn Pro Cys
            660                 665                 670

Tyr Ile Gly Thr His Gly Cys Asp Thr Asn Ala Ala Cys Arg Pro Gly
            675                 680                 685

Pro Arg Thr Gln Phe Thr Cys Glu Cys Ser Ile Gly Phe Arg Gly Asp
            690                 695                 700

Gly Arg Thr Cys Tyr Asp Ile Asp Glu Cys Ser Glu Gln Pro Ser Val
705                 710                 715                 720

Cys Gly Ser His Thr Ile Cys Asn Asn His Pro Gly Thr Phe Arg Cys
                725                 730                 735

Glu Cys Val Glu Gly Tyr Gln Phe Ser Asp Glu Gly Thr Cys Val Ala
            740                 745                 750

Val Val Asp Gln Arg Pro Ile Asn Tyr Cys Glu Thr Gly Leu His Asn
            755                 760                 765

Cys Asp Ile Pro Gln Arg Ala Gln Cys Ile Tyr Thr Gly Gly Ser Ser
770                 775                 780

Tyr Thr Cys Ser Cys Leu Pro Gly Phe Ser Gly Asp Gly Gln Ala Cys
785                 790                 795                 800

Gln Asp Val Asp Glu Cys Gln Pro Ser Arg Cys His Pro Asp Ala Phe
                805                 810                 815

Cys Tyr Asn Thr Pro Gly Ser Phe Thr Cys Gln Cys Lys Pro Gly Tyr
            820                 825                 830

Gln Gly Asp Gly Phe Arg Cys Val Pro Gly Glu Val Glu Lys Thr Arg
            835                 840                 845

Cys Gln His Glu Arg Glu His Ile Leu Gly Ala Ala Gly Ala Thr Asp
850                 855                 860

Pro Gln Arg Pro Ile Pro Pro Gly Leu Phe Val Pro Glu Cys Asp Ala
865                 870                 875                 880

His Gly His Tyr Ala Pro Thr Gln Cys His Gly Ser Thr Gly Tyr Cys
                885                 890                 895
```

-continued

```
Trp Cys Val Asp Arg Asp Gly Arg Glu Val Glu Gly Thr Arg Thr Arg
                900                 905                 910

Pro Gly Met Thr Pro Pro Cys Leu Ser Thr Val Ala Pro Pro Ile His
            915                 920                 925

Gln Gly Pro Ala Val Pro Thr Ala Val Ile Pro Leu Pro Pro Gly Thr
        930                 935                 940

His Leu Leu Phe Ala Gln Thr Gly Lys Ile Glu Arg Leu Pro Leu Glu
945                 950                 955                 960

Gly Asn Thr Met Arg Lys Thr Glu Ala Lys Ala Phe Leu His Val Pro
                965                 970                 975

Ala Lys Val Ile Ile Gly Leu Ala Phe Asp Cys Val Asp Lys Met Val
            980                 985                 990

Tyr Trp Thr Asp Ile Thr Glu Pro Ser Ile Gly Arg Ala Ser Leu His
        995                 1000                1005

Gly Gly Glu Pro Thr Thr Ile Ile Arg Gln Asp Leu Gly Ser Pro
1010                1015                1020

Glu Gly Ile Ala Val Asp His Leu Gly Arg Asn Ile Phe Trp Thr
1025                1030                1035

Asp Ser Asn Leu Asp Arg Ile Glu Val Ala Lys Leu Asp Gly Thr
1040                1045                1050

Gln Arg Arg Val Leu Phe Glu Thr Asp Leu Val Asn Pro Arg Gly
1055                1060                1065

Ile Val Thr Asp Ser Val Arg Gly Asn Leu Tyr Trp Thr Asp Trp
1070                1075                1080

Asn Arg Asp Asn Pro Lys Ile Glu Thr Ser Tyr Met Asp Gly Thr
1085                1090                1095

Asn Arg Arg Ile Leu Val Gln Asp Asp Leu Gly Leu Pro Asn Gly
1100                1105                1110

Leu His Phe Asp Ala Phe Ser Ser Gln Leu Cys Trp Val Asp Ala
1115                1120                1125

Gly Thr Asn Arg Ala Glu Cys Leu Asn Pro Ser Gln Pro Ser Arg
1130                1135                1140

Arg Lys Ala Leu Glu Gly Leu Gln Tyr Pro Phe Ala Val Thr Ser
1145                1150                1155

Tyr Gly Lys Asn Leu Tyr Phe Thr Asp Trp Lys Met Asn Ser Val
1160                1165                1170

Val Ala Leu Asp Leu Ala Ile Ser Lys Glu Thr Asp Ala Phe Gln
1175                1180                1185

Pro His Lys Gln Thr Arg Leu Tyr Gly Ile Thr Thr Ala Leu Ser
1190                1195                1200

Gln Cys Pro Gln Gly His Asn Tyr Cys Ser Val Asn Asn Gly Gly
1205                1210                1215

Cys Thr His Leu Cys Leu Ala Thr Pro Gly Ser Arg Thr Cys Arg
1220                1225                1230

Cys Pro Asp Asn Thr Leu Gly Val Asp Cys Ile Glu Arg
1235                1240                1245

<210> SEQ ID NO 86
<211> LENGTH: 423
<212> TYPE: PRT
<213> ORGANISM: Homo sapiens

<400> SEQUENCE: 86

Met Ala Met Val Val Ser Ser Trp Arg Asp Pro Gln Asp Asp Val Ala
1               5                   10                  15
```

```
Gly Gly Asn Pro Gly Gly Pro Asn Pro Ala Ala Gln Ala Ala Arg Gly
             20                  25                  30

Gly Gly Gly Gly Ala Gly Glu Gln Gln Gln Gln Ala Gly Ser Gly Ala
         35                  40                  45

Pro His Thr Pro Gln Thr Pro Gly Gln Pro Gly Ala Pro Ala Thr Pro
     50                  55                  60

Gly Thr Ala Gly Asp Lys Gly Gln Gly Pro Pro Gly Ser Gly Gln Ser
 65              70                  75                  80

Gln Gln His Ile Glu Cys Val Val Cys Gly Asp Lys Ser Ser Gly Lys
                 85                  90                  95

His Tyr Gly Gln Phe Thr Cys Glu Gly Cys Lys Ser Phe Phe Lys Arg
            100                 105                 110

Ser Val Arg Arg Asn Leu Thr Tyr Thr Cys Arg Ala Asn Arg Asn Cys
        115                 120                 125

Pro Ile Asp Gln His His Arg Asn Gln Cys Gln Tyr Cys Arg Leu Lys
    130                 135                 140

Lys Cys Leu Lys Val Gly Met Arg Arg Glu Ala Val Gln Arg Gly Arg
145                 150                 155                 160

Met Pro Pro Thr Gln Pro Asn Pro Gly Gln Tyr Ala Leu Thr Asn Gly
                165                 170                 175

Asp Pro Leu Asn Gly His Cys Tyr Leu Ser Gly Tyr Ile Ser Leu Leu
            180                 185                 190

Leu Arg Ala Glu Pro Tyr Pro Thr Ser Arg Tyr Gly Ser Gln Cys Met
        195                 200                 205

Gln Pro Asn Asn Ile Met Gly Ile Glu Asn Ile Cys Glu Leu Ala Ala
    210                 215                 220

Arg Leu Leu Phe Ser Ala Val Glu Trp Ala Arg Asn Ile Pro Phe Phe
225                 230                 235                 240

Pro Asp Leu Gln Ile Thr Asp Gln Val Ser Leu Leu Arg Leu Thr Trp
                245                 250                 255

Ser Glu Leu Phe Val Leu Asn Ala Ala Gln Cys Ser Met Pro Leu His
            260                 265                 270

Val Ala Pro Leu Leu Ala Ala Ala Gly Leu His Ala Ser Pro Met Ser
        275                 280                 285

Ala Asp Arg Val Val Ala Phe Met Asp His Ile Arg Ile Phe Gln Glu
    290                 295                 300

Gln Val Glu Lys Leu Lys Ala Leu His Val Asp Ser Ala Glu Tyr Ser
305                 310                 315                 320

Cys Leu Lys Ala Ile Val Leu Phe Thr Ser Asp Ala Cys Gly Leu Ser
                325                 330                 335

Asp Ala Ala His Ile Glu Ser Leu Gln Glu Lys Ser Gln Cys Ala Leu
            340                 345                 350

Glu Glu Tyr Val Arg Ser Gln Tyr Pro Asn Gln Pro Ser Arg Phe Gly
        355                 360                 365

Lys Leu Leu Leu Arg Leu Pro Ser Leu Arg Thr Val Ser Ser Ser Val
    370                 375                 380

Ile Glu Gln Leu Phe Phe Val Arg Leu Val Gly Lys Thr Pro Ile Glu
385                 390                 395                 400

Thr Leu Ile Arg Asp Met Leu Leu Ser Gly Ser Ser Phe Asn Trp Pro
                405                 410                 415

Tyr Met Ser Ile Gln Cys Ser
            420
```

<210> SEQ ID NO 87
<211> LENGTH: 534
<212> TYPE: PRT
<213> ORGANISM: Homo sapiens

<400> SEQUENCE: 87

```
Met Ile Trp Tyr Ile Leu Ile Ile Gly Ile Leu Leu Pro Gln Ser Leu
  1               5                  10                  15

Ala His Pro Gly Phe Phe Thr Ser Ile Gly Gln Met Thr Asp Leu Ile
             20                  25                  30

His Thr Glu Lys Asp Leu Val Thr Ser Leu Lys Asp Tyr Ile Lys Ala
         35                  40                  45

Glu Glu Asp Lys Leu Glu Gln Ile Lys Lys Trp Ala Glu Lys Leu Asp
     50                  55                  60

Arg Leu Thr Ser Thr Ala Thr Lys Asp Pro Glu Gly Phe Val Gly His
 65                  70                  75                  80

Pro Val Asn Ala Phe Lys Leu Met Lys Arg Leu Asn Thr Glu Trp Ser
                 85                  90                  95

Glu Leu Glu Asn Leu Val Leu Lys Asp Met Ser Asp Gly Phe Ile Ser
            100                 105                 110

Asn Leu Thr Ile Gln Arg Pro Val Leu Ser Asn Asp Glu Asp Gln Val
        115                 120                 125

Gly Ala Ala Lys Ala Leu Leu Arg Leu Gln Asp Thr Tyr Asn Leu Asp
    130                 135                 140

Thr Asp Thr Ile Ser Lys Gly Asn Leu Pro Gly Val Lys His Lys Ser
145                 150                 155                 160

Phe Leu Thr Ala Glu Asp Cys Phe Glu Leu Gly Lys Val Ala Tyr Thr
                165                 170                 175

Glu Ala Asp Tyr Tyr His Thr Glu Leu Trp Met Glu Gln Ala Leu Arg
            180                 185                 190

Gln Leu Asp Glu Gly Glu Ile Ser Thr Ile Asp Lys Val Ser Val Leu
        195                 200                 205

Asp Tyr Leu Ser Tyr Ala Val Tyr Gln Gln Gly Asp Leu Asp Lys Ala
    210                 215                 220

Leu Leu Leu Thr Lys Lys Leu Leu Glu Leu Asp Pro Glu His Gln Arg
225                 230                 235                 240

Ala Asn Gly Asn Leu Lys Tyr Phe Glu Tyr Ile Met Ala Lys Glu Lys
                245                 250                 255

Asp Val Asn Lys Ser Ala Ser Asp Asp Gln Ser Asp Gln Lys Thr Thr
            260                 265                 270

Pro Lys Lys Lys Gly Val Ala Val Asp Tyr Leu Pro Glu Arg Gln Lys
        275                 280                 285

Tyr Glu Met Leu Cys Arg Gly Glu Gly Ile Lys Met Thr Pro Arg Arg
    290                 295                 300

Gln Lys Lys Leu Phe Cys Arg Tyr His Asp Gly Asn Arg Asn Pro Lys
305                 310                 315                 320

Phe Ile Leu Ala Pro Ala Lys Gln Glu Asp Glu Trp Asp Lys Pro Arg
                325                 330                 335

Ile Ile Arg Phe His Asp Ile Ile Ser Asp Ala Glu Ile Glu Ile Val
            340                 345                 350

Lys Asp Leu Ala Lys Pro Arg Leu Ser Arg Ala Thr Val His Asp Pro
        355                 360                 365

Glu Thr Gly Lys Leu Thr Thr Ala Gln Tyr Arg Val Ser Lys Ser Ala
    370                 375                 380
```

```
Trp Leu Ser Gly Tyr Glu Asn Pro Val Val Ser Arg Ile Asn Met Arg
385                 390                 395                 400

Ile Gln Asp Leu Thr Gly Leu Asp Val Ser Thr Ala Glu Glu Leu Gln
                405                 410                 415

Val Ala Asn Tyr Gly Val Gly Gly Gln Tyr Glu Pro His Phe Asp Phe
            420                 425                 430

Ala Arg Lys Asp Glu Pro Asp Ala Phe Lys Glu Leu Gly Thr Gly Asn
        435                 440                 445

Arg Ile Ala Thr Trp Leu Phe Tyr Met Ser Asp Val Ser Ala Gly Gly
    450                 455                 460

Ala Thr Val Phe Pro Glu Val Gly Ala Ser Val Trp Pro Lys Lys Gly
465                 470                 475                 480

Thr Ala Val Phe Trp Tyr Asn Leu Phe Ala Ser Gly Glu Gly Asp Tyr
                485                 490                 495

Ser Thr Arg His Ala Ala Cys Pro Val Leu Val Gly Asn Lys Trp Val
                500                 505                 510

Ser Asn Lys Trp Leu His Glu Arg Gly Gln Glu Phe Arg Arg Pro Cys
            515                 520                 525

Thr Leu Ser Glu Leu Glu
        530

<210> SEQ ID NO 88
<211> LENGTH: 162
<212> TYPE: PRT
<213> ORGANISM: Homo sapiens

<400> SEQUENCE: 88

Met Asp Ile Pro Gln Thr Lys Gln Asp Leu Glu Leu Pro Lys Leu Ala
1               5                   10                  15

Gly Thr Trp His Ser Met Ala Met Ala Thr Asn Asn Ile Ser Leu Met
            20                  25                  30

Ala Thr Leu Lys Ala Pro Leu Arg Val His Ile Thr Ser Leu Leu Pro
        35                  40                  45

Thr Pro Glu Asp Asn Leu Glu Ile Val Leu His Arg Trp Glu Asn Asn
    50                  55                  60

Ser Cys Val Glu Lys Lys Val Leu Gly Glu Lys Thr Gly Asn Pro Lys
65                  70                  75                  80

Lys Phe Lys Ile Asn Tyr Thr Val Ala Asn Glu Ala Thr Leu Leu Asp
                85                  90                  95

Thr Asp Tyr Asp Asn Phe Leu Phe Leu Cys Leu Gln Asp Thr Thr Thr
            100                 105                 110

Pro Ile Gln Ser Met Met Cys Gln Tyr Leu Ala Arg Val Leu Val Glu
        115                 120                 125

Asp Asp Glu Ile Met Gln Gly Phe Ile Arg Ala Phe Arg Pro Leu Pro
    130                 135                 140

Arg His Leu Trp Tyr Leu Leu Asp Leu Lys Gln Met Glu Glu Pro Cys
145                 150                 155                 160

Arg Phe

<210> SEQ ID NO 89
<211> LENGTH: 449
<212> TYPE: PRT
<213> ORGANISM: Homo sapiens
```

-continued

```
<400> SEQUENCE: 89

Met Leu Pro Ala Ala Thr Ala Ser Leu Leu Gly Pro Leu Leu Thr Ala
1               5                   10                  15

Cys Ala Leu Leu Pro Phe Ala Gln Gly Gln Thr Pro Asn Tyr Thr Arg
                20                  25                  30

Pro Val Phe Leu Cys Gly Gly Asp Val Lys Gly Glu Ser Gly Tyr Val
            35                  40                  45

Ala Ser Glu Gly Phe Pro Asn Ser Tyr Pro Pro Asn Lys Glu Cys Ile
    50                  55                  60

Trp Thr Ile Thr Val Pro Glu Gly Gln Thr Val Ser Leu Ser Phe Arg
65                  70                  75                  80

Val Phe Asp Leu Glu Leu His Pro Ala Cys Arg Tyr Asp Ala Leu Glu
                85                  90                  95

Val Phe Ala Gly Ser Gly Thr Ser Gly Gln Arg Leu Gly Arg Phe Cys
            100                 105                 110

Gly Thr Phe Arg Pro Ala Pro Leu Val Ala Pro Gly Asn Gln Val Thr
        115                 120                 125

Leu Arg Met Thr Thr Asp Glu Gly Thr Gly Gly Arg Gly Phe Leu Leu
    130                 135                 140

Trp Tyr Ser Gly Arg Ala Thr Ser Gly Ser Glu His Gln Phe Cys Gly
145                 150                 155                 160

Gly Arg Leu Glu Lys Ala Gln Gly Thr Leu Thr Thr Pro Asn Trp Pro
                165                 170                 175

Glu Ser Asp Tyr Pro Pro Gly Ile Ser Cys Ser Trp His Ile Ile Ala
            180                 185                 190

Pro Pro Asp Gln Val Ile Ala Leu Thr Phe Glu Lys Phe Asp Leu Glu
        195                 200                 205

Pro Asp Thr Tyr Cys Arg Tyr Asp Ser Val Ser Val Phe Asn Gly Ala
    210                 215                 220

Val Ser Asp Asp Ser Arg Arg Leu Gly Lys Phe Cys Gly Asp Ala Val
225                 230                 235                 240

Pro Gly Ser Ile Ser Ser Glu Gly Asn Glu Leu Leu Val Gln Phe Val
                245                 250                 255

Ser Asp Leu Ser Val Thr Ala Asp Gly Phe Ser Ala Ser Tyr Lys Thr
            260                 265                 270

Leu Pro Arg Gly Thr Ala Lys Glu Gly Gln Gly Pro Gly Pro Lys Arg
        275                 280                 285

Gly Thr Glu Pro Lys Val Lys Leu Pro Pro Lys Ser Gln Pro Pro Glu
    290                 295                 300

Lys Thr Glu Glu Ser Pro Ser Ala Pro Asp Ala Pro Thr Cys Pro Lys
305                 310                 315                 320

Gln Cys Arg Arg Thr Gly Thr Leu Gln Ser Asn Phe Cys Ala Ser Ser
                325                 330                 335

Leu Val Val Thr Ala Thr Val Lys Ser Met Val Arg Glu Pro Gly Glu
            340                 345                 350

Gly Leu Ala Val Thr Val Ser Leu Ile Gly Ala Tyr Lys Thr Gly Gly
        355                 360                 365

Leu Asp Leu Pro Thr Pro Pro Thr Gly Ala Ser Leu Lys Phe Tyr Val
    370                 375                 380

Pro Cys Lys Gln Cys Pro Pro Met Lys Lys Gly Val Ser Tyr Leu Leu
385                 390                 395                 400

Met Gly Gln Val Glu Glu Asn Arg Gly Pro Val Leu Pro Pro Glu Ser
                405                 410                 415
```

-continued

```
Phe Val Val Leu His Arg Pro Asn Gln Asp Gln Ile Leu Thr Asn Leu
            420                 425                 430

Ser Lys Arg Lys Cys Pro Ser Gln Pro Val Arg Ala Ala Ala Ser Gln
            435                 440                 445

Asp

<210> SEQ ID NO 90
<211> LENGTH: 1089
<212> TYPE: PRT
<213> ORGANISM: Homo sapiens

<400> SEQUENCE: 90

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335
```

```
Val Glu Val Arg Ala Tyr Pro Pro Arg Ile Ser Trp Leu Lys Asn
            340             345             350

Asn Leu Thr Leu Ile Glu Asn Leu Thr Glu Ile Thr Thr Asp Val Glu
            355             360             365

Lys Ile Gln Glu Ile Arg Tyr Arg Ser Lys Leu Lys Leu Ile Arg Ala
            370             375             380

Lys Glu Glu Asp Ser Gly His Tyr Thr Ile Val Ala Gln Asn Glu Asp
385             390             395             400

Ala Val Lys Ser Tyr Thr Phe Glu Leu Leu Thr Gln Val Pro Ser Ser
            405             410             415

Ile Leu Asp Leu Val Asp Asp His His Gly Ser Thr Gly Gly Gln Thr
            420             425             430

Val Arg Cys Thr Ala Glu Gly Thr Pro Leu Pro Asp Ile Glu Trp Met
            435             440             445

Ile Cys Lys Asp Ile Lys Lys Cys Asn Asn Glu Thr Ser Trp Thr Ile
            450             455             460

Leu Ala Asn Asn Val Ser Asn Ile Ile Thr Glu Ile His Ser Arg Asp
465             470             475             480

Arg Ser Thr Val Glu Gly Arg Val Thr Phe Ala Lys Val Glu Glu Thr
            485             490             495

Ile Ala Val Arg Cys Leu Ala Lys Asn Leu Leu Gly Ala Glu Asn Arg
            500             505             510

Glu Leu Lys Leu Val Ala Pro Thr Leu Arg Ser Glu Leu Thr Val Ala
            515             520             525

Ala Ala Val Leu Val Leu Leu Val Ile Val Ile Ile Ser Leu Ile Val
            530             535             540

Leu Val Val Ile Trp Lys Gln Lys Pro Arg Tyr Glu Ile Arg Trp Arg
545             550             555             560

Val Ile Glu Ser Ile Ser Pro Asp Gly His Glu Tyr Ile Tyr Val Asp
            565             570             575

Pro Met Gln Leu Pro Tyr Asp Ser Arg Trp Glu Phe Pro Arg Asp Gly
            580             585             590

Leu Val Leu Gly Arg Val Leu Gly Ser Gly Ala Phe Gly Lys Val Val
            595             600             605

Glu Gly Thr Ala Tyr Gly Leu Ser Arg Ser Gln Pro Val Met Lys Val
            610             615             620

Ala Val Lys Met Leu Lys Pro Thr Ala Arg Ser Ser Glu Lys Gln Ala
625             630             635             640

Leu Met Ser Glu Leu Lys Ile Met Thr His Leu Gly Pro His Leu Asn
            645             650             655

Ile Val Asn Leu Leu Gly Ala Cys Thr Lys Ser Gly Pro Ile Tyr Ile
            660             665             670

Ile Thr Glu Tyr Cys Phe Tyr Gly Asp Leu Val Asn Tyr Leu His Lys
            675             680             685

Asn Arg Asp Ser Phe Leu Ser His His Pro Glu Lys Pro Lys Lys Glu
            690             695             700

Leu Asp Ile Phe Gly Leu Asn Pro Ala Asp Glu Ser Thr Arg Ser Tyr
705             710             715             720

Val Ile Leu Ser Phe Glu Asn Asn Gly Asp Tyr Met Asp Met Lys Gln
            725             730             735

Ala Asp Thr Thr Gln Tyr Val Pro Met Leu Glu Arg Lys Glu Val Ser
            740             745             750
```

```
Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
        770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
        820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
        850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
                900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
        930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
                980                 985                 990

Tyr Lys Asn Glu Glu Asp Lys Leu  Lys Asp Trp Glu Gly  Gly Leu Asp
        995                 1000                1005

Glu Gln  Arg Leu Ser Ala Asp  Ser Gly Tyr Ile Ile  Pro Leu Pro
        1010                1015                1020

Asp Ile  Asp Pro Val Pro Glu  Glu Glu Asp Leu Gly  Lys Arg Asn
        1025                1030                1035

Arg His  Ser Ser Gln Thr Ser  Glu Glu Ser Ala Ile  Glu Thr Gly
        1040                1045                1050

Ser Ser  Ser Ser Thr Phe Ile  Lys Arg Glu Asp Glu  Thr Ile Glu
        1055                1060                1065

Asp Ile  Asp Met Met Asp Asp  Ile Gly Ile Asp Ser  Ser Asp Leu
        1070                1075                1080

Val Glu  Asp Ser Phe Leu
        1085

<210> SEQ ID NO 91
<211> LENGTH: 318
<212> TYPE: PRT
<213> ORGANISM: Homo sapiens

<400> SEQUENCE: 91

Met Pro Asn Ile Lys Ile Phe Ser Gly Ser Ser His Gln Asp Leu Ser
1               5                   10                  15

Gln Lys Ile Ala Asp Arg Leu Gly Leu Glu Leu Gly Lys Val Val Thr
            20                  25                  30
```

```
Lys Lys Phe Ser Asn Gln Glu Thr Cys Val Glu Ile Gly Glu Ser Val
            35                  40                  45

Arg Gly Glu Asp Val Tyr Ile Val Gln Ser Gly Cys Gly Glu Ile Asn
        50                  55                  60

Asp Asn Leu Met Glu Leu Leu Ile Met Ile Asn Ala Cys Lys Ile Ala
65                  70                  75                  80

Ser Ala Ser Arg Val Thr Ala Val Ile Pro Cys Phe Pro Tyr Ala Arg
                85                  90                  95

Gln Asp Lys Lys Asp Lys Ser Arg Ala Pro Ile Ser Ala Lys Leu Val
            100                 105                 110

Ala Asn Met Leu Ser Val Ala Gly Ala Asp His Ile Ile Thr Met Asp
        115                 120                 125

Leu His Ala Ser Gln Ile Gln Gly Phe Phe Asp Ile Pro Val Asp Asn
    130                 135                 140

Leu Tyr Ala Glu Pro Ala Val Leu Lys Trp Ile Arg Glu Asn Ile Ser
145                 150                 155                 160

Glu Trp Arg Asn Cys Thr Ile Val Ser Pro Asp Ala Gly Gly Ala Lys
                165                 170                 175

Arg Val Thr Ser Ile Ala Asp Arg Leu Asn Val Asp Phe Ala Leu Ile
            180                 185                 190

His Lys Glu Arg Lys Lys Ala Asn Glu Val Asp Arg Met Val Leu Val
        195                 200                 205

Gly Asp Val Lys Asp Arg Val Ala Ile Leu Val Asp Asp Met Ala Asp
    210                 215                 220

Thr Cys Gly Thr Ile Cys His Ala Ala Asp Lys Leu Leu Ser Ala Gly
225                 230                 235                 240

Ala Thr Arg Val Tyr Ala Ile Leu Thr His Gly Ile Phe Ser Gly Pro
                245                 250                 255

Ala Ile Ser Arg Ile Asn Asn Ala Cys Phe Glu Ala Val Val Val Thr
            260                 265                 270

Asn Thr Ile Pro Gln Glu Asp Lys Met Lys His Cys Ser Lys Ile Gln
        275                 280                 285

Val Ile Asp Ile Ser Met Ile Leu Ala Glu Ala Ile Arg Arg Thr His
    290                 295                 300

Asn Gly Glu Ser Val Ser Tyr Leu Phe Ser His Val Pro Leu
305                 310                 315

<210> SEQ ID NO 92
<211> LENGTH: 318
<212> TYPE: PRT
<213> ORGANISM: Homo sapiens

<400> SEQUENCE: 92

Met Pro Asn Ile Val Leu Phe Ser Gly Ser Ser His Gln Asp Leu Ser
1               5                   10                  15

Gln Arg Val Ala Asp Arg Leu Gly Leu Glu Leu Gly Lys Val Val Thr
            20                  25                  30

Lys Lys Phe Ser Asn Gln Glu Thr Ser Val Glu Ile Gly Glu Ser Val
        35                  40                  45

Arg Gly Glu Asp Val Tyr Ile Ile Gln Ser Gly Cys Gly Glu Ile Asn
    50                  55                  60

Asp Asn Leu Met Glu Leu Leu Ile Met Ile Asn Ala Cys Lys Ile Ala
65                  70                  75                  80

Ser Ser Ser Arg Val Thr Ala Val Ile Pro Cys Phe Pro Tyr Ala Arg
                85                  90                  95
```

-continued

```
Gln Asp Lys Lys Asp Lys Ser Arg Ala Pro Ile Ser Ala Lys Leu Val
            100                 105                 110

Ala Asn Met Leu Ser Val Ala Gly Ala Asp His Ile Ile Thr Met Asp
        115                 120                 125

Leu His Ala Ser Gln Ile Gln Gly Phe Phe Asp Ile Pro Val Asp Asn
    130                 135                 140

Leu Tyr Ala Glu Pro Ala Val Leu Gln Trp Ile Arg Glu Asn Ile Ala
145                 150                 155                 160

Glu Trp Lys Asn Cys Ile Ile Val Ser Pro Asp Ala Gly Gly Ala Lys
                165                 170                 175

Arg Val Thr Ser Ile Ala Asp Arg Leu Asn Val Glu Phe Ala Leu Ile
            180                 185                 190

His Lys Glu Arg Lys Lys Ala Asn Glu Val Asp Arg Met Val Leu Val
        195                 200                 205

Gly Asp Val Lys Asp Arg Val Ala Ile Leu Val Asp Asp Met Ala Asp
    210                 215                 220

Thr Cys Gly Thr Ile Cys His Ala Ala Asp Lys Leu Leu Ser Ala Gly
225                 230                 235                 240

Ala Thr Lys Val Tyr Ala Ile Leu Thr His Gly Ile Phe Ser Gly Pro
                245                 250                 255

Ala Ile Ser Arg Ile Asn Asn Ala Ala Phe Glu Ala Val Val Val Thr
            260                 265                 270

Asn Thr Ile Pro Gln Glu Asp Lys Met Lys His Cys Thr Lys Ile Gln
        275                 280                 285

Val Ile Asp Ile Ser Met Ile Leu Ala Glu Ala Ile Arg Arg Thr His
    290                 295                 300

Asn Gly Glu Ser Val Ser Tyr Leu Phe Ser His Val Pro Leu
305                 310                 315

<210> SEQ ID NO 93
<211> LENGTH: 244
<212> TYPE: PRT
<213> ORGANISM: Homo sapiens

<400> SEQUENCE: 93

Met Ala Ala Ala Ala Ala Gly Glu Ala Arg Arg Val Leu Val Tyr
1               5                   10                  15

Gly Gly Arg Gly Ala Leu Gly Ser Arg Cys Val Gln Ala Phe Arg Ala
            20                  25                  30

Arg Asn Trp Trp Val Ala Ser Val Asp Val Val Glu Asn Glu Glu Ala
        35                  40                  45

Ser Ala Thr Ile Ile Val Lys Met Thr Asp Ser Phe Thr Glu Gln Ala
    50                  55                  60

Asp Gln Val Thr Ala Glu Val Gly Lys Leu Leu Gly Glu Lys Val
65                  70                  75                  80

Asp Ala Ile Leu Cys Val Ala Gly Gly Trp Ala Gly Gly Asn Ala Lys
                85                  90                  95

Ser Lys Ser Leu Phe Lys Asn Cys Asp Leu Met Trp Lys Gln Ser Ile
            100                 105                 110

Trp Thr Ser Thr Ile Ser Ser His Leu Ala Thr Lys His Leu Lys Glu
        115                 120                 125

Gly Gly Leu Leu Thr Leu Ala Gly Ala Lys Ala Ala Leu Asp Gly Thr
    130                 135                 140

Pro Gly Met Ile Gly Tyr Gly Met Ala Lys Gly Ala Val His Gln Leu
145                 150                 155                 160
```

-continued

```
Cys Gln Ser Leu Ala Gly Lys Asn Ser Gly Met Pro Pro Gly Ala Ala
                165                 170                 175

Ala Ile Ala Val Leu Pro Val Thr Leu Asp Thr Pro Met Asn Arg Lys
            180                 185                 190

Ser Met Pro Glu Ala Asp Phe Ser Ser Trp Thr Pro Leu Glu Phe Leu
        195                 200                 205

Val Glu Thr Phe His Asp Trp Ile Thr Gly Lys Asn Arg Pro Ser Ser
    210                 215                 220

Gly Ser Leu Ile Gln Val Val Thr Thr Glu Gly Arg Thr Glu Leu Thr
225                 230                 235                 240

Pro Ala Tyr Phe

<210> SEQ ID NO 94
<211> LENGTH: 331
<212> TYPE: PRT
<213> ORGANISM: Homo sapiens

<400> SEQUENCE: 94

Met Gly Thr Pro Gln Lys Asp Val Ile Ile Lys Ser Asp Ala Pro Asp
1               5                   10                  15

Thr Leu Leu Leu Glu Lys His Ala Asp Tyr Ile Ala Ser Tyr Gly Ser
            20                  25                  30

Lys Lys Asp Asp Tyr Glu Tyr Cys Met Ser Glu Tyr Leu Arg Met Ser
        35                  40                  45

Gly Ile Tyr Trp Gly Leu Thr Val Met Asp Leu Met Gly Gln Leu His
    50                  55                  60

Arg Met Asn Arg Glu Glu Ile Leu Ala Phe Ile Lys Ser Cys Gln His
65                  70                  75                  80

Glu Cys Gly Gly Ile Ser Ala Ser Ile Gly His Asp Pro His Leu Leu
                85                  90                  95

Tyr Thr Leu Ser Ala Val Gln Ile Leu Thr Leu Tyr Asp Ser Ile Asn
            100                 105                 110

Val Ile Asp Val Asn Lys Val Val Glu Tyr Val Lys Gly Leu Gln Lys
        115                 120                 125

Glu Asp Gly Ser Phe Ala Gly Asp Ile Trp Gly Glu Ile Asp Thr Arg
    130                 135                 140

Phe Ser Phe Cys Ala Val Ala Thr Leu Ala Leu Leu Gly Lys Leu Asp
145                 150                 155                 160

Ala Ile Asn Val Glu Lys Ala Ile Glu Phe Val Leu Ser Cys Met Asn
                165                 170                 175

Phe Asp Gly Gly Phe Gly Cys Arg Pro Gly Ser Glu Ser His Ala Gly
            180                 185                 190

Gln Ile Tyr Cys Cys Thr Gly Phe Leu Ala Ile Thr Ser Gln Leu His
        195                 200                 205

Gln Val Asn Ser Asp Leu Leu Gly Trp Trp Leu Cys Glu Arg Gln Leu
    210                 215                 220

Pro Ser Gly Gly Leu Asn Gly Arg Pro Glu Lys Leu Pro Asp Val Cys
225                 230                 235                 240

Tyr Ser Trp Trp Val Leu Ala Ser Leu Lys Ile Ile Gly Arg Leu His
                245                 250                 255

Trp Ile Asp Arg Glu Lys Leu Arg Asn Phe Ile Leu Ala Cys Gln Asp
            260                 265                 270

Glu Glu Thr Gly Gly Phe Ala Asp Arg Pro Gly Asp Met Val Asp Pro
        275                 280                 285
```

-continued

```
Phe His Thr Leu Phe Gly Ile Ala Gly Leu Ser Leu Leu Gly Glu Glu
    290                 295                 300

Gln Ile Lys Pro Val Asn Pro Val Phe Cys Met Pro Glu Glu Val Leu
305                 310                 315                 320

Gln Arg Val Asn Val Gln Pro Glu Leu Val Ser
                325                 330

<210> SEQ ID NO 95
<211> LENGTH: 93
<212> TYPE: PRT
<213> ORGANISM: Homo sapiens

<400> SEQUENCE: 95

Met Asn Ala Lys Val Val Val Leu Val Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 96
<211> LENGTH: 381
<212> TYPE: PRT
<213> ORGANISM: Homo sapiens
<220> FEATURE:
<221> NAME/KEY: UNSURE
<222> LOCATION: (59)..(59)
<223> OTHER INFORMATION: Xaa = any amino acid
<221> NAME/KEY: UNSURE
<222> LOCATION: (300)..(300)
<223> OTHER INFORMATION: Xaa = any amino acid
<221> NAME/KEY: UNSURE
<222> LOCATION: (318)..(318)
<223> OTHER INFORMATION: Xaa = any amino acid
<221> NAME/KEY: UNSURE
<222> LOCATION: (330)..(330)
<223> OTHER INFORMATION: Xaa = any amino acid
<221> NAME/KEY: UNSURE
<222> LOCATION: (345)..(345)
<223> OTHER INFORMATION: Xaa = any amino acid
<221> NAME/KEY: UNSURE
<222> LOCATION: (352)..(352)
<223> OTHER INFORMATION: Xaa = any amino acid
<221> NAME/KEY: UNSURE
<222> LOCATION: (367)..(367)
<223> OTHER INFORMATION: Xaa = any amino acid
<221> NAME/KEY: UNSURE
<222> LOCATION: (369)..(369)
<223> OTHER INFORMATION: Xaa = any amino acid
<221> NAME/KEY: UNSURE
<222> LOCATION: (376)..(376)
<223> OTHER INFORMATION: Xaa = any amino acid
<221> NAME/KEY: UNSURE
<222> LOCATION: (378)..(378)
<223> OTHER INFORMATION: Xaa = any amino acid

<400> SEQUENCE: 96

Met Trp Arg Ser Leu Gly Leu Ala Leu Ala Leu Cys Leu Leu Pro Ser
1               5                   10                  15

Gly Gly Thr Glu Ser Gln Asp Gln Ser Ser Leu Cys Lys Gln Pro Pro
                20                  25                  30
```

-continued

```
Ala Trp Ser Ile Arg Asp Gln Asp Pro Met Leu Asn Ser Asn Gly Ser
        35                  40                  45

Val Thr Val Val Ala Leu Leu Gln Ala Ser Xaa Tyr Leu Cys Ile Ile
 50                  55                  60

Glu Ala Ser Lys Leu Glu Asp Leu Arg Val Lys Leu Lys Lys Glu Gly
 65                  70                  75                  80

Tyr Ser Asn Ile Ser Tyr Ile Val Val Asn His Gln Gly Ile Ser Ser
                 85                  90                  95

Arg Leu Lys Tyr Thr His Leu Lys Asn Lys Val Ser Glu His Ile Pro
            100                 105                 110

Val Tyr Gln Gln Glu Glu Asn Gln Thr Asp Val Trp Thr Leu Leu Asn
            115                 120                 125

Gly Ser Lys Asp Asp Phe Leu Ile Tyr Asp Arg Cys Gly Arg Leu Val
130                 135                 140

Tyr His Leu Gly Leu Pro Phe Ser Phe Leu Thr Phe Pro Tyr Val Glu
145                 150                 155                 160

Glu Ala Ile Lys Ile Ala Tyr Cys Glu Lys Lys Cys Gly Asn Cys Ser
                165                 170                 175

Leu Thr Thr Leu Lys Asp Glu Asp Phe Cys Lys Arg Val Ser Leu Ala
            180                 185                 190

Thr Val Asp Lys Thr Val Glu Thr Pro Ser Pro His Tyr His His Glu
            195                 200                 205

His His His Asn His Gly His Gln His Leu Gly Ser Ser Glu Leu Ser
            210                 215                 220

Glu Asn Gln Gln Pro Gly Ala Pro Asn Ala Pro Thr His Pro Ala Pro
225                 230                 235                 240

Pro Gly Leu His His His His Lys His Lys Gly Gln His Arg Gln Gly
                245                 250                 255

His Pro Glu Asn Arg Asp Met Pro Ala Ser Glu Asp Leu Gln Asp Leu
            260                 265                 270

Gln Lys Lys Leu Cys Arg Lys Arg Cys Ile Asn Gln Leu Leu Cys Lys
            275                 280                 285

Leu Pro Thr Asp Ser Glu Leu Ala Pro Arg Ser Xaa Cys Cys His Cys
290                 295                 300

Arg His Leu Ile Phe Glu Lys Thr Gly Ser Ala Ile Thr Xaa Gln Cys
305                 310                 315                 320

Lys Glu Asn Leu Pro Ser Leu Cys Ser Xaa Gln Gly Leu Arg Ala Glu
                325                 330                 335

Glu Asn Ile Thr Glu Ser Cys Gln Xaa Arg Leu Pro Pro Ala Ala Xaa
            340                 345                 350

Gln Ile Ser Gln Gln Leu Ile Pro Thr Glu Ala Ser Ala Ser Xaa Arg
            355                 360                 365

Xaa Lys Asn Gln Ala Lys Lys Xaa Glu Xaa Pro Ser Asn
370                 375                 380

<210> SEQ ID NO 97
<211> LENGTH: 220
<212> TYPE: PRT
<213> ORGANISM: Homo sapiens

<400> SEQUENCE: 97

Met Ala Ile Leu Phe Ala Val Val Ala Arg Gly Thr Thr Ile Leu Ala
 1               5                  10                  15

Lys His Ala Trp Cys Gly Gly Asn Phe Leu Glu Val Thr Glu Gln Ile
                 20                  25                  30
```

```
Leu Ala Lys Ile Pro Ser Glu Asn Asn Lys Leu Thr Tyr Ser His Gly
            35                  40                  45

Asn Tyr Leu Phe His Tyr Ile Cys Gln Asp Arg Ile Val Tyr Leu Cys
        50                  55                  60

Ile Thr Asp Asp Phe Glu Arg Ser Arg Ala Phe Asn Phe Leu Asn
65                  70                  75                  80

Glu Ile Lys Lys Arg Phe Gln Thr Thr Tyr Gly Ser Arg Ala Gln Thr
                85                  90                  95

Ala Leu Pro Tyr Ala Met Asn Ser Glu Phe Ser Ser Val Leu Ala Ala
            100                 105                 110

Gln Leu Lys His His Ser Glu Asn Lys Gly Leu Asp Lys Val Met Glu
            115                 120                 125

Thr Gln Ala Gln Val Asp Glu Leu Lys Gly Ile Met Val Arg Asn Ile
        130                 135                 140

Asp Leu Val Ala Gln Arg Gly Glu Arg Leu Glu Leu Leu Ile Asp Lys
145                 150                 155                 160

Thr Glu Asn Leu Val Asp Ser Ser Val Thr Phe Lys Thr Thr Ser Arg
                165                 170                 175

Asn Leu Ala Arg Ala Met Cys Met Lys Asn Leu Lys Leu Thr Ile Ile
            180                 185                 190

Ile Ile Ile Val Ser Ile Val Phe Ile Tyr Ile Val Ser Pro Leu
        195                 200                 205

Cys Gly Gly Phe Thr Trp Pro Ser Cys Val Lys Lys
            210                 215                 220

<210> SEQ ID NO 98
<211> LENGTH: 1736
<212> TYPE: PRT
<213> ORGANISM: Homo sapiens

<400> SEQUENCE: 98

Met Glu Glu Thr Ala Ile Trp Glu Gln His Thr Val Thr Leu His Arg
1               5                   10                  15

Ala Pro Gly Phe Gly Phe Gly Ile Ala Ile Ser Gly Gly Arg Asp Asn
            20                  25                  30

Pro His Phe Gln Ser Gly Glu Thr Ser Ile Val Ile Ser Asp Val Leu
        35                  40                  45

Lys Gly Gly Pro Ala Glu Gly Gln Leu Gln Glu Asn Asp Arg Val Ala
    50                  55                  60

Met Val Asn Gly Val Ser Met Asp Asn Val Glu His Ala Phe Ala Val
65                  70                  75                  80

Gln Gln Leu Arg Lys Ser Gly Lys Asn Ala Lys Ile Thr Ile Arg Arg
                85                  90                  95

Lys Lys Lys Val Gln Ile Pro Val Ser Arg Pro Asp Pro Glu Pro Val
            100                 105                 110

Ser Asp Asn Glu Glu Asp Ser Tyr Asp Glu Glu Ile His Asp Pro Arg
        115                 120                 125

Ser Gly Arg Ser Gly Val Val Asn Arg Ser Glu Lys Ile Trp Pro
    130                 135                 140

Arg Asp Arg Ser Ala Ser Arg Glu Arg Ser Leu Ser Pro Arg Ser Asp
145                 150                 155                 160

Arg Arg Ser Val Ala Ser Ser Gln Pro Ala Lys Pro Thr Lys Val Thr
                165                 170                 175

Leu Val Lys Ser Arg Lys Asn Glu Glu Tyr Gly Leu Arg Leu Ala Ser
            180                 185                 190
```

```
His Ile Phe Val Lys Glu Ile Ser Gln Asp Ser Leu Ala Ala Arg Asp
        195                 200                 205

Gly Asn Ile Gln Glu Gly Asp Val Val Leu Lys Ile Asn Gly Thr Val
        210                 215                 220

Thr Glu Asn Met Ser Leu Thr Asp Ala Lys Thr Leu Ile Glu Arg Ser
225                 230                 235                 240

Lys Gly Lys Leu Lys Met Val Val Gln Arg Asp Glu Arg Ala Thr Leu
                245                 250                 255

Leu Asn Val Pro Asp Leu Ser Asp Ser Ile His Ser Ala Asn Ala Ser
                260                 265                 270

Glu Arg Asp Asp Ile Ser Glu Ile Gln Ser Leu Ala Ser Asp His Ser
        275                 280                 285

Gly Arg Ser His Asp Arg Pro Pro Arg Ser Arg Ser Arg Ser Pro
        290                 295                 300

Asp Gln Arg Ser Glu Pro Ser Asp His Ser Arg His Ser Pro Gln Gln
305                 310                 315                 320

Pro Ser Asn Gly Ser Leu Arg Ser Arg Asp Glu Arg Ile Ser Lys
                325                 330                 335

Pro Gly Ala Val Ser Thr Pro Val Lys His Ala Asp Asp His Thr Pro
                340                 345                 350

Lys Thr Val Glu Glu Val Thr Val Glu Arg Asn Glu Lys Gln Thr Pro
                355                 360                 365

Ser Leu Pro Glu Pro Lys Pro Val Tyr Ala Gln Val Gly Asn Gln Met
        370                 375                 380

Trp Ile Tyr Leu Ser Val His Leu Met Val Ser Tyr Leu Ile Gln Leu
385                 390                 395                 400

Met Lys Met Gly Phe Leu Arg Pro Ser Met Lys Leu Val Lys Phe Arg
                405                 410                 415

Lys Gly Asp Ser Val Gly Leu Arg Leu Ala Gly Gly Asn Asp Val Gly
                420                 425                 430

Ile Phe Val Ala Gly Val Leu Glu Asp Ser Pro Ala Ala Lys Glu Gly
        435                 440                 445

Leu Glu Glu Gly Asp Gln Ile Leu Arg Val Asn Asn Val Asp Phe Thr
        450                 455                 460

Asn Ile Ile Arg Glu Glu Ala Val Leu Phe Leu Leu Asp Leu Pro Lys
465                 470                 475                 480

Gly Glu Glu Val Thr Ile Leu Ala Gln Lys Lys Asp Val Tyr Arg
                485                 490                 495

Arg Ile Val Glu Ser Asp Val Gly Asp Ser Phe Tyr Ile Arg Thr His
                500                 505                 510

Phe Glu Tyr Glu Lys Glu Ser Pro Tyr Gly Leu Ser Phe Asn Lys Gly
        515                 520                 525

Glu Val Phe Arg Ala Val Asp Thr Leu Tyr Asn Gly Lys Leu Gly Ser
        530                 535                 540

Trp Leu Ala Ile Arg Ile Gly Lys Asn His Lys Glu Val Glu Arg Gly
545                 550                 555                 560

Ile Ile Pro Asn Lys Asn Arg Ala Glu Gln Leu Ala Ser Val Gln Tyr
                565                 570                 575

Thr Leu Pro Lys Thr Ala Gly Gly Asp Arg Ala Asp Phe Trp Arg Phe
                580                 585                 590

Arg Gly Leu Arg Ser Ser Lys Arg Asn Leu Arg Lys Ser Arg Glu Asp
                595                 600                 605
```

-continued

```
Leu Ser Ala Gln Pro Val Gln Thr Lys Phe Pro Ala Tyr Glu Arg Val
610                 615                 620
Val Leu Arg Glu Ala Gly Phe Leu Arg Pro Val Thr Ile Phe Gly Pro
625                 630                 635                 640
Ile Ala Asp Val Ala Arg Glu Lys Leu Ala Arg Glu Pro Asp Ile
            645                 650                 655
Tyr Gln Ile Ala Lys Ser Glu Pro Arg Asp Ala Gly Thr Asp Gln Arg
            660                 665                 670
Ser Ser Gly Tyr Ile Arg Leu His Thr Ile Lys Gln Ile Ile Asp Gln
            675                 680                 685
Asp Lys His Ala Leu Leu Asp Val Thr Pro Asn Ala Val Asp Arg Leu
690                 695                 700
Asn Tyr Ala Gln Trp Tyr Pro Ile Val Val Phe Leu Asn Pro Asp Ser
705                 710                 715                 720
Lys Gln Gly Val Lys Thr Met Arg Met Arg Leu Cys Pro Glu Ser Arg
            725                 730                 735
Lys Ser Ala Arg Lys Leu Tyr Glu Arg Ser His Lys Leu Ala Lys Asn
            740                 745                 750
Asn His His Leu Phe Thr Thr Ile Asn Leu Asn Ser Met Asn Asp
            755                 760                 765
Gly Trp Tyr Gly Ala Leu Lys Glu Ala Val Gln Gln Gln Asn Gln
770                 775                 780
Leu Val Trp Val Ser Glu Gly Lys Ala Asp Gly Ala Thr Ser Asp Asp
785                 790                 795                 800
Leu Asp Leu His Asp Asp Arg Leu Ser Tyr Leu Ser Ala Pro Gly Ser
            805                 810                 815
Glu Tyr Ser Met Tyr Ser Thr Asp Ser Arg His Thr Ser Asp Tyr Glu
            820                 825                 830
Asp Thr Asp Thr Glu Gly Gly Ala Tyr Thr Asp Gln Glu Leu Asp Glu
            835                 840                 845
Thr Leu Asn Asp Glu Val Gly Thr Pro Pro Glu Ser Ala Ile Thr Arg
850                 855                 860
Ser Ser Glu Pro Val Arg Glu Asp Ser Ser Gly Met His His Glu Asn
865                 870                 875                 880
Gln Thr Tyr Pro Pro Tyr Ser Pro Gln Ala Gln Pro Gln Pro Ile His
            885                 890                 895
Arg Ile Asp Ser Pro Gly Phe Lys Pro Ala Ser Gln Gln Lys Ala Glu
            900                 905                 910
Ala Ser Ser Pro Val Pro Tyr Leu Ser Pro Glu Thr Asn Pro Ala Ser
            915                 920                 925
Ser Thr Ser Ala Val Asn His Asn Val Asn Leu Thr Asn Val Arg Leu
930                 935                 940
Glu Glu Pro Thr Pro Ala Pro Ser Thr Ser Tyr Ser Pro Gln Ala Asp
945                 950                 955                 960
Ser Leu Arg Thr Pro Ser Thr Glu Ala Ala His Ile Met Leu Arg Asp
            965                 970                 975
Gln Glu Pro Ser Leu Ser Ser His Val Asp Pro Thr Lys Val Tyr Arg
            980                 985                 990
Lys Asp Pro Tyr Pro Glu Glu Met  Met Arg Gln Asn His  Val Leu Lys
            995                 1000                1005
Gln Pro  Ala Val Ser His Pro  Gly His Arg Pro  Asp Lys Glu Pro
   1010              1015              1020
```

-continued

```
Asn Leu Thr Tyr Glu Pro Gln Leu Pro Tyr Val Glu Lys Gln Ala
    1025                1030                1035

Ser Arg Asp Leu Glu Gln Pro Thr Tyr Arg Tyr Glu Ser Ser Ser
    1040                1045                1050

Tyr Thr Asp Gln Phe Ser Arg Asn Tyr Glu His Arg Leu Arg Tyr
    1055                1060                1065

Glu Asp Arg Val Pro Met Tyr Glu Glu Gln Trp Ser Tyr Tyr Asp
    1070                1075                1080

Asp Lys Gln Pro Tyr Pro Ser Arg Pro Pro Phe Asp Asn Gln His
    1085                1090                1095

Ser Gln Asp Leu Asp Ser Arg Gln His Pro Glu Glu Ser Ser Glu
    1100                1105                1110

Arg Gly Tyr Phe Pro Arg Phe Glu Glu Pro Ala Pro Leu Ser Tyr
    1115                1120                1125

Asp Ser Arg Pro Arg Tyr Glu Gln Ala Pro Arg Ala Ser Ala Leu
    1130                1135                1140

Arg His Glu Glu Gln Pro Ala Pro Gly Tyr Asp Thr His Gly Arg
    1145                1150                1155

Leu Arg Pro Glu Ala Gln Pro His Pro Ser Ala Gly Pro Lys Pro
    1160                1165                1170

Ala Glu Ser Lys Gln Tyr Phe Glu Gln Tyr Ser Arg Ser Tyr Glu
    1175                1180                1185

Gln Val Pro Pro Gln Gly Phe Thr Ser Arg Ala Gly His Phe Glu
    1190                1195                1200

Pro Leu His Gly Ala Ala Ala Val Pro Pro Leu Ile Pro Ser Ser
    1205                1210                1215

Gln His Lys Pro Glu Ala Leu Pro Ser Asn Thr Lys Pro Leu Pro
    1220                1225                1230

Pro Pro Pro Thr Gln Thr Glu Glu Glu Glu Asp Pro Ala Met Lys
    1235                1240                1245

Pro Gln Ser Val Leu Thr Arg Val Lys Met Phe Glu Asn Lys Arg
    1250                1255                1260

Ser Ala Ser Leu Glu Thr Lys Lys Asp Val Asn Asp Thr Gly Ser
    1265                1270                1275

Phe Lys Pro Pro Glu Val Ala Ser Lys Pro Ser Gly Ala Pro Ile
    1280                1285                1290

Ile Gly Pro Lys Pro Thr Ser Gln Asn Gln Phe Ser Glu His Asp
    1295                1300                1305

Lys Thr Leu Tyr Arg Ile Pro Glu Pro Gln Lys Pro Gln Leu Lys
    1310                1315                1320

Pro Pro Glu Asp Ile Val Arg Ser Asn His Tyr Asp Pro Glu Glu
    1325                1330                1335

Asp Glu Glu Tyr Tyr Arg Lys Gln Leu Ser Tyr Phe Asp Arg Arg
    1340                1345                1350

Ser Phe Glu Asn Lys Pro Pro Ala His Ile Ala Ala Ser His Leu
    1355                1360                1365

Ser Glu Pro Ala Lys Pro Ala His Ser Gln Asn Gln Ser Asn Phe
    1370                1375                1380

Ser Ser Tyr Ser Ser Lys Gly Lys Pro Pro Glu Ala Asp Gly Val
    1385                1390                1395

Asp Arg Ser Phe Gly Glu Lys Arg Tyr Glu Pro Ile Gln Ala Thr
    1400                1405                1410
```

-continued

```
Pro Pro Pro Pro Leu Pro Ser Gln Tyr Ala Gln Pro Ser Gln
    1415            1420                1425

Pro Val Thr Ser Ala Ser Leu His Ile His Ser Lys Gly Ala His
    1430            1435                1440

Gly Glu Gly Asn Ser Val Ser Leu Asp Phe Gln Asn Ser Leu Val
    1445            1450                1455

Ser Lys Pro Asp Pro Pro Ser Gln Asn Lys Pro Ala Thr Phe
    1460            1465                1470

Arg Pro Pro Asn Arg Glu Asp Thr Ala Gln Ala Ala Phe Tyr Pro
    1475            1480                1485

Gln Lys Ser Phe Pro Asp Lys Ala Pro Val Asn Gly Thr Glu Gln
    1490            1495                1500

Thr Gln Lys Thr Val Thr Pro Ala Tyr Asn Arg Phe Thr Pro Lys
    1505            1510                1515

Pro Tyr Thr Ser Ser Ala Arg Pro Phe Glu Arg Lys Phe Glu Ser
    1520            1525                1530

Pro Lys Phe Asn His Asn Leu Leu Pro Ser Glu Thr Ala His Lys
    1535            1540                1545

Pro Asp Leu Ser Ser Lys Thr Pro Thr Ser Pro Lys Thr Leu Val
    1550            1555                1560

Lys Ser His Ser Leu Ala Gln Pro Pro Glu Phe Asp Ser Gly Val
    1565            1570                1575

Glu Thr Phe Ser Ile His Ala Glu Lys Pro Lys Tyr Gln Ile Asn
    1580            1585                1590

Asn Ile Ser Thr Val Pro Lys Ala Ile Pro Val Ser Pro Ser Ala
    1595            1600                1605

Val Glu Glu Asp Glu Asp Asp Gly His Thr Val Val Ala Thr
    1610            1615                1620

Ala Arg Gly Ile Phe Asn Ser Asn Gly Gly Val Leu Ser Ser Ile
    1625            1630                1635

Glu Thr Gly Val Ser Ile Ile Ile Pro Gln Gly Ala Ile Pro Glu
    1640            1645                1650

Gly Val Glu Gln Glu Ile Tyr Phe Lys Val Cys Arg Asp Asn Ser
    1655            1660                1665

Ile Leu Pro Pro Leu Asp Lys Glu Lys Gly Glu Thr Leu Leu Ser
    1670            1675                1680

Pro Leu Val Met Cys Gly Pro His Gly Leu Lys Phe Leu Lys Pro
    1685            1690                1695

Val Glu Leu Arg Leu Pro His Cys Asp Pro Lys Thr Trp Gln Asn
    1700            1705                1710

Lys Cys Leu Pro Gly Asp Pro Asn Tyr Leu Val Gly Ala Asn Cys
    1715            1720                1725

Val Ser Val Leu Ile Asp His Phe
    1730            1735
```

<210> SEQ ID NO 99
<211> LENGTH: 93
<212> TYPE: PRT
<213> ORGANISM: Homo sapiens

<400> SEQUENCE: 99

```
Met Gln Arg Arg Gly Gln Pro Leu Glu Asn His Val Ala Leu Ile His
1               5                   10                  15

Trp Gln Ser Ala Gly Ile Pro Ala Ser Lys Val His Asn Tyr Cys Asn
            20                  25                  30
```

-continued

Met Lys Lys Ser Arg Leu Gly Arg Ser Arg Ala Val Arg Ile Ser Gln
                35                  40                  45

Pro Leu Leu Ser Pro Arg Arg Cys Pro Leu His Leu Thr Glu Arg Gly
         50                  55                  60

Ala Gly Leu Leu Gln Pro Gln Pro Gln Gly Pro Val Arg Thr Pro Gly
 65                  70                  75                  80

Pro Pro Pro Gly Val Thr Gln Arg Pro Arg Thr Thr Glu
                 85                  90

<210> SEQ ID NO 100
<211> LENGTH: 582
<212> TYPE: PRT
<213> ORGANISM: Homo sapiens

<400> SEQUENCE: 100

Asp Val Ser Arg Cys Ala His Arg Ala Arg Pro Gly Ala Ile Met Leu
 1               5                  10                  15

Leu Leu Pro Ser Ala Ala Asp Gly Arg Gly Thr Ala Ile Thr His Ala
                20                  25                  30

Leu Thr Ser Ala Ser Thr Leu Cys Gln Val Glu Pro Val Gly Arg Trp
                35                  40                  45

Phe Glu Ala Phe Val Lys Arg Arg Asn Arg Asn Ala Ser Ala Ser Phe
         50                  55                  60

Gln Glu Leu Glu Asp Lys Lys Glu Leu Ser Glu Ser Glu Asp Glu
 65                  70                  75                  80

Glu Leu Gln Leu Glu Glu Phe Pro Met Leu Lys Thr Leu Asp Pro Lys
                85                  90                  95

Asp Trp Lys Asn Gln Asp His Tyr Ala Val Leu Gly Leu Gly His Val
                100                 105                 110

Arg Tyr Lys Ala Thr Gln Arg Gln Ile Lys Ala Ala His Lys Ala Met
            115                 120                 125

Val Leu Lys His His Pro Asp Lys Arg Lys Ala Ala Gly Glu Pro Ile
        130                 135                 140

Lys Glu Gly Asp Asn Asp Tyr Phe Thr Cys Ile Thr Lys Ala Tyr Glu
145                 150                 155                 160

Met Leu Ser Asp Pro Val Lys Arg Arg Ala Phe Asn Ser Val Asp Pro
                165                 170                 175

Thr Phe Asp Asn Ser Val Pro Ser Lys Ser Glu Ala Lys Asp Asn Phe
            180                 185                 190

Phe Glu Val Phe Thr Pro Val Phe Glu Arg Asn Ser Arg Trp Ser Asn
        195                 200                 205

Lys Lys Asn Val Pro Lys Leu Gly Asp Met Asn Ser Ser Phe Glu Asp
    210                 215                 220

Val Asp Ile Phe Tyr Ser Phe Trp Tyr Asn Phe Asp Ser Trp Arg Glu
225                 230                 235                 240

Phe Ser Tyr Leu Asp Glu Glu Lys Glu Lys Ala Glu Cys Arg Asp
                245                 250                 255

Glu Arg Arg Trp Ile Glu Lys Gln Asn Gly Ala Thr Arg Ala Gln Arg
            260                 265                 270

Lys Lys Glu Glu Met Asn Arg Ile Arg Thr Leu Val Asp Asn Ala Tyr
    275                 280                 285

Ser Cys Asp Pro Arg Ile Lys Lys Phe Lys Glu Glu Lys Ala Lys
        290                 295                 300

Lys Glu Ala Glu Lys Lys Ala Lys Ala Glu Ala Lys Arg Lys Glu Gln
305                 310                 315                 320

-continued

```
Glu Ala Lys Glu Lys Gln Arg Gln Ala Glu Leu Glu Ala Ala Arg Leu
            325                 330                 335

Ala Lys Glu Lys Glu Glu Glu Val Arg Gln Gln Ala Leu Leu Ala
            340             345                 350

Lys Lys Glu Lys Asp Ile Gln Lys Lys Ala Ile Lys Lys Glu Arg Gln
            355                 360                 365

Lys Leu Arg Asn Ser Cys Lys Ile Glu Glu Ile Asn Glu Gln Ile Arg
            370             375                 380

Lys Glu Lys Glu Glu Ala Glu Ala Arg Met Arg Gln Ala Ser Lys Asn
385                 390                 395                 400

Thr Glu Lys Ser Thr Gly Gly Gly Asn Gly Ser Lys Asn Trp Ser
                405                 410                 415

Glu Asp Asp Leu Gln Leu Leu Ile Lys Ala Val Asn Leu Phe Pro Ala
            420                 425                 430

Arg Thr Asn Ser Arg Trp Glu Val Ile Ala Asn Tyr Met Asn Ile His
            435             440                 445

Ser Ser Ser Gly Val Lys Arg Thr Ala Lys Asp Val Ile Gly Lys Ala
    450             455                 460

Lys Ser Leu Gln Lys Leu Asp Pro His Gln Lys Asp Asp Ile Asn Lys
465             470                 475                 480

Lys Ala Phe Asp Lys Phe Lys Lys Glu His Gly Val Val Pro Gln Ala
            485                 490                 495

Asp Asn Ala Thr Pro Ser Glu Arg Phe Glu Gly Pro Tyr Thr Asp Phe
            500                 505             510

Thr Pro Trp Thr Thr Glu Glu Gln Lys Leu Leu Glu Gln Ala Leu Lys
        515                 520                 525

Thr Tyr Pro Val Asn Thr Pro Glu Arg Trp Glu Lys Ile Ala Glu Ala
    530                 535                 540

Val Pro Gly Arg Thr Lys Lys Asp Cys Met Lys Arg Tyr Lys Glu Leu
545                 550                 555                 560

Val Glu Met Val Lys Ala Lys Ala Ala Gln Glu Gln Val Leu Asn
                565                 570                 575

Ala Ser Arg Ala Lys Lys
                580
```